United States Patent
Lim et al.

(10) Patent No.: US 11,787,810 B2
(45) Date of Patent: Oct. 17, 2023

(54) DIACYLGLYCERIDE O-ACYLTRANSFERASE 2 INHIBITORS

(71) Applicant: Merck Sharp & Dohme Corp., Rahway, NJ (US)

(72) Inventors: Yeon-Hee Lim, South San Francisco, CA (US); Cedric Lorenz Hugelshofer, Oakland, CA (US); Victor W. Mak, South San Francisco, CA (US); James Patrick Roane, Brisbane, CA (US); Jillian R. Sanzone, San Francisco, CA (US); Samantha E. Shockley, San Francisco, CA (US); Rose Yen, San Francisco, CA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/319,121

(22) Filed: May 13, 2021

(65) Prior Publication Data

US 2021/0363147 A1    Nov. 25, 2021

Related U.S. Application Data

(60) Provisional application No. 63/026,263, filed on May 18, 2020.

(51) Int. Cl.
| | |
|---|---|
| *C07D 231/56* | (2006.01) |
| *C07D 471/04* | (2006.01) |
| *C07D 487/04* | (2006.01) |
| *C07D 409/14* | (2006.01) |

(52) U.S. Cl.
CPC ......... *C07D 487/04* (2013.01); *C07D 231/56* (2013.01); *C07D 409/14* (2013.01); *C07D 471/04* (2013.01)

(58) Field of Classification Search
CPC .............................. C07D 231/56; C07D 471/04
See application file for complete search history.

(56) References Cited

U.S. PATENT DOCUMENTS

| | | | |
|---|---|---|---|
| 8,569,512 B2 * | 10/2013 | Burgey | A61P 25/00 548/361.1 |
| 9,296,745 B2 | 3/2016 | Ahn et al. | |
| 10,947,222 B2 * | 3/2021 | Shen | C07D 209/10 |
| 11,104,690 B2 * | 8/2021 | Shen | C07D 515/08 |
| 2015/0259323 A1 | 9/2015 | Cabral et al. | |
| 2019/0330239 A1 | 10/2019 | Shen et al. | |

FOREIGN PATENT DOCUMENTS

| | | |
|---|---|---|
| WO | 2003053363 A2 | 7/2003 |
| WO | 2013150416 A1 | 10/2013 |
| WO | 2015077299 A1 | 5/2015 |
| WO | 2016036633 A1 | 3/2016 |
| WO | 2016036636 A1 | 3/2016 |
| WO | 2016036638 A1 | 3/2016 |
| WO | 2017011276 A1 | 1/2017 |
| WO | 2018033832 A1 | 2/2018 |
| WO | 2018093696 A1 | 5/2018 |
| WO | 2018093698 A1 | 5/2018 |

OTHER PUBLICATIONS

Chemical Abstracts Registry No. 924738-74-9, indexed in the Registry file on STN CAS Online Mar. 5, 2007. (Year: 2007).*
Chemical Abstracts Registry No. 2226397-88-0, indexed in the Registry file on STN CAS Online Jun. 5, 2018. (Year: 2018).*
Pubchem SID 389814512, Available Date: Dec. 6, 2019 [retrieved on Jul. 21, 2021], Retrieved from the Internet URL: https://pubchem.ncbi.nlm.nih.gov/substance/389814512 entire document, 5 pages.
Choi et al., Suppression of Diacylglycerol Acyltransferase-2 (DGAT2), but Not DGAT1, with Antisense Oligonucleotides Reverses Diet-induced Hepatic Steatosis and Insulin Resistance, Journal of Biological Chemistry, 2007, 22678-22688, 282(31).
Li, Chen et al., Roles of Acyl-CoA:Diacylglycerol Acyltransferases 1 and 2 in Triacylglycerol Synthesis and Secretion in Primary Hepatocytes, Arterioscler. Thromb. Vasc. Biol., 2015, 1080-1091, 35.
Liu et al., Knockdown of Acyl-CoA:diacylglycerol acyltransferase 2 with antisense oligonucleotide reduces VLDL TG and ApoB secretion in mice, Biochimica et Biophysica Acta, Molecular and Cell Biology of Lipids, 2008, 97-104, 1781 (3).
Yen, Chi-Liang Eric et al., DGAT enzymes and triacylglycerol biosynthesis, Journal of Lipid Research, 2008, 2283-2301, 49.
Yu, Xing Xian et al., Antisense Oligonucleotide Reduction of DGAT2 Expression Improves Hepatic Steatosis and Hyperlipidemia in Obese Mice, Hepatology, 2005, 362-371, 42.
Ciapetti, Paola et al., Molecular Variations Based on Isosteric Replacements, The Practice of Medicinal Chemistry (Third Edition), 2008, 290-342, Chapter 15.

* cited by examiner

*Primary Examiner* — Laura L Stockton
(74) *Attorney, Agent, or Firm* — Kristi K. Harman; Catherine D. Fitch

(57) ABSTRACT

Invented are compounds of formula I

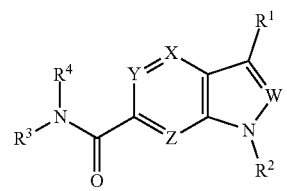

and the pharmaceutically acceptable salts, esters, and prodrugs thereof, which are DGAT2 inhibitors. Also provided are methods of making compounds of Formula I, pharmaceutical compositions comprising compounds of Formula I, and methods of using these compounds to treat hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases and heart failure and related diseases and conditions, comprising administering a compound of Formula I to a patient in need thereof.

13 Claims, No Drawings

DIACYLGLYCERIDE O-ACYLTRANSFERASE 2 INHIBITORS

CROSS-REFERENCE TO RELATED APPLICATIONS

This application is a Non-Provisional application, which claims the benefit of priority to U.S. Provisional Patent Application No. 63/062,263, filed May 18, 2020, the contents of which is hereby incorporated by reference in its entirety.

FIELD OF THE INVENTION

The present invention is directed to novel pharmaceutical compounds which inhibit diacylglyceride O-acyltransferase 2 ("DGAT2"), and may be useful for preventing, treating or acting as a reversing agent for hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases and heart failure, and related diseases and conditions, as well as methods of making such compounds and pharmaceutical compositions comprising such a compound and a pharmaceutical carrier.

BACKGROUND OF THE INVENTION

Triacylglycerols ("TGs") serve several functions in living organisms. One such function of TGs is in the storage of energy. TGs also play a role in the synthesis of membrane lipids. TG synthesis in cells may protect them from the potentially toxic effects of excess fatty acid ("FA"). In enterocytes and hepatocytes, TGs are synthesized for the assembly and secretion of lipoproteins which transport FA between tissues. TGs play a role in the skin's surface water barrier, and TGs in adipose tissue provide insulation for organisms.

The glycerol phosphate and the monoacylglycerol pathways are the major pathways for the biosynthesis of TG. However, the last step in the synthesis of TG involves the reaction of a fatty acyl-CoA and diacylglycerol ("DAG") to form TG. The reaction is catalyzed by acyl-CoA:diacylglycerol acyltransferase ("DGAT") enzymes. There have been identified two DGAT enzymes, DGAT1 and DGAT2. Although DGAT1 and DGAT2 catalyze the same reaction, they differ significantly at the level of DNA and protein sequences. DGAT2 can utilize endogenous fatty acid to synthesize TG in in vitro assays, whereas DGAT1 appears to be more dependent on exogenous fatty acid (Yen et al., *J. Lipid Research*, 2008, 49, 2283). Inactivation of DGAT2 impaired cytosolic lipid droplet growth, whereas inactivation of DGAT1 exerts opposite effect. (Li et al., *Arterioscler. Thromb. Vasc. Biol.* 2015, 35, 1080).

DGAT2 is an integral membrane protein of the endoplasmic reticulum and is expressed strongly in adipose tissue and the liver. DGAT2 appears to be the dominant DGAT enzyme controlling TG homeostasis in vivo. DGAT2 deficient mice survive for only a few hours after birth. On the other hand, DGAT1 deficient mice are viable (Yen et al., *J. Lipid Research*, 2008, 49, 2283).

Despite this perinatal lethal phenotype, the metabolic role of DGAT2 has been mostly comprehended from effort exploiting anti-sense oligonucleotides (ASO) in rodents. In this setting, DGAT2 knockdown in ob/ob mice with a DGAT2 gene-specific ASO resulted in a dose dependent decrease in very low density lipoprotein ("VLDL") and a reduction in plasma TG, total cholesterol, and ApoB (Liu, et al., *Biochim. Biophys Acta* 2008, 1781, 97). In the same study, DGAT2 antisense oligonucleotide treatment of ob/ob mice showed a decrease in weight gain, adipose weight and hepatic TG content. Id. In another study, antisense treatment of ob/ob mice improved hepatic steatosis and hyperlipidemia (Yu, et al., *Hepatology,* 2005, 42, 362). Another study showed that diet-induced hepatic steatosis and insulin resistance was improved by knocking down DGAT2 in rats. These effects seem to be unique to inhibition of DGAT2, as ASO against DGAT1 did not lead to similar beneficial effects. Although the molecular mechanism behind these observations remains uncertain, the collective data suggest that suppression of DGAT2 is associated with reduced expression of lipogenic genes (SREBP1c, ACC1, SCD1, and mtGPAT) and increased expression of oxidative/thermogenic genes (CPT1, UCP2) (Choi et al., *J. Bio. Chem.,* 2007, 282, 22678).

In light of the above description, inhibitors of DGAT2 are useful for treating disease related to the spectrum of metabolic syndrome such as hepatic steatosis, non-alcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases and heart failure and related diseases and conditions.

DGAT2 inhibitor compounds are described in WO2016036633, WO2016036636, WO2016036638, WO2018093696, WO2018093698, WO2013150416, US20150259323, WO2015077299, WO2017011276, WO2018033832, US201801628, WO2003053363.

SUMMARY OF THE INVENTION

The present invention relates to compounds represented by Formula I.

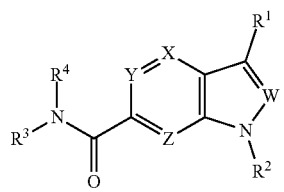

as well as pharmaceutically acceptable salts, esters, and prodrugs thereof, which are DGAT2 inhibitors. Also provided are methods of making compounds of Formula I, pharmaceutical compositions comprising compounds of Formula I, and methods of using these compounds to treat hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases and heart failure and related diseases and conditions, comprising administering a compound of formula I to a patient in need thereof.

DETAILED DESCRIPTION OF THE INVENTION

The present disclosure is directed to compounds having structural Formula I:

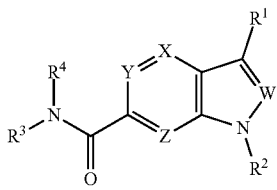

or pharmaceutically acceptable salts thereof wherein:
W is selected from N or C(H);
X, Y, and Z are independently selected from N or C($R^5$); and
$R^1$ is
  (1) phenyl unsubstituted or substituted with 1, 2, or 3 $R^6$, or
  (2) 5- or 6-membered heteroaryl containing 1, 2, 3 or 4 heteroatoms independently selected from N, O, and S, wherein the heteroaryl is unsubstituted or substituted with 1, 2, or 3 $R^6$, or
  (3) 8- to 10-membered fused heteroaryl containing 1, 2, 3 heteroatoms independently selected from N, O, and S, wherein the heteroaryl is unsubstituted or substituted with 1, 2, or 3 $R^6$;
$R^2$ is
  (1) phenyl optionally mono-substituted or disubstituted with halogen,
  (2) 5- or 6-membered heteroaryl containing 1, 2 or 3 heteroatoms independently selected from N, O, and S, wherein the heteroaryl is optionally mono-substituted or disubstituted with halogen, $C_{1-6}$haloalkyl, $C_{1-6}$alkyl, C(O)$C_{1-6}$alkyl, C(O)(OH), or OH,
  (3) $C_{1-6}$alkyl unsubstituted or optionally mono-substituted, disubstituted or trisubstituted with halogen, OH, $CF_3$, —CN, or ($C_{3-6}$)cycloalkyl,
  (4) ($C_{3-6}$)cycloalkyl unsubstituted or optionally mono-substituted, disubstituted or trisubstituted with $C_{1-6}$alkyl, halogen, OH, $CF_3$, or —CN,
  (5) 4- to 6-membered heterocyclyl containing 1 or 2 heteroatoms independently selected from N, O and S wherein the heterocyclyl is unsubstituted or substituted by 1, 2, or 3 $R^7$,
  (6) —$CH_2$-aryl optionally mono-substituted or disubstituted with halogen,
  (7) —$CH_2$-heterocyclyl containing 1 or 2 heteroatoms independently selected from N, O, and S, or
  (8) —$C_{1-6}$alkylC(O)$NH_2$;
$R^3$ is
  (1) 4- to 7-membered heterocyclyl containing 1 or 2 heteroatoms independently selected from N, O and S,
  (2) —($C_{1-6}$)alkyl-heterocyclyl, wherein the heterocyclyl is a 3- to 6-membered ring containing 1 or 2 heteroatoms independently selected from N, O and S,
  (3) —($C_{1-6}$)alkyl,
  (4) —($C_{3-6}$)cycloalkyl,
  (5) —($C_{3-6}$)cycloalkyl-heterocyclyl wherein the heterocyclyl is a 3- to 6-membered ring containing 1 or 2 heteroatoms independently selected from N, O and S,
  (6) —($C_{1-6}$)hydroxyalkyl,
  (7) —($C_{1-6}$)cyanoalkyl,
  (8) —($C_{1-6}$)alkyl-S(O)$_2$—($C_{1-3}$)alkyl,
  (9) —($C_{1-6}$)alkyl-($C_{3-6}$)cycloalkyl, or
  (10) —C(1-6)alkyl-N($R^{11}$)$_2$,
wherein each cycloalkyl, or heterocyclyl is unsubstituted or substituted with 1, 2, 3, or 4 $R^9$, and wherein each alkyl is unsubstituted or substituted with 1, 2, or 3 $R^{10}$;
$R^4$ is
  (1) hydrogen,
  (2) ($C_{1-3}$)alkyl,
or $R^3$ and $R^4$, together with the nitrogen atom to which they are attached, combine to form a mono- or bicyclic heterocyclyl ring containing 1 N and optionally containing 1 additional heteroatoms independently selected from N, O and S, wherein the heterocyclyl ring is unsubstituted or substituted by 1, 2, or 3 $R^{11}$;
when present, each $R^5$ is selected from
  (1) hydrogen,
  (2) ($C_{1-3}$)alkyl,
  (3) cyano, or
  (4) halogen,
when present, each $R^6$ is independently selected from
  (1) cyano,
  (2) halogen,
  (3) ($C_{1-6}$)alkyl or $OC_{1-6}$alkyl wherein the alkyl moiety is optionally substituted with cyano,
  (4) ($C_{3-6}$)cycloalkyl, optionally substituted with halogen, $C_{1-6}$alkyl, $C_{1-6}$haloalkyl, cyano, OH or $OC_{1-6}$alkyl,
  (5) —C(O)$NH_2$,
  (6) O($C_{3-6}$)cycloalkyl wherein the cycloalkyl is optionally substituted with halogen, $C_{1-6}$alkyl, $C_{1-6}$haloalkyl, cyano, OH, or $OC_{1-6}$alkyl,
  (7) hydroxy,
  (8) —N($R^{11}$)$_2$
  (9) ($C_{1-6}$)haloalkyl-,
  (10) $OC_{1-6}$haloalkyl,
  (11) —$SO_2$($C_{1-6}$)alkyl, or
  (12) —SONH($C_{1-6}$)alkyl;
when present, each $R^7$ is independently selected from
  (1) ($C_{1-6}$)alkyl,
  (2) halo,
  (3) ($C_{1-6}$)alkoxy-,
  (4) ($C_{1-6}$)haloalkyl-,
  (5) ($C_{3-6}$)cycloalkyl,
  (6) hydroxy, or
  (7) C(O)$C_{1-6}$alkyl;
when present, each $R^9$ is independently selected from
  (1) ($C_{1-6}$)alkyl,
  (2) ($C_{1-3}$)haloalkyl-,
  (3) oxo,
  (4) ($C_{3-6}$)cycloalkyl,
  (5) —N($R^{11}$)$_2$,
  (6) hydroxy,
  (7) $C_{1-6}$alkyl(OH),
  (8) cyano,
  (9) halo, or
  (10) morpholinyl;
when present, $R^{10}$ is
  (1) ($C_{1-3}$)alkyl,
  (2) ($C_{1-3}$) hydroxy alkyl-,
  (3) ($C_{1-3}$)alkoxy-,
  (4) hydroxy,
  (5) halogen,
  (6) ($C_{1-3}$)haloalkyl-, or
  (7) N($R^{11}$)$_2$,
  (8) C(O)$NH_2$;
when present, $R^{11}$ is independently
  (1) hydrogen,
  (2) ($C_{1-3}$)alkyl, or
  (3) C(O)$C_{1-6}$alkyl.

In Embodiment 1 of this disclosure are compounds of Formula I, or a pharmaceutically acceptable salt of any of the foregoing, wherein $R^1$ is
(1) phenyl unsubstituted or substituted with one to three substituents independently selected from halogen, hydroxy, $N(C_{1-3}alkyl)_2$, CN, $C_{1-6}alkyl$, $C_{1-6}haloalkyl$, $C_{3-6}cycloalkyl$, $OC_{1-6}alkyl$, $OC_{1-6}haloalkyl$, $OC_{3-6}cycloalkyl$, $S(O)_2C_{1-6}alkyl$, $OC_{1-6}alkyl$-CN, $C_{1-6}alkyl$-CN, $NHC(O)C_{1-6}alkyl$, and wherein the cycloalkyl is optionally substituted with $C_{1-6}alkyl$, $C_{1-6}haloalkyl$, CN, OH, $OC_{1-6}alkyl$; or
(2) 5- or 6-membered heteroaryl containing 1 or 2 N atoms, wherein the heteroaryl is unsubstituted or substituted with 1, 2, or 3 substituents independently selected from halogen, $C_{1-6}alkyl$, $C_{1-6}haloalkyl$, $C_{3-6}cycloalkyl$, $OC_{1-6}alkyl$, $OC_{1-6}haloalkyl$, $O-C_{3-6}cycloalkyl$, $OC_{1-6}alkyl$-CN, or CN, and when the cycloalkyl is cyclopropyl, the cyclopropyl is optionally substituted with halogen, $C_{1-6}alkyl$, $C_{1-6}haloalkyl$, CN, OH, or $OC_{1-6}alkyl$.

In Embodiment 2 of this disclosure are compounds of Formula I, or a pharmaceutically acceptable salt of any of the foregoing, wherein $R^1$ is
(1) phenyl optionally substituted with one to three substituents independently selected from halogen, hydroxy, $N(C_{1-3}alkyl)_2$, CN, $C_{1-6}alkyl$, $C_{1-6}haloalkyl$, $C_{3-6}cycloalkyl$, $OC_{1-6}alkyl$, $OC_{1-6}haloalkyl$, $OC_{3-6}cycloalkyl$, $S(O)_2C_{1-6}alkyl$, $OC_{1-6}alkyl$-CN, $C_{1-6}alkyl$-CN, $NHC(O)C_{1-6}alkyl$, and wherein the cycloalkyl is optionally substituted with $C_{1-6}alkyl$, $C_{1-6}haloalkyl$, CN, OH, $OC_{1-6}alkyl$;
(2) 6 membered heteroaryl containing one nitrogen atom optionally substituted with one to three substituents independently selected from halogen, hydroxy, $C_{1-6}alkyl$, $C_{1-6}haloalkyl$, $C_{3-6}cycloalkyl$, $OC_{1-6}alkyl$, $OC_{1-6}haloalkyl$, $O-C_{3-6}cycloalkyl$, $OC_{1-6}alkyl$-CN or CN, and when the cycloalkyl is cyclopropyl, the cyclopropyl is optionally substituted with halogen, $C_{1-6}alkyl$, $C_{1-6}haloalkyl$, CN, OH, or $OC_{1-6}alkyl$; or
(3) 5 membered heteroaryl containing 2 N atoms optionally substituted with $C_{1-6}alkyl$.

In Embodiment 3 of this disclosure are compounds of Formula I, or any one of Embodiments 1-2 or a pharmaceutically acceptable salt of any of the foregoing, wherein $R^1$ is
(1) phenyl optionally substituted with one to three substituents independently selected from halogen, OH, $NH_2$, $NC_{1-6}alkyl$, CN, $CH_3$, $CHF_2$, $CF_3$, $OC_{1-6}alkyl$, $OC_{1-6}alkylF_2$, $(C_{1-6}alky)CHF_2$, $O(C_{1-6}alky)CHF_2$, $O(C_{1-6}alky)CF_3$, cyclopropyl, O-cyclopropyl, O-cyclobutyl, $C(F)_2CH_3$, $S(O)_2CH_3$, $OCH_3CN$, $NHC(O)CH_3$, and wherein the cyclopropyl is optionally substituted with $CH_3$, $CF_3$, CN, OH, or $OCH_3$;
(2) a 6 membered heteroaryl containing one nitrogen atom optionally substituted with one to three substituents independently selected from halogen, OH, CN $CH_3$, cyclopropyl, $OCHF_2$, $OCF_3$, $OCH_2CH_3$, $OCH_2CHF_2$, $OCH_2CF_3$, O-cyclobutyl, O-cyclopropyl, wherein the O-cyclopropyl is optionally substituted with halogen, $CH_3$, $CF_3$, CN, OH, or $OCH_3$; or
(3) a 5 membered heteroaryl containing 2 N atoms optionally substituted with $CH_3$.

In Embodiment 4 of this disclosure are compounds of Formula I, or any one of Embodiments 1-3 or a pharmaceutically acceptable salt of any of the foregoing, wherein $R^1$ is
(1) phenyl optionally substituted with one to three substituents independently selected from F, OH, $NH_2$, $N(CH_3)_2$, CN, Cl, $OCHF_2$, $OCH_2CHF_2$, $OCH_2CF_3$, O-cyclobutyl, $OCH_2CH_3$, cyclopropyl, O-cyclopropyl, $C(F)_2CH_3$, $S(O)_2CH_3$, $OCH_2CN$, $NHC(O)CH_3$, wherein the cyclopropyl is additionally optionally substituted with $CF_3$, CN, OH, $OCH_3$, or $CH_3$;
(2) a 6 membered heteroaryl containing one nitrogen atom optionally substituted with one to three substituents independently selected from halogen, CN, OH, $CH_3$, cyclopropyl, $OCHF_2$, $OCF_3$, $OCH_2CH_3$, $OCH_2CHF_2$, $OCH_2CF_3$, O-cyclobutyl, O-cyclopropyl, wherein the O-cyclopropyl is optionally substituted with halogen, $CH_3$, $CF_3$, CN, OH, or $OCH_3$; or
(3) a 5 membered heteroaryl containing 2 N atoms optionally substituted with $CH_3$.

In Embodiment 5 of this disclosure are compounds of Formula I, or any one of Embodiments 1-4, or a pharmaceutically acceptable salt of any of the foregoing, wherein $R^1$ is

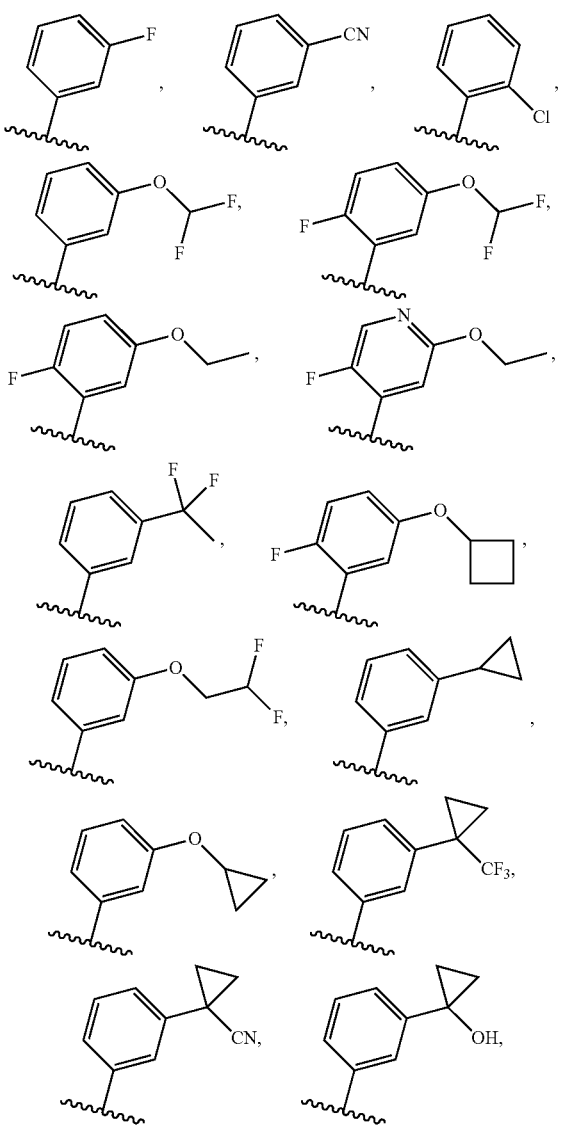

-continued

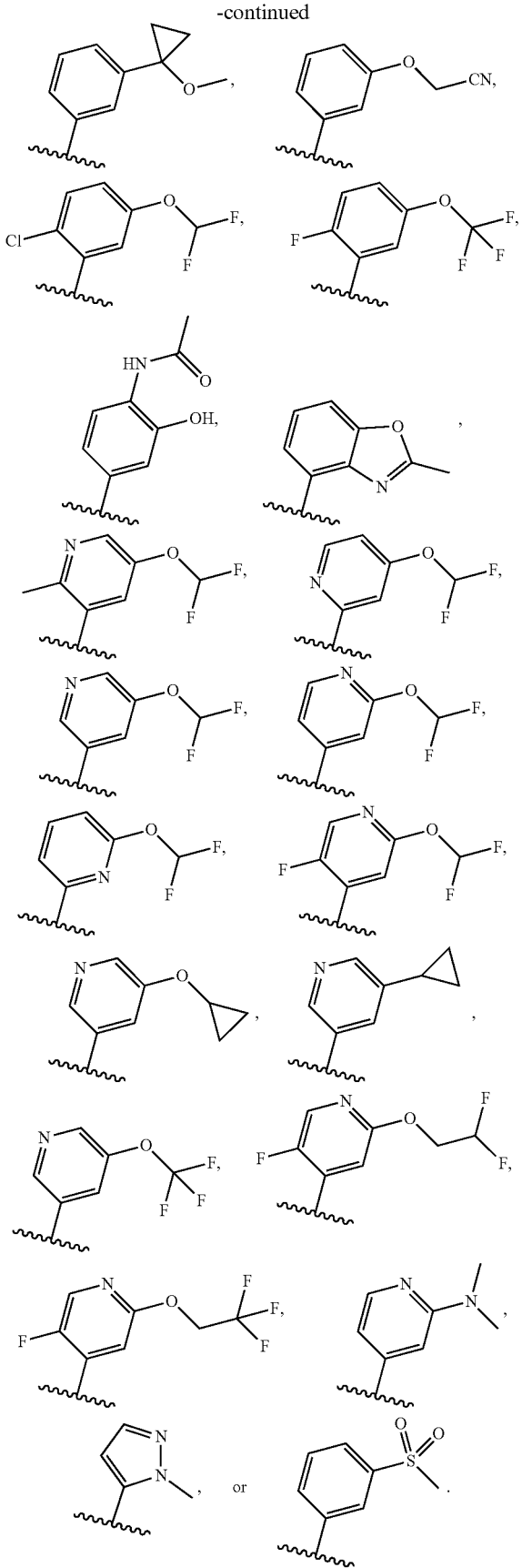

In Embodiment 6 of this disclosure are compounds of Formula I or a pharmaceutically acceptable salt of any of the foregoing, wherein $R^1$ is

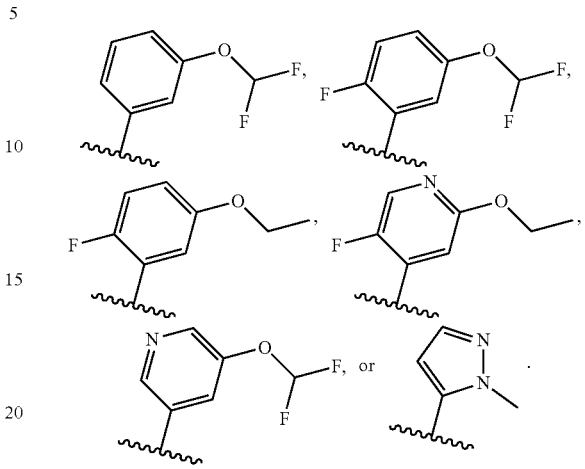

In Embodiment 7 of this disclosure are compounds of Formula I, or Embodiments 1-6, or a class thereof, or a pharmaceutically acceptable salt of any of the foregoing, wherein $R^2$ is
  (1) 5- or 6-membered heteroaryl containing zero or one oxygen atoms and/or zero, one or two nitrogen atoms optionally mono-substituted or disubstituted with halogen, $C_{1-6}$haloalkyl, $C_{1-6}$alkyl, $C(O)C_{1-6}$alkyl, $C(O)(OH)$, or OH,
  (2) $C_{1-6}$alkyl unsubstituted or optionally mono-substituted, disubstituted or trisubstituted with halogen, OH, $CF_3$, or CN,
  (3) $C_{3-6}$cycloalkyl optionally mono-substituted, disubstituted or trisubstituted with $C_{1-6}$alkyl, halogen, OH, $CF_3$, or CN,
  (4) 4 to 6 membered heterocycle containing zero or one oxygen atoms and/or zero, one, or two nitrogen atoms optionally mono-substituted or disubstituted with halogen, $C_{1-6}$haloalkyl, $C_{1-6}$alkyl, $C(O)C_{1-6}$alkyl, $C(O)(OH)$, or OH,
  (5) $CH_2$-aryl substituted with halogen,
  (6) $CH_2$— heterocyclyl containing 1 or 2 heteroatoms independently selected from N, O, and S, or
  (7) $C_{1-6}$alkyl-$C(O)NH_2$.

In Embodiment 8 of this disclosure are compounds of Formula I, or Embodiments 1-6 or a class thereof, or a pharmaceutically acceptable salt of any of the foregoing, wherein $R^2$ is
  (1) 5 or 6-membered heteroaryl containing 2 N atoms optionally substituted with $C_{1-6}$alkyl or halogen,
  (2) phenyl substituted with halogen,
  (3) $C_{1-6}$alkyl optionally mono-substituted, disubstituted or trisubstituted with halogen, OH, $CF_3$, or CN,
  (4) $C_{3-6}$cycloalkyl optionally mono-substituted, disubstituted or trisubstituted with $C_{1-6}$alkyl, halogen, OH, $CF_3$, or CN,
  (5) 4 membered saturated heterocycle containing one oxygen atom or one nitrogen atom optionally substituted with $C(O)CH_3$,
  (6) 5 membered saturated heterocycle containing one oxygen atom, optionally substituted with OH,
  (7) 6 membered saturated heterocycle containing zero or one oxygen atom and zero or one nitrogen atoms optionally mono-substituted or disubstituted with halogen, $C_{1-6}$haloalkyl, or $C_{1-6}$alkyl,
(8) $CH_2$-aryl substituted with halogen,
(9) $CH_2$— tetrahydropyran, or
(10) $C_{1-6}$alkyl-C(O)NH$_2$.

In Embodiment 9 of this disclosure are compounds of Formula I, or any one of Embodiments 1-6, or a pharmaceutically acceptable salt of any of the foregoing, wherein $R^2$ is
(1) 5 or 6-membered heteroaryl containing 2 N atoms optionally substituted with $CH_3$ or fluoro,
(2) phenyl substituted with halogen,
(3) $CH_3$, $CH_2CH_3$, $CH_2CH(CH_3)_2$, $CH_2C(CH_3)_3$, $CH(CH_3)_2$, $CH(CH_3)CH_2CH_3$, $CH_2CH(OH)(CH_3)$, $CH_2C(OH)(CH_3)_2$, $CH(CH_3)CH(OH)(CH_3)$, $(CH_3)_2C(CH_3)_2(OH)$, $CH(CH_3)C(CH_3)_2OH$, $CH_2CH(OH)(CF_3)$, cyclobutyl, cyclopropyl wherein the cyclobutyl is optionally mono-substituted or disubstituted selected from OH, fluoro, $CH_3$, or CN,
(4) 4 membered saturated heterocycle containing one oxygen atom or one nitrogen atom optionally substituted with C(O)CH$_3$,
(5) 5 membered saturated heterocycle containing one oxygen atom, optionally substituted with OH,
(6) 6 membered saturated heterocycle containing zero or one oxygen atom and zero or one nitrogen atoms optionally mono-substituted or disubstituted with F, $CF_3$, or $CH_3$,
(7) $C_{1-6}$alkyl substituted with phenyl substituted with halogen, or 6 membered saturated heterocycle containing one oxygen atom, or
(8) $C_{1-6}$alkyl-C(O)NH$_2$.

In Embodiment 10 of this disclosure are compounds of Formula I, or any one of Embodiments 1-6, or a pharmaceutically acceptable salt of any of the foregoing, wherein $R^2$ is

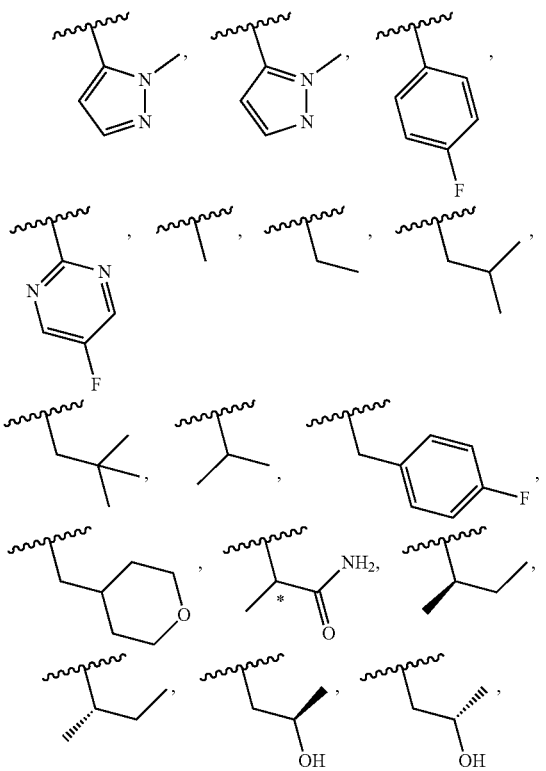

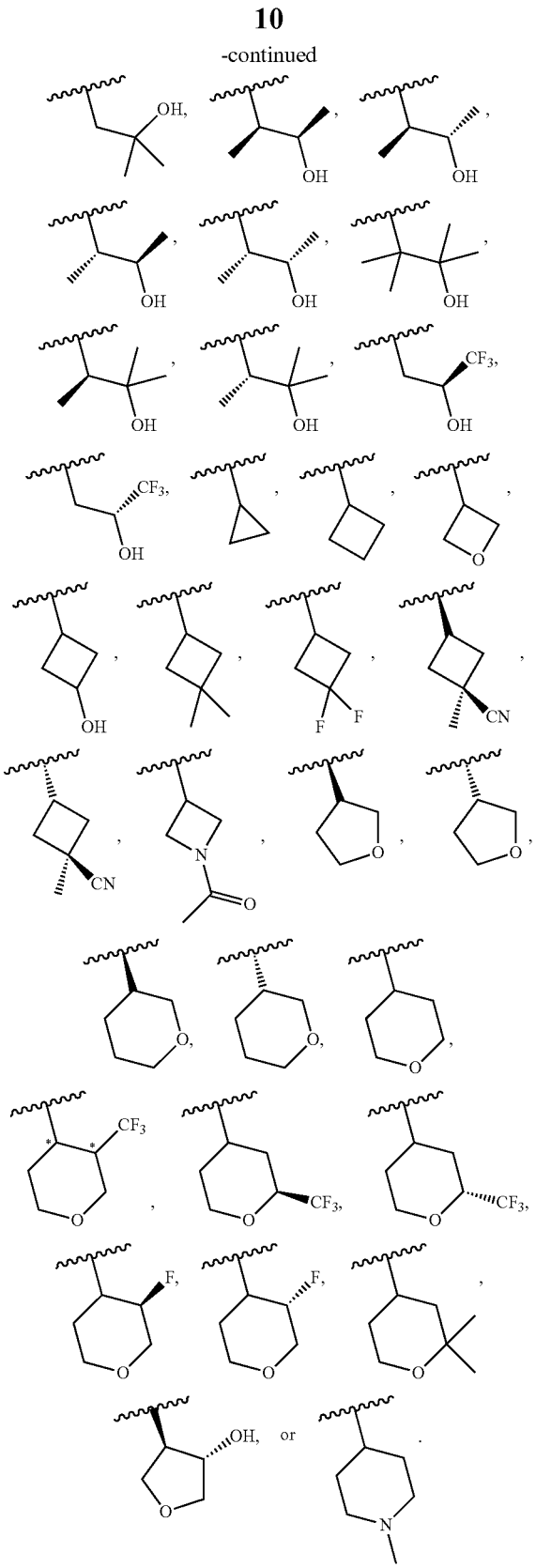

In Embodiment 11 of this disclosure are compounds of Formula I, or any of embodiments 1-6, or a pharmaceutically acceptable salt of any of the foregoing, wherein $R^2$ is

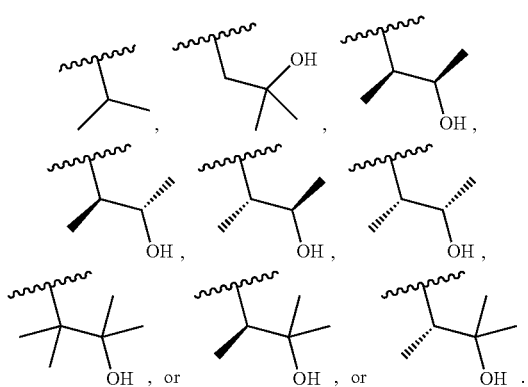

In Embodiment 12 of this disclosure are compounds of Formula I, or any of embodiments 1-6, or a pharmaceutically acceptable salt of any of the foregoing, wherein $R^2$ is

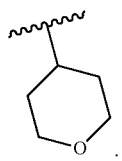

In Embodiment 13 of this disclosure are compounds of Formula I, or any one of Embodiments 1-12, or a pharmaceutically acceptable salt of any of the foregoing, wherein $R^3$ is
(1) 4- to 7-membered heterocyclyl containing 1 or 2 heteroatoms independently selected from N, O and S,
(2) —($C_{1-6}$)alkyl-heterocyclyl, wherein the heterocyclyl is a 3- to 6-membered ring containing 1 or 2 heteroatoms independently selected from N, O and S,
(3) —($C_{1-6}$)alkyl,
(4) —($C_{3-6}$)cycloalkyl,
(5) —($C_{3-6}$)cycloalkyl-heterocyclyl wherein the heterocyclyl is a 3- to 6-membered ring containing 1 or 2 heteroatoms independently selected from N, O and S,
(6) ($C_{1-6}$)hydroxyalkyl,
(7) —($C_{1-6}$)alkyl-N($R^{11}$)$_2$, or
(8) $C_{1-6}$alkyl-C(O)NH$_2$,
wherein each aryl, cycloalkyl, or heterocyclyl is optionally mono-substituted, disubstituted, trisubstituted, or quad-substituted with $C_{1-6}$alkyl, $C_{1-3}$haloalkyl, oxo, $C_{3-6}$cycloalkyl, N(CH$_3$)$_2$, NH$_2$, OH, $C_{1-6}$alkyl(OH), CN, halogen, or morpholinyl, and wherein each alkyl is optionally mono-substituted, disubstituted, or trisubstituted with ($C_{1-3}$)alkyl, ($C_{1-3}$) hydroxy alkyl-, ($C_{1-3}$)alkoxy-, OH, halogen, ($C_{1-3}$)haloalkyl-, N(CH$_3$)$_2$, or NH$_2$.

In Embodiment 14 of this disclosure are compounds of Formula I, or any one of Embodiments 1-12, or a pharmaceutically acceptable salt of any of the foregoing, wherein $R^3$ is
(1) 4- to 6-membered heterocyclyl containing 1 or 2 heteroatoms independently selected from N, O and S;
(2) —($C_{3-6}$)cycloalkyl;
(3) —($C_{3-6}$)cycloalkyl-heterocyclyl wherein the heterocyclyl is a 3- to 6-membered ring containing 1 or 2 heteroatoms independently selected from N, O and S;
(4) ($C_{1-6}$)hydroxyalkyl;
(5) —($C_{1-6}$)alkyl-N(CH$_3$)$_2$; or
(6) $C_{1-6}$alkyl-C(O)NH$_2$, wherein each aryl, cycloalkyl, or heterocyclyl is optionally mono-substituted, disubstituted, trisubstituted, or quad-substituted with $C_{1-3}$haloalkyl, halogen, $C_{1-6}$alkyl, $C_{1-6}$alkyl (OH), OH, NH$_2$, N(CH$_3$)$_2$, CN, oxo or morpholinyl, and wherein each alkyl is optionally mono-substituted, disubstituted, or trisubstituted with halogen, CF$_3$, $C_{1-6}$alkyl, $C_{1-3}$haloalkyl, NH$_2$, N(CH$_3$)$_2$, or OH.

In Embodiment 15 of this disclosure are compounds of Formula I, or any one of Embodiments 1-12, or a pharmaceutically acceptable salt of any of the foregoing, wherein $R^3$ is
(1) 4 to 6 membered cycloalkyl optionally substituted with halogen, $C_{1-6}$alkyl, $C_{1-6}$alkyl(OH), OH, NH$_2$, or morpholinyl;
(2) 4, 5, or 6 membered heterocyclyl containing 1 sulfur atom or 1 oxygen atom optionally mono-substituted, disubstituted, trisubstituted, or quad-substituted with $C_{1-6}$alkyl, $C_{1-3}$alkyl (OH), OH, NH$_2$, N(CH$_3$)$_2$, CN, or oxo;
(3) $C_{1-6}$alkyl(OH) wherein the alkyl moiety is optionally mono-substituted, disubstituted, or trisubstituted with halogen, CF$_3$, $C_{1-6}$alkyl, or OH;
(4) $C_{1-6}$alkyl-N(CH$_3$)$_2$; or
(5) $C_{1-6}$alkyl-C(O)NH$_2$.

In Embodiment 16 of this disclosure are compounds of Formula I, or any one of Embodiments 1-12 or a pharmaceutically acceptable salt of any of the foregoing, wherein $R^3$ is
(1) 4 to 6 membered cycloalkyl optionally substituted with F, CH$_2$(OH), OH, NH$_2$, or morpholinyl,
(2) 4 or 5 membered heterocyclyl containing 1 sulfur atom optionally mono-substituted, disubstituted, trisubstituted, or quad-substituted with oxo, OH, or CH$_3$,
(3) 5 or 6 membered heterocyclyl containing 1 oxygen atom optionally mono-substituted, disubstituted, or trisubstituted with CH$_3$, NH$_2$, CN, CH$_2$OH, N(CH$_3$) (CH$_3$), CH(CH$_3$)(OH), C(CH$_3$)(CH$_3$)(OH),
(4) $C_{1-6}$alkyl(OH), wherein the alkyl moiety is optionally mono-substituted, disubstituted, or trisubstituted with halogen, CF$_3$, CH$_3$, OH,
(5) $C_{1-6}$alkyl-N(CH$_3$)$_2$, or
(6) $C_{1-6}$alkyl-C(O)NH$_2$.

In Embodiment 17 of this disclosure are compounds of Formula I, or any one of Embodiments 1-12, or a pharmaceutically acceptable salt of any of the foregoing, wherein $R^3$ is

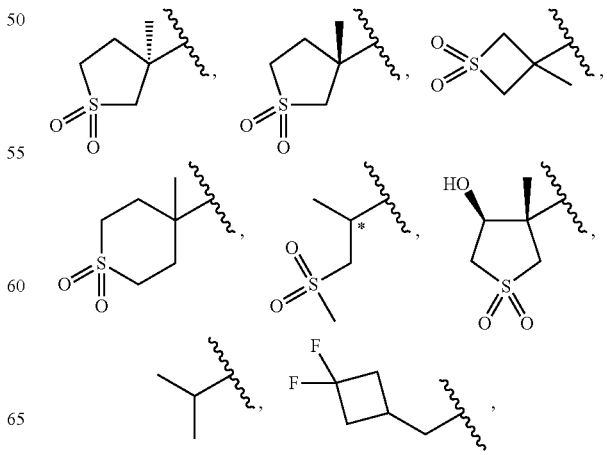

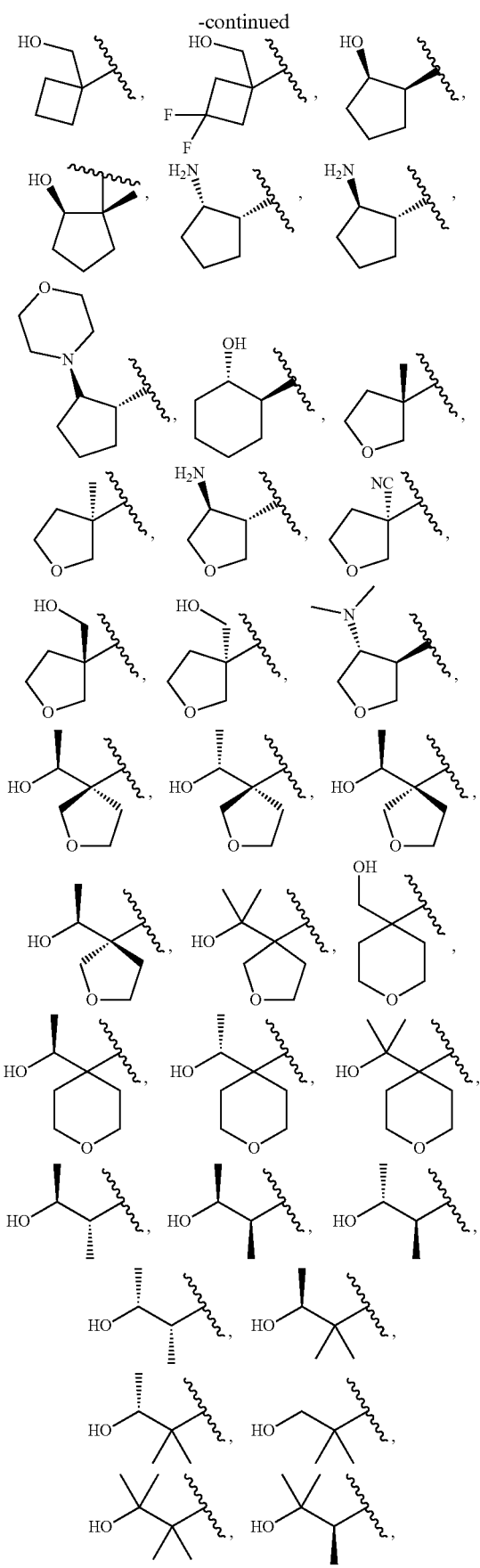

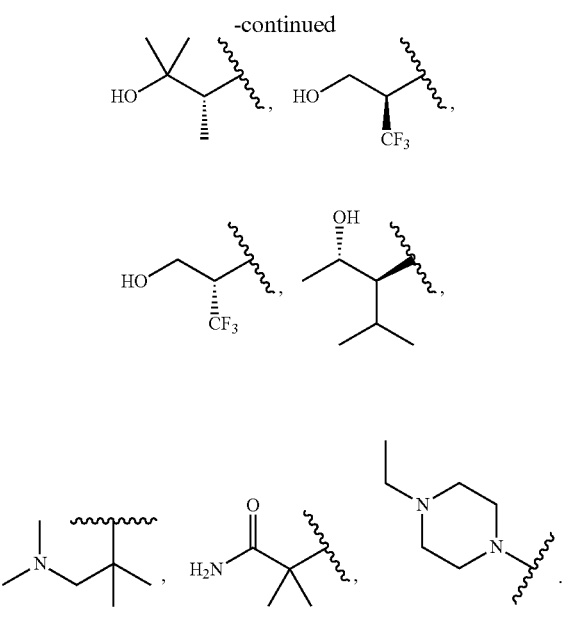

In Embodiment 18 of this disclosure are compounds of Formula I, or any one of Embodiments

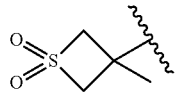

In Embodiment 19 of this disclosure are compounds of Formula I, or any one of Embodiments 1-17, or a pharmaceutically acceptable salt of any of the foregoing, wherein $R^3$ is

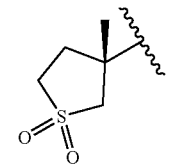

In Embodiment 20 of this disclosure are compounds of Formula I, or any one of Embodiments 1-17, or a pharmaceutically acceptable salt of any of the foregoing, wherein $R^3$ is

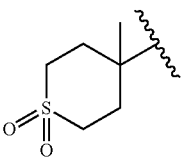

In Embodiment 21 of this disclosure are compounds of Formula I, or any one of Embodiments 1-20, or a pharmaceutically acceptable salt of any of the foregoing, wherein $R^1$ is In Embodiment 22 of this disclosure are compounds of Formula I, or any one of Embodiments 1-20, or a pharmaceutically acceptable salt of any of the foregoing, wherein $R^1$ is

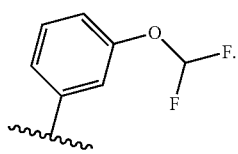 [SMILES: *c1cccc(OC(F)F)c1]

In Embodiment 23 of this disclosure are compounds of Formula I, or any one of Embodiments 1-20, or a pharmaceutically acceptable salt of any of the foregoing, wherein is $R^1$ is

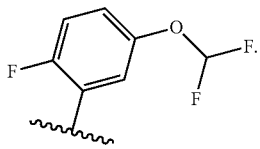

In Embodiment 24 of this disclosure are compounds of Formula I, or any one of Embodiments 1-20, or a pharmaceutically acceptable salt of any of the foregoing, wherein $R^1$ is

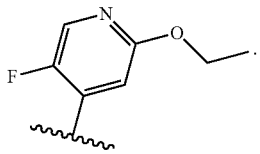 [SMILES: *c1cc(OCC)ncc1F]

In Embodiment 25 of this disclosure are compounds of Formula I, or any one of Embodiments 1-20, or a pharmaceutically acceptable salt of any of the foregoing, wherein $R^1$ is

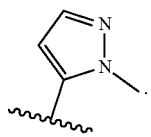 [SMILES: *c1ccnn1C]

In Embodiment 26 of this disclosure are compounds of Formula I, or any one of Embodiment 1-25, or a pharmaceutically acceptable salt of any of the foregoing, wherein $R^2$ is

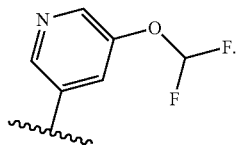 [SMILES: *c1cncc(OC(F)F)c1]

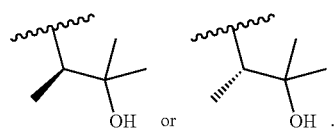

In Embodiment 27 of this disclosure are compounds of Formula I, or any one of Embodiments 1-25, or a pharmaceutically acceptable salt of any of the foregoing, wherein $R^2$ is

In Embodiment 28 of this disclosure are compounds of Formula I, or any one of Embodiments 1-25, or a pharmaceutically acceptable salt of any of the foregoing, wherein $R^2$ is

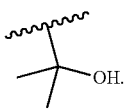

In Embodiment 29 of this disclosure are compounds of Formula I, or any one of Embodiments 1-25, or a pharmaceutically acceptable salt of any of the foregoing, wherein $R^2$ is

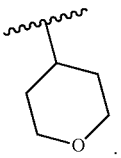 [SMILES: *C1CCOCC1]

In Embodiment 30 of this disclosure are compounds of Formula I, or any one of Embodiment 1-29, or a pharmaceutically acceptable salt of any of the foregoing, wherein W is N.

In Embodiment 31 of this disclosure are compounds of Formula I, or any one of Embodiments 1-29, or a pharmaceutically acceptable salt of any of the foregoing, wherein W is C(H).

In Embodiment 32 of this disclosure are compounds of Formula I, or any one of Embodiments 1-31, or a pharmaceutically acceptable salt of any of the foregoing, wherein X is N, Y is $C(R^5)$, and Z is $C(R^5)$.

In Embodiment 33 of this disclosure are compounds of Formula I, or any one of Embodiments 1-31, or a pharmaceutically acceptable salt of any of the foregoing, wherein X is $C(R^5)$, Y is N, and Z is $C(R^5)$.

In Embodiment 34 of this disclosure are compounds of Formula I, or any one of Embodiments 1-31, or a pharmaceutically acceptable salt of any of the foregoing, wherein X is $C(R^5)$, Y is $C(R^5)$ and Z is N.

In Embodiment 35 of this disclosure are compounds of Formula I, or any one of Embodiments 1-31, or a pharmaceutically acceptable salt of any of the foregoing, wherein X, Y, and Z are $C(R^5)$.

In Embodiment 36 of this disclosure are compounds of Formula I, or any one of Embodiments 1-31, or a pharmaceutically acceptable salt of any of the foregoing, wherein X is N, Y is N and Z is C(R$^5$).

In Embodiment 37 of this disclosure are compounds of Formula I, or any one of Embodiments 1-31, or a pharmaceutically acceptable salt of any of the foregoing, wherein X is N, Y is C(R$^5$) and Z is N.

In Embodiment 38 of this disclosure are compounds of Formula I, or any one of Embodiments 1-31, or a pharmaceutically acceptable salt of any of the foregoing, wherein X is C(R$^5$), Y is N and Z is N.

In Embodiment 39 of this disclosure are compounds of Formula I, or any one of Embodiments 1-31, or a pharmaceutically acceptable salt of any of the foregoing, wherein R$^5$ is selected from hydrogen, halogen, cyano, or (C$_{1-3}$)alkyl.

In Embodiment 40 of this disclosure are compounds of Formula I, or any one of Embodiments 1-31, or a pharmaceutically acceptable salt of any of the foregoing, wherein R$^5$ is selected from hydrogen, halogen, cyano, or C$_{1-3}$alkyl.

In Embodiment 41 of this disclosure are compounds of Formula I, or any one of Embodiments 1-31, or a pharmaceutically acceptable salt of any of the foregoing, wherein R$^5$ is selected from H, CN, CH$_3$, or F.

In Embodiment 42 of this disclosure are compounds of Formula I, or any one of Embodiments 1-31, or a pharmaceutically acceptable salt of any of the foregoing, wherein R$^4$ is selected from H or C$_{1-3}$alkyl.

In Embodiment 43 of this disclosure are compounds of Formula I, or any one of Embodiments 1-31, or a pharmaceutically acceptable salt of any of the foregoing, wherein R$^4$ is selected from H or CH$_3$.

In Embodiment 44, the compound of Formula (I) has the Formula (Ia)

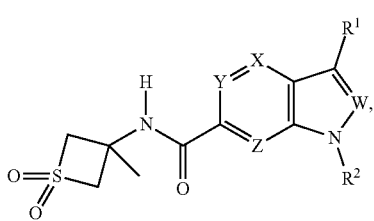

(Ia)

wherein the group R$^1$, R$^2$, X, Y, Z, and W are set forth in Embodiment 1

In Embodiment 45, the compound of Formula (I) has the Formula (Ib)

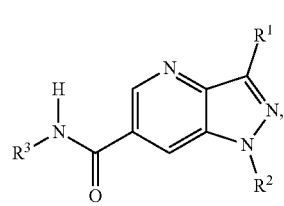

(Ib)

acceptable salt thereof, wherein

R$^1$ is

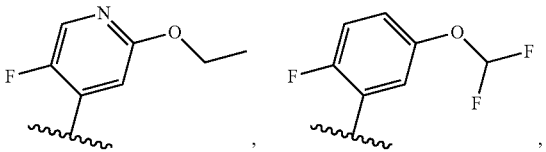

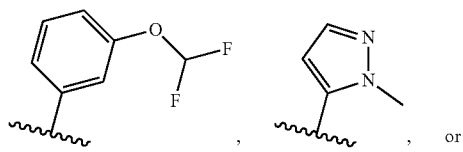

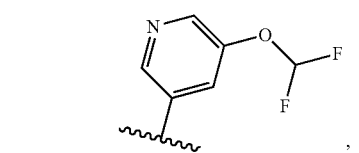

R$^2$ is

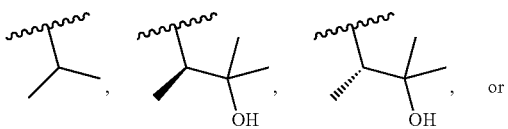

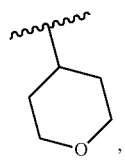

and
R$^3$ is

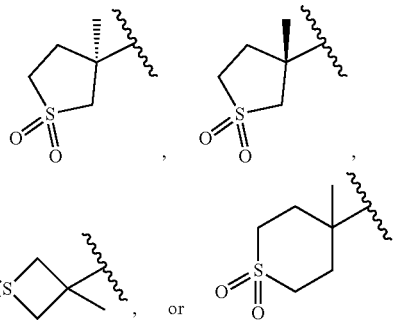

In Embodiment 46, the present invention provides a compound as described in any one of Examples 1-137 as set forth below, or a pharmaceutically acceptable salt thereof.

In Embodiment 47, the present invention is a compound, or a pharmaceutically acceptable salt thereof, which is

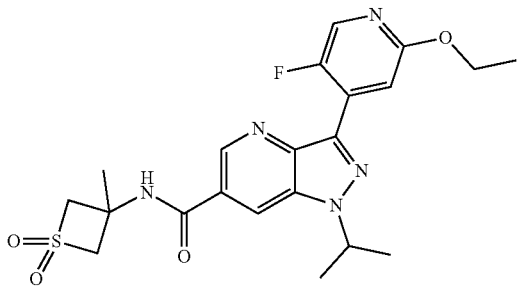

In Embodiment 48, the present invention is a compound, or a pharmaceutically acceptable salt thereof, which is

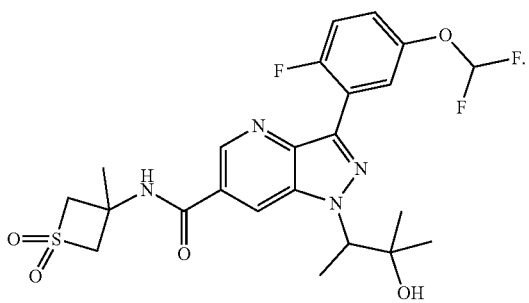 [SMILES: CC(n1nc(-c2cc(OC(F)F)ccc2F)c2ncc(C(=O)NC3(C)CS(=O)(=O)C3)cc21)C(C)(C)O]

In Embodiment 49, the present invention is a compound, or a pharmaceutically acceptable salt thereof, which is

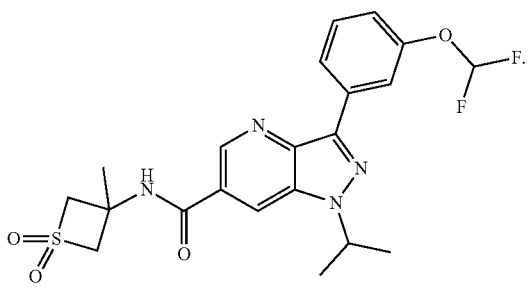 [SMILES: CC(C)n1nc(-c2cccc(OC(F)F)c2)c2ncc(C(=O)NC3(C)CS(=O)(=O)C3)cc21]

In Embodiment 50, the present invention is a compound, or a pharmaceutically acceptable salt thereof, which is

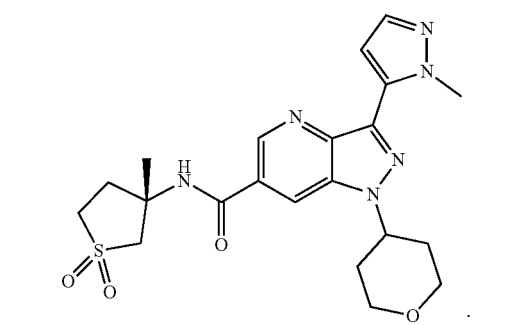 [SMILES: Cn1nccc1-c1nn(C2CCOCC2)c2cc(C(=O)N[C@@]3(C)CCS(=O)(=O)C3)cnc12]

In Embodiment 51, the present invention is a compound, or a pharmaceutically acceptable salt thereof, which is

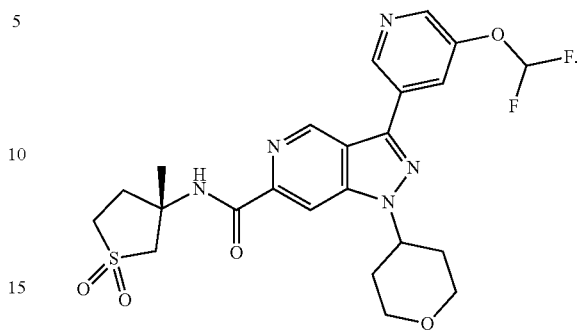

In Embodiment 52 of the invention, the compound of formula I, or a pharmaceutically acceptable salt thereof, is:
- (S)-3-(3-(difluoromethoxy)phenyl)-1-(4-fluorophenyl)-N-(3-methyl-1,1-dioxidotetrahydrothiophen-3-yl)-1H-pyrazolo[4,3-b]pyridine-6-carboxamide,
- (S)-1-(4-fluorophenyl)-N-(3-methyl-1,1-dioxidotetrahydrothiophen-3-yl)-3-(1-methyl-1H-pyrazol-5-yl)-1H-pyrazolo[4,3-b]pyridine-6-carboxamide,
- (S)-3-(3-(difluoromethoxy)phenyl)-1-(4-fluorophenyl)-N-(3-methyl-1,1-dioxidotetrahydrothiophen-3-yl)-1H-pyrazolo[4,3-b]pyridine-6-carboxamide,
- (S)-1-(4-fluorophenyl)-N-(3-methyl-1,1-dioxidotetrahydrothiophen-3-yl)-3-(1-methyl-1H-pyrazol-5-yl)-1H-pyrazolo[4,3-b]pyridine-6-carboxamide,
- (S)-3-(3-(difluoromethoxy)phenyl)-1-(5-fluoropyrimidin-2-yl)-N-(3-methyl-1,1-dioxidotetrahydrothiophen-3-yl)-1H-pyrazolo[4,3-b]pyridine-6-carboxamide,
- 3-(3-(difluoromethoxy)phenyl)-1-(5-fluoropyrimidin-2-yl)-N-(3-methyl-1,1-dioxidothietan-3-yl)-1H-pyrazolo[4,3-b]pyridine-6-carboxamide,
- (S)-3-(3-(difluoromethoxy)phenyl)-1-(4-fluorophenyl)-N-(3-methyl-1,1-dioxidotetrahydrothiophen-3-yl)-1H-pyrazolo[4,3-c]pyridine-6-carboxamide,
- (S)-3-(5-(difluoromethoxy)pyridin-3-yl)-1-(4-fluorophenyl)-N-(3-methyl-1,1-dioxidotetrahydrothiophen-3-yl)-1H-pyrazolo[4,3-c]pyridine-6-carboxamide,
- 3-(3-(difluoromethoxy)phenyl)-1-(5-fluoropyrimidin-2-yl)-N-((1R,2R)-2-morpholinocyclopentyl)-1H-pyrrolo[3,2-b]pyridine-6-carboxamide,
- 3-(3-(difluoromethoxy)phenyl)-N-((3R,4R)-4-(dimethylamino)tetrahydrofuran-3-yl)-1-(5-fluoropyrimidin-2-yl)-1H-pyrrolo[3,2-b]pyridine-6-carboxamide,
- (S)-3-(3-(difluoromethoxy)phenyl)-1-(4-fluorophenyl)-N-(3-methyl-1,1-dioxidotetrahydrothiophen-3-yl)-1H-pyrrolo[3,2-b]pyridine-6-carboxamide,
- (S)-3-(2-chlorophenyl)-1-(4-fluorophenyl)-N-(3-methyl-1,1-dioxidotetrahydrothiophen-3-yl)-1H-pyrrolo[2,3-b]pyridine-6-carboxamide,
- (S)-3-(2-chlorophenyl)-1-(4-fluorophenyl)-N-(3-methyl-1,1-dioxidotetrahydrothiophen-3-yl)-1H-pyrrolo[3,2-b]pyridine-6-carboxamide,
- (R)-3-(2-chlorophenyl)-1-(4-fluorophenyl)-N-(3-methyl-1,1-dioxidotetrahydrothiophen-3-yl)-1H-pyrrolo[3,2-b]pyridine-6-carboxamide,
- (S)-1-(4-fluorophenyl)-N-(3-methyl-1,1-dioxidotetrahydrothiophen-3-yl)-3-(1-methyl-1H-pyrazol-5-yl)-1H-pyrrolo[3,2-b]pyridine-6-carboxamide, (S)-3-(2-chlorophenyl)-1-(4-fluorophenyl)-N-(3-methyl-1,1-dioxidotetrahydrothiophen-3-yl)-1H-pyrrolo[3,2-c]pyridine-6-carboxamide, (S)-3-(3-(difluoromethoxy)phenyl)-1-(4-fluorophenyl)-N-(3-methyl-1,1-dioxidotetrahydrothiophen-3-yl)-1H-pyrrolo[3,2-c]pyridine-6-carboxamide, N-((1R,2S)-2-aminocyclopentyl)-3-(3-(difluoromethoxy)phenyl)-1-(5-fluoropyrimidin-2-yl)-1H-pyrrolo[3,2-b]pyridine-6-carboxamide, N-((1R,2R)-2-aminocyclopentyl)-3-(3-(difluoromethoxy)phenyl)-1-(5-fluoropyrimidin-2-yl)-1H-pyrrolo[3,2-b]pyridine-6-carboxamide, N-((3S,4S)-4-aminotetrahydrofuran-3-yl)-3-(3-(difluoromethoxy)phenyl)-1-(5-fluoropyrimidin-2-yl)-1H-pyrrolo[3,2-b]pyridine-6-carboxamide, N-((1S,2R)-2-aminocyclopentyl)-3-(3-(difluoromethoxy)phenyl)-1-(5-fluoropyrimidin-2-yl)-1H-pyrrolo[3,2-b]pyridine-6-carboxamide, (S)-7-(3-(difluoromethoxy)phenyl)-5-(4-fluorophenyl)-N-(3-methyl-1,1-dioxidotetrahydrothiophen-3-yl)-5H-pyrrolo[2,3-b]pyrazine-3-carboxamide, (S)-3-(3-(difluoromethoxy)phenyl)-1-isopropyl-N-(3-methyl-1,1-dioxidotetrahydrothiophen-3-yl)-1H-pyrazolo[4,3-b]pyridine-6-carboxamide, 3-[3-(difluoromethoxy)phenyl]-1-isopropyl-N-(3-methyl-1,1-dioxidothietan-3-yl)-1H-pyrazolo[4,3-b]pyridine-6-carboxamide, 3-(3-(difluoromethoxy)phenyl)-1-isopropyl-N-(4-methyl-1,1-dioxidotetrahydro-2H-thiopyran-4-yl)-1H-pyrazolo[4,3-b]pyridine-6-carboxamide, 3-(3-(difluoromethoxy)phenyl)-4-fluoro-1-isopropyl-N-(3-methyl-1,1-dioxidothietan-3-yl)-1H-indazole-6-carboxamide, 3-(3-(difluoromethoxy)phenyl)-7-fluoro-1-isopropyl-N-(3-methyl-1,1-dioxidothietan-3-yl)-1H-indazole-6-carboxamide, 3-(5-(difluoromethoxy)-2-methylpyridin-3-yl)-1-isopropyl-N-(3-methyl-1,1-dioxidothietan-3-yl)-1H-pyrazolo[4,3-c]pyridine-6-carboxamide, 3-(5-(difluoromethoxy)-2-fluorophenyl)-1-isopropyl-N-(3-methyl-1,1-dioxidothietan-3-yl)-1H-pyrazolo[4,3-c]pyridine-6-carboxamide, 3-(3-(difluoromethoxy)phenyl)-1-isopropyl-N-(3-methyl-1,1-dioxidothietan-3-yl)-1H-pyrrolo[3,2-b]pyridine-6-carboxamide, N-[(3S)-3-cyanotetrahydrofuran-3-yl]-3-[3-(difluoromethoxy)phenyl]-1-isopropyl-pyrazolo[4,3-b]pyridine-6-carboxamide, (S)-3-(3-(difluoromethoxy)phenyl)-N-(3-(hydroxymethyl)tetrahydrofuran-3-yl)-1-isopropyl-1H-pyrazolo[4,3-b]pyridine-6-carboxamide, (R)-3-(3-(difluoromethoxy)phenyl)-N-(3-(hydroxymethyl)tetrahydrofuran-3-yl)-1-isopropyl-1H-pyrazolo[4,3-b]pyridine-6-carboxamide, 3-[3-(difluoromethoxy)phenyl]-N-[(1S,2S)-2-hydroxycyclohexyl]-1-isopropyl-pyrazolo[4,3-b]pyridine-6-carboxamide, 3-[3-(difluoromethoxy)phenyl]-1-isopropyl-N-[(1R,2R)-2-morpholinocyclopentyl]pyrazolo[4,3-b]pyridine-6-carboxamide, 3-(3-(difluoromethoxy)phenyl)-N-(1-hydroxy-2-methylpropan-2-yl)-1-isopropyl-1H-pyrazolo[4,3-b]pyridine-6-carboxamide, 3-(3-(difluoromethoxy)phenyl)-N-(3-hydroxy-2,3-dimethylbutan-2-yl)-1-isopropyl-1H-pyrazolo[4,3-b]pyridine-6-carboxamide, 3-(3-(difluoromethoxy)phenyl)-N-((1S,2R)-2-hydroxycyclopentyl)-1-isopropyl-1H-pyrazolo[4,3-b]pyridine-6-carboxamide, 3-(3-(difluoromethoxy)phenyl)-N-((2R,3S)-3-hydroxybutan-2-yl)-1-isopropyl-1H-pyrazolo[4,3-b]pyridine-6-carboxamide, 3-(3-(difluoromethoxy)phenyl)-N-((2R,3R)-3-hydroxybutan-2-yl)-1-isopropyl-1H-pyrazolo[4,3-b]pyridine-6-carboxamide, 3-(3-(difluoromethoxy)phenyl)-N-((2S,3S)-3-hydroxybutan-2-yl)-1-isopropyl-1H-pyrazolo[4,3-b]pyridine-6-carboxamide, 3-(3-(difluoromethoxy)phenyl)-N-((2S,3R)-3-hydroxybutan-2-yl)-1-isopropyl-1H-pyrazolo[4,3-b]pyridine-6-carboxamide, (R)-3-(3-(difluoromethoxy)phenyl)-N-(3-hydroxy-2-methylbutan-2-yl)-1-isopropyl-1H-pyrazolo[4,3-b]pyridine-6-carboxamide, (S)-3-(3-(difluoromethoxy)phenyl)-N-(3-hydroxy-2-methylbutan-2-yl)-1-isopropyl-1H-pyrazolo[4,3-b]pyridine-6-carboxamide, (R)-3-(3-(difluoromethoxy)phenyl)-N-(3-(2-hydroxypropan-2-yl)tetrahydrofuran-3-yl)-1-isopropyl-1H-pyrazolo[4,3-b]pyridine-6-carboxamide, (S)-3-(3-(difluoromethoxy)phenyl)-N-(3-(2-hydroxypropan-2-yl)tetrahydrofuran-3-yl)-1-isopropyl-1H-pyrazolo[4,3-b]pyridine-6-carboxamide, (R)-3-(3-(difluoromethoxy)phenyl)-1-isopropyl-N-(3-methyltetrahydrofuran-3-yl)-1H-pyrazolo[4,3-b]pyridine-6-carboxamide, (S)-3-(3-(difluoromethoxy)phenyl)-1-isopropyl-N-(3-methyltetrahydrofuran-3-yl)-1H-pyrazolo[4,3-b]pyridine-6-carboxamide, 3-(3-(difluoromethoxy)phenyl)-N-(1-(hydroxymethyl)cyclobutyl)-1-isopropyl-1H-pyrazolo[4,3-b]pyridine-6-carboxamide, 3-(3-(difluoromethoxy)phenyl)-N—((R)-3-((R)-1-hydroxyethyl)tetrahydrofuran-3-yl)-1-isopropyl-1H-pyrazolo[4,3-b]pyridine-6-carboxamide, 3-(3-(difluoromethoxy)phenyl)-N—(S)-3-((R)-1-hydroxyethyl)tetrahydrofuran-3-yl)-1-isopropyl-1H-pyrazolo[4,3-b]pyridine-6-carboxamide, 3-(3-(difluoromethoxy)phenyl)-N—((R)-3-((S)-1-hydroxyethyl)tetrahydrofuran-3-yl)-1-isopropyl-1H-pyrazolo[4,3-b]pyridine-6-carboxamide, 3-(3-(difluoromethoxy)phenyl)-N—((S)-3-((S)-1-hydroxyethyl)tetrahydrofuran-3-yl)-1-isopropyl-1H-pyrazolo[4,3-b]pyridine-6-carboxamide, N-(3,3-difluoro-1-(hydroxymethyl)cyclobutyl)-3-(3-(difluoromethoxy)phenyl)-1-isopropyl-1H-pyrazolo[4,3-b]pyridine-6-carboxamide, 3-(3-(difluoromethoxy)phenyl)-1-isopropyl-N-(1,1,1-trifluoro-3-hydroxypropan-2-yl)-1H-pyrazolo[4,3-b]pyridine-6-carboxamide (racemic mixture), 3-(3-(difluoromethoxy)phenyl)-1-((trans)-4-hydroxytetrahydrofuran-3-yl)-N-(3-methyl-1,1-dioxidothietan-3-yl)-1H-pyrazolo[4,3-b]pyridine-6-carboxamide, 3-(5-(difluoromethoxy)pyridin-3-yl)-N-((2S,3S)-2-hydroxy-4-methylpentan-3-yl)-1-isopropyl-1H-pyrazolo[4,3-b]pyridine-6-carboxamide, 3-(5-(difluoromethoxy)-2-fluorophenyl)-N-(1-(dimethylamino)-2-methylpropan-2-yl)-1-isopropyl-1H-pyrazolo[4,3-b]pyridine-6-carboxamide, 1-cyclobutyl-3-(3-(difluoromethoxy)phenyl)-N-(3-methyl-1,1-dioxidothietan-3-yl)-1H-pyrazolo[4,3-b]pyridine-6-carboxamide, 3-(3-(difluoromethoxy)phenyl)-N—((S)-3-methyl-1,1-dioxidotetrahydrothiophen-3-yl)-1-((S)-tetrahydrofuran-3-yl)-1H-pyrazolo[4,3-b]pyridine-6-carboxamide, 3-(3-(difluoromethoxy)phenyl)-N—((S)-3-methyl-1,1-dioxidotetrahydrothiophen-3-yl)-1-((R)-tetrahydrofuran-3-yl)-1H-pyrazolo[4,3-b]pyridine-6-carboxamide, 3-[3-(difluoromethoxy)phenyl]-N-(3-methyl-1,1-dioxo-thietan-3-yl)-1-(oxetan-3-yl)pyrazolo[4,3-b]pyridine-6-carboxamide, 3-(3-(difluoromethoxy)phenyl)-N—((S)-3-methyl-1,1-dioxidotetrahydrothiophen-3-yl)-1-((R)-tetrahydro-2H-pyran-3-yl)-1H-pyrazolo[4,3-b]pyridine-6-carboxamide, 3-(3-(difluoromethoxy)phenyl)-N—((S)-3-methyl-1,1-dioxidotetrahydrothiophen-3-yl)-1-((S)-tetrahydro-2H-pyran-3-yl)-1H-pyrazolo[4,3-b]pyridine-6-carboxamide, 3-(3-(difluoromethoxy)phenyl)-N-(3-methyl-1,1-dioxidothietan-3-yl)-1-(tetrahydro-2H-pyran-4-yl)-1H-pyrazolo[4,3-b]pyridine-6-carboxamide, 3-[5-(difluoromethoxy)-3-pyridyl]-N-(3-methyl-1,1-dioxo-thietan-3-yl)-1-tetrahydropyran-4-yl-pyrazolo[4,3-b]pyridine-6-carboxamide, N-[(3S)-3-methyl-1,1-dioxo-thiolan-3-yl]-3-(2-methylpyrazol-3-yl)-1-tetrahydropyran-4-yl-pyrazolo[4,3-b]pyridine-6-carboxamide, (R)-1-(sec-butyl)-3-(3-(difluoromethoxy)phenyl)-N-(3-methyl-1,1-dioxidothietan-3-yl)-1H-pyrazolo[4,3-b]pyridine-6-carboxamide, (S)-1-(sec-butyl)-3-(3-(difluoromethoxy)phenyl)-N-(3-methyl-1,1-dioxidothietan-3-yl)-1H-pyrazolo[4,3-b]pyridine-6-carboxamide, (R)-3-(3-(difluoromethoxy)phenyl)-N-(3-methyl-1,1-dioxidothietan-3-yl)-1-(3,3,3-trifluoro-2-hydroxypropyl)-1H-pyrazolo[4,3-b]pyridine-6-carboxamide, (S)-3-(3-(difluoromethoxy)phenyl)-N-(3-methyl-1,1-dioxidothietan-3-yl)-1-(3,3,3-trifluoro-2-hydroxypropyl)-1H-pyrazolo[4,3-b]pyridine-6-carboxamide, (R)-3-(3-(difluoromethoxy)phenyl)-1-(2-hydroxypropyl)-N-(3-methyl-1,1-dioxidothietan-3-yl)-1H-pyrazolo[4,3-b]pyridine-6-carboxamide, (S)-3-(3-(difluoromethoxy)phenyl)-1-(2-hydroxypropyl)-N-(3-methyl-1,1-dioxidothietan-3-yl)-1H-pyrazolo[4,3-b]pyridine-6-carboxamide, 3-(3-(difluoromethoxy)phenyl)-N-(3-methyl-1,1-dioxidothietan-3-yl)-1-(3-(trifluoromethyl)tetrahydro-2H-pyran-4-yl)-1H-pyrazolo[4,3-b]pyridine-6-carboxamide, 3-(3-(difluoromethoxy)phenyl)-N-(4-(2-hydroxypropan-2-yl)tetrahydro-2H-pyran-4-yl)-1-isopropyl-1H-pyrazolo[4,3-b]pyridine-6-carboxamide, (R)-3-(3-(difluoromethoxy)phenyl)-N-(4-(1-hydroxyethyl)tetrahydro-2H-pyran-4-yl)-1-isopropyl-1H-pyrazolo[4,3-b]pyridine-6-carboxamide, (S)-3-(3-(difluoromethoxy)phenyl)-N-(4-(1-hydroxyethyl)tetrahydro-2H-pyran-4-yl)-1-isopropyl-1H-pyrazolo[4,3-b]pyridine-6-carboxamide, 3-(3-(difluoromethoxy)phenyl)-N-(4-(hydroxymethyl)tetrahydro-2H-pyran-4-yl)-1-isopropyl-1H-pyrazolo[4,3-b]pyridine-6-carboxamide, 3-(3-(difluoromethoxy)phenyl)-1-((3R)-3-fluorotetrahydro-2H-pyran-4-yl)-N-(3-methyl-1,1-dioxidothietan-3-yl)-1H-pyrazolo[4,3-b]pyridine-6-carboxamide, 3-(3-(difluoromethoxy)phenyl)-1-((3S)-3-fluorotetrahydro-2H-pyran-4-yl)-N-(3-methyl-1,1-dioxidothietan-3-yl)-1H-pyrazolo[4,3-b]pyridine-6-carboxamide, 3-(3-(difluoromethoxy)phenyl)-N-(3-methyl-1,1-dioxidothietan-3-yl)-1-((2R)-2-(trifluoromethyl)tetrahydro-2H-pyran-4-yl)-1H-pyrazolo[4,3-b]pyridine-6-carboxamide, 3-(3-(difluoromethoxy)phenyl)-N-(3-methyl-1,1-dioxidothietan-3-yl)-1-((2S)-2-(trifluoromethyl)tetrahydro-2H-pyran-4-yl)-1H-pyrazolo[4,3-b]pyridine-6-carboxamide, (R)-3-(3-(difluoromethoxy)phenyl)-1-(2,2-dimethyltetrahydro-2H-pyran-4-yl)-N-(3-methyl-1,1-dioxidothietan-3-yl)-1H-pyrazolo[4,3-b]pyridine-6-carboxamide, (S)-3-(3-(difluoromethoxy)phenyl)-1-(2,2-dimethyltetrahydro-2H-pyran-4-yl)-N-(3-methyl-1,1-dioxidothietan-3-yl)-1H-pyrazolo[4,3-b]pyridine-6-carboxamide, 3-(3-(difluoromethoxy)phenyl)-1-((2S,3R)-3-hydroxybutan-2-yl)-N-(3-methyl-1,1-dioxidothietan-3-yl)-1H-pyrazolo[4,3-b]pyridine-6-carboxamide, 3-(3-(difluoromethoxy)phenyl)-1-((2S,3S)-3-hydroxybutan-2-yl)-N-(3-methyl-1,1-dioxidothietan-3-yl)-1H-pyrazolo[4,3-b]pyridine-6-carboxamide, 3-(3-(difluoromethoxy)phenyl)-1-((2R,3R)-3-hydroxybutan-2-yl)-N-(3-methyl-1,1-dioxidothietan-3-yl)-1H-pyrazolo[4,3-b]pyridine-6-carboxamide, 3-(3-(difluoromethoxy)phenyl)-1-((2R,3S)-3-hydroxybutan-2-yl)-N-(3-methyl-1,1-dioxidothietan-3-yl)-1H-pyrazolo[4,3-b]pyridine-6-carboxamide, (S)-3-(5-(difluoromethoxy)pyridin-3-yl)-N-(3-methyl-1,1-dioxidotetrahydrothiophen-3-yl)-1-(tetrahydro-2H-pyran-4-yl)-1H-pyrazolo[4,3-c]pyridine-6-carboxamide, (S)-3-(5-(difluoromethoxy)pyridin-3-yl)-N-(3-methyl-1,1-dioxidotetrahydrothiophen-3-yl)-1-(tetrahydro-2H-pyran-4-yl)-1H-pyrrolo[3,2-b]pyridine-6-carboxamide, (S)-3-(3-(difluoromethoxy)phenyl)-N-(3-methyl-1,1-dioxidotetrahydrothiophen-3-yl)-1-(tetrahydro-2H-pyran-4-yl)-1H-pyrrolo[3,2-b]pyridine-6-carboxamide, (S)-3-(3-(difluoromethoxy)phenyl)-N-(3-methyl-1,1-dioxidotetrahydrothiophen-3-yl)-1-(tetrahydro-2H-pyran-4-yl)-1H-pyrrolo[3,2-c]pyridine-6-carboxamide, (S)-3-(3-(difluoromethoxy)phenyl)-4-methyl-N-(3-methyl-1,1-dioxidotetrahydrothiophen-3-yl)-1-(tetrahydro-2H-pyran-4-yl)-1H-indazole-6-carboxamide, 1-(3,3-difluorocyclobutyl)-3-(3-(difluoromethoxy)phenyl)-N-(3-methyl-1,1-dioxidothietan-3-yl)-1H-pyrazolo[4,3-b]pyridine-6-carboxamide, trans-1-((3-cyano-3-methylcyclobutyl)-3-(3-(difluoromethoxy)phenyl)-N-(3-methyl-1,1-dioxidothietan-3-yl)-1H-indazole-6-carboxamide, cis-1-((3-cyano-3-methylcyclobutyl)-3-(3-(difluoromethoxy)phenyl)-N-(3-methyl-1,1-dioxidothietan-3-yl)-1H-indazole-6-carboxamide, 3-(3-(difluoromethoxy)phenyl)-1-(3-hydroxycyclobutyl)-N-(3-methyl-1,1-dioxidothietan-3-yl)-1H-pyrazolo[4,3-b]pyridine-6-carboxamide, 3-(3-(difluoromethoxy)phenyl)-1-(3,3-dimethylcyclobutyl)-N-(3-methyl-1,1-dioxidothietan-3-yl)-1H-pyrazolo[4,3-b]pyridine-6-carboxamide, 4-cyano-3-(3-(difluoromethoxy)phenyl)-1-isopropyl-N-(3-methyl-1,1-dioxidothietan-3-yl)-1H-indazole-6-carboxamide, 3-(3-cyclopropylphenyl)-1-isopropyl-N-(3-methyl-1,1-dioxidothietan-3-yl)-1H-pyrazolo[4,3-b]pyridine-6-carboxamide, 3-[3-(1,1-difluoroethyl)phenyl]-1-isopropyl-N-(3-methyl-1,1-dioxo-thietan-3-yl)pyrazolo[4,3-b]pyridine-6-carboxamide, 3-[3-(2,2-difluoroethoxy)phenyl]-1-isopropyl-N-(3-methyl-1,1-dioxo-thietan-3-yl)pyrazolo[4,3-b]pyridine-6-carboxamide, 3-[5-(difluoromethoxy)-3-pyridyl]-1-isopropyl-N-(3-methyl-1,1-dioxo-thietan-3-yl)pyrazolo[4,3-b]pyridine-6-carboxamide, 3-[6-(difluoromethoxy)-2-pyridyl]-1-isopropyl-N-(3-methyl-1,1-dioxo-thietan-3-yl)pyrazolo[4,3-b]pyridine-6-carboxamide, 3-[3-(cyclopropoxy)phenyl]-1-isopropyl-N-(3-methyl-1,1-dioxo-thietan-3-yl)pyrazolo[4,3-b]pyridine-6-carboxamide, 3-[4-(difluoromethoxy)-2-pyridyl]-1-isopropyl-N-(3-methyl-1,1-dioxo-thietan-3-yl)pyrazolo[4,3-b]pyridine-6-carboxamide, 3-[5-(difluoromethoxy)-3-pyridyl]-N-[(1S,2S)-2-hydroxycyclohexyl]-1-isopropyl-pyrazolo[4,3-b]pyridine-6-carboxamide, 3-[2-(difluoromethoxy)-4-pyridyl]-1-isopropyl-N-(3-methyl-1,1-dioxo-thietan-3-yl)pyrazolo[4,3-b]pyridine-6-carboxamide, 3-(5-cyclopropyl-3-pyridyl)-1-isopropyl-N-(3-methyl-1,1-dioxo-thietan-3-yl)pyrazolo[4,3-b]pyridine-6-carboxamide, 1-isopropyl-N-(3-methyl-1,1-dioxo-thietan-3-yl)-3-(3-methylsulfonylphenyl)pyrazolo[4,3-b]pyridine-6-carboxamide, 3-[3-(cyanomethoxy)phenyl]-1-isopropyl-N-(3-methyl-1,1-dioxo-thietan-3-yl)pyrazolo[4,3-b]pyridine-6-carboxamide, 3-(3-fluorophenyl)-1-isopropyl-N-(3-methyl-1,1-dioxo-thietan-3-yl)pyrazolo[4,3-b]pyridine-6-carboxamide, 3-(5-(difluoromethoxy)pyridin-3-yl)-N-((1S,2R)-2-hydroxycyclopentyl)-1-isopropyl-1H-pyrazolo[4,3-b]pyridine-6-carboxamide, 3-(5-cyclopropoxypyridin-3-yl)-1-isopropyl-N-(3-methyl-1,1-dioxidothietan-3-yl)-1H-pyrazolo[4,3-b]pyridine-6-carboxamide, 1-isopropyl-N-(3-methyl-1,1-dioxidothietan-3-yl)-3-(3-(1-(trifluoromethyl)cyclopropyl)phenyl)-1H-pyrazolo[4,3-b]pyridine-6-carboxamide, 3-(3-cyanophenyl)-1-isopropyl-N-(3-methyl-1,1-dioxidothietan-3-yl)-1H-pyrazolo[4,3-b]pyridine-6-carboxamide, 3-(5-cyclobutoxy-2-fluorophenyl)-1-isopropyl-N-(3-methyl-1,1-dioxidothietan-3-yl)-1H-pyrazolo[4,3-b]pyridine-6-carboxamide, 3-(3-(1-cyanocyclopropyl)phenyl)-1-isopropyl-N-(3-methyl-1,1-dioxidothietan-3-yl)-1H-pyrazolo[4,3-b]pyridine-6-carboxamide, 3-(3-(difluoromethoxy)phenyl)-1-(2-hydroxy-2-methylpropyl)-N-(3-methyl-1,1-dioxidothietan-3-yl)-1H-pyrazolo[4,3-b]pyridine-6-carboxamide, 3-(3-cyclopropylphenyl)-1-(2-hydroxy-2-methylpropyl)-N-(3-methyl-1,1-dioxidothietan-3-yl)-1H-pyrazolo[4,3-b]pyridine-6-carboxamide, 3-(5-(difluoromethoxy)-2-fluorophenyl)-1-isopropyl-N-(3-methyl-1,1-dioxidothietan-3-yl)-1H-pyrazolo[4,3-b]pyridine-6-carboxamide, 1-isopropyl-N-(3-methyl-1,1-dioxidothietan-3-yl)-3-(5-(trifluoromethoxy)pyridin-3-yl)-1H-pyrazolo[4,3-b]pyridine-6-carboxamide, 3-(5-ethoxy-2-fluorophenyl)-1-isopropyl-N-(3-methyl-1,1-dioxidothietan-3-yl)-1H-pyrazolo[4,3-b]pyridine-6-carboxamide, (S)-1-(sec-butyl)-3-(2-(difluoromethoxy)-5-fluoropyridin-4-yl)-N-(4-methyl-1,1-dioxidotetrahydro-2H-thiopyran-4-yl)-1H-pyrazolo[4,3-b]pyridine-6-carboxamide, 3-(5-cyclopropyl-2-fluorophenyl)-1-isopropyl-N-(3-methyl-1,1-dioxidothietan-3-yl)-1H-pyrazolo[4,3-b]pyridine-6-carboxamide, 3-(2-fluoro-5-(trifluoromethoxy)phenyl)-1-isopropyl-N-(4-methyl-1,1-dioxidotetrahydro-2H-thiopyran-4-yl)-1H-pyrazolo[4,3-b]pyridine-6-carboxamide, 1-isopropyl-N-(3-methyl-1,1-dioxidothietan-3-yl)-3-(3-(trifluoromethoxy)phenyl)-1H-pyrazolo[4,3-b]pyridine-6-carboxamide, 3-(2-chloro-5-(difluoromethoxy)phenyl)-1-isopropyl-N-(3-methyl-1,1-dioxidothietan-3-yl)-1H-pyrazolo[4,3-b]pyridine-6-carboxamide, 3-(2-ethoxy-5-fluoropyridin-4-yl)-1-isopropyl-N-(3-methyl-1,1-dioxidothietan-3-yl)-1H-pyrazolo[4,3-b]pyridine-6-carboxamide, 3-(3-(1-Hydroxycyclopropyl)phenyl)-1-isopropyl-N-(3-methyl-1,1-dioxidothietan-3-yl)-1H-pyrazolo[4,3-b]pyridine-6-carboxamide, 1-isopropyl-3-(3-(1-methoxycyclopropyl)phenyl)-N-(3-methyl-1,1-dioxidothietan-3-yl)-1H-pyrazolo[4,3-b]pyridine-6-carboxamide, 3-(3-(difluoromethoxy)phenyl)-1-(3-hydroxy-2,3-dimethylbutan-2-yl)-N-(3-methyl-1,1-dioxidothietan-3-yl)-1H-pyrazolo[4,3-b]pyridine-6-carboxamide, (R)-3-(3-(difluoromethoxy)phenyl)-1-(3-hydroxy-3-methylbutan-2-yl)-N-(3-methyl-1,1-dioxidothietan-3-yl)-1H-pyrazolo[4,3-b]pyridine-6-carboxamide, (S)-3-(3-(difluoromethoxy)phenyl)-1-(3-hydroxy-3-methylbutan-2-yl)-N-(3-methyl-1,1-dioxidothietan-3-yl)-1H-pyrazolo[4,3-b]pyridine-6-carboxamide, (R)-3-(5-(difluoromethoxy)-2-fluorophenyl)-1-(3-hydroxy-3-methylbutan-2-yl)-N-(3-methyl-1,1-dioxidothietan-3-yl)-1H-pyrazolo[4,3-b]pyridine-6-carboxamide, (S)-3-(5-(difluoromethoxy)-2-fluorophenyl)-1-(3-hydroxy-3-methylbutan-2-yl)-N-(3-methyl-1,1-dioxidothietan-3-yl)-1H-pyrazolo[4,3-b]pyridine-6-carboxamide, 3-(3-(difluoromethoxy)phenyl)-N-(3-methyl-1,1-dioxidothietan-3-yl)-1-(1-methylpiperidin-4-yl)-1H-pyrazolo[4,3-b]pyridine-6-carboxamide, 1-(1-acetylazetidin-3-yl)-3-(3-(difluoromethoxy)phenyl)-N-(3-methyl-1,1-dioxidothietan-3-yl)-1H-pyrazolo[4,3-b]pyridine-6-carboxamide, 3-(3-(difluoromethoxy)phenyl)-1-(5-fluoropyrimidin-2-yl)-N-isopropyl-1H-pyrrolo[3,2-b]pyridine-6-carboxamide, 3-(3-(difluoromethoxy)phenyl)-1-(5-fluoropyrimidin-2-yl)-N-(1-(methylsulfonyl)propan-2-yl)-1H-pyrrolo[3,2-b]pyridine-6-carboxamide, N-(1-amino-2-methyl-1-oxopropan-2-yl)-3-(3-(difluoromethoxy)phenyl)-1-(5-fluoropyrimidin-2-yl)-1H-pyrrolo[3,2-b]pyridine-6-carboxamide, N-((3,3-difluorocyclobutyl)methyl)-3-(3-(difluoromethoxy)phenyl)-1-(5-fluoropyrimidin-2-yl)-1H-pyrrolo[3,2-b]pyridine-6-carboxamide, 3-(5-(difluoromethoxy)-2-methylpyridin-3-yl)-N-((3S,4S)-4-hydroxy-3-methyl-1,1-dioxidotetrahydrothiophen-3-yl)-1-isopropyl-1H-pyrazolo[4,3-b]pyridine-6-carboxamide, 3-(2-ethoxy-5-fluoropyridin-4-yl)-N-((1S,2R)-2-hydroxy-1-methylcyclopentyl)-1-isopropyl-1H-pyrazolo[4,3-b]pyridine-6-carboxamide, (3-(5-(difluoromethoxy)pyridin-3-yl)-1-isopropyl-1H-pyrazolo[4,3-b]pyridin-6-yl)(4-ethylpiperazin-1-yl)methanone, 3-(3-(difluoromethoxy)phenyl)-N-(3-methyl-1,1-dioxidothietan-3-yl)-1-((tetrahydro-2H-pyran-4-yl)methyl)-1H-pyrazolo[4,3-b]pyridine-6-carboxamide, 3-(3-(difluoromethoxy)phenyl)-1-(4-fluorobenzyl)-N-(3-methyl-1,1-dioxidothietan-3-yl)-1H-pyrazolo[4,3-b]pyridine-6-carboxamide, (S)-5-fluoro-N-(3-methyl-1,1-dioxidotetrahydrothiophen-3-yl)-3-(1-methyl-1H-pyrazol-5-yl)-1-(tetrahydro-2H-pyran-4-yl)-1H-indole-6-carboxamide, 3-(2-(difluoromethoxy)-5-fluoropyridin-4-yl)-1-isopropyl-N-(4-methyl-1,1-dioxidotetrahydro-2H-thiopyran-4-yl)-1H-pyrazolo[4,3-c]pyridazine-6-carboxamide, 1-(1-amino-1-oxopropan-2-yl)-3-(5-(difluoromethoxy)-2-fluorophenyl)-N-(3-methyl-1,1-dioxidothietan-3-yl)-1H-pyrazolo[4,3-b]pyridine-6-carboxamide, 3-(2-(2,2-difluoroethoxy)-5-fluoropyridin-4-yl)-1-isopropyl-N-(3-methyl-1,1-dioxidothietan-3-yl)-1H-pyrazolo[4,3-b]pyridine-6-carboxamide, 3-(5-fluoro-2-(2,2,2-trifluoroethoxy)pyridin-4-yl)-1-isopropyl-N-(3-methyl-1,1-dioxidothietan-3-yl)-1H-pyrazolo[4,3-b]pyridine-6-carboxamide, 1-isopropyl-N-(3-methyl-1,1-dioxidothietan-3-yl)-3-(2-methylbenzo[d]oxazol-4-yl)-1H-pyrazolo[4,3-b]pyridine-6-carboxamide, 3-(4-acetamido-3-hydroxyphenyl)-1-isopropyl-N-(3-methyl-1,1-dioxidothietan-3-yl)-1H-pyrazolo[4,3-b]pyridine-6-carboxamide, 3-(2-(dimethylamino)pyridin-4-yl)-1-isopropyl-N-(3-methyl-1,1-dioxidothietan-3-yl)-1H-pyrazolo[4,3-b]pyridine-6-carboxamide, (R)-3-(2-fluoro-5-(trifluoromethoxy)phenyl)-1-(3-hydroxy-3-methylbutan-2-yl)-N-(3-methyl-1,1-dioxidothietan-3-yl)-1H-pyrazolo[4,3-b]pyridine-6-carboxamide, (S)-3-(2-fluoro-5-(trifluoromethoxy)phenyl)-1-(3-hydroxy-3-methylbutan-2-yl)-N-(3-methyl-1,1-dioxidothietan-3-yl)-1H-pyrazolo[4,3-b]pyridine-6-carboxamide, (R)-3-(2-(difluoromethoxy)-5-fluoropyridin-4-yl)-1-(3-hydroxy-3-methylbutan-2-yl)-N-(3-methyl-1,1-dioxidothietan-3-yl)-1H-pyrazolo[4,3-c]pyridine-6-carboxamide, (S)-3-(2-(difluoromethoxy)-5-fluoropyridin-4-yl)-1-(3-hydroxy-3-methylbutan-2-yl)-N-(3-methyl-1,1-dioxidothietan-3-yl)-1H-pyrazolo[4,3-c]pyridine-6-carboxamide, 3-(3-(difluoromethoxy)phenyl)-1-methyl-N-(3-methyl-1,1-dioxidothietan-3-yl)-1H-pyrazolo[4,3-b]pyridine-6-carboxamide, 3-(3-(difluoromethoxy)phenyl)-1-ethyl-N-(3-methyl-1,1-dioxidothietan-3-yl)-1H-pyrazolo[4,3-b]pyridine-6-carboxamide, 3-(3-(difluoromethoxy)phenyl)-1-isobutyl-N-(3-methyl-1,1-dioxidothietan-3-yl)-1H-pyrazolo[4,3-b]pyridine-6-carboxamide, 3-(3-(difluoromethoxy)phenyl)-N-(3-methyl-1,1-dioxidothietan-3-yl)-1-neopentyl-1H-pyrazolo[4,3-b]pyridine-6-carboxamide, or 1-cyclopropyl-3-(3-(difluoromethoxy)phenyl)-N-(3-methyl-1,1-dioxidothietan-3-yl)-1H-pyrazolo[4,3-b]pyridine-6-carboxamide.

In Embodiment 53 of the invention, the compound of formula I, or a pharmaceutically acceptable salt thereof, is:

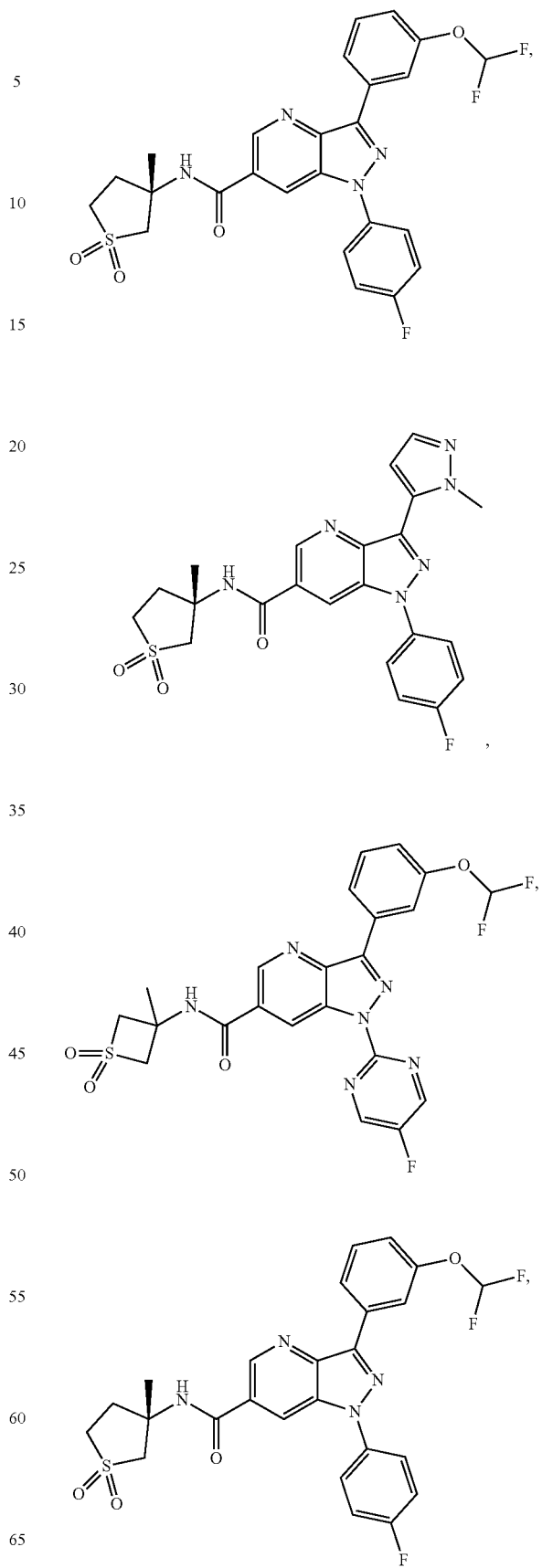

29
-continued
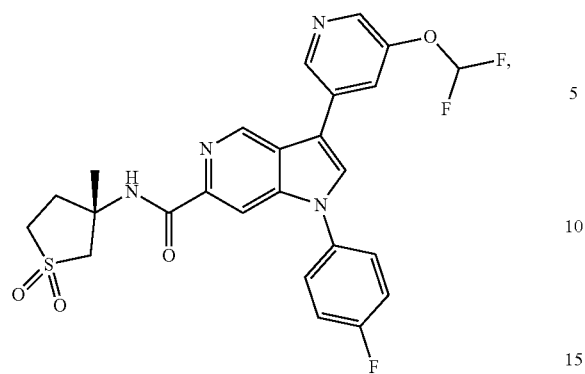
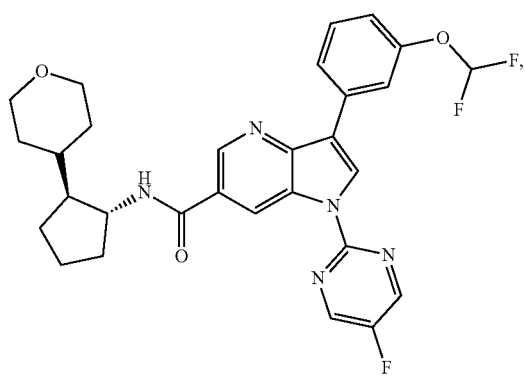
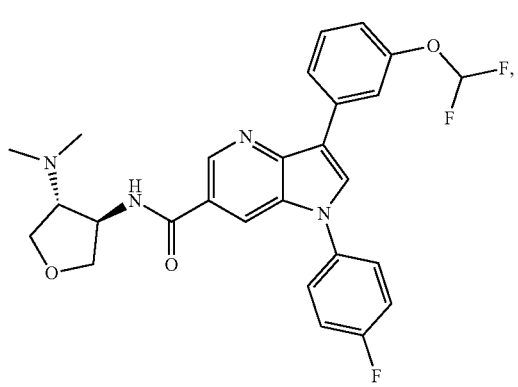
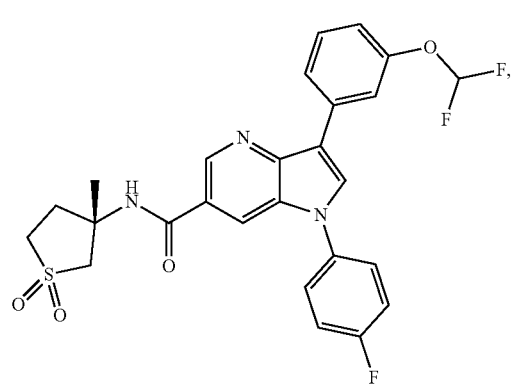
30
-continued
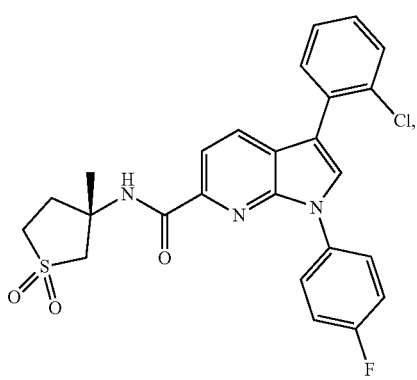
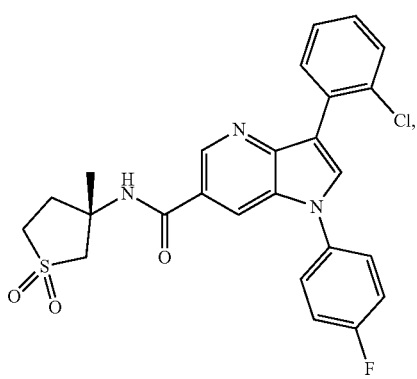
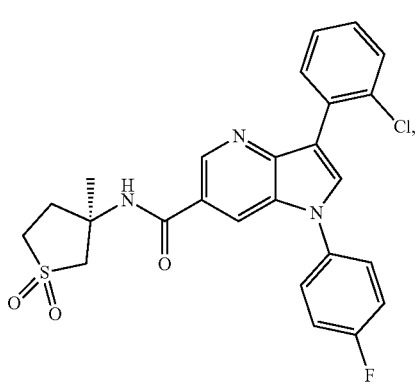
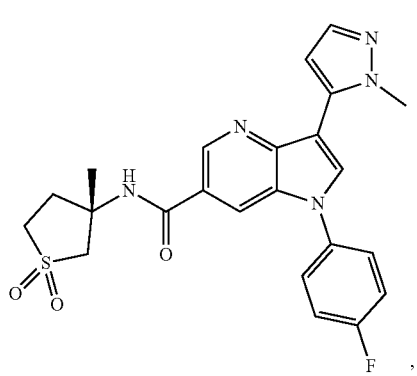

31
-continued
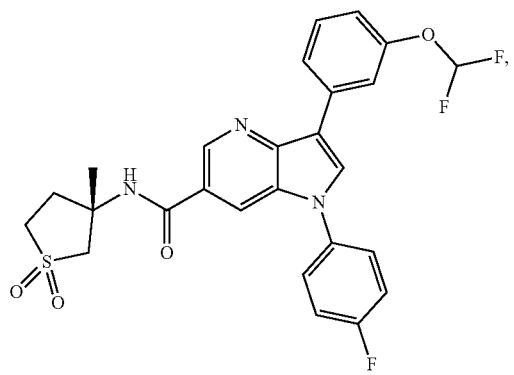
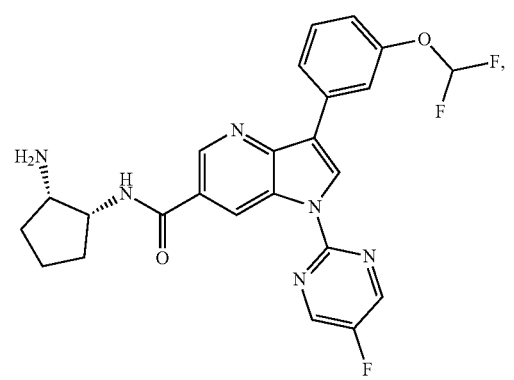
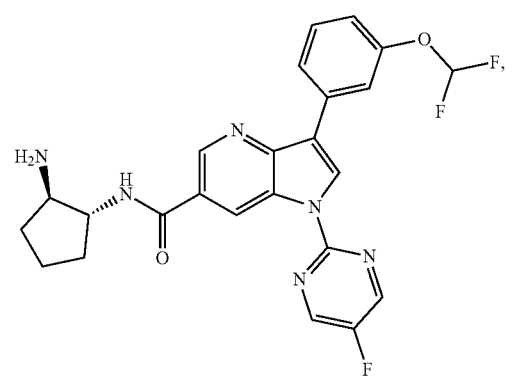
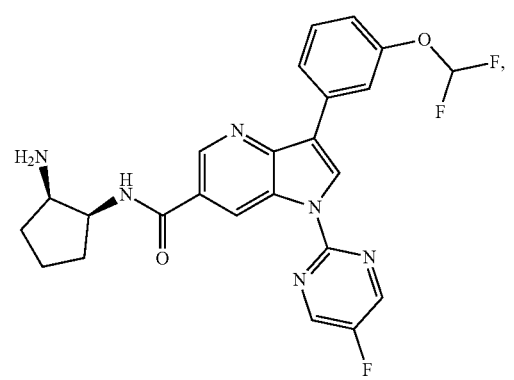
32
-continued
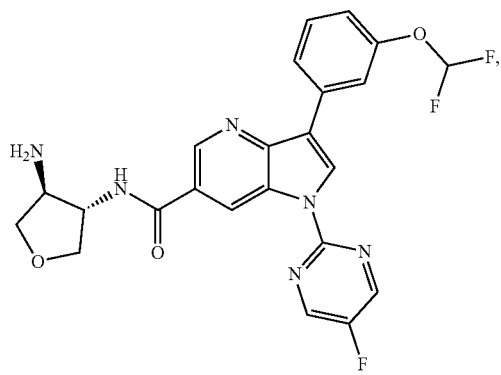
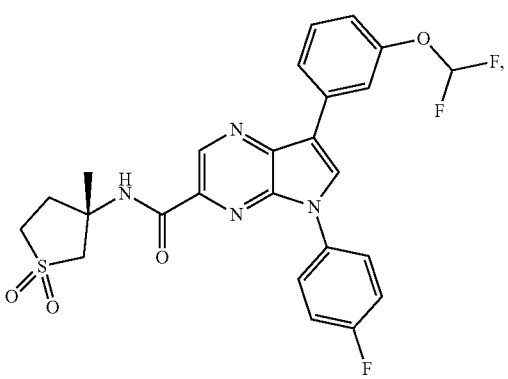
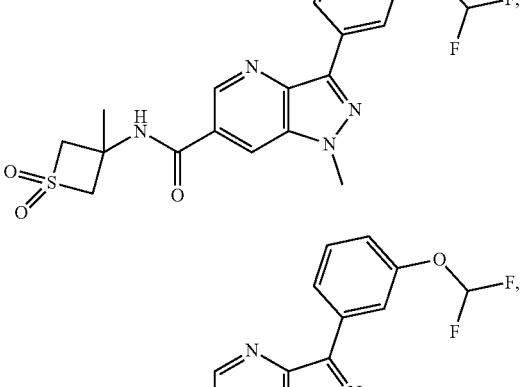
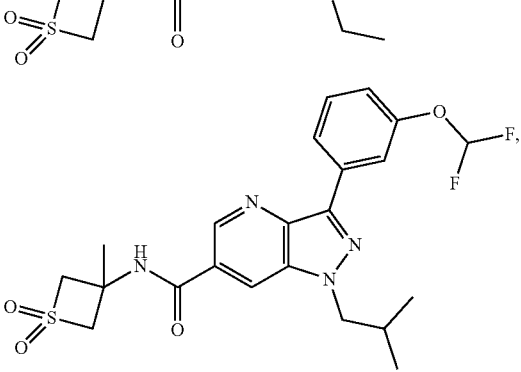
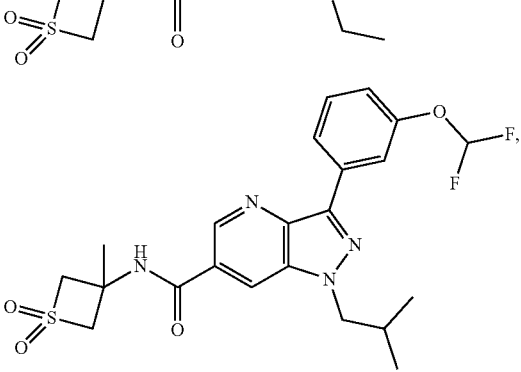

33
-continued
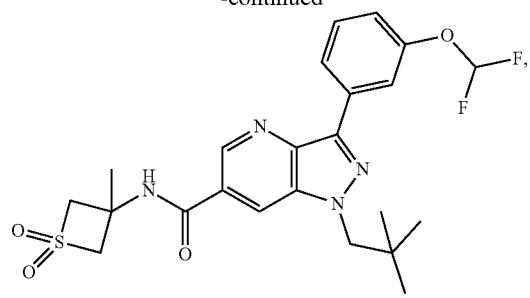
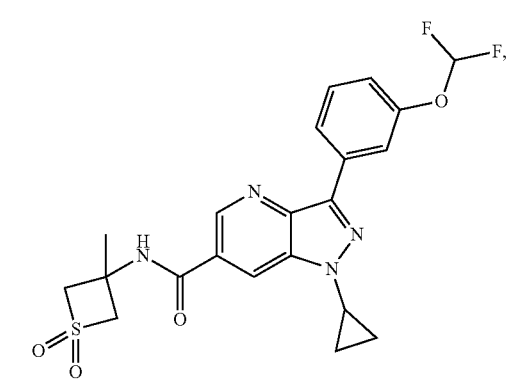
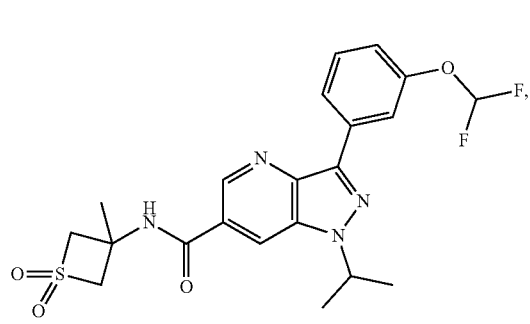
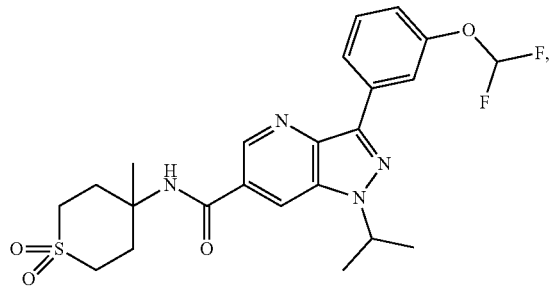
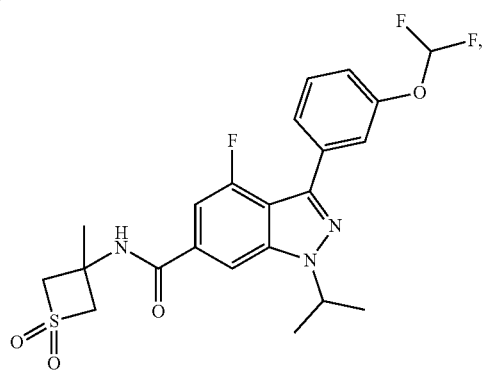
34
-continued
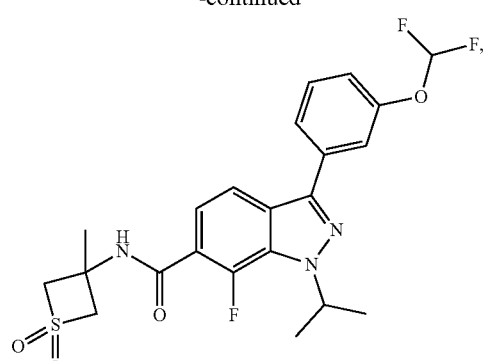
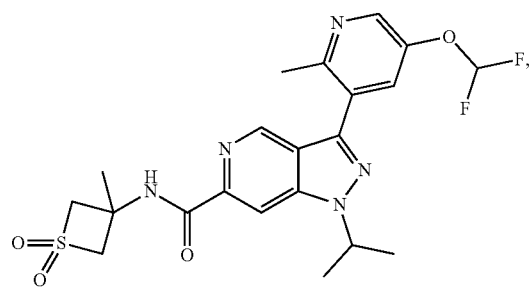
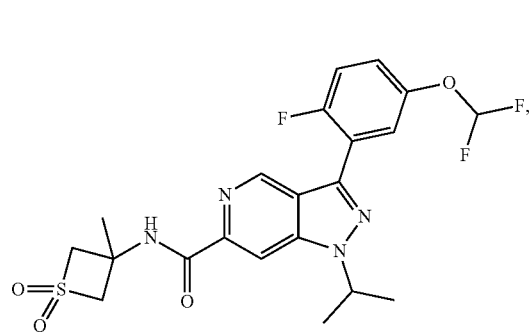
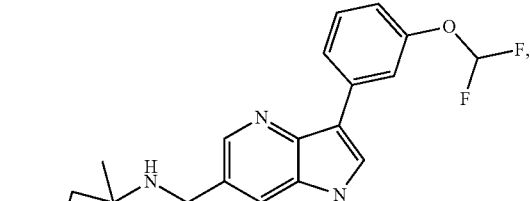
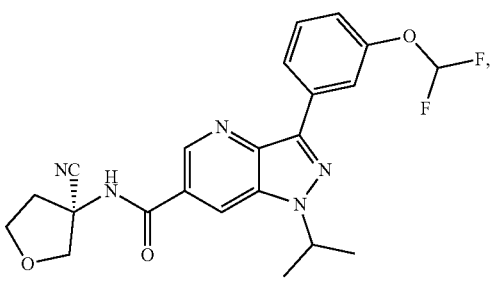

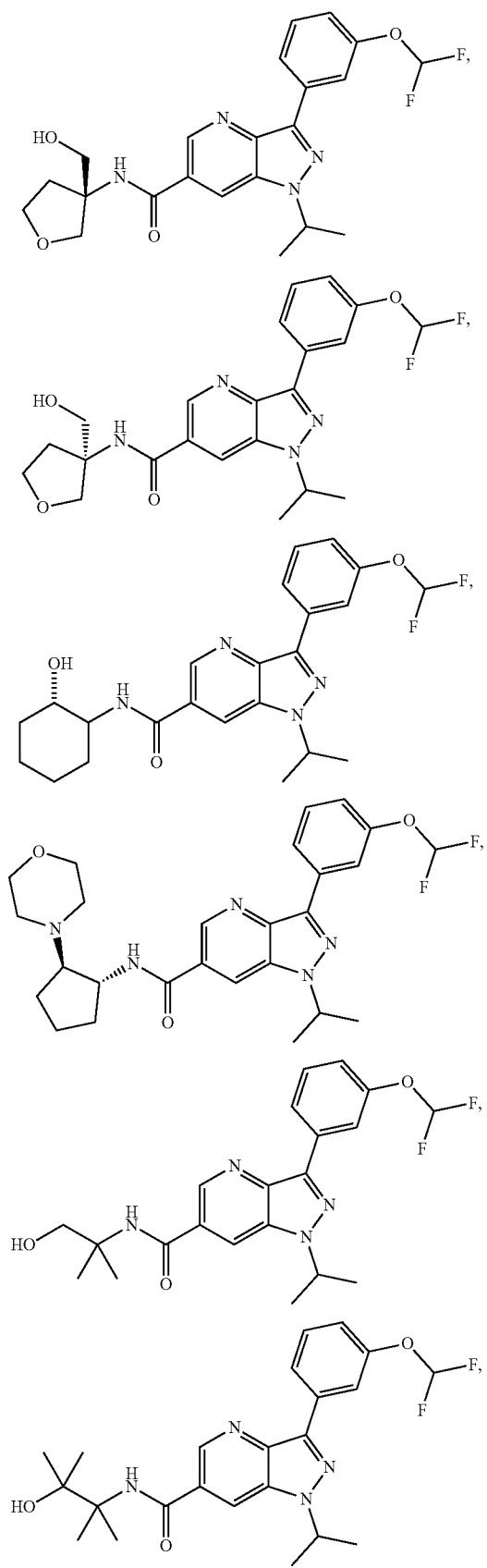
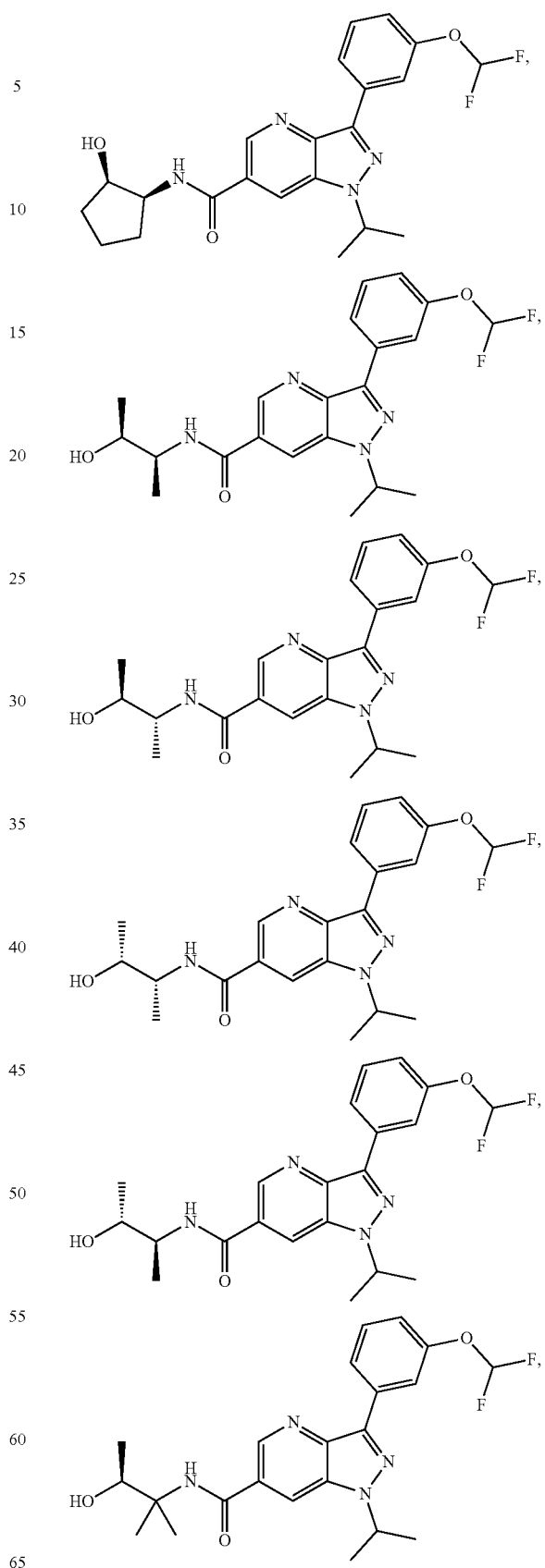

37
-continued
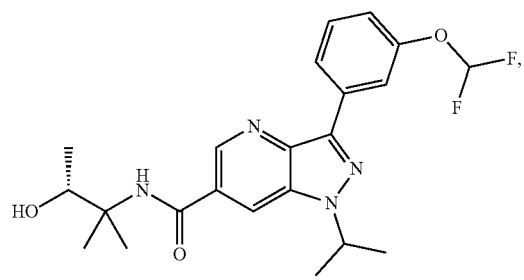
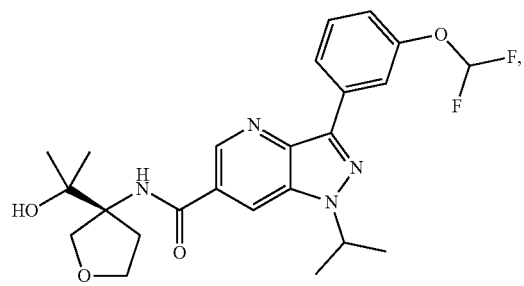
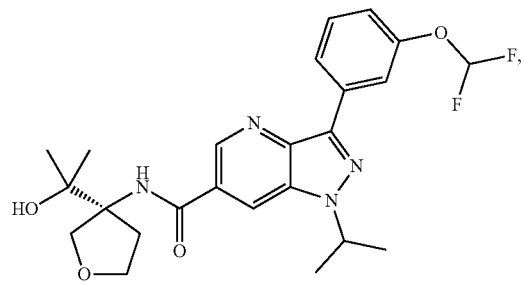
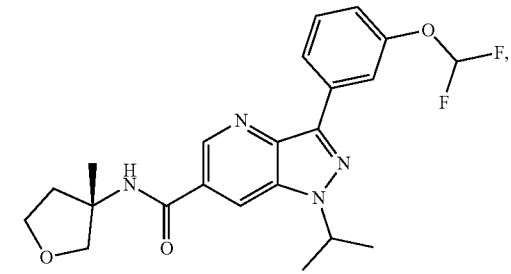
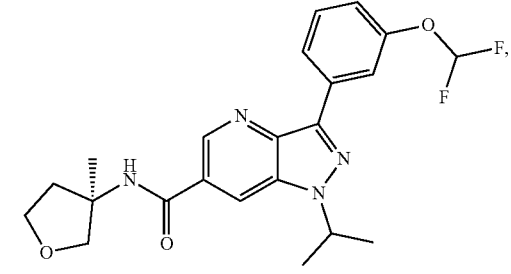
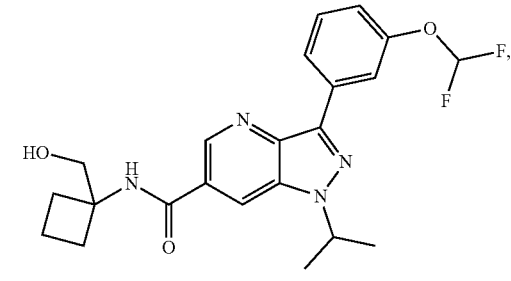
38
-continued
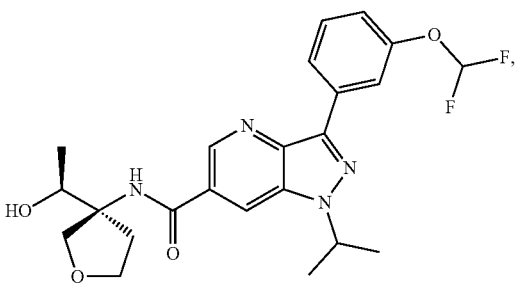
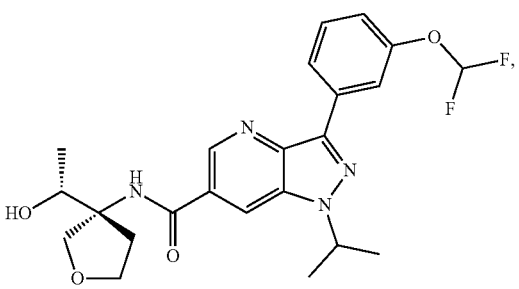
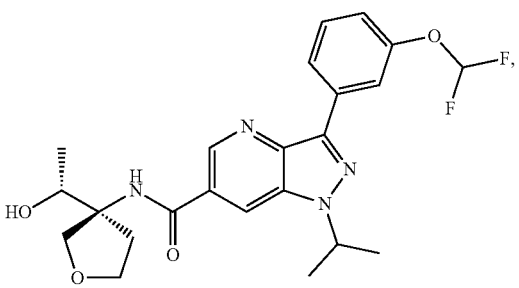
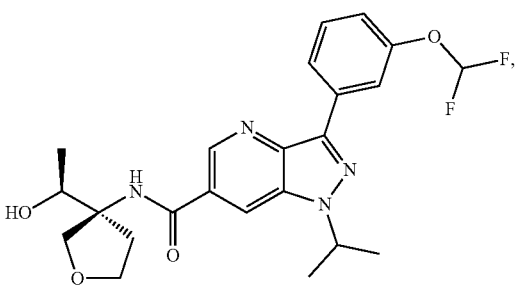
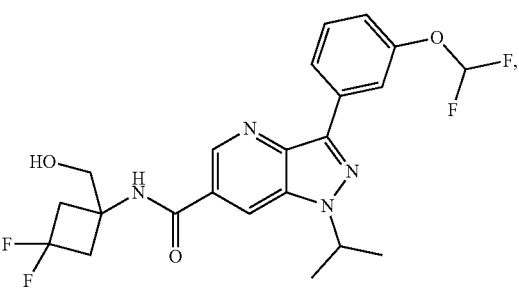
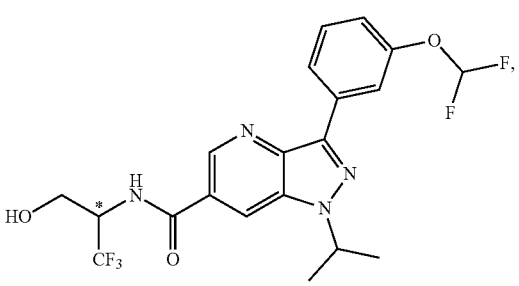

39
-continued
40
-continued
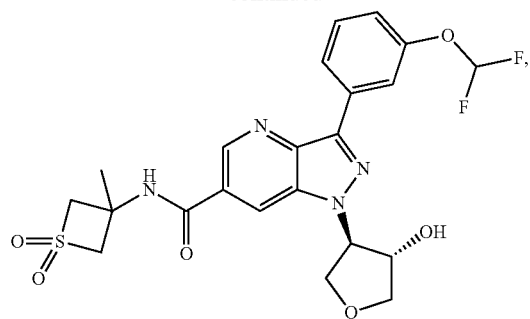
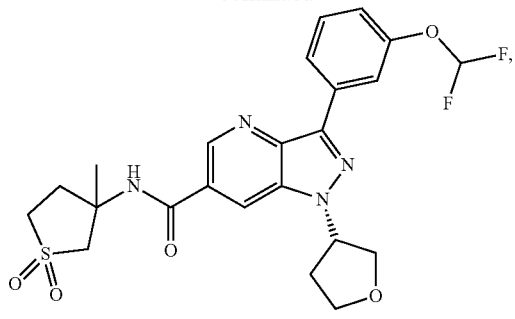

41
-continued
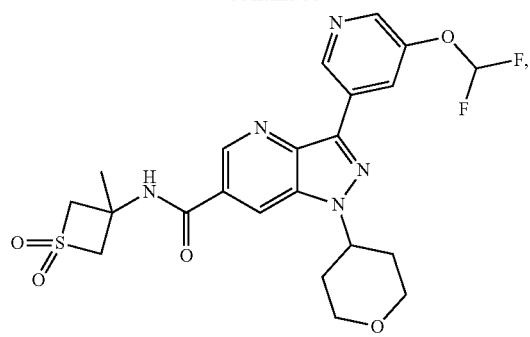
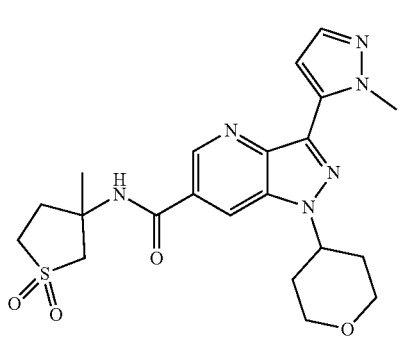
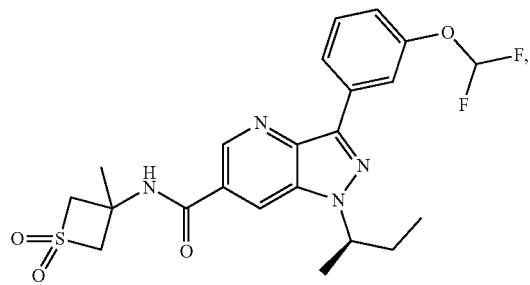
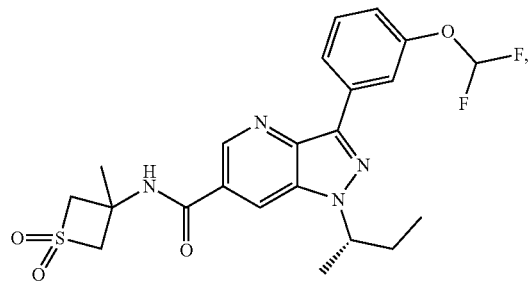
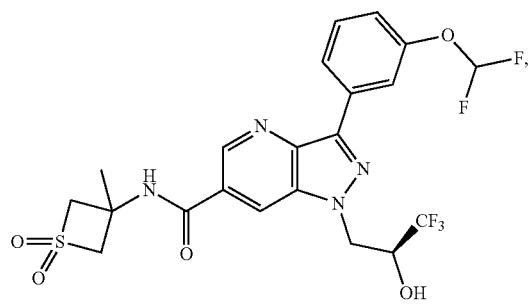
42
-continued
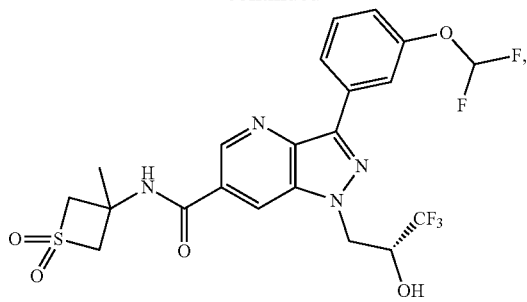
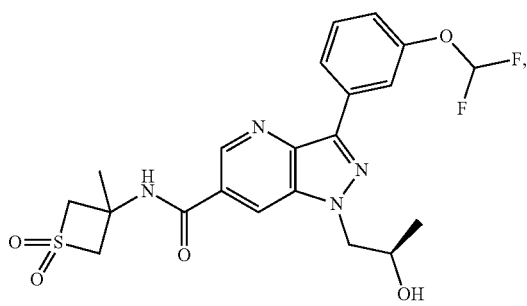
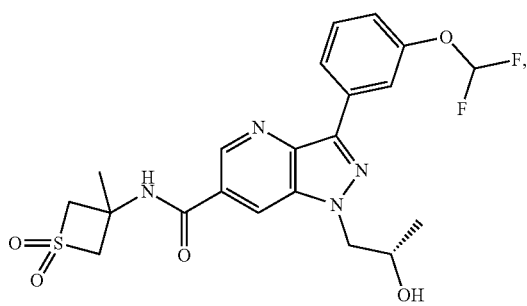
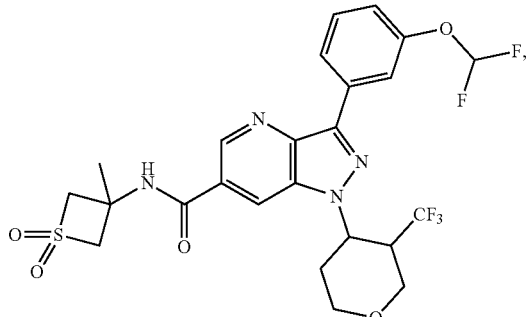
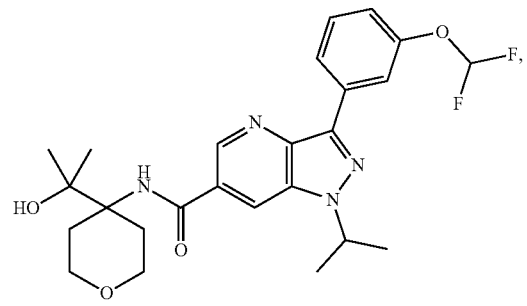

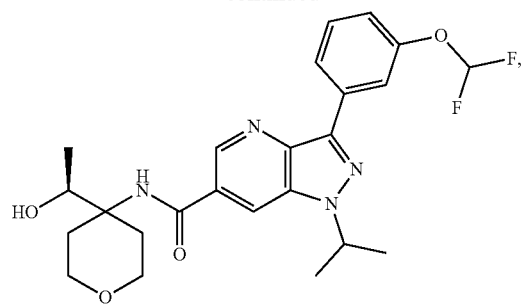
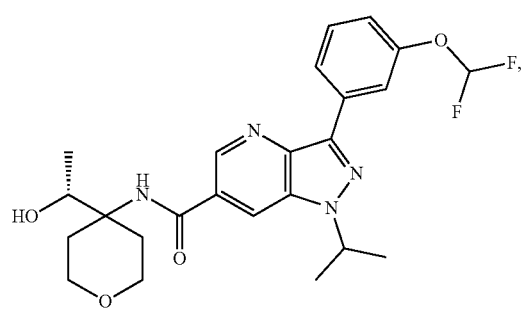
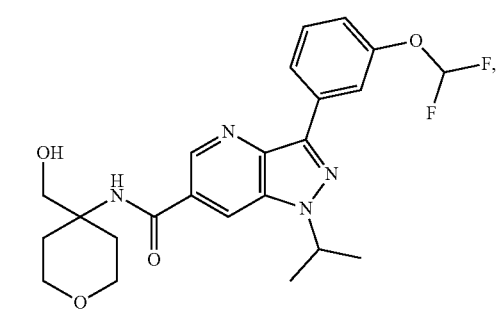
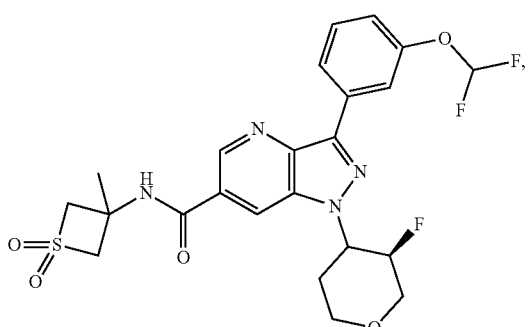
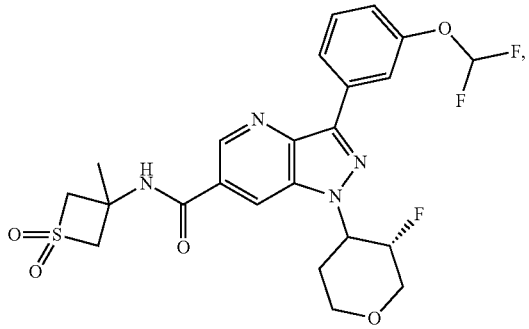
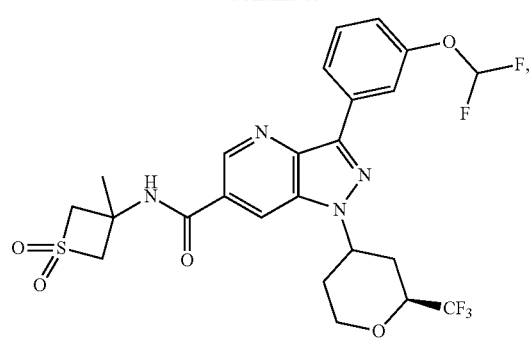
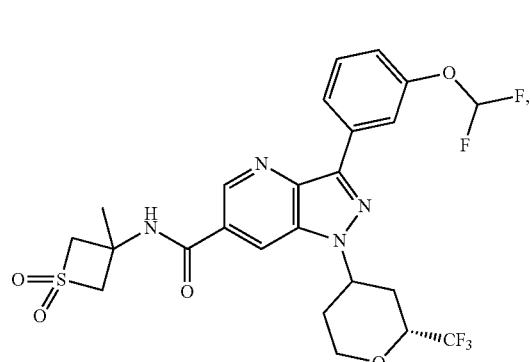
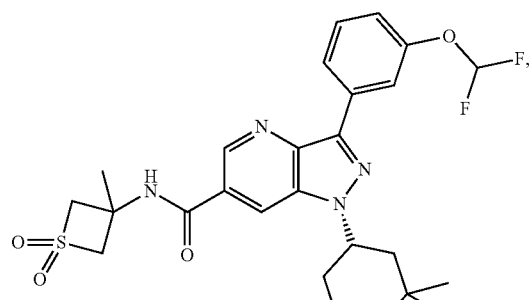
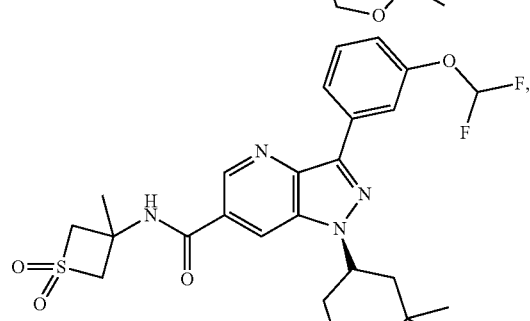
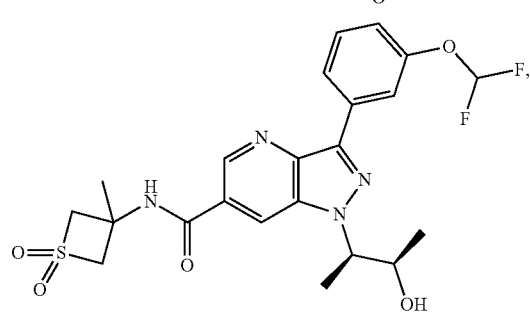

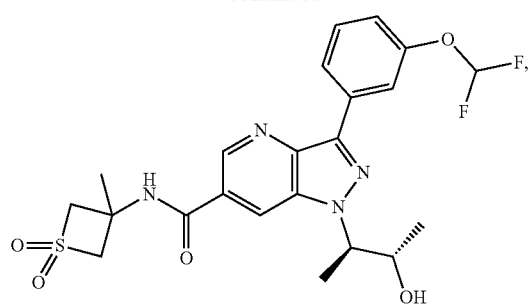
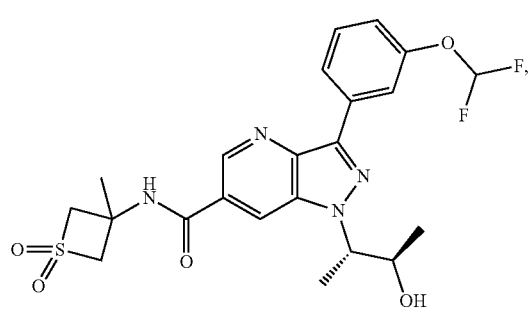
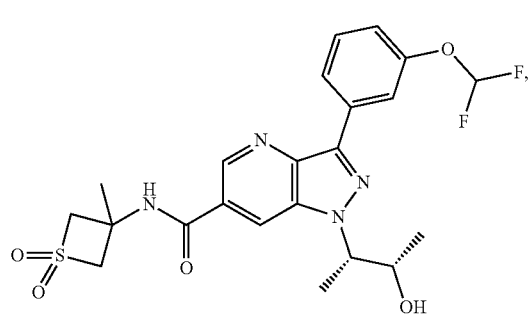
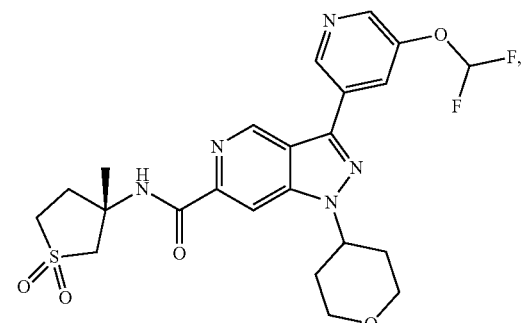
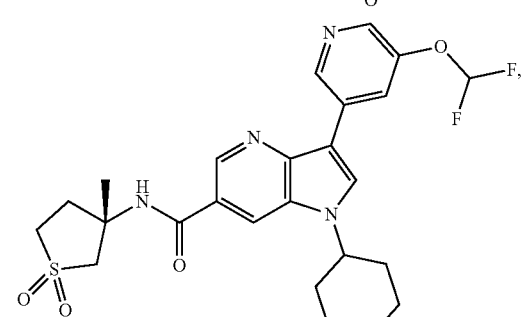
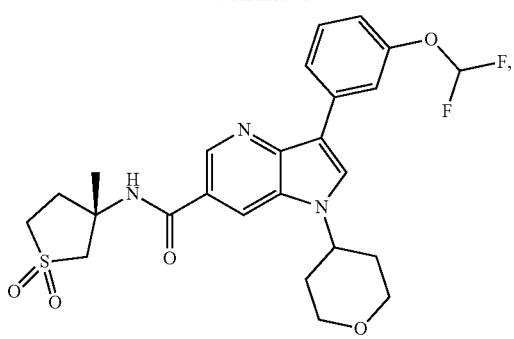 [SMILES: C[C@]1(NC(=O)c2cc3c(cn2)c(-c2cncc(OC(F)F)c2)nn3C2CCOCC2)CCS(=O)(=O)C1]
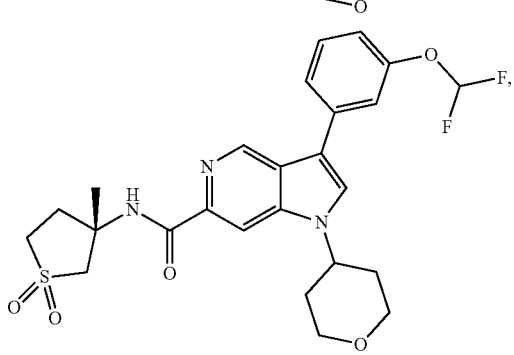
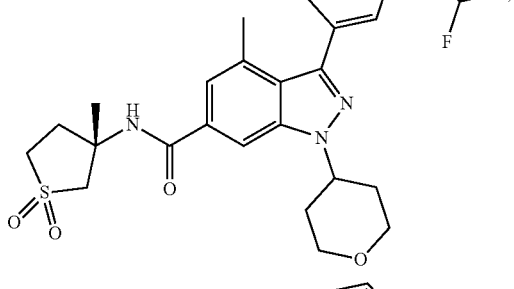
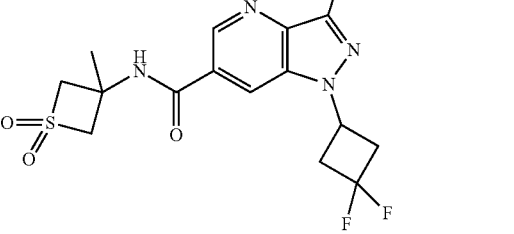
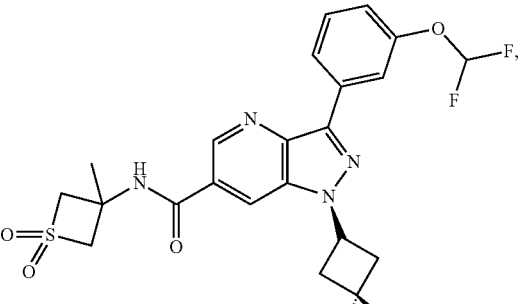

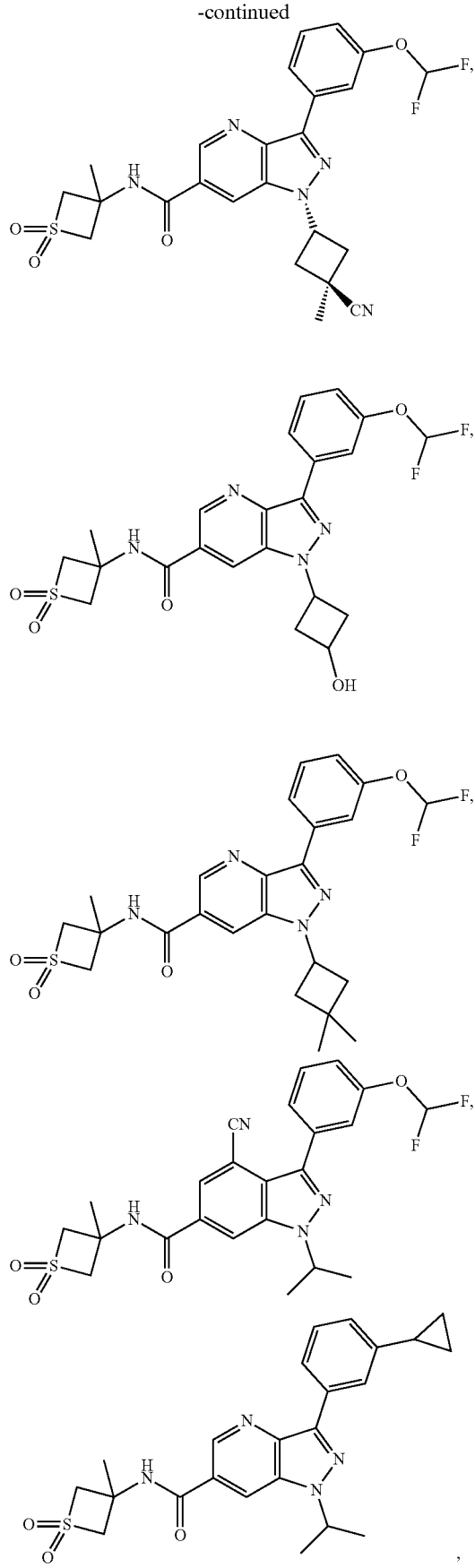
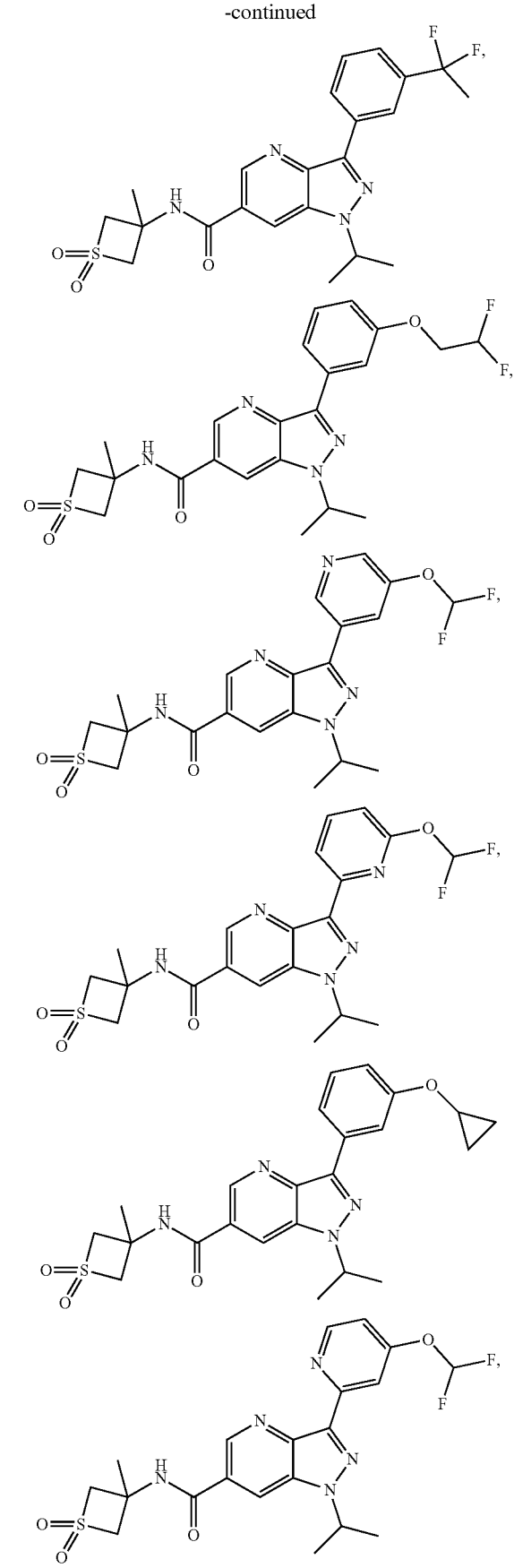

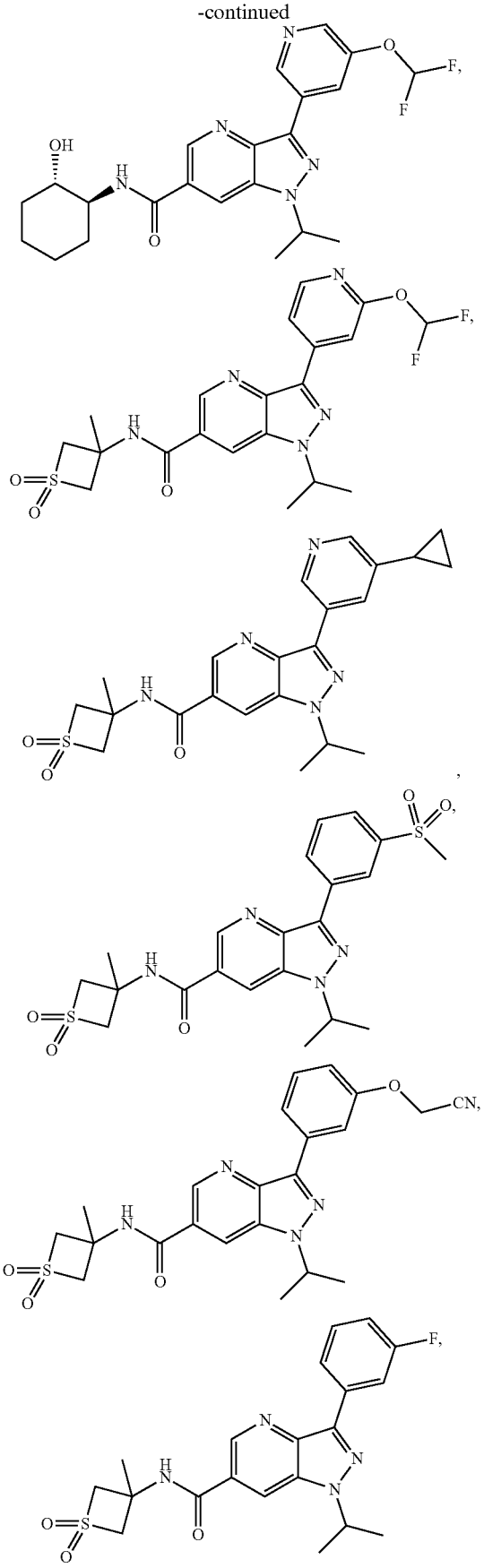
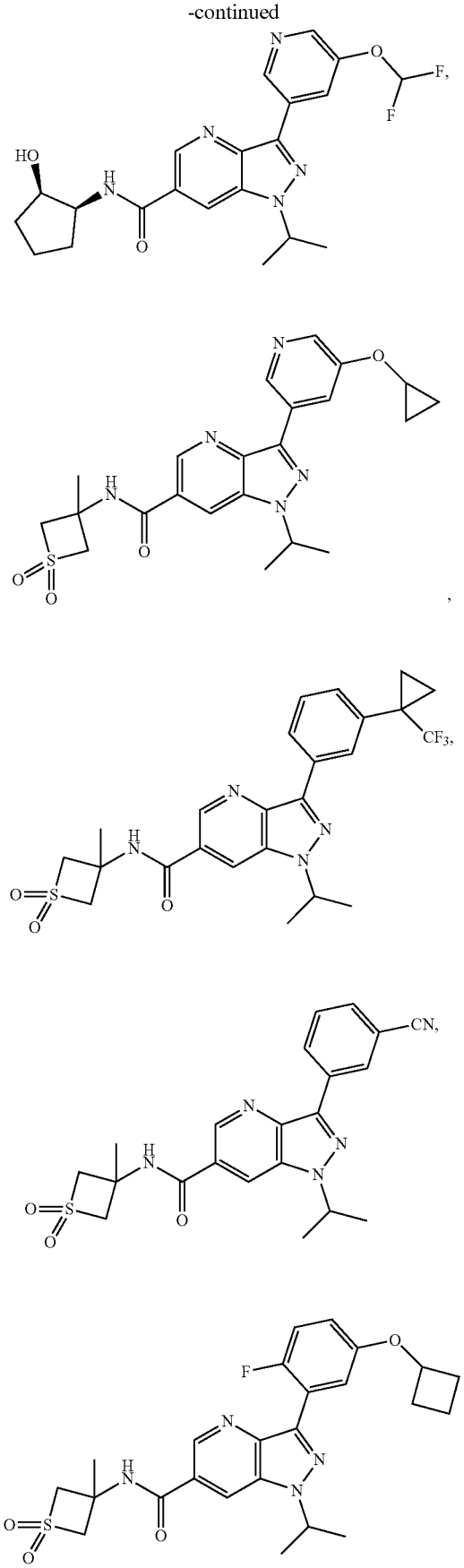

51
-continued
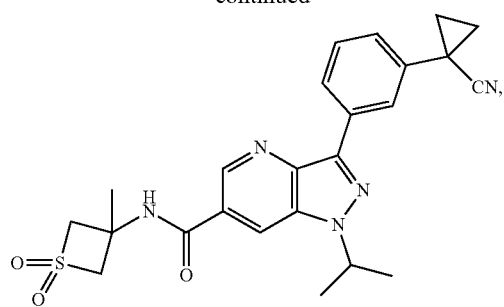
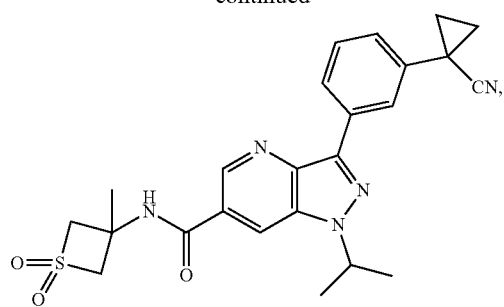
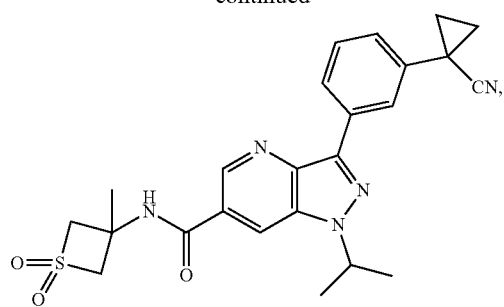
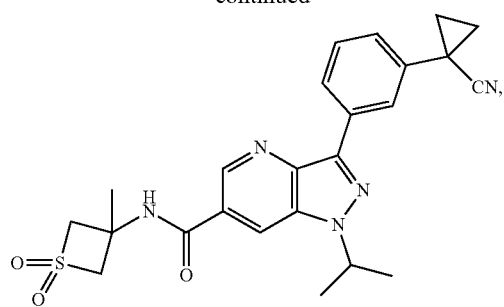
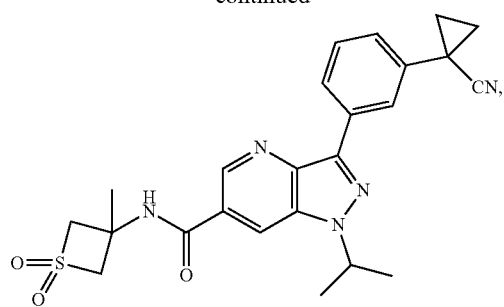
52
-continued
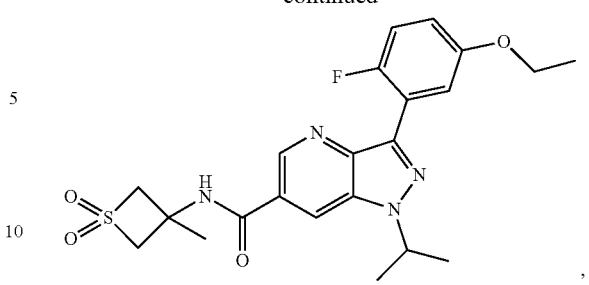
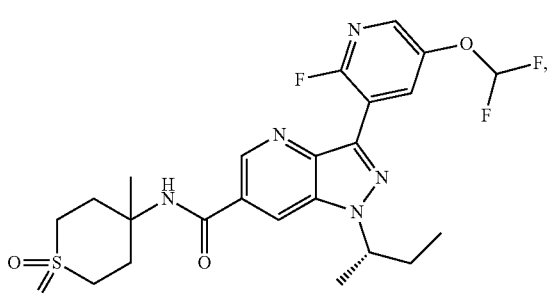
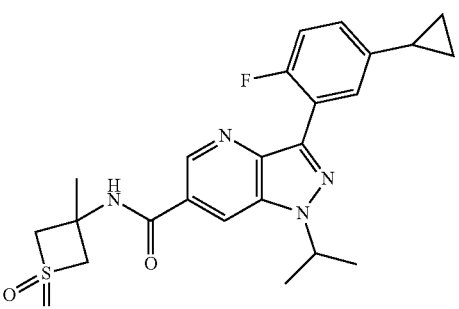
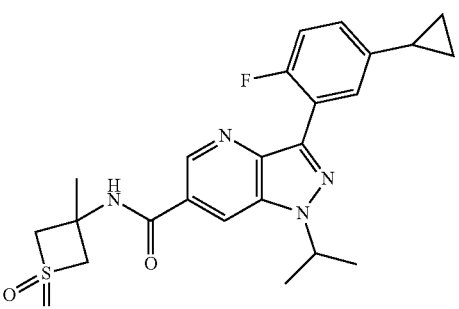
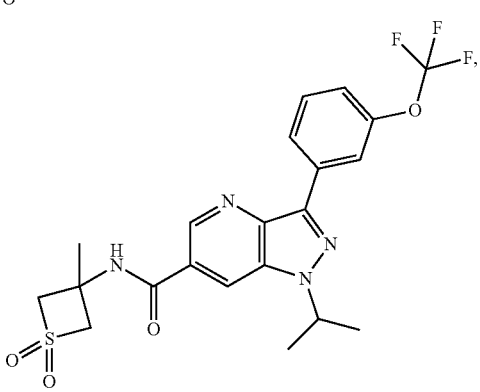

53
-continued
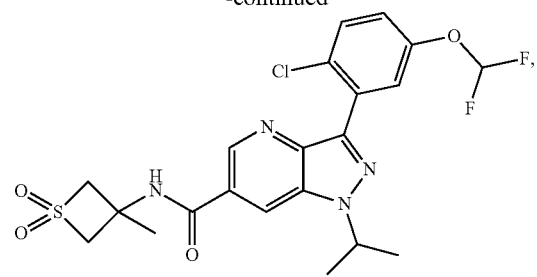
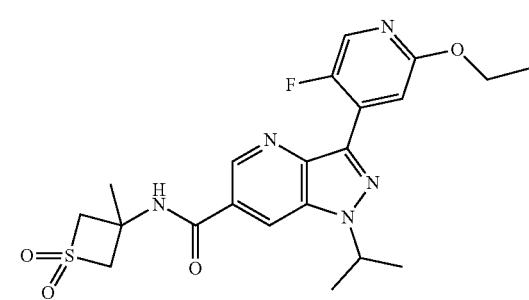
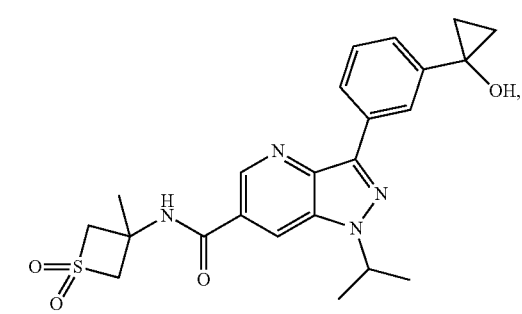
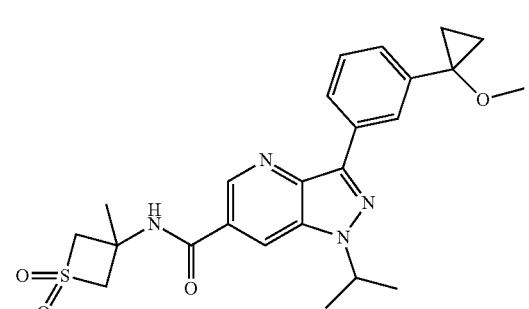
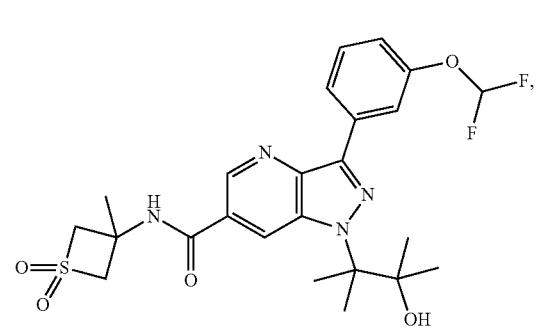
54
-continued
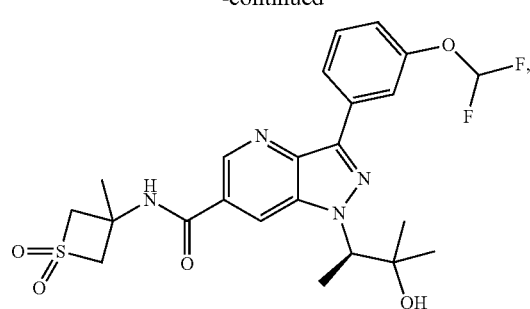
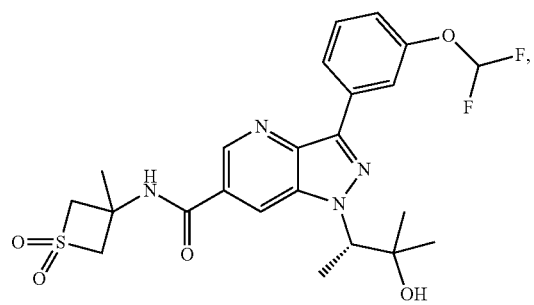
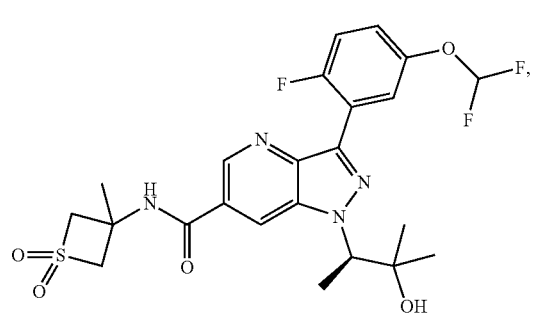
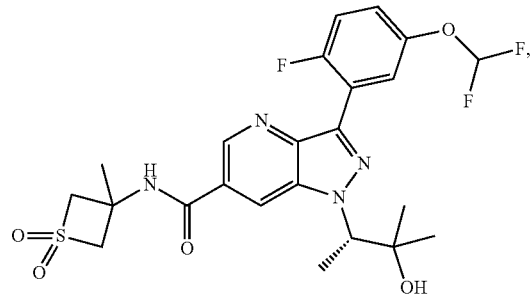
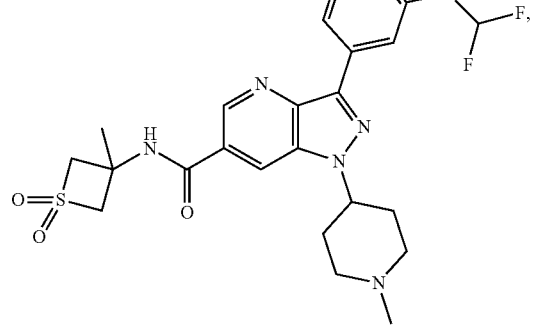

55
-continued
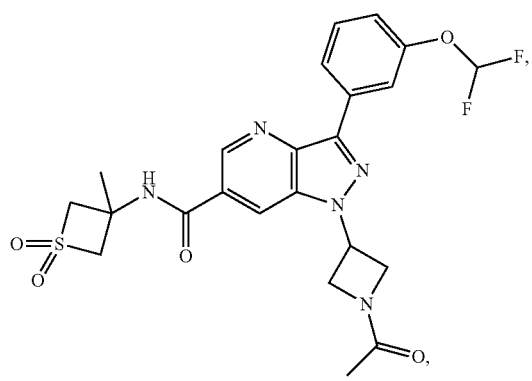
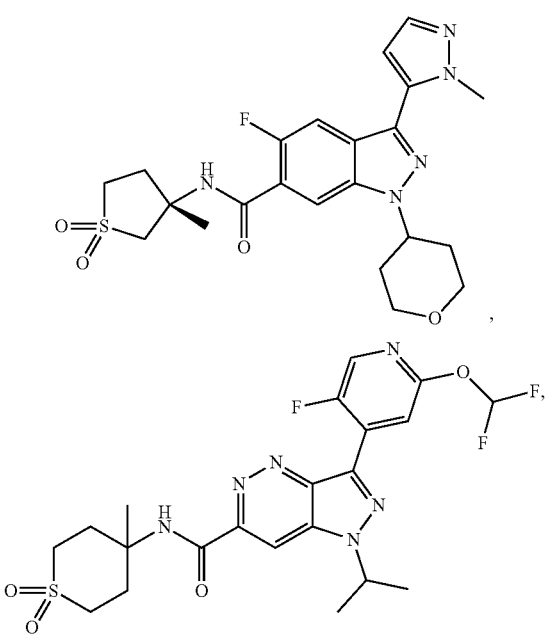
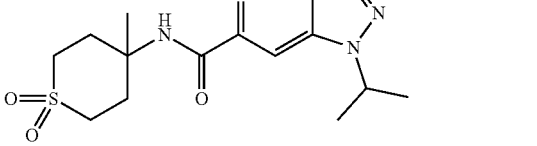
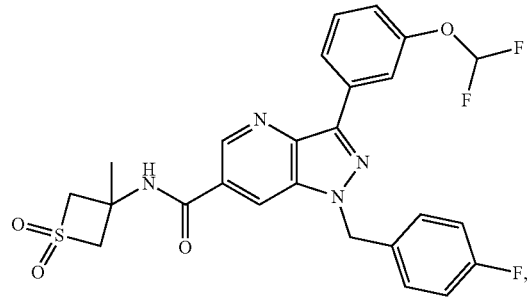
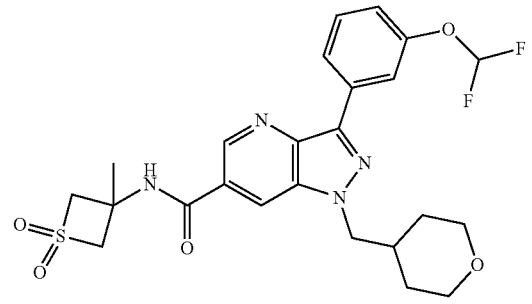
56
-continued
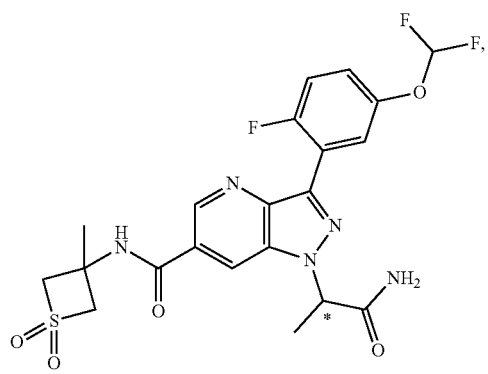
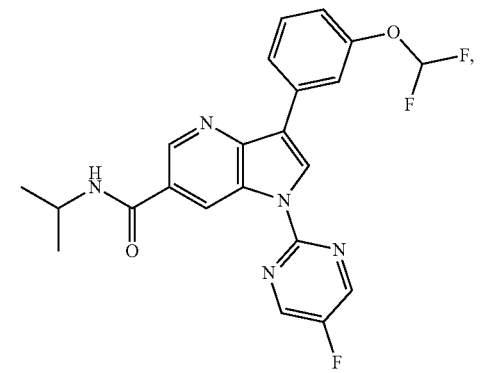
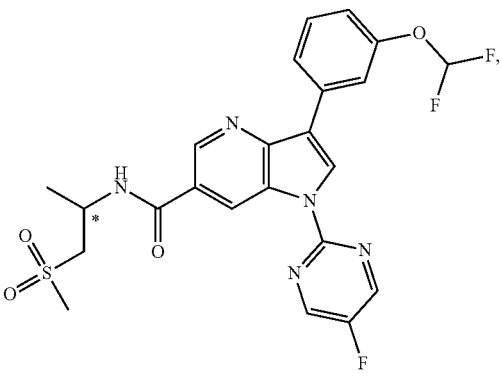
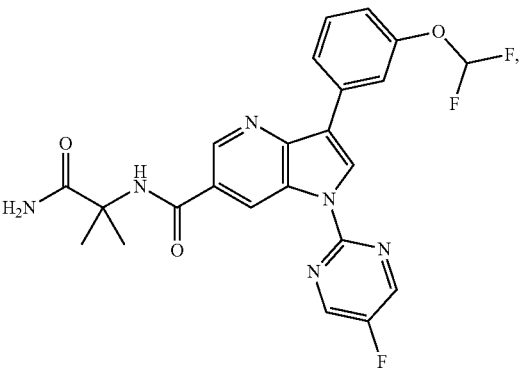

57
-continued
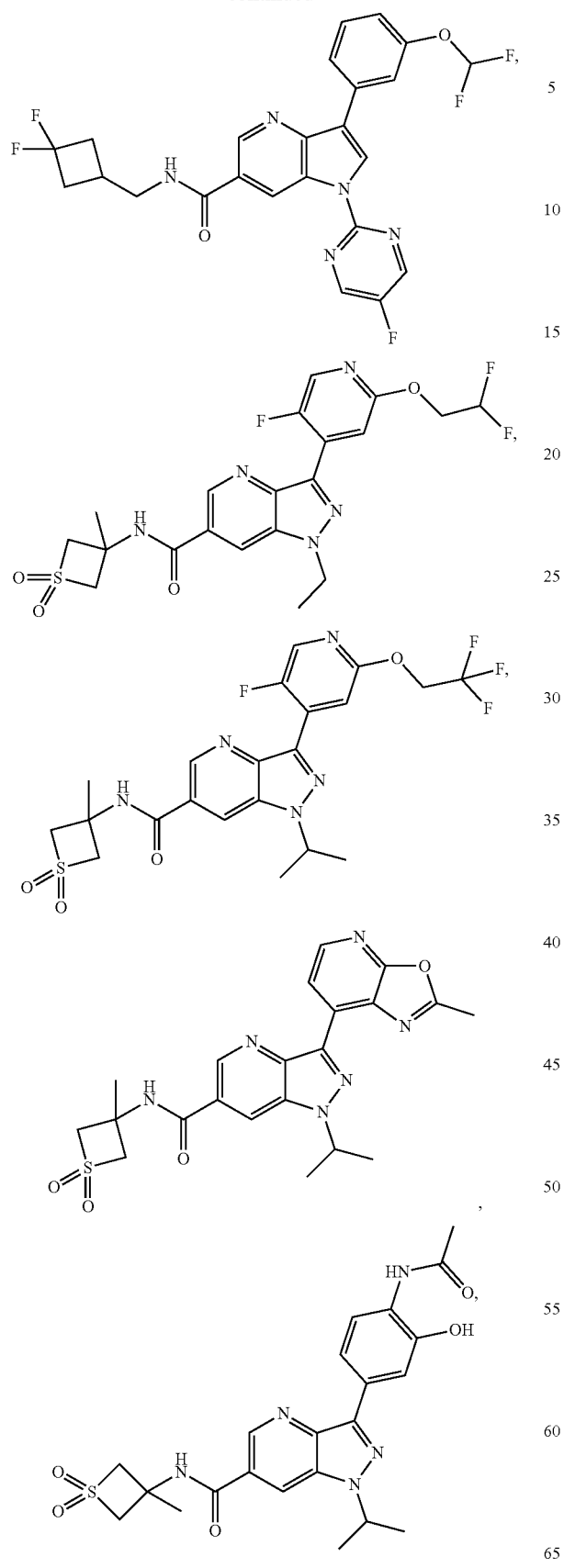
58
-continued
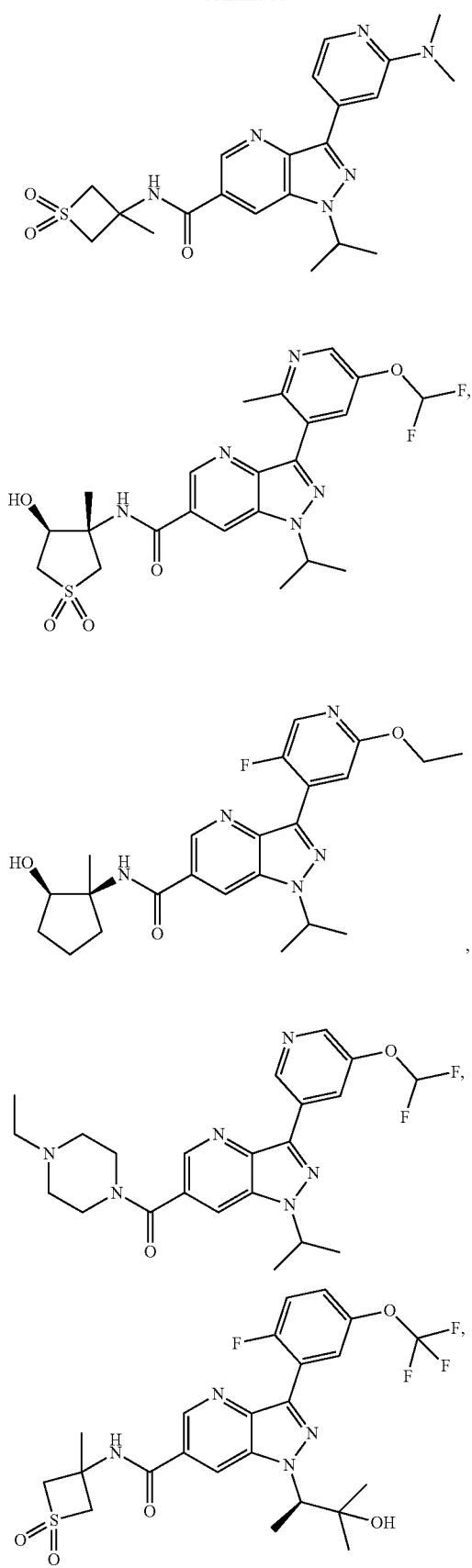

-continued

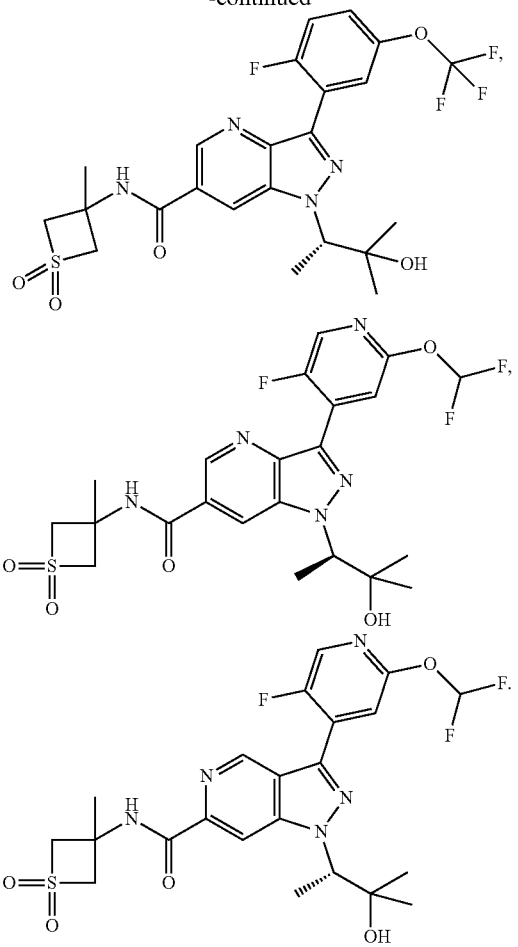

The present invention includes the pharmaceutically acceptable salts of the compounds defined therein. Reference to the compounds of structural Formula (I) includes the compounds of other generic structural Formulas, such as Formula I-a and I-b, and embodiments that fall within the scope of Formula (I). Reference to the compounds of structural Formulas I, I-a, I-b, (hereinafter "Formulas I to I-b" or "Formulas I, Ia, and Ib") includes the compounds of other generic structural Formulas and embodiments that fall within the scope of Formulas I to I-b.

In one embodiment, the present invention is a composition comprising an effective amount of at least one compound of formula I, I-a, or I-b, or a pharmaceutically acceptable salt thereof.

The invention also provides a pharmaceutical composition comprising a therapeutically effective amount of at least one compound of Formula I, I-a, I-b, or a pharmaceutically acceptable salt thereof, and a pharmaceutically acceptable carrier.

The invention also provides a pharmaceutical composition comprising a therapeutically effective amount of at least one compound of formula I, I-a, I-b, or a pharmaceutically acceptable salt thereof, and an effective amount of at least one other pharmaceutically active ingredient (such as, for example, a chemotherapeutic agent).

The invention also provides a pharmaceutical composition comprising an therapeutically effective amount of at least one compound of formula I, I-a, I-b, or a pharmaceutically acceptable salt thereof, and an therapeutically effective amount of at least one other pharmaceutically active ingredient (such as, for example, a chemotherapeutic agent), and a pharmaceutically acceptable carrier.

In one embodiment, the present invention provides a composition for treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure.

In one embodiment, the present invention provides a composition for treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure, comprising a compound of formula I, I-a, I-b, or a pharmaceutically acceptable salt thereof.

In one embodiment, the present invention provides a composition for treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure, comprising a compound of formula I, I-a, I-b, or a pharmaceutically acceptable salt thereof, and a pharmaceutically acceptable carrier.

In one embodiment, the present invention provides a method of treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure in a patient in need thereof, comprising administering to said patient a therapeutically effective amount of at least one compound of formula I, I-a, I-b, or a pharmaceutically acceptable salt thereof.

In one embodiment, the present invention provides a method of treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure in a patient in need thereof, comprising administering to said patient a therapeutically effective amount of at least one compound of formula I, I-a, I-b, or a pharmaceutically acceptable salt thereof, and a pharmaceutically acceptable carrier.

The methods of the invention include the administration of a pharmaceutical composition comprising at least one compound of the invention, or a pharmaceutically acceptable salt thereof, and a pharmaceutically acceptable carrier.

In another embodiment, the present invention includes a method of treating NASH and/or fibrosis, comprising administering to a patient in need thereof a compound of formula I, I-a, I-b, or a pharmaceutically acceptable salt thereof.

In another embodiment, the present invention includes a method of treating NASH and/or fibrosis, comprising administering to a patient in need thereof a compound of formula I, I-a, I-b, or a pharmaceutically acceptable salt thereof, and a pharmaceutically acceptable carrier.

In another embodiment, the present invention includes a method of treating NASH and/or fibrosis, comprising administering to a patient in need thereof a composition comprising formula I, I-a, I-b, or a pharmaceutically acceptable salt thereof.

In another embodiment, the present invention includes a method of treating NASH and/or fibrosis, comprising administering to a patient in need thereof a composition comprising formula I, I-a, I-b, or a pharmaceutically acceptable salt thereof, and a pharmaceutically acceptable carrier.

In another embodiment, the present invention is the use of a compound of formula I, I-a, I-b, or a pharmaceutically acceptable salt thereof, in the manufacture of a medicament for treating NASH and/or fibrosis, In another embodiment, the present invention includes the use of a compound of formula I, I-a, I-b, or a pharmaceutically acceptable salt thereof, for the preparation of a medicament for the treatment of NASH and/or fibrosis, Formula numbers and letter abbreviations can be written in different way with the same meaning. For example, Formula IA is the same as Formula I-A and the same as Formula Ia.

"Alkyl" means branched- and straight-chain saturated aliphatic hydrocarbon groups having the specified number of carbon atoms when noted. If no number is specified, 1-6 carbon atoms are intended for linear and 3-7 carbon atoms for branched alkyl groups. Examples of alkyl groups include methyl, ethyl, propyl, isopropyl, cyclopropyl, butyl, sec- and tert-butyl, pentyl, hexyl, octyl, nonyl, and the like. For example, the term "$C_{1-6}$alkyl" includes all of "$C_{1-4}$alkyl" defined as follows, plus the linear or branched chain alkyl groups, including all possible isomers, having 5 or 6 carbon atoms "$C_{1-6}$alkyl" means linear or branched chain alkyl groups, including all possible isomers, having 1, 2, 3, 4, 5 or 6 carbon atoms, and includes each of the alkyl groups within $C_{1-6}$alkyl including each of the hexyl and pentyl isomers as well as n-, iso-, sec- and tert-butyl (butyl, i-butyl, s-butyl, t-butyl, collectively "$C_4$alkyl"; Bu=butyl), n- and i-propyl (propyl, i-propyl, collectively "$C_3$alkyl"; Pr=propyl), ethyl (Et) and methyl (Me). Commonly used abbreviations for alkyl groups are used throughout the specification, e.g. methyl may be represented by conventional abbreviations including "Me" or $CH_3$ or a symbol that is an extended bond as the terminal group, e.g.,

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. For example, the structures

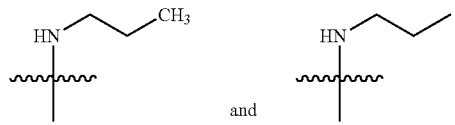

have equivalent meanings. If no number is specified, 1-6 carbon atoms are intended for linear or branched alkyl groups.

"Alkoxy" refers to an alkyl group linked to oxygen. Examples of alkoxy groups include methoxy, ethoxy, propoxy and the like.

"Aryl" refers to an aromatic monocyclic or multicyclic ring moiety comprising 6 to 14 ring carbon atoms. In one embodiment, an aryl group contains from about 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Fused Aryl" refers to an aryl ring fused with heterocyclyl or cycloalkyl.

"Halogen" or "Halo" includes fluorine, chlorine, bromine and iodine.

"Cycloalkyl" refers to a non-aromatic mono- or multicyclic ring system comprising about 3 to 10 ring carbon atoms. If no number of atoms is specified, 3-10 carbon atoms are intended. Cycloalkyl may also be fused, forming 1-3 carbocyclic rings. Non-limiting examples of monocyclic cycloalkyl include cyclopropyl, cyclobutyl, cyclopentyl, cyclohexyl, cycloheptyl, and cyclooctyl. A cycloalkyl group is unsubstituted or substituted with one or more ring system substituents which may be the same or different, and are as defined within. The term $C_{1-6}$cycloalkyl" refers to a cycloalkyl group having 1 to 6 ring carbon atoms. The term $C_{3-6}$cycloalkyl" refers to a cycloalkyl group having 3 to 6 ring carbon atoms. Thus, for example, "$C_{3-6}$ cycloalkyl" includes each of cyclopropyl, cyclobutyl, cyclopentyl, and cyclohexyl. A cycloalkyl group is unsubstituted or substituted with one or more ring system substituents which may be the same or different, and are as defined within. When cycloalkyl is a substituent on an alkyl group in a compound of Formula I-Ib, the cycloalkyl substituent can be bonded to any available carbon in the alkyl group. The following are illustrations of —$C_{3-6}$cycloalkyl substituents on an alkyl group wherein the substituent is cyclopropyl in bold:

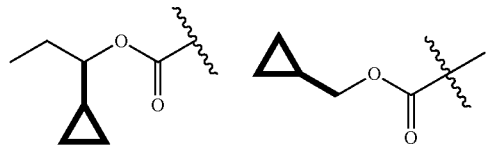

"Haloalkyl" refers to an alkyl group as defined within, wherein one or more of the alkyl group's hydrogen atoms has been replaced with a halogen. In one embodiment, a haloalkyl group has from 1 to 6 carbon atoms. Non-limiting examples of haloalkyl groups include $CH_2F$, $CHF_2$, $CF_3$, $CH_2CF_3$, $CH_2CHF_2$, $CF_2CF_3$, $CF_2CHF_2$, $CH_2Cl$ and $CCl_3$. The term "$C_{1-6}$haloalkyl" or "halo$C_{1-6}$alkyl" refers to a haloalkyl group having from 1 to 6 carbons.

"Haloalkoxy," "haloalkyl-O" and derivatives such as "halo($C_{1-6}$)alkoxy" or "O$C_{1-6}$haloalkkyl" are used interchangeably and refer to halo substituted alkyl groups linked through the oxygen atom. Haloalkoxy include mono-substituted as well as multiple halo substituted alkoxy groups. For example, trifluoromethoxy, chloromethoxy, and bromomethoxy are included as well as $OCHF_2$, $OCH_2CF_3$, $OCH_2CHF_2$, $OCF_3$, $OCF_2CF_3$, and $OCF_2CHF_2$.

"Heterocyclyl," "heterocycle" or "heterocyclic" refers to monocyclic ring structures in which one or more atoms in the ring, the heteroatom(s), is an element other than carbon. Heteroatoms are typically O, S or N atoms. A heterocycle containing more than one heteroatom may contain different heteroatoms. Bicyclic ring moieties include fused, spirocyclic and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or unsaturated. The heterocycle may be attached to the rest of the molecule via a ring carbon atom, a ring oxygen atom or a ring nitrogen atom. Examples of heterocyclyl groups include: piperidine, piperazine, morpholine, pyrrolidine, tetrahydrofuran, tetrahydropyran, thietane, tetrahydrothiophene, thiane, azetidine, oxirane, oxetane, or aziridine, and the like.

"Bicyclic heterocyclyl," "bicyclic heterocycle" or "bicyclic heterocyclic" refers to a heterocyclic ring fused to another ring system. The fusion may be bridged or unbridged.

"Heteroaryl" unless otherwise indicated, means a monocyclic-aromatic ring or ring system, wherein the ring or ring system is made up of a specified number of atoms when noted, and which contains at least one heteroatom selected from O, S and N or a specified number and selection of heteroatoms when noted. Examples include, but are not limited to, pyrrolyl, isoxazolyl, isothiazolyl, pyrazolyl, pyridyl, oxazolyl, oxadiazolyl, 1,3,4-oxadiazolyl-2(3H)-one, thiadiazolyl, thiazolyl, imidazolyl, triazolyl, tetrazolyl, furanyl, triazinyl, thienyl, pyridinyl, pyrimidinyl, pyridazinyl, pyrazinyl, and the like.

"Fused heteroaryl" is heteroaryl fused with a heteroaryl.

"Oxo" means an oxygen linked to an atom by a double bond. An example of an oxo group is a doubly bonded oxygen in a ketone, sulfoxide, sulfone and sulfate.

"Hydroxyalkyl" or "hydroxy($C_{1-3}$)alkyl" means an alkyl group having one or more hydrogen atoms replaced by hydroxyl (—OH) groups "Cyanoalkyl" means an alkyl group having one or more hydrogen atoms replaced by cyano (—CN) groups.

"Hydroxyhaloalkyl" means an alkyl group having one or more hydrogen atoms replaced by hydroxyl (—OH) groups, and one or more hydrogen atoms replaced by a halogen.

"Hydroxycycloalkyl" means a cyclic alkyl group having one or more hydrogen atoms replaced by hydroxyl (—OH) groups.

The term "composition" is intended to encompass a product comprising the specified ingredients in the specified amounts, as well as any product which results, directly or indirectly, from combination of the specified ingredients in the specified amounts.

The term "anti-cancer agent" means a drug (medicament or pharmaceutically active ingredient), or antibody for treating cancer.

The term "compound" with reference to the antineoplastic agents, includes the agents that are antibodies.

The term "at least one" means one or more than one. The meaning of "at least one" with reference to the number of compounds of the invention is independent of the meaning with reference to the number of chemotherapeutic agents.

The term "chemotherapeutic agent" means a drug (medicament or pharmaceutically active ingredient) for treating cancer (i.e., an antineoplastic agent).

The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

Except where noted herein, the term "carbocycle" (and variations thereof such as "carbocyclic" or "carbocyclyl") as used herein, unless otherwise indicated, refers to a $C_3$ to $C_6$ monocyclic ring, e.g., $C_{3-6}$ monocyclic carbocycle. The carbocycle may be attached to the rest of the molecule at any carbon atom which results in a stable compound. Saturated carbocyclic rings include, for example, "cycloalkyl" rings, e.g., cyclopropyl, cyclobutyl, etc. Unsaturated carbocyclic rings include, for example

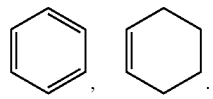

Except where noted, the term "saturated heterocycle" refers to a stable 4- to 7-membered mono-cyclic heteroatom-containing ring system, and which consists of carbon atoms and from one to four heteroatoms independently selected from the group consisting of N, O and S, and wherein the nitrogen and sulfur heteroatoms may optionally be oxidized, and the nitrogen heteroatom may optionally be quaternized. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Representative examples include azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, trithiane, azepane, oxepane, thiepane and homopiperazine. For example, a "saturated 6 membered heterocycle" is a stable 6-membered mono-cyclic heteroatom-containing ring system. An example of a saturated 6 membered heterocycle is piperdine. Likewise, but not limiting, a "saturated 4 membered heterocycle" is a stable 4-membered mono-cyclic heteroatom-containing ring system.

Except where noted herein, the term "unsaturated heterocycle" refers to a monocyclic unsaturated heterocycle having a specified number of atom members (e.g., 5 membered), including a specified number of heteroatoms (e.g., 1, 2, 3 or 4 heteroatoms independently selected from N, O or S), e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen (triazole) atoms, five-membered aromatic rings containing one oxygen, one nitrogen or one sulfur atom, five-membered aromatic rings containing two heteroatoms independently selected from oxygen, nitrogen and sulfur (e.g., oxazole), Additional examples are thiophene, imidazole, isothiazole, oxadiazole, and isoxazole. For example, a "unsaturated 6 membered heterocycle" is a 6 membered ring containing 6 atom members including at least one heteroatom. Likewise, an "unsaturated 5 membered heterocycle" is a 5 membered ring containing 5 atom members including at least one heteroatom.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The compounds of the present disclosure are limited to stable compounds embraced by Formula I and its embodiments. For example, certain moieties as defined in Formula I, I-a, I-b, may be unsubstituted or substituted, and the latter is intended to encompass substitution patterns (i.e., number and kind of substituents) that are chemically possible for the moiety and that result in a stable compound.

The term "substituted" means that one or more hydrogens on the designated atom is replaced with a selected from the indicated group, provided that the designated atom's normal valency under the existing circumstances is not exceeded, and that the substitution results in a stable compound. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different. Combinations of substituents and/or variables are permissible only if such combinations result in stable compounds. If a substituent is itself substituted with more than one group, it is understood that these multiple groups may be on the same carbon or on different carbons, so long as a stable structure result. By optionally substituted, it is meant that compounds containing the specified optional substituent(s) as well as compounds that do not contain the optional substituent(s).

The wavy line  as used herein, indicates a point of attachment to the rest of the compound.

Where ring atoms are represented by variables such as "X", e.g.,

the variables are defined by indicating the atom located at the variable ring position without depicting the ring bonds associated with the atom. For example, when X in the above ring is nitrogen, the definition will show "N" and will not depict the bonds associated with it, e.g., will not show "=N—". Likewise, when X is a carbon atom that is substituted with bromide, the definition will show "C—Br" and will not depict the bonds associated with it, e.g., will not show

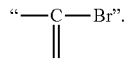

The invention also includes derivatives of the compound of formula I, I-a, I-b, acting as prodrugs and solvates. Any pharmaceutically acceptable pro-drug modification of a compound of the invention which results in conversion in vivo to a compound within the scope of the invention is also within the scope of the invention. Prodrugs, following administration to the patient, are converted in the body by normal metabolic or chemical processes, such as through hydrolysis in the blood, to the compound of formula I, I-a, or I-b. Such prodrugs include those that demonstrate enhanced bioavailability, tissue specificity, and/or cellular delivery, to improve drug absorption of the compound of I, IA, or IB. The effect of such prodrugs may result from modification of physicochemical properties such as lipophilicity, molecular weight, charge, and other physicochemical properties that determine the permeation properties of the drug.

For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of the invention. Included are those esters and acyl groups known in the art for modifying the solubility or hydrolysis characteristics for use as sustained-release or prodrug formulations. Examples of pharmaceutically acceptable pro-drug modifications include, but are not limited to, —$C_{1-6}$alkyl esters and —$C_{1-6}$alkyl substituted with phenyl esters.

"Celite®" (Fluka) diatomite is diatomaceous earth, and can be referred to as "celite".

When any variable (e.g., $R^1$ etc.) occurs more than one time in any constituent or in Formulas I to Ib or other generic Formula herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e. $R^1$ etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound.

It should be noted that, if a discrepancy between the chemical name and structure exists, the structure is understood to dominate.

Compounds of structural Formulas I to Ib may contain one or more asymmetric centers and can thus occur as racemates and racemic mixtures, single enantiomers, diastereoisomeric mixtures and individual diastereoisomers. Centers of asymmetry that are present in the compounds of Formulas I to Ib can all independently of one another have S configuration or R configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formulas. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

The compounds of this invention include all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereo-isomeric forms of the compounds of structural Formulas I to Ib.

Compounds of structural Formulas I to Ib may be separated into their individual diastereoisomers by, for example, fractional crystallization from a suitable solvent, for example MeOH or EtOAc or a mixture thereof, or via chiral chromatography using an optically active stationary phase. Optionally a derivatization can be carried out before a separation of stereoisomers. The separation of a mixture of stereoisomers can be carried out at an intermediate step during the synthesis of a compound of formula I, I-a, I-b, or it can be done on a final racemic product. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formulas I to Ib may be obtained by stereospecific synthesis using optically pure starting materials or reagents of known absolute configuration. The present invention includes all such isomers, as well as salts, solvates (including hydrates) and solvated salts of such racemates, enantiomers, diastereomers and tautomers and mixtures thereof.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formulas I to Ib described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formulas I to Ib of the present invention.

In the compounds of structural Formulas I to Ib, the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of structural Formulas I to Ib and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formulas I to Ib, can be prepared without undue experimentation by conventional techniques well known to those skilled in the art or by processes analogous to those described in the Schemes and Examples herein using appropriate isotopically-enriched reagents and/or intermediates.

It will be understood that the compounds of structural Formulas I to Ib may be prepared as pharmaceutically acceptable salts or as salts that are not pharmaceutically acceptable when they are used as precursors to the free compounds or their pharmaceutically acceptable salts or in other synthetic manipulations. The compounds of the present invention, including the compounds of the Examples, may also include all salts of the compounds of Formulas I to Ib which, owing to low physiological compatibility, are not directly suitable for use in pharmaceuticals but which can be used, for example, as intermediates for chemical reactions or for the preparation of physiologically acceptable salts.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids.

Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In one embodiment, the salts of acidic compounds are as follows, the ammonium, calcium, magnesium, potassium, and sodium salts.

With basic reagents such as hydroxides, carbonates, hydrogencarbonates, alkoxides and ammonia, organic bases or alternatively basic amino acids the compounds of the formula I, I-a, I-b, form stable alkali metal, alkaline earth metal or optionally substituted ammonium salts.

Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The preparation of pharmacologically acceptable salts from compounds of the formula I, I-a, I-b, capable of salt formation, including their stereoisomeric forms is carried out known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formulas I to Ib simultaneously contain acidic and basic groups in the molecule the invention also includes, in addition to the salt forms mentioned, inner salts or betaines (zwitterions). Salts can be obtained from the compounds of Formulas I to Ib by customary methods which are known to the person skilled in the art, for example by combination with an organic or inorganic acid or base in a solvent or dispersant, or by anion exchange or cation exchange from other salts.

The present invention includes compounds of structural formula I, I-a, I-b, as well as salts thereof, particularly pharmaceutically acceptable salts, solvates of such compounds and solvated salt forms thereof, where such forms are possible unless specified otherwise.

Furthermore, compounds of the present invention may exist in amorphous form and/or one or more crystalline forms, and as such all amorphous and crystalline forms and mixtures thereof of the compounds of Formulas I to Ib, including the Examples, are intended to be included within the scope of the present invention. In addition, some of the compounds of the instant invention may form solvates with water (i.e., a hydrate) or common organic solvents such as but not limited to EtOAc. Such solvates and hydrates, particularly the pharmaceutically acceptable solvates and hydrates, of the instant compounds are likewise encompassed within the scope of this invention, along with un-solvated and anhydrous forms.

Accordingly, the compounds within the generic structural formulas, embodiments and specific compounds described in the Examples and claimed herein encompass salts, all possible stereoisomers and tautomers, physical forms (e.g., amorphous and crystalline forms), solvate and hydrate forms thereof and any combination of these forms, as well as the salts, pro-drug forms thereof, and salts of pro-drug forms thereof, where such forms are possible unless specified otherwise, The invention also relates to medicaments containing at least one compound of the Formulas I to Ib and/or of a pharmaceutically acceptable salt of the compound of the Formulas I to Ib and/or an optionally stereoisomeric form of the compound of the Formulas I to Ib or a pharmaceutically acceptable salt of the stereoisomeric form of the compound of Formulas I to Ib, together with a pharmaceutically acceptable vehicle, carrier, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds of the Formulas I to Ib and other surfaces which come into contact with blood in the body is possible.

The invention also relates to a process for the production of a medicament, which comprises bringing at least one compound of the Formulas I to Ib into a suitable administration form using a pharmaceutically acceptable carrier and optionally further suitable active substances, additives or auxiliaries.

The present invention also relates to processes for the preparation of the compounds of Formulas I to Ib which are described in the following and by which the compounds of the invention are obtainable.

The terms "therapeutically effective (or efficacious) amount" and similar descriptions such as "an amount efficacious for treatment" are intended to mean that amount of a pharmaceutical drug that will alleviate the symptoms of the disorder, condition or disease being treated (i.e., disorder, condition or disease associated with DGAT2 activity) in an animal or human. The terms "prophylactically effective (or efficacious) amount" and similar descriptions such as "an amount efficacious for prevention" are intended to mean that amount of a pharmaceutical drug that will prevent or reduce the symptoms or occurrence of the disorder, condition or disease being treated (i.e., disorder, condition or disease associated with DGAT2 activity) in an animal or human. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hepatic steatosis, diabetes mellitus, obesity, hyperlipidemia, hypercholesterolemia, and a prophylactically effective amount, e.g., for treatment of NASH.

Disorders, conditions and diseases which can be treated or prevented by inhibiting DGAT2 by using the compounds of Formulas I to Ib are, for example, diseases such as non-alcoholic steatohepatitis (NASH), fibrosis, hyperlipidemia, type I diabetes, type II diabetes mellitus, cognitive decline, dementia, coronary heart disease, ischemic stroke, restenosis, peripheral vascular disease, intermittent claudication, myocardial infarction, dyslipidemia, post-prandial lipemia, obesity, osteoporosis, hypertension, congestive heart failure, left ventricular hypertrophy, peripheral arterial disease, diabetic retinopathy, diabetic nephropathy, glomerulosclerosis, chronic renal failure, diabetic neuropathy, metabolic syndrome, syndrome X, coronary heart disease, angina pectoris, thrombosis, atherosclerosis, myocardial infarction, transient ischemic attacks, stroke, hyperglycemia, hyperinsulinemia, hypertriglyceridemia, hypertriglyceridemia, insulin resistance, impaired glucose tolerance, erectile dysfunction, skin and connective tissue disorders, hyper-apo B lipoproteinemia, non-alcoholic fatty liver disease, cardiorenal diseases such as chronic kidney diseases and heart failure, and related diseases and conditions.

The compounds of Formulas I to Ib and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may need, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

Furthermore, a subject of the present invention are pharmaceutical preparations (or pharmaceutical compositions) which comprise as active component a therapeutically effective dose of at least one compound of Formulas I to Ib and/or a pharmaceutically acceptable salt thereof and a customary pharmaceutically acceptable carrier, i.e., one or more pharmaceutically acceptable carrier substances and/or additives.

Thus, a subject of the invention is, for example, said compound and its pharmaceutically acceptable salts for use as a pharmaceutical, pharmaceutical preparations which comprise as active component a therapeutically effective dose of said compound and/or a pharmaceutically acceptable salt thereof and a customary pharmaceutically acceptable carrier, and the uses of said compound and/or a pharmaceutically acceptable salt thereof in the therapy or prophylaxis of the above mentioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formulas I to Ib and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formulas I to Ib and/or of a pharmaceutically acceptable salt thereof to be administered depends on the individual case and is, as is customary, to be adapted to the individual circumstances to achieve an optimum effect. Thus, it depends on the nature and the severity of the disorder, condition or disease to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formulas I to Ib.

Combination Agents

The compounds of the present invention can be administered alone or in combination with one or more additional therapeutic agents disclosed herein or other suitable agents, depending on the condition being treated. Hence, in some embodiments the one or more compounds of the invention will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound of Formula (I) and any of the agents described above can be formulated together in the same dosage form and administered simultaneously. Alternatively, a compound of Formula (I) and any of the agents described above can be simultaneously administered, wherein both the agents are present in separate formulations. In another alternative, a compound of Formula (I) can be administered just followed by and any of the agents described above, or vice versa. In some embodiments of the separate administration protocol, a compound of Formula (I) and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of Formula (I), and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral, parenteral; IV, transdermal and subcutaneous), are administered at different dosage intervals, or when titration of the individual components of the combination is desired by the prescribing health care professional.

One or more additional pharmacologically active agents may be administered in combination with a compound of Formulas I to Ib. An additional active agent (or agents) is intended to mean a pharmaceutically active agent (or agents) that is active in the body, including pro-drugs that convert to pharmaceutically active form after administration, which are different from the compound of Formulas I to Ib, and also includes free-acid, free-base and pharmaceutically acceptable salts of said additional active agents. Generally, any suitable additional active agent or agents, including but not limited to anti-hypertensive agents, anti-obetic, anti-inflammatory, anti-fibrotic, and anti-atherosclerotic agents such as a lipid modifying compound, anti-diabetic agents and/or anti-obesity agents may be used in any combination with the compound of Formulas I to Ib in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides, amino acids and derivatives, amino acid chains linked by non-peptidic bonds, di- and tri-peptide derivatives, peptidyl amino diols and peptidyl beta-aminoacyl aminodiol carbamates; also, and small molecule renin inhibitors including diol sulfonamides and, N-morpholino derivatives, N-heterocyclic alcohols and pyrolimidazolones; also, pepstatin derivatives and fluoro- and chloro-derivatives of statone-containing peptides, enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazosin, prazosin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), cerivastatin, and pitavastatin; a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and/or with an HMG-CoA reductase inhibitor; niacin receptor agonists such as acipimox and acifran, as well as niacin receptor partial agonists; anti-cholesterol agents such as PCSK9 inhibitors (alirocumab, evolocumab), Nexletol™ (bempedoic acid, ACL inhibitor), and Vascepa® (Icosapent ethyl); metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) β-klotho/FGFRT activating monoclonal antibody (e.g. MK-3655), pan FGFR1-4/KLB modulators, FGF19 analogue (e.g. Aldafermin) (ii) PPARγ agonists, such as the glitazones (e.g. pioglitazone, AMG 131, CHS 131, MBX2044, mitoglitazone, lobeglitazone, IDR-105, rosiglitazone, and balaglitazone), and other PPAR ligands, including (1) PPARα/γ dual agonists (e.g. ZYH2, ZYH1, GFT505, chiglitazar, muraglitazar, aleglitazar, sodelglitazar, and naveglitazar); (2) PPARU agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); (4) PPARγ partial agonists, (5) PPAR α/δ dual agonists (e.g. Elafibranor); (iii) biguanides, such as metformin and its pharmaceutically acceptable salts, in particular, metformin hydrochloride, and extended-release formulations thereof, such as Glumetza™, Fortamet™, and GlucophageXR™; and (iv) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof), bile acid sequestering agents (e.g., colestilan, colestimide, colesevalam hydrochloride, colestipol, cholestyramine, and dialkylaminoalkyl derivatives of a cross-linked dextran), acyl CoA:cholesterol acyltransferase inhibitors, (e.g., avasimibe); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, torcetrapib, and evacetrapib): inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators (e.g. Aramchol); GPR-105 antagonists (e.g., such as those disclosed in WO 2009/000087); SGLT inhibitors (e.g., ASP1941, SGLT-3, SGLT-2 such as empagliflozin, dapagliflozin, canagliflozin, and ertugliflozin, BI-10773, remogloflozin, TS-071, tofogliflozin, ipragliflozin, and LX-4211); inhibitors of acyl coenzyme A carboxylase (ACC, MK-4074); inhibitors of diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; bile acid modulators; PACAP, PACAP mimetics, and PACAP receptor 3 agonists; IL-1b antibodies, (e.g., XOMA052 and canakinumab), anti-fibrotic and/or anti-inflammatory agents (CCR2/CCR5 dual receptor antagonist (e.g. cenicriviroc); galectin 3 inhibitor (e.g. belapectin, GB-1107, GB-1211), siRNA against HSP 47 (e.g. BMS-986263); NSAID derived from pirfenidone (e.g. hydronidone), A3AR agonist (e.g. namodenoson, FM101); TGFTX4 (e.g. nitazoxanide); 5-lipoxygenase inhibitor (e.g. tipelukast), Bifunctional urate inhibitor (e.g. ACQT1127), adiponectin receptor agonist (e.g. ALY688), TNF receptor antagonist (e.g. atrosimab), Autotaxin inhibitor (e.g. BLD-0409, TJC 0265, TJC 0316), CCL24 blocking monoclonal antibody (e.g. CM101), IL-11 inhibitor (e.g. ENx 108A), LPA1 receptor antagonist (e.g. EPGN 696), Dual JAK1/2 inhibitor (e.g. EX 76545), GPR antagonist (e.g. GPR91 antagonist), Integrin αvβ1, αvβ3 and αvβ6 inhibitor (e.g. IDL 2965), NLRP3 antagonist (e.g. IFM-514), inflammasome inhibitors (e.g. JT194, JT349), Cell membrane permeability inhibitor (e.g. Larazotide), CCR5 antagonist (e.g. Ieronlimab), TNF inhibitor (e.g. LIVNate), integrin αvβ6 inhibitor (e.g. MORF beta6), NLRP inflammasome antagonists, siRNA (e.g. OLX 701), dual TFGβ/Hedgehog inhibitor (e.g. Oxy 200), GPR40 agonist/GPR84 antagonist (e.g. PBI-4547), neutrophil elastase inhibitor (e.g. PHP-303), integrin inhibitor (e.g. PLN-1474), TGFβ1 modulator (e.g. PRM-151), CCK receptor antagonist (e.g. proglumide), LOXL2 inhibitor (e.g. PXS-5338K, PXS-5382A), IL-11 inhibitors, MPYS protein inhibitor (e.g. cGAS/STING antagonists), kinase inhibiting RNase, membrane protein mAbs, tumor necrosis factor inhibitor, NRF2 activator (e.g. SCO 116), SSAO inhibitor (e.g. TERN 201), TRAIL2 agonist (e.g. TLY012), IL-6 receptor antagonist (e.g. TZLS 501), AOC3 inhibitor (e.g. UD-014), SSAO/VAP-1 inhibitor, TREM2); anti-oxidant (e.g. vitamin E); anti-inflammatory agents (e.g. norfloxacin, ciprofloxacin, ceftriaxone); coagulation modifiers (e.g. anti-coagulants, anti-platelet agents, pentoxifylline, vitamin K, DDAVP); dual GIP and GLP-1 receptor agonist (e.g. tirzepetide); dual GLP-1/GRA (e.g. cotadutide, ALT-801, DD 01, G49, PB-718); dual GLP-1 (e.g. CT 868); GLP-1/GRA/GIP triple agonist (e.g. HM15211); GRP120 stimulant/inflammasome modulator/PPARγ dual agonist (e.g. KDT501); GLP-1/FGF21 (e.g. YH25724); GLP-1 agonist (e.g. Ozempic (semaglutide sc), XW 003); selective thyroid hormone receptor-β agonist (e.g. resmetirom); apoptosis modulators (JNK-1 inhibitor (e.g. CC-90001), Peroxidase inhibitor (e.g. AZM198), ASK-1 inhibitor (e.g. CS-17919, SRT 015)); erythropoietin-stimulating agents (erythropoietin receptor agonist (e.g. cibinetide)); glucose pathway modulators (SGLT-2 inhibitor (e.g. Forxiga, Farxiga (dapagliflozin)); dual SGLT-1/2 inhibitor (e.g. licogliflozin), Glucose-6-P dehydrogenase inhibitor (e.g. fluasterone) LAPS glucagon combo (e.g. HM14320), SGLT-1 inhibitor (e.g. SGL5213)); immune modulators (TLR4 inhibitor (e.g. GBK-233), immunomodulatory polyclonal antibody (e.g. IMM-124E), TLR4 antagonist (e.g. JKB-122), CD3 monoclonal antibody (e.g. foralumab), TLR4 antagonist (e.g. JKB 133), TLR4 inhibitor (e.g. mosedipimod), Macrophage inhibitor via CD206 targeting (e.g. MT2002), TLR2/4 antagonist (e.g. VB-201, VB-703), immunomodulatory polyclonal antibody (e.g. IMM-124E)); incretin-based therapies (GLP-1 agonist (e.g. Ozempic (semaglutide sc), XW 003), GLP-1/glucagon dual receptor agonist (e.g. H1M12525A), prandial insulin (e.g. ORMD 0801)); lipid modulators (AMPK Activator/Glutathione transferase (e.g. oltipraz), THR-beta agonist (e.g. resmetirom, VK2809, MGL-3745, ALG-009, ASC41, CNPT-101101, TERN 501), IBAT inhibitor (e.g. elobixibat, CJ 14199), omega-6-fatty acid (e.g. epeleuton), FASN inhibitor (e.g. TVB2640, FT 4101, FT 8225), ANGPTL3 inhibitor (e.g. vupanorsen), PNPLA3 inhibitor (e.g. AZD2693), RAS domain kinase inhibitor (e.g. BioE1115), NTCP inhibitor (e.g. bulevirtide), P2Y13 receptor agonist (e.g. CER-209), omega-3 fatty acid, HSD1713 inhibitor; metabolism modulators (FXR agonist (e.g. Ocaliva (obeticholic acid), IOT022), recombinant variant of FGF19 (e.g. aldafermin), bi-specific FGFR1/KLB antibody (e.g. BFKB8488A), mTOT modulator (e.g. MSDC-0602K), pegylated analog of FGF21 (e.g. pegbelfermin, BMS-986171), non-bile FXR agonist (e.g. cilofexor, EDP-305, EYP 001, tropifexor, MET409, AGN-242256, AGN-242266, EDP 297, HPG 1860, MET642, RDX023, TERN 101), ACC inhibitor (e.g. firsocostat, PF-05221304), keto-hexokinase inhibitor (e.g. PF-06835919), AMPK activator (e.g. PXL770, MSTM 101, 0304), bile acid modulator (e.g. Albiero), FGF21 analog (e.g. BI089-100), MOTSc analog (e.g. CB4211), cyclophilin inhibitor (e.g. CRV 431), FGF19 (e.g. DEL 30), mitochondrial uncoupler (e.g. GEN 3026), FXR/GPCR dual agonist (e.g. INT-767), Cysteamine derivative (e.g. KB-GE-001), dual amylin and calcitonin receptor agonist (e.g. KBP-089), transient FXR agonist (e.g. M 1217), anti-beta-klotho (KLB)-FGFR1c receptor complex mAb (e.g. MK3655), GDF15 analog (e.g. NGM395), cyclophilin inhibitor (e.g. NV556), LXR modulator (e.g. PX 329, PX 655, PX 788), LXR inverse agonist (e.g. PX016), deuterated obeticholic acid (e.g. ZG 5216)); PPAR modulators (dual PPARα/γ agonist (e.g. elafibranor), PPAR pan agonist (e.g. lanifibranor), PPARα agonists (e.g. Parmodia), PPARγ agonist (e.g. CHS 131), MPC inhibitor (e.g. PXL065), PPARδ/γ agonist (e.g.T3D 959)); RAAS mIM- Modulators (mineralocorticoid receptor antagonist (e.g. apararenone, eplerenone, spironolactone), angiotensin receptor blocker (e.g. losartan potassium)); neurotransmitter modulators (cannabinoid receptor modulator, CBT receptor antagonist (e.g. CRB-4001, IM-102, nimacimab), TPH1 inhibitor (e.g. CU 02), GPR120 agonist (e.g. KBR2001), combination of cannabinoid and botanical anti-inflammatory compound (e.g. SCN 002)); PDE Modulator (PDE4 inhibitor (e.g. ART 648)); CYP2E1 inhibitor (e.g. SNP-610); cell therapies (e.g. HepaStem) and bromocriptine mesylate and rapid-release formulations thereof; or with other drugs beneficial for the prevention or the treatment of the above-mentioned diseases including nitroprusside and diazoxide the free-acid, free-base, and pharmaceutically acceptable salt forms of the above active agents where chemically possible.

The present invention includes the pharmaceutically acceptable salts of the compounds defined herein, including the pharmaceutically acceptable salts of all structural formulas, embodiments and classes defined herein. Reference to the compounds of structural Formula (I) includes the compounds of other generic structural Formulas, such as Formulas and embodiments that fall within the scope of Formula (I).

Dosages of the Compounds of Formula (I)

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician considers such factors as the patient's age, condition and size, as well as the severity of the condition being treated and the response of the patient to the treatment.

The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of an oncological condition, and a prophylactically effective amount, e.g., for prevention of an oncological condition.

While individual needs vary, determination of optimal ranges of effective amounts of the compound of the invention is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or may be divided into multiple doses.

Pharmaceutical Compositions

The compounds of Formula I to I-b and their pharmaceutically acceptable salts can be administered to animals, preferably to mammals, and in particular to humans, as pharmaceuticals by themselves, in mixtures with one another or in the form of pharmaceutical compositions. The term "subject" or "patient" includes animals, preferably mammals and especially humans, who use the instant active agents for the prevention or treatment of a medical condition.

Administering of the compound of Formula I to I-b to the subject includes both self-administration and administration to the patient by another person. The subject may need, or desire, treatment for an existing disease or medical condition, or may be in need of or desire prophylactic treatment to prevent or reduce the risk of occurrence of said disease or medical condition. As used herein, a subject "in need" of treatment of an existing condition or of prophylactic treatment encompasses both a determination of need by a medical professional as well as the desire of a patient for such treatment.

Methods for the safe and effective administration of most of these agents are known to those skilled in the art. In addition, their administration is described in the standard literature.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the condition being treated and the response of the patient to the treatment.

The amount and frequency of administration of the compound of formula I, I-a, I-b, and any additional agents will be regulated according to the judgment of the attending clinician (physician) considering such factors as age, condition and size of the patient as well as severity of the condition being treated.

The compounds of the invention are also useful in preparing a medicament that is useful in treating NASH and fibrosis.

The instant compounds are also useful in combination with therapeutic, chemotherapeutic and anti-cancer agents for the treatment of hepatic cellular carcinoma. Combinations of the presently disclosed compounds with therapeutic, chemotherapeutic and anti-cancer agents are within the scope of the invention. Examples of such agents can be found in Cancer Principles and Practice of Oncology by V. T. Devita and S. Hellman (editors), $9^{th}$ edition (May 16, 2011), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents. The particular choice of chemotherapeutic agent will depend upon the diagnosis of the attending physicians and their judgment of the condition of the patient and the appropriate treatment protocol.

The initial administration can be made according to established protocols known in the art, and then, based upon the observed effects, the dosage, modes of administration and times of administration can be modified by the skilled clinician.

The determination of the order of administration, and the number of repetitions of administration of the chemotherapeutic agent during a treatment protocol, is well within the knowledge of the skilled physician after evaluation of the condition being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The agent can be administered according to therapeutic protocols well known in the art. It will be apparent to those skilled in the art that the administration of the anti-cancer agent can be varied depending on the cancer being treated and the known effects of the anti-cancer agent on that disease.

The initial administration can be made according to established protocols known in the art, and then, based upon the observed effects, the dosage, modes of administration and times of administration can be modified by the skilled clinician.

The particular choice of agent will depend upon the diagnosis of the attending physicians and their judgment of the condition of the patient and the appropriate treatment protocol.

The determination of the order of administration, and the number of repetitions of administration of the agent during a treatment protocol, is well within the knowledge of the skilled physician after evaluation of the cancer being treated and the condition of the patient.

Thus, in accordance with experience and knowledge, the practicing physician can modify each protocol for the administration of an anti-cancer agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds, compositions and methods provided herein are useful for the treatment of cancer. Cancers that may be treated by the compounds, compositions and methods disclosed herein include, but are not limited to: Liver: hepatoma (hepatocellular carcinoma), cholangiocarcinoma, hepatoblastoma, angiosarcoma, hepatocellular adenoma, hemangioma. Cancers that also may be treated by the compounds, compositions and methods disclosed herein include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

PD-1 inhibitors include pembrolizumab (lambrolizumab), nivolumab and MPDL3280A. PDL-inhibitors include atezolizumab, avelumab, and durvalumab.

The invention further relates to a method of treating cancer in a human patient comprising administration of a compound of the invention (i.e., a compound of Formula I-I-b) and a PD-1 antagonist to the patient. The compound of the invention and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, N.J., USA), nivolumab (OPDIVO™, Bristol-Myers Squibb Company, Princeton, N.J., USA), cemiplimab (LIBTAYO™, Regeneron Pharmaceuticals, Inc., Tarrytown, N.Y., USA), atezolizumab (TECENTRIQ™, Genentech, San Francisco, Calif., USA), durvalumab (IMFINZI™, AstraZeneca Pharmaceuticals LP, Wilmington, Del.), or avelumab (BAVENCIO™, Merck KGaA, Darmstadt, Germany).

In some embodiments, the PD-1 antagonist is pembrolizumab. In particular sub-embodiments, the method comprises administering 200 mg of pembrolizumab to the patient about every three weeks. In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks. In other sub-embodiments, the method comprises administering 480 mg of nivolumab to the patient about every four weeks.

In some embodiments, the PD-1 antagonist is cemiplimab. In particular embodiments, the method comprises administering 350 mg of cemiplimab to the patient about every 3 weeks.

In some embodiments, the PD-1 antagonist is atezolizumab. In particular sub-embodiments, the method comprises administering 1200 mg of atezolizumab to the patient about every three weeks.

In some embodiments, the PD-1 antagonist is durvalumab. In particular sub-embodiments, the method comprises administering 10 mg/kg of durvalumab to the patient about every two weeks.

In some embodiments, the PD-1 antagonist is avelumab. In particular sub-embodiments, the method comprises administering 800 mg of avelumab to the patient about every two weeks.

A compound of the instant invention, or a pharmaceutically acceptable salt thereof, may also be useful for treating cancer in combination with the following therapeutic agents: pembrolizumab (Keytruda®), abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®), or a pharmaceutically acceptable salt thereof.

Methods for Making the Compounds of Present Invention

The following examples are provided so that the invention might be more fully understood. Unless otherwise indicated, the starting materials are commercially available. They should not be construed as limiting the invention in any way.

Several methods for preparing the compounds of this invention are described in the following Schemes and Examples. Starting materials and intermediates are purchased, made from known procedures, or as otherwise illustrated. Some frequently applied routes to the compounds of Formulas I to Ib are also described by the Schemes as follows. In some cases, the order of carrying out the steps of reaction schemes may be varied to facilitate the reaction or to avoid unwanted reaction products. For stereoisomers, enantiomer A refers to the faster/earlier eluting enantiomer and enantiomer B refers to the slower/later eluting enantiomer at the point of separation and this nomenclature is maintained through the remainder of a synthetic sequence for a given enantiomeric series regardless of the possibility that subsequent intermediates and final compounds may have the same or opposite orders of elution.

Throughout the synthetic schemes and examples, abbreviations and acronyms may be used with the following meanings unless otherwise indicated:
ACN, MeCN=acetonitrile
Boc=tert-butyloxycarbonyl
$Cu(OAc)_2$=copper acetate
DMF=dimethylformamide
DCM=dichloromethane
DIPEA=N,N-diisopropylethylamine
DPPA=diphenylphosphoryl azide
DMAP=4-(dimethylamino)pyridine
dppf=1,1'-bis(diphenylphosphino)ferrocene
EtOAc=ethyl acetate
$Fe(acac)_3$=ferric acetylacetonate
THF=tetrahydrofuran
HPLC=high pressure liquid chromatography
HATU=1-[bis(dimethylamino)methylene]-1H-1,23-triazolo [4,5-b]pyridinium 3-oxid-hexafluorophosphate
Hex=hexanes
IPA=isopropyl alcohol
Me=methyl
MeOH=methanol
MsCl=methanesulfonyl chloride
NBS=N-bromosuccinimide
NIS=N-Iodosuccinimide
rt or RT=room temperature
SFC=supercritical fluid chromatography
TBAF=tetrabutylammonium fluoride
THF=tetrahydrofuran
TFA=trifluoroacetic acid
TsCl=4-methylbenzenesulfonyl chloride
$Pd_2(dba)_3$=tris(dibenylideneacetone)dipalladium (0)
$Pd(dppf)Cl_2$=bis(diphenylphosphino)ferrocene]dichloropalladium(II)
Xantphos=4,5-bis(diphenylphosphino)-9,9-dimethylxanthene
XPhos Pd G2=chloro(2-dicyclohexylphosphino-2',4',6'-triisopropyl-1,1'-biphenyl)[2-(2'-amino-1,1'-biphenyl)]palladium(II)
$Zn(OAc)_2$=zinc acetate Also, aq. is aqueous, TLC is thin layer chromatography; Ts is tosyl; UV is ultraviolet; W is watts; wt. % is percentage by weight; x g is times gravity; $\alpha_D$ is the specific rotation of polarized light at 589 nm; ° C. is degrees Celsius; % w/v is percentage in weight of the former agent relative to the volume of the latter agent.

LCMS conditions: column: ACQUITY UPLC-QDa BEH C18, 1.7 mm, 2.1×50 mm.

Solvent system: A: Water 0.1% FA, B: ACN 0.1% FA

Gradient condition: 10-90% B, in 1.7 min, total run time 2.4 min

General Synthetic Schemes

While the present invention has been described in conjunction with the specific examples set forth above, many alternatives, modifications and variations thereof will be apparent to those of ordinary skill in the art. In some cases, the order of carrying out the steps of the reaction schemes may be varied to facilitate the reaction or to avoid unwanted reaction products. All such alternatives, modifications and variations are intended to fall within the spirit and scope of the present invention.

85

[General Scheme 1]

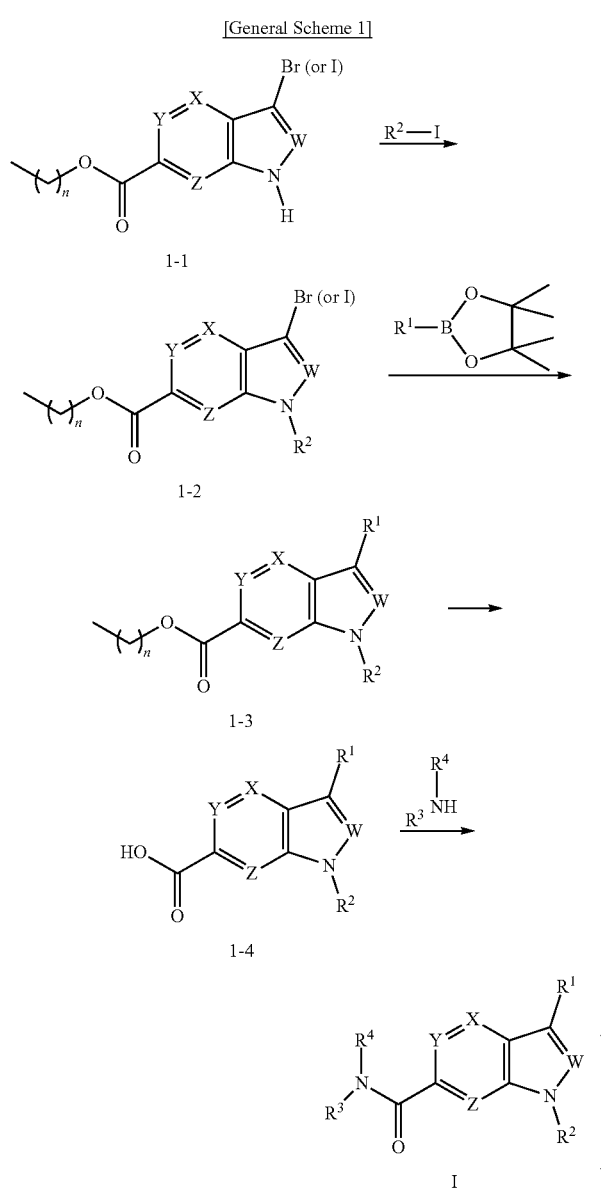

Compounds of formula I were prepared from 1-1 with $R^2$—I via $SN_2$ for alkyl substituents or copper-mediated C—N coupling (Chan-Lam or Buchwald N-arylation) for aromatic substituents. N-substituted compounds (1-2) were prepared by C—C coupling with $R^1$-boronic acid or ester to provide 1-3. Saponification of 1-3 provided the corresponding carboxylic acid (1-4) and subsequent amide coupling with the appropriate amines provided compounds of formula (I-a) as described by the general scheme. The order of steps for some examples may be varied to facilitate the syntheses.

EXAMPLES

The following experimental procedures detail the preparation of specific examples of the instant disclosure. The examples are for illustrative purposes only and are not intended to limit the scope of the instant disclosure in any way.

Example 1: (S)-3-(3-(difluoromethoxy)phenyl)-1-(4-fluorophenyl)-N-(3-methyl-1,1-dioxidotetrahydrothiophen-3-yl)-1H-pyrazolo[4,3-b]pyridine-6-carboxamide

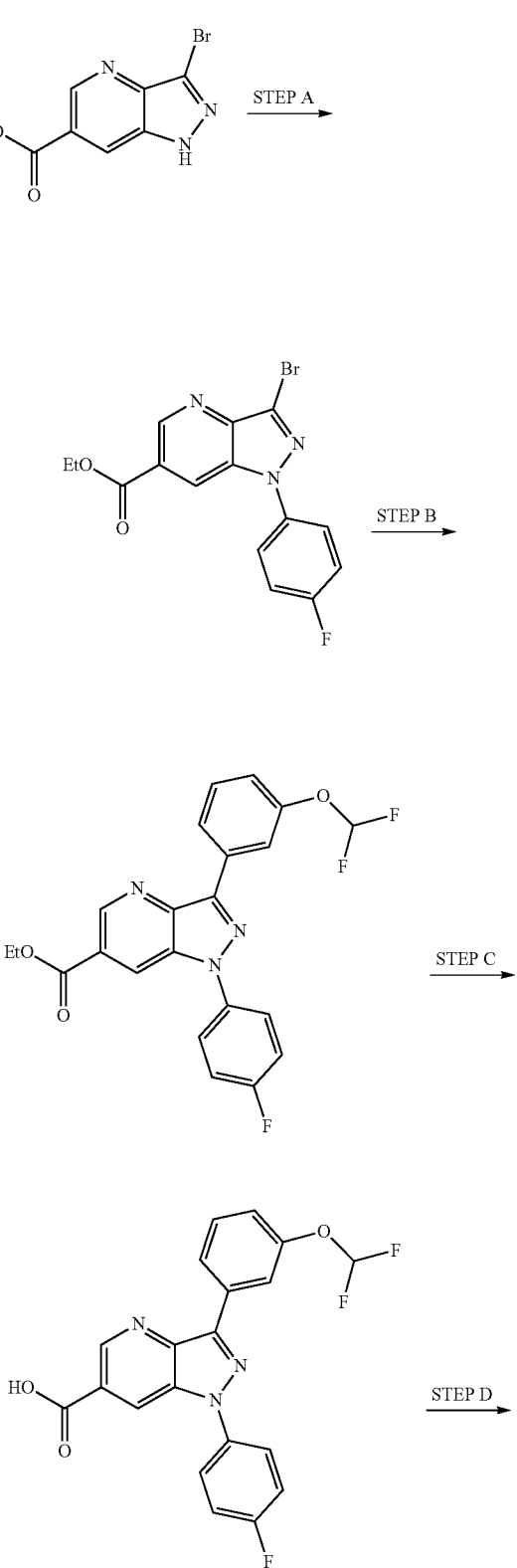

87

-continued

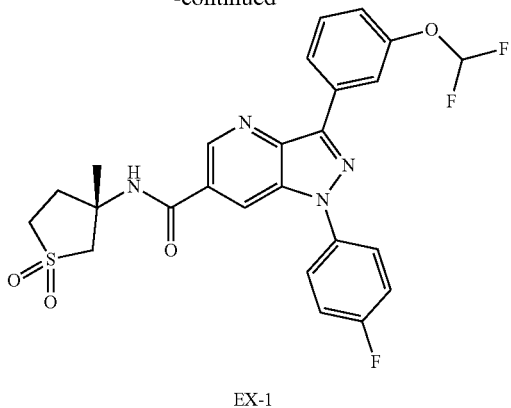

EX-1

Step A: Ethyl 3-bromo-1-(4-fluorophenyl)-1H-pyrazolo[4,3-b]pyridine-6-carboxylate To a mixture of ethyl 3-bromo-1H-pyrazolo[4,3-b]pyridine-6-carboxylate (250 mg, 0.926 mmol), CuI (17.6 mg, 0.093 mmol), and $K_3PO_4$ (413 mg, 1.94 mmol) under $N_2$ was added a solution of 1-fluoro-4-iodobenzene (247 mg, 1.11 mmol) and (R,R)—N,N'-dimethylcyclohexane-1,2-diamine (52.7 mg, 0.37 mmol) in toluene (1.9 mL). The reaction mixture was heated to 110° C. for 36 h, then cooled to RT, and directly purified by flash silica gel chromatography (0-100% EtOAc in hexanes) to afford the title compound. LC/MS=364/366 [M+1].

Step B: Ethyl 3-(3-(difluoromethoxy)phenyl)-1-(4-fluorophenyl)-1H-pyrazolo[4,3-b]pyridine-6-carboxylate To a mixture of ethyl 3-bromo-1-(4-fluorophenyl)-1H-pyrazolo[4,3-b]pyridine-6-carboxylate (73 mg, 0.20 mmol), 2-(3-(difluoromethoxy)phenyl)-4,4,5,5-tetramethyl-1,3,2-dioxaborolane (81 mg, 0.30 mmol), Pd(dppf)Cl$_2$ (14.7 mg, 0.02 mmol), and Na$_2$CO$_3$ (63.7 mg, 0.60 mmol) was added dioxane (1.7 mL), and water (0.33 mL). The reaction mixture was heated to 100° C. for 18 h, then cooled to RT. The mixture was diluted with EtOAc, dried over MgSO$_4$ (s), filtered, and concentrated in vacuo to afford the title compound. LC/MS=428 [M+1].

Step C: 3-(3-(Difluoromethoxy)phenyl)-1-(4-fluorophenyl)-1H-pyrazolo[4,3-b]pyridine-6-carboxylic acid To a solution of crude ethyl 3-(3-(difluoromethoxy)phenyl)-1-(4-fluorophenyl)-1H-pyrazolo[4,3-b]pyridine-6-carboxylate (73 mg, 0.20 mmol) in THF (0.8 mL) and MeOH (0.1 mL) was added NaOH (100 mg, 2.50 mmol) in water (0.6 mL). The reaction was heated to 55° C. for 24 h, then cooled to RT. The resulting mixture was diluted with aq. HCl (1N), extracted with EtOAc, dried over Na$_2$SO$_4$ (s), filtered and concentrated in vacuo to afford the title compound. LC/MS=400 [M+1].

Step D: (S)-3-(3-(Difluoromethoxy)phenyl)-1-(4-fluorophenyl)-N-(3-methyl-1,1-dioxidotetrahydrothiophen-3-yl)-1H-pyrazolo[4,3-b]pyridine-6-carboxamide To a solution of 3-(3-(difluoromethoxy)phenyl)-1-(4-fluorophenyl)-1H-pyrazolo[4,3-b]pyridine-6-carboxylic acid (80 mg, 0.20 mmol) in DMF (2.0 mL) was added (S)-3-amino-3-methyltetrahydrothiophene 1,1-dioxide (35.8 mg, 0.240 mmol), HATU (114 mg, 0.300 mmol), and DIPEA (0.087 mL, 0.50 mmol). Stirred at RT for 24 h. The crude mixture was purified by mass triggered reverse phase HPLC (ACN/water with 0.1% TFA modifier) to afford the title compound. LC/MS=531 [M+1]. $^1$H NMR (600 MHz, Chloroform-d) δ 9.02 (d, J=1.7 Hz, 1H), 8.49 (q, J=2.8, 2.4 Hz, 2H), 8.41 (s, 1H), 7.75 (dd, J=8.9, 4.6 Hz, 2H), 7.54 (t, J=8.0 Hz, 1H), 7.31 (t, J=8.5 Hz, 2H), 7.21 (d, J=7.8 Hz, 1H), 6.65 (t, J=74.0 Hz, 1H), 6.52 (s, 1H), 3.71 (d, J=13.5 Hz, 1H), 3.49-3.42 (m, 1H), 3.33 (ddd, J=12.9, 8.3, 3.8 Hz, 1H), 3.20 (d, J=13.8 Hz, 1H), 3.16-3.08 (m, 1H), 2.32 (ddd, J=14.1, 10.4, 9.0 Hz, 1H), 1.83 (s, 3H). Human DGAT2 IC$_{50}$=0.8 nM By using procedures similar to those described in Example 1 with appropriate reagents, the following compounds were synthesized. These compounds were characterized by LC/MS.

| Example | Structure | Name | LCMS [M + 1] | Human DGAT2 IC$_{50}$ (nM) |
|---|---|---|---|---|
| 2 | 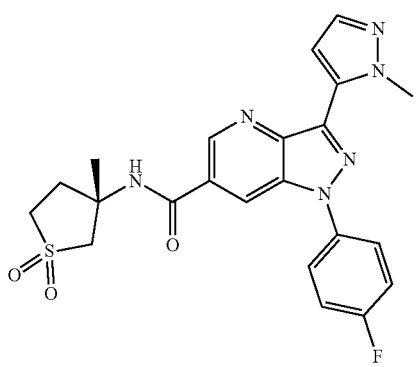 [SMILES: Cn1nccc1-c1nn(-c2ccc(F)cc2)c2cc(C(=O)N[C@@]3(C)CCS(=O)(=O)C3)cnc12] | (S)-1-(4-fluorophenyl)-N-(3-methyl-1,1-dioxidotetrahydrothiophen-3-yl)-3-(1-methyl-1H-pyrazol-5-yl)-1H-pyrazolo[4,3-b]pyridine-6-carboxamide | 469 | 142 |

-continued

| Example | Structure | Name | LCMS [M + 1] | Human DGAT2 IC$_{50}$ (nM) |
|---|---|---|---|---|
| 3 | 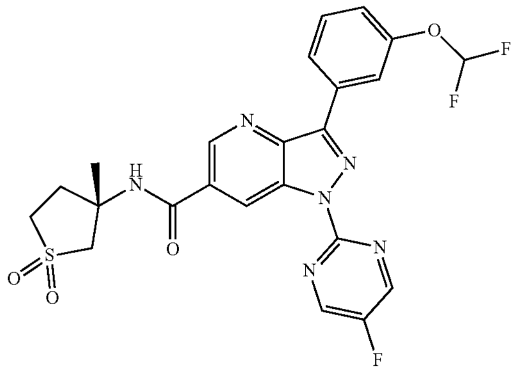 [SMILES: C[C@]1(NC(=O)c2cnc3c(-c4cccc(OC(F)F)c4)nn(-c4ncc(F)cn4)c3c2)CCS(=O)(=O)C1] | (S)-3-(3-(difluoromethoxy)phenyl)-1-(5-fluoropyrimidin-2-yl)-N-(3-methyl-1,1-dioxidotetrahydrothiophen-3-yl)-1H-pyrazolo[4,3-b]pyridine-6-carboxamide | 533 | 57 |
| 4 | 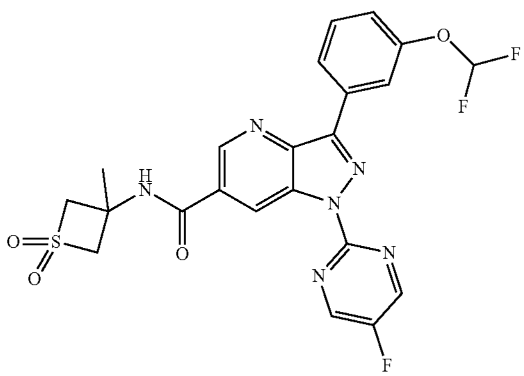 [SMILES: CC1(NC(=O)c2cnc3c(-c4cccc(OC(F)F)c4)nn(-c4ncc(F)cn4)c3c2)CS(=O)(=O)C1] | 3-(3-(difluoromethoxy)phenyl)-1-(5-fluoropyrimidin-2-yl)-N-(3-methyl-1,1-dioxidothietan-3-yl)-1H-pyrazolo[4,3-b]pyridine-6-carboxamide | 519 | 17 |
| 5 | 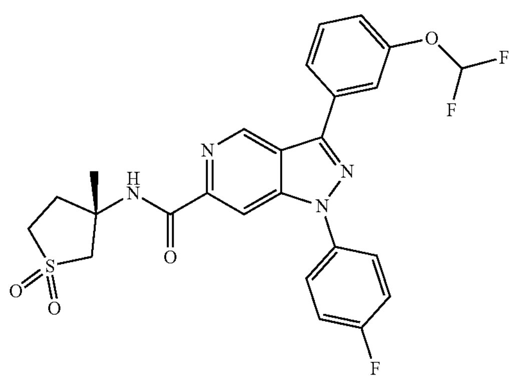 [SMILES: C[C@]1(NC(=O)c2cc3c(cn2)c(-c2cccc(OC(F)F)c2)nn3-c2ccc(F)cc2)CCS(=O)(=O)C1] | (S)-3-(3-(difluoromethoxy)phenyl)-1-(4-fluorophenyl)-N-(3-methyl-1,1-dioxidotetrahydrothiophen-3-yl)-1H-pyrazolo[4,3-c]pyridine-6-carboxamide | 531 | 11 |
| 6 | 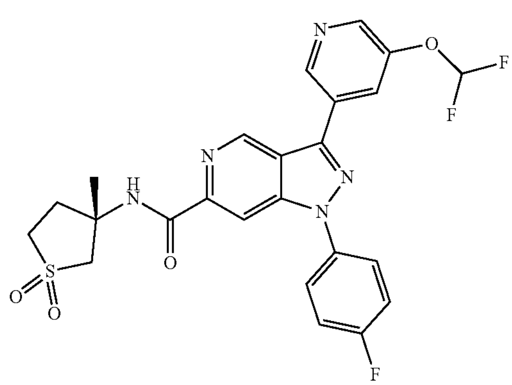 [SMILES: C[C@]1(NC(=O)c2cc3c(cn2)c(-c2cncc(OC(F)F)c2)nn3-c2ccc(F)cc2)CCS(=O)(=O)C1] | (S)-3-(5-(difluoromethoxy)pyridin-3-yl)-1-(4-fluorophenyl)-N-(3-methyl-1,1-dioxidotetrahydrothiophen-3-yl)-1H-pyrazolo[4,3-c]pyridine-6-carboxamide | 532 | 89 |

91

Example 7: 3-(3-(difluoromethoxy)phenyl)-1-(5-fluoropyrimidin-2-yl)-N-((1R,2R)-2-morpholinocyclopentyl)-1H-pyrrolo[3,2-b]pyridine-6-carboxamide

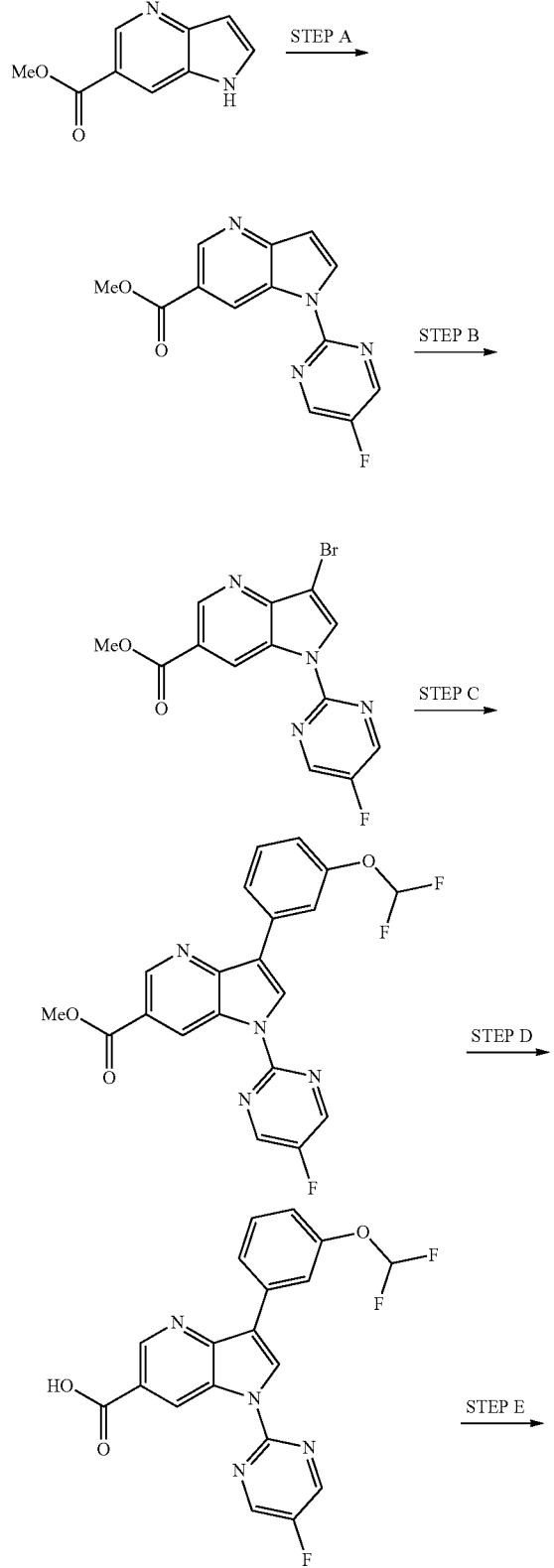

92

-continued

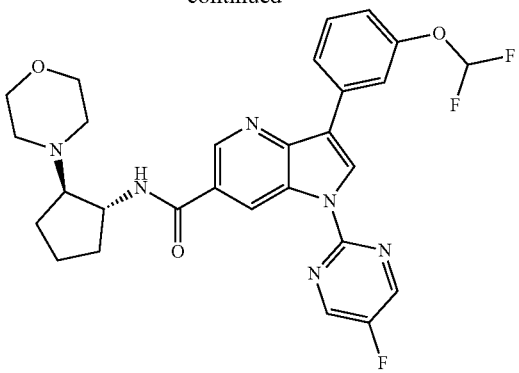

EX-7

Step A: Methyl 1-(5-fluoropyrimidin-2-yl)-1H-pyrrolo[3,2-b]pyridine-6-carboxylate To a mixture of methyl 1H-pyrrolo[3,2-b]pyridine-6-carboxylate (1.00 g, 5.68 mmol), 2-bromo-5-fluoropyrimidine (1.20 g, 6.81 mmol), $K_3PO_4$ (1.20 g, 5.68 mmol), (R,R)—N,N'-dimethylcyclohexane-1,2-diamine (0.323 g, 2.27 mmol) in toluene (57 mL) under $N_2$ was added CuI (0.216 g, 1.13 mmol). The mixture was heated at 100° C. for 72 h. After cooling to RT, Celite® was added, and the mixture was filtered and concentrated. The crude residue was purified by flash silica gel chromatography (0-100% EtOAc/hexanes) to afford the title compound.
LC/MS=273 [M+1].

Step B: Methyl 3-bromo-1-(5-fluoropyrimidin-2-yl)-1H-pyrrolo[3,2-b]pyridine-6-carboxylate To a mixture of methyl 1-(5-fluoropyrimidin-2-yl)-1H-pyrrolo[3,2-b]pyridine-6-carboxylate (0.7 g, 2.57 mmol) in DCM (25.7 mL) was added NBS (0.549 g, 3.09 mmol). The solution was stirred for 16 h, then diluted with DCM and washed with sat. aq. $Na_2S_2O_3$, dried over $Na_2SO_4$ (s), concentrated and purified by flash silica gel chromatography (0-90% EtOAc/hexanes) to afford the title compound.
LC/MS=351/353 [M+1].

Step C: Methyl 3-(3-(difluoromethoxy)phenyl)-1-(5-fluoropyrimidin-2-yl)-1H-pyrrolo[3,2-b]pyridine-6-carboxylate A mixture of methyl 3-bromo-1-(5-fluoropyrimidin-2-yl)-1H-pyrrolo[3,2-b]pyridine-6-carboxylate (602 mg, 1.71 mmol), 2-(3-(difluoromethoxy)phenyl)-4,4,5,5-tetramethyl-1,3,2-dioxaborolane (556 mg, 2.05 mmol), 2 M aq. $K_3PO_4$ (1.7 mL, 3.43 mmol) and XPhos Pd G2 (67.4 mg, 0.086 mmol) in dioxane (20 mL) was heated to 100° C. for 90 min. After cooling to RT, $Na_2SO_4$ (s) was added, the reaction was filtered, concentrated, and purified by flash silica gel chromatography (0-100% EtOAc/hexanes) to afford the title compound. LC/MS=415 [M+1].

Step D: 3-(3-(Difluoromethoxy)phenyl)-1-(5-fluoropyrimidin-2-yl)-1H-pyrrolo[3,2-b]pyridine-6-carboxylic acid To a solution of methyl 3-(3-(difluoromethoxy)phenyl)-1-(5-fluoropyrimidin-2-yl)-1H-pyrrolo[3,2-b]pyridine-6- carboxylate (0.7 g, 1.68 mmol) in THF (60 mL) and MeOH (20 mL) was added 2 M aq. LiOH (12.6 mL, 25.3 mmol). After stirring for 16 h, the aqueous layer was acidified to pH 4 with 3 N aq. HCl and the precipitate was collected to afford the title compound.

LC/MS=401 [M+1].

Step E: 3-(3-(difluoromethoxy)phenyl)-1-(5-fluoropyrimidin-2-yl)-N-((1R,2R)-2-morpholinocyclopentyl)-1H-pyrrolo[3,2-b]pyridine-6-carboxamide To a solution of 3-(3-(difluoromethoxy)phenyl)-1-(5-fluoropyrimidin-2-yl)-1H-pyrrolo[3,2-b]pyridine-6-carboxylic acid (30 mg, 0.075 mmol), HATU (37.0 mg, 0.097 mmol) and (1R,2R)-2-morpholinocyclopentan-1-amine hydrochloride in DMF (1 mL) was added DIPEA (0.039 mL, 0.22 mmol). The reaction was stirred for 16 h, and then purified by mass triggered reverse phase HPLC (ACN/water with 0.1% formic acid modifier) to afford the title compound. LC/MS=553 [M+1]. $^1$H NMR (600 MHz, Methanol-d4) δ 9.42 (s, 1H), 8.95 (s, 2H), 8.81 (s, 2H), 8.39 (s, 1H), 8.05 (s, 1H), 7.97 (d, J=6.7 Hz, 1H), 7.48 (t, J=7.9 Hz, 1H), 7.11 (d, J=8.1 Hz, 1H), 6.93 (t, J=74.3 Hz, 1H), 4.58 (q, J=7.0 Hz, 1H), 3.77 (t, J=4.5 Hz, 4H), 3.06 (q, J=7.7 Hz, 1H), 2.88-2.74 (m, 4H), 2.22 (dq, J=15.6, 7.1 Hz, 1H), 2.10 (dq, J=12.5, 7.3 Hz, 1H), 1.78 (dddd, J=50.6, 26.6, 12.7, 6.7 Hz, 4H). Human DGAT2 IC$_{50}$=45 nM By using procedures similar to those described in Example 7 with appropriate reagents, the following compounds were synthesized. These compounds were characterized by LC/MS.

| Example | Structure | Name | LCMS [M + 1] | Human DGAT2 IC$_{50}$ (nM) |
|---|---|---|---|---|
| 8 | 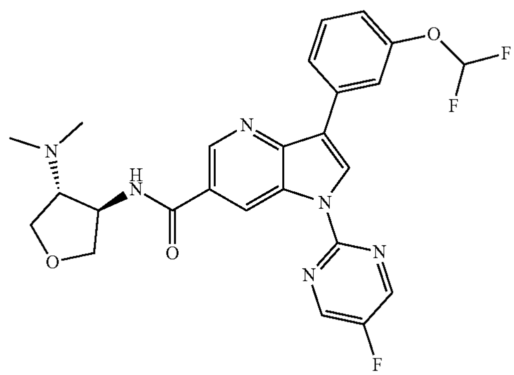 [SMILES: CN(C)[C@H]1COC[C@@H]1NC(=O)c1cnc2c(-c3cccc(OC(F)F)c3)cn(-c3ncc(F)cn3)c2c1] | 3-(3-(difluoromethoxy)phenyl)-N-((3R,4R)-4-(dimethylamino)tetrahydrofuran-3-yl)-1-(5-fluoropyrimidin-2-yl)-1H-pyrrolo[3,2-b]pyridine-6-carboxamide | 513 | 119 |
| 9 | 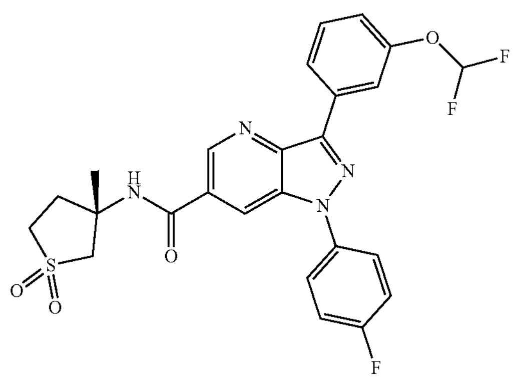 [SMILES: C[C@]1(NC(=O)c2cnc3c(-c4cccc(OC(F)F)c4)nn(-c4ccc(F)cc4)c3c2)CCS(=O)(=O)C1] | (S)-3-(3-(difluoromethoxy)phenyl)-1-(4-fluorophenyl)-N-(3-methyl-1,1-dioxidotetrahydrothiophen-3-yl)-1H-pyrrolo[3,2-b]pyridine-6-carboxamide | 530 | 6.8 |
| 10 | 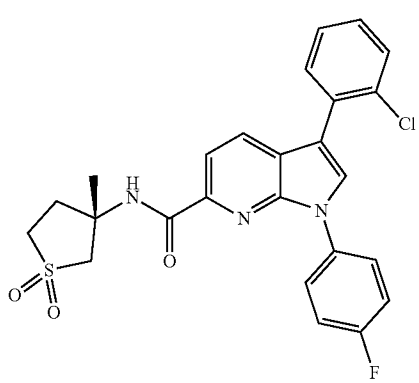 [SMILES: C[C@]1(NC(=O)c2ccc3c(-c4ccccc4Cl)cn(-c4ccc(F)cc4)c3n2)CCS(=O)(=O)C1] | (S)-3-(2-chlorophenyl)-1-(4-fluorophenyl)-N-(3-methyl-1,1-dioxidotetrahydrothiophen-3-yl)-1H-pyrrolo[2,3-b]pyridine-6-carboxamide | 498 | 3696 |

-continued

| Example | Structure | Name | LCMS [M + 1] | Human DGAT2 IC$_{50}$ (nM) |
|---|---|---|---|---|
| 11 | 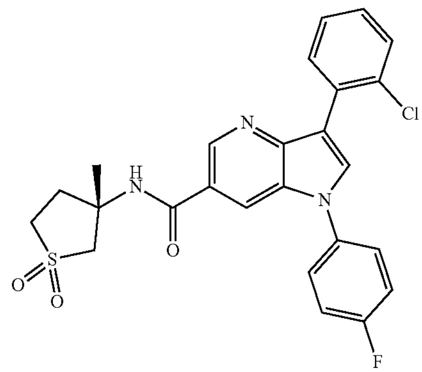 [SMILES: C[C@]1(NC(=O)c2cnc3c(-c4ccccc4Cl)cn(-c4ccc(F)cc4)c3c2)CCS(=O)(=O)C1] | (S)-3-(2-chlorophenyl)-1-(4-fluorophenyl)-N-(3-methyl-1,1-dioxidotetrahydrothiophen-3-yl)-1H-pyrrolo[3,2-b]pyridine-6-carboxamide | 498 | 186 |
| 12 | 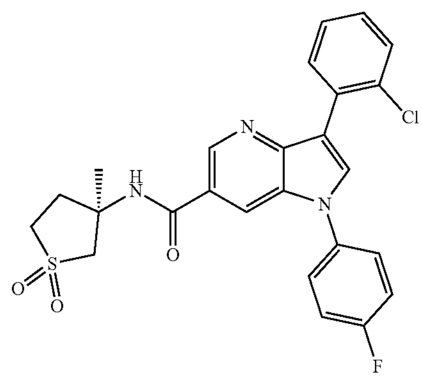 [SMILES: C[C@@]1(NC(=O)c2cnc3c(-c4ccccc4Cl)cn(-c4ccc(F)cc4)c3c2)CCS(=O)(=O)C1] | (R)-3-(2-chlorophenyl)-1-(4-fluorophenyl)-N-(3-methyl-1,1-dioxidotetrahydrothiophen-3-yl)-1H-pyrrolo[3,2-b]pyridine-6-carboxamide | 498 | 356 |
| 13 | 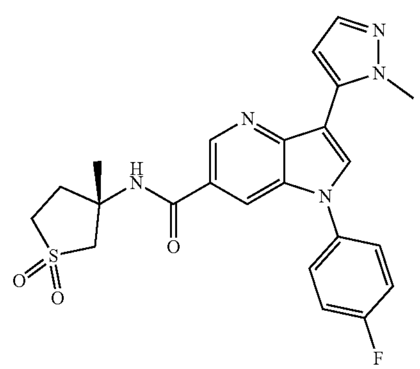 [SMILES: Cn1nccc1-c1cn(-c2ccc(F)cc2)c2cc(C(=O)N[C@@]3(C)CCS(=O)(=O)C3)cnc12] | (S)-1-(4-fluorophenyl)-N-(3-methyl-1,1-dioxidotetrahydrothiophen-3-yl)-3-(1-methyl-1H-pyrazol-5-yl)-1H-pyrrolo[3,2-b]pyridine-6-carboxamide | 468 | 89 |
| 14 | 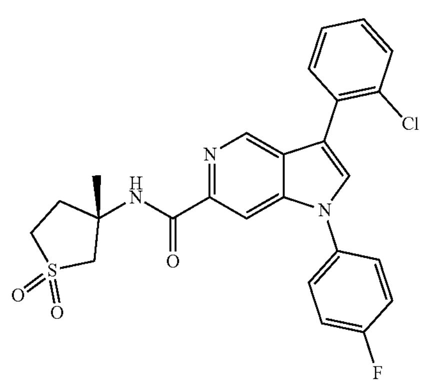 [SMILES: C[C@]1(NC(=O)c2cc3c(cn2)c(-c2ccccc2Cl)cn3-c2ccc(F)cc2)CCS(=O)(=O)C1] | (S)-3-(2-chlorophenyl)-1-(4-fluorophenyl)-N-(3-methyl-1,1-dioxidotetrahydrothiophen-3-yl)-1H-pyrrolo[3,2-c]pyridine-6-carboxamide | 498 | 292 |

-continued

| Example | Structure | Name | LCMS [M + 1] | Human DGAT2 IC$_{50}$ (nM) |
|---|---|---|---|---|
| 15 | 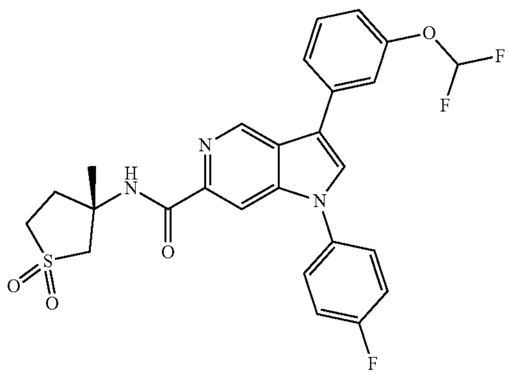 [SMILES: C[C@]1(NC(=O)c2cc3c(cn2)c(-c2cccc(OC(F)F)c2)cn3-c2ccc(F)cc2)CCS(=O)(=O)C1] | (S)-3-(3-(difluoromethoxy)phenyl)-1-(4-fluorophenyl)-N-(3-methyl-1,1-dioxidotetrahydrothiophen-3-yl)-1H-pyrrolo[3,2-c]pyridine-6-carboxamide | 530 | 23 |
| 16 | 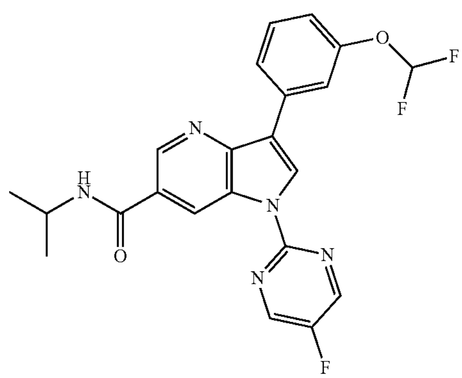 [SMILES: CC(C)NC(=O)c1cnc2c(-c3cccc(OC(F)F)c3)cn(-c3ncc(F)cn3)c2c1] | 3-(3-(difluoromethoxy)phenyl)-1-(5-fluoropyrimidin-2-yl)-N-isopropyl-1H-pyrrolo[3,2-b]pyridine-6-carboxamide | 442 | 209 |
| 17 | 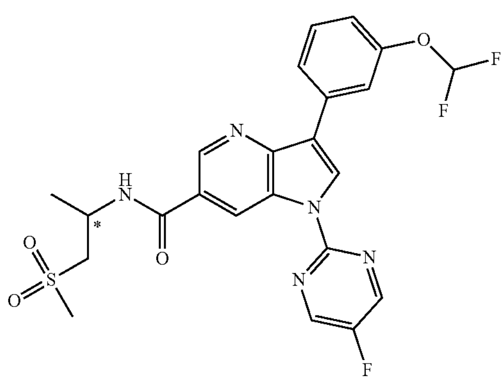 [SMILES: CC(CS(C)(=O)=O)NC(=O)c1cnc2c(-c3cccc(OC(F)F)c3)cn(-c3ncc(F)cn3)c2c1] | 3-(3-(difluoromethoxy)phenyl)-1-(5-fluoropyrimidin-2-yl)-N-(1-(methylsulfonyl)propan-2-yl)-1H-pyrrolo[3,2-b]pyridine-6-carboxamide | 520 | 72 |

| Example | Structure | Name | LCMS [M + 1] | Human DGAT2 IC$_{50}$ (nM) |
|---|---|---|---|---|
| 18 | 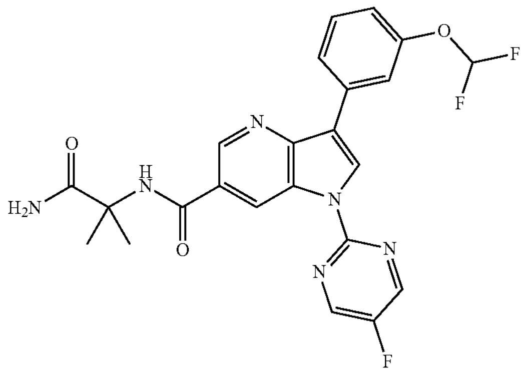 [SMILES: CC(C)(NC(=O)c1cnc2c(-c3cccc(OC(F)F)c3)cn(-c3ncc(F)cn3)c2c1)C(N)=O] | N-(1-amino-2-methyl-1-oxopropan-2-yl)-3-(3-(difluoromethoxy)phenyl)-1-(5-fluoropyrimidin-2-yl)-1H-pyrrolo[3,2-b]pyridine-6-carboxamide | 485 | 3418 |
| 19 | 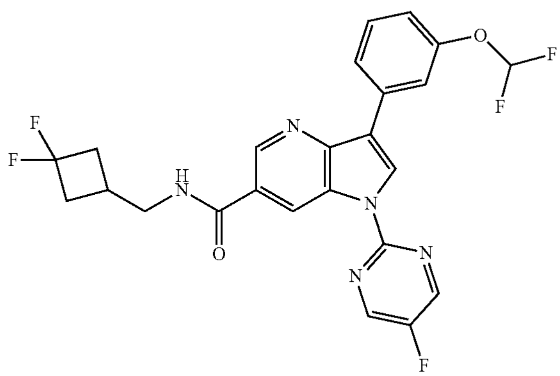 [SMILES: O=C(NCC1CC(F)(F)C1)c1cnc2c(-c3cccc(OC(F)F)c3)cn(-c3ncc(F)cn3)c2c1] | N-((3,3-difluorocyclobutyl)methyl)-3-(3-(difluoromethoxy)phenyl)-1-(5-fluoropyrimidin-2-yl)-1H-pyrrolo[3,2-b]pyridine-6-carboxamide | 504 | >1000 |

Example 20: N-((1R,2S)-2-aminocyclopentyl)-3-(3-(difluoromethoxy)phenyl)-1-(5-fluoropyrimidin-2-yl)-1H-pyrrolo[3,2-b]pyridine-6-carboxamide

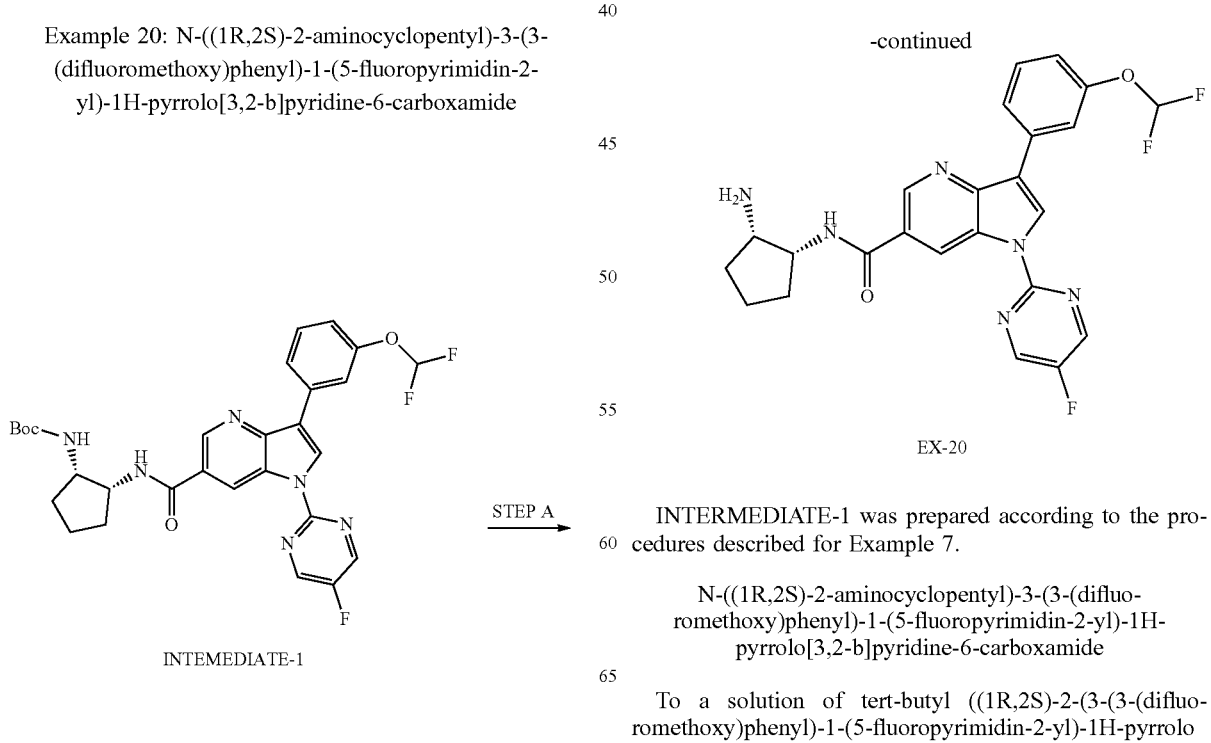

INTERMEDIATE-1 was prepared according to the procedures described for Example 7.

N-((1R,2S)-2-aminocyclopentyl)-3-(3-(difluoromethoxy)phenyl)-1-(5-fluoropyrimidin-2-yl)-1H-pyrrolo[3,2-b]pyridine-6-carboxamide To a solution of tert-butyl ((1R,2S)-2-(3-(3-(difluoromethoxy)phenyl)-1-(5-fluoropyrimidin-2-yl)-1H-pyrrolo

[3,2-b]pyridine-6-carboxamido)cyclopentyl)carbamate (0.175 g, 0.30 mmol) in DCM (2 mL) was added TFA (0.6 mL, 0.30 mmol). The reaction was stirred for 16 h. An aliquot of ~20 mg was taken, concentrated in vacuo, and purified by mass triggered reverse phase HPLC (ACN/water with 0.1% formic acid modifier) to afford the title compound as the formic acid salt. LC/MS=483 [M+1]. $^1$H NMR (600 MHz, Methanol-d4) δ 9.49 (br s, 1H), 9.05 (s, 1H), 8.98 (br s, 1H), 8.82 (s, 2H), 8.07 (s, 1H), 7.97 (br s, 1H), 7.49 (t, J=7.9 Hz, 1H), 7.13 (d, J=8.2 Hz, 1H), 6.93 (t, J=74.3 Hz, 1H), 4.55 (q, J=7.0 Hz, 1H), 3.86 (q, J=6.6 Hz, 1H), 2.29-2.19 (m, 2H), 2.10-1.94 (m, 2H), 1.89-1.75 (m, 2H). Human DGAT2 IC$_{50}$=189 nM.

By using procedures similar to those described in Example 20 with appropriate reagents, the following compounds were synthesized. These compounds were characterized by LC/MS.

Example 24: (S)-7-(3-(difluoromethoxy)phenyl)-5-(4-fluorophenyl)-N-(3-methyl-1,1-dioxidotetrahydrothiophen-3-yl)-5H-pyrrolo[2,3-b]pyrazine-3-carboxamide

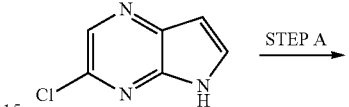
STEP A

| Example | Structure | Name | LCMS [M + 1] | Human DGAT2 IC$_{50}$ (nM) |
|---|---|---|---|---|
| 21 | 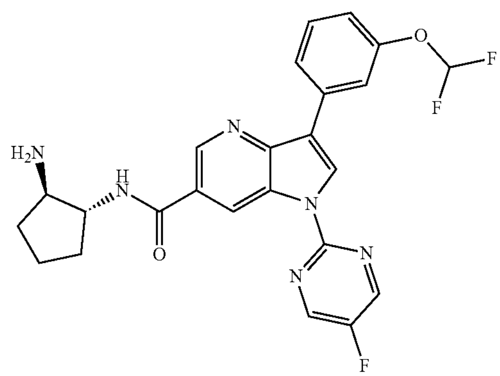 [SMILES: N[C@@H]1CCC[C@H]1NC(=O)c1cnc2c(-c3cccc(OC(F)F)c3)cn(-c3ncc(F)cn3)c2c1] | N-((1R,2R)-2-aminocyclopentyl)-3-(3-(difluoromethoxy)phenyl)-1-(5-fluoropyrimidin-2-yl)-1H-pyrrolo[3,2-b]pyridine-6-carboxamide | 483 | 6530 |
| 22 | 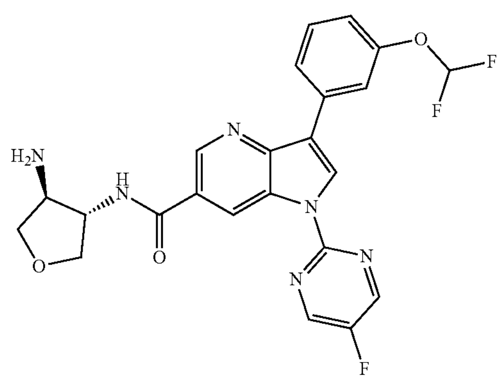 [SMILES: N[C@@H]1COC[C@H]1NC(=O)c1cnc2c(-c3cccc(OC(F)F)c3)cn(-c3ncc(F)cn3)c2c1] | N-((3S,4S)-4-aminotetrahydrofuran-3-yl)-3-(3-(difluoromethoxy)phenyl)-1-(5-fluoropyrimidin-2-yl)-1H-pyrrolo[3,2-b]pyridine-6-carboxamide | 485 | 630 |
| 23 | 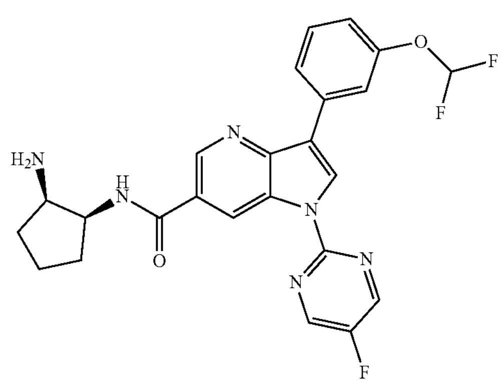 [SMILES: N[C@@H]1CCC[C@@H]1NC(=O)c1cnc2c(-c3cccc(OC(F)F)c3)cn(-c3ncc(F)cn3)c2c1] | N-((1S,2R)-2-aminocyclopentyl)-3-(3-(difluoromethoxy)phenyl)-1-(5-fluoropyrimidin-2-yl)-1H-pyrrolo[3,2-b]pyridine-6-carboxamide | 483 | 173 |

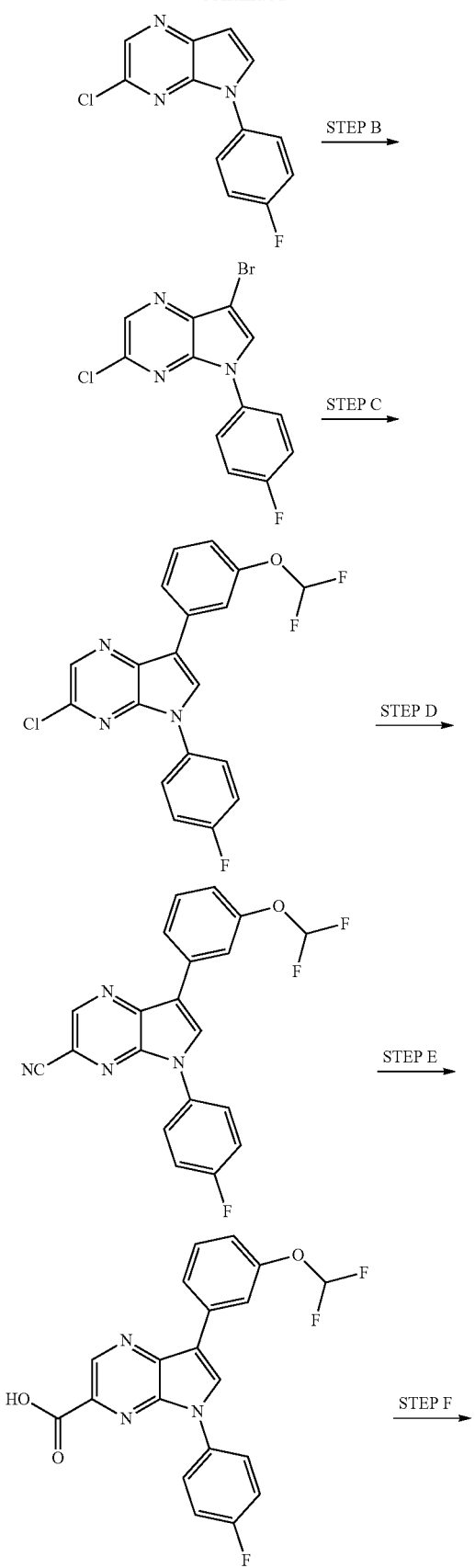

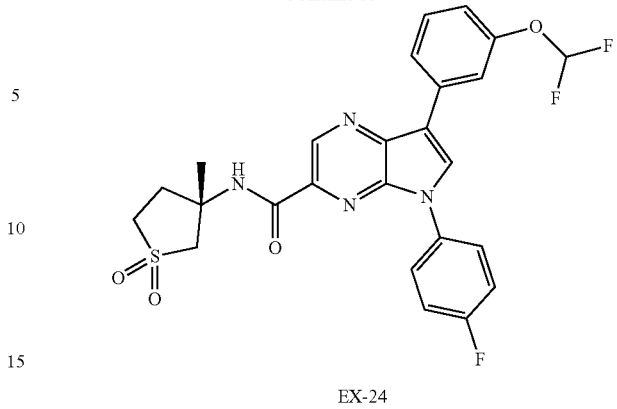

EX-24

Step A: 3-chloro-5-(4-fluorophenyl)-5H-pyrrolo[2,3-b]pyrazine

To mixture of 3-chloro-5H-pyrrolo[2,3-b]pyrazine (1.00 g, 6.51 mmol), CuI (124 mg, 0.65 mmol), and $K_3PO_4$ (2.90 g, 13.7 mmol) under $N_2$ was added a solution of 1-fluoro-4-iodobenzene (1.74 g, 7.81 mmol) and (R,R)—N,N'-dimethylcyclohexane-1,2-diamine (371 mg, 2.60 mmol) in toluene (6.5 mL). The reaction mixture was heated to 110° C. for 24 h, then cooled to RT, filtered over a pad of silica and concentrated in vacuo. The crude residue was purified by flash silica gel chromatography (0-100% EtOAc/hexanes) to afford the title compound. LC/MS=248 [M+1].

Step B: 7-bromo-3-chloro-5-(4-fluorophenyl)-5H-pyrrolo[2,3-b]pyrazine

To a solution of 3-chloro-5-(4-fluorophenyl)-5H-pyrrolo[2,3-b]pyrazine (500 mg, 2.02 mmol) in DCM (6.7 mL) was added NBS (539 mg, 3.03 mmol). The reaction was stirred for 20 h, then concentrated in vacuo and purified by flash silica gel chromatography (0-100% EtOAc/hexanes) to afford the title compound. LC/MS=326/328 [M+1].

Step C: 3-chloro-7-(3-(difluoromethoxy)phenyl)-5-(4-fluorophenyl)-5H-pyrrolo[2,3-b]pyrazine To a mixture of 7-bromo-3-chloro-5-(4-fluorophenyl)-5H-pyrrolo[2,3-b]pyrazine (250 mg, 0.766 mmol), 2-(3-(difluoromethoxy)phenyl)-4,4,5,5-tetramethyl-1,3,2-dioxaborolane (248 mg, 0.92 mmol), Pd(dppf)$Cl_2$ (56 mg, 0.077 mmol), and $Na_2CO_3$ (243 mg, 2.30 mmol) was added dioxane (6.4 mL), and water (1.3 mL). The reaction mixture was heated to 100° C. for 20 h, then cooled to RT. The mixture was diluted with EtOAc, dried over $MgSO_4$, filtered over a pad of Celite®, and concentrated in vacuo. The crude residue was purified by flash silica gel chromatography (0-100% EtOAc/hexanes) to afford the title compound. LC/MS=390 [M+1].

Step D: 7-(3-(difluoromethoxy)phenyl)-5-(4-fluorophenyl)-5H-pyrrolo[2,3-b]pyrazine-3-carbonitrile To a mixture of 3-chloro-7-(3-(difluoromethoxy)phenyl)-5-(4-fluorophenyl)-5H-pyrrolo[2,3-b]pyrazine (90 mg, 0.17 mmol), Pd(dppf)$Cl_2$ (16.9 mg, 0.023 mmol), and CuCN (41.4 mg, 0.462 mmol) was added DMF (2.3 mL). The reaction was heated to 110° C. for 18 h, then cooled to rt and concentrated in vacuo. The crude residue was purified by flash silica gel chromatography (0-100% EtOAc/hexanes) to afford the title compound. LC/MS=381 [M+1].

Step E: 7-(3-(difluoromethoxy)phenyl)-5-(4-fluorophenyl)-5H-pyrrolo[2,3-b]pyrazine-3-carboxylic acid To a solution of 7-(3-(difluoromethoxy)phenyl)-5-(4-fluorophenyl)-5H-pyrrolo[2,3-b]pyrazine-3-carbonitrile (38 mg, 0.10 mmol) in dioxane (0.5 mL) was added a mixture of NaOH (200 mg, 5.00 mmol) in water (0.5 mL). The reaction was heated to 65° C. for 48 h, then cooled to RT and adjusted to pH 3 using 1 N aq. HCl. The resulting mixture was extracted with EtOAc, and the combined organics were dried over $Na_2SO_4$ (s) and concentrated in vacuo to afford the crude title compound. LC/MS=400 [M+1].

Step F: (S)-7-(3-(difluoromethoxy)phenyl)-5-(4-fluorophenyl)-N-(3-methyl-1,1-dioxidotetrahydrothiophen-3-yl)-5H-pyrrolo[2,3-b]pyrazine-3-carboxamide To a solution of 7-(3-(difluoromethoxy)phenyl)-5-(4-fluorophenyl)-5H-pyrrolo[2,3-b]pyrazine-3-carboxylic acid (39.9 mg, 0.10 mmol) in DMF (1.0 mL) was added (S)-3-amino-3-methyltetrahydrothiophene 1,1-dioxide (29.8 mg, 0.20 mmol), HATU (49.4 mg, 0.13 mmol), and DIPEA (52 µL, 0.300 mmol). The reaction mixture was stirred at RT for 24 h, then directly purified by mass triggered reverse phase HPLC (ACN/water with 0.1% TFA modifier) to afford the title compound as the TFA salt. LC/MS=531 [M+1]. $^1$H NMR (600 MHz, Chloroform-d) δ 9.44 (s, 1H), 8.24 (s, 1H), 8.08 (s, 1H), 8.02 (d, J=7.8 Hz, 1H), 7.94 (s, 1H), 7.79-7.73 (m, 2H), 7.50 (t, J=8.0 Hz, 1H), 7.34 (t, J=8.5 Hz, 2H), 7.12 (dd, J=8.2, 1.5 Hz, 1H), 6.62 (t, J=73.9 Hz, 1H), 3.61 (d, J=13.8 Hz, 1H), 3.39 (ddd, J=13.0, 10.8, 8.3 Hz, 1H), 3.30 (ddd, J=13.5, 8.3, 3.2 Hz, 1H), 3.21-3.14 (m, 2H), 2.27 (ddd, J=13.7, 10.8, 8.4 Hz, 1H), 1.80 (s, 3H). Human DGAT2 $IC_{50}$=50 nM.

Example 25: 3-[3-(difluoromethoxy)phenyl]-1-isopropyl-N-(3-methyl-1,1-dioxidothietan-3-yl)-1H-pyrazolo[4,3-b]pyridine-6-carboxamide

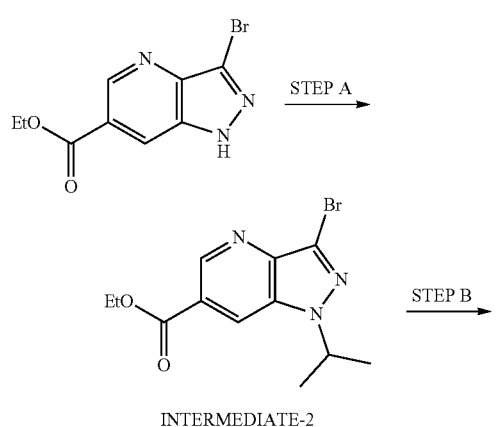

INTERMEDIATE-2

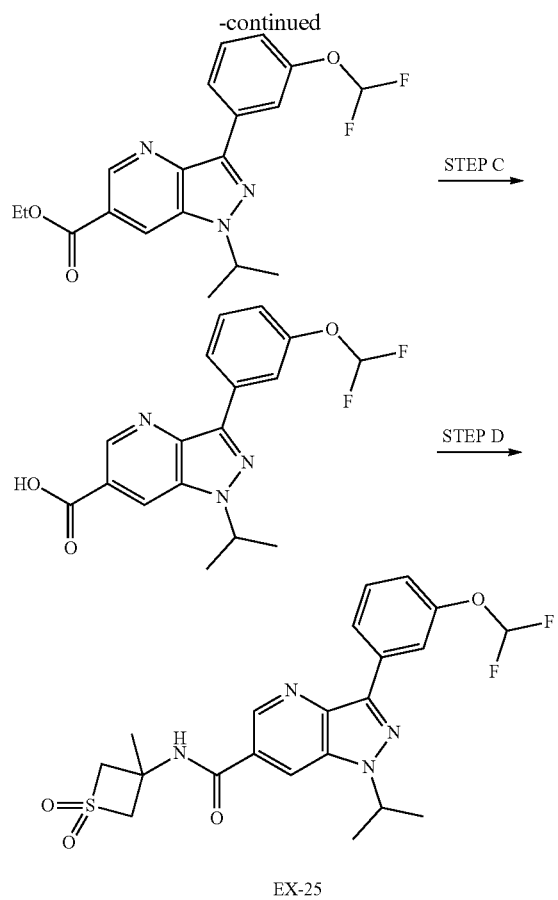

EX-25

Step A: Ethyl 3-bromo-1-isopropyl-1H-pyrazolo[4,3-b]pyridine-6-carboxylate (Intermediate-2)

To a suspension of ethyl 3-bromo-1H-pyrazolo[4,3-b]pyridine-6-carboxylate (1.0 g, 3.70 mmol) and $K_3CO_2$ (1.02 g, 7.41 mmol) in DMF (12 mL) was added a solution of 2-iodopropane (0.944 g, 5.55 mmol) in DMF (2 mL) and stirred for 16 h at RT. After dilution with water and EtOAc, the solution was washed with saturated aq. $NaHCO_3$, and the organic layer was washed with brine, dried over $Na_2SO_4$, filtered, and concentrated in vacuo. The resulting mixture was purified by flash silica gel chromatography (0-35% EtOAc/hexanes) to afford the title compound. LC/MS=314 [M+1].

Step B: Ethyl 3-(3-(difluoromethoxy)phenyl)-1-isopropyl-1H-pyrazolo[4,3-b]pyridine-6-carboxylate To a mixture of ethyl 3-bromo-1-isopropyl-1H-pyrazolo[4,3-b]pyridine-6-carboxylate (625 mg, 2.00 mmol), (3-(difluoromethoxy)phenyl)boronic acid (564 mg, 3.00 mmol), and aq. $Na_2CO_3$ (2 M, 2.25 mL, 4.50 mmol) in dioxane (19 mL) under $N_2$(g) was added $Pd(dppf)Cl_2$ (146 mg, 0.200 mmol). Reaction was heated to 90° C. for 6 h. The reaction mixture was filtered through Celite®, dried over $Na_2SO_4$, concentrated in vacuo, and purified by flash silica gel chromatography (0-40% EtOAc/hexanes) to afford the title compound. LC/MS=376 [M+1].

Step C: 3-(3-(Difluoromethoxy)phenyl)-1-isopropyl-1H-pyrazolo[4,3-b]pyridine-6-carboxylic acid To a solution of ethyl 3-(3-(difluoromethoxy)phenyl)-1-isopropyl-1H-pyrazolo[4,3-b]pyridine-6-carboxylate (676 mg, 1.80 mmol) in THF (12 mL) and MeOH (4 mL) was added 2 M aq. LiOH (4.5 mL, 9.0 mmol) followed by water (4 mL), and the resulting mixture was stirred at RT for 16 h. The reaction was concentrated and adjusted to pH 4 with 3 N aq. HCl (3N), then extracted with EtOAc. The combined organic phases were washed with brine, dried over $Na_2SO_4$, filtered and concentrated in vacuo to afford the title compound. LC/MS=348 [M+1].

Step D: 3-[3-(difluoromethoxy)phenyl]-1-isopropyl-N-(3-methyl-1,1-dioxidothietan-3-yl)-1H-pyrazolo[4,3-b]pyridine-6-carboxamide To a solution of 3-(3-(difluoromethoxy)phenyl)-1-isopropyl-1H-pyrazolo[4,3-b]pyridine-6-carboxylic acid (0.056 g, 0.16 mmol), 3-amino-3-methylthietane 1,1-dioxide (0.032 mg, 0.24 mmol), and HATU (0.091 g, 0.24 mmol) in DMF (1.0 mL) was added DIPEA (0.07 mL, 0.40 mmol) and stirred for 24 h at RT. The reaction mixture was filtered and purified by mass triggered reverse phase HPLC (ACN/water with 0.1% TFA modifier) to afford the title compound. LC/MS=465 [M+1]. $^1$H NMR (600 MHz, Chloroform-d) δ 9.01-8.94 (m, 1H), 8.40 (s, 1H), 8.38-8.32 (m, 1H), 8.30-8.24 (m, 1H), 7.48 (t, J=6.5 Hz, 1H), 7.14 (d, J=8.0 Hz, 1H), 6.97-6.77 (m, 1H), 6.63 (t, J=74.0 Hz, 1H), 4.94 (p, J=6.6 Hz, 1H), 4.69 (d, J=14.0 Hz, 2H), 4.25 (d, J=14.0 Hz, 2H), 1.98 (s, 3H), 1.67 (d, J=6.7 Hz, 6H). Human DGAT2 $IC_{50}$=4.7 nM.

By using procedures similar to those described in Example 25 with appropriate reagents, the following compounds were synthesized. These compounds were characterized by LC/MS.

| Example | Structure | Name | LCMS [M + 1] | Human DGAT2 $IC_{50}$ (nM) |
|---|---|---|---|---|
| 26 | 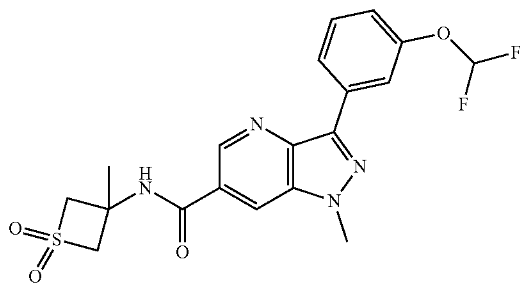 [SMILES: Cn1nc(-c2cccc(OC(F)F)c2)c2ncc(C(=O)NC3(C)CS(=O)(=O)C3)cc21] | 3-(3-(difluoromethoxy)phenyl)-1-methyl-N-(3-methyl-1,1-dioxidothietan-3-yl)-1H-pyrazolo[4,3-b]pyridine-6-carboxamide | 437 | 153 |
| 27 | 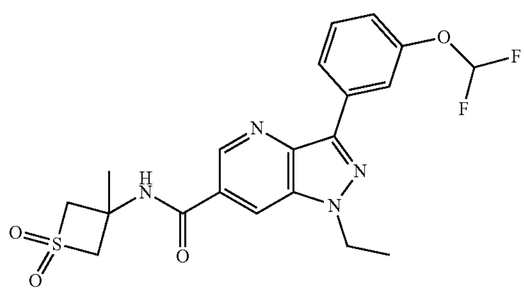 [SMILES: CCn1nc(-c2cccc(OC(F)F)c2)c2ncc(C(=O)NC3(C)CS(=O)(=O)C3)cc21] | 3-(3-(difluoromethoxy)phenyl)-1-ethyl-N-(3-methyl-1,1-dioxidothietan-3-yl)-1H-pyrazolo[4,3-b]pyridine-6-carboxamide | 451 | 111 |
| 28 | 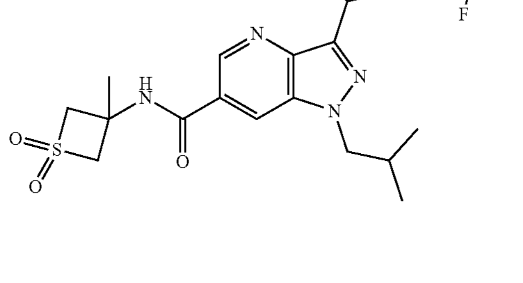 | 3-(3-(difluoromethoxy)phenyl)-1-isobutyl-N-(3-methyl-1,1-dioxidothietan-3-yl)-1H-pyrazolo[4,3-b]pyridine-6-carboxamide | 479 | 29 |

-continued

| Example | Structure | Name | LCMS [M + 1] | Human DGAT2 IC₅₀ (nM) |
|---|---|---|---|---|
| 29 | 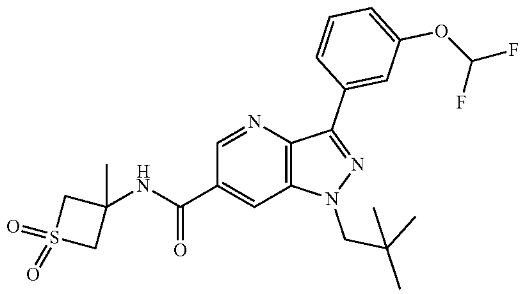 [SMILES: CC(C)(C)Cn1nc(-c2cccc(OC(F)F)c2)c2ncc(C(=O)NC3(C)CS(=O)(=O)C3)cc21] | 3-(3-(difluoromethoxy)phenyl)-N-(3-methyl-1,1-dioxidothietan-3-yl)-1-neopentyl-1H-pyrazolo[4,3-b]pyridine-6-carboxamide | 493 | 388 |
| 30 | 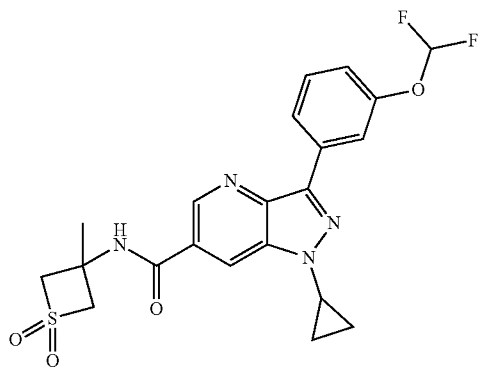 [SMILES: CC1(NC(=O)c2cnc3c(-c4cccc(OC(F)F)c4)nn(C4CC4)c3c2)CS(=O)(=O)C1] | 1-cyclopropyl-3-(3-(difluoromethoxy)phenyl)-N-(3-methyl-1,1-dioxidothietan-3-yl)-1H-pyrazolo[4,3-b]pyridine-6-carboxamide | 463 | 99 |
| 31 | 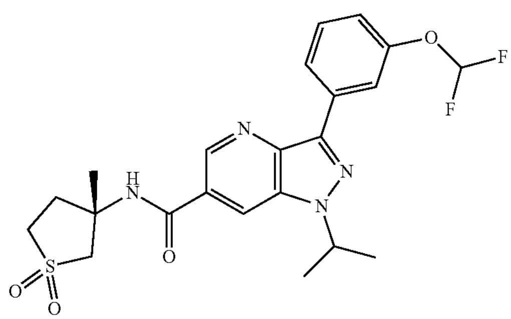 [SMILES: CC(C)n1nc(-c2cccc(OC(F)F)c2)c2ncc(C(=O)N[C@@]3(C)CCS(=O)(=O)C3)cc21] | (S)-3-(3-(difluoromethoxy)phenyl)-1-isopropyl-N-(3-methyl-1,1-dioxidotetrahydrothiophen-3-yl)-1H-pyrazolo[4,3-b]pyridine-6-carboxamide | 479 | 7.2 |
| 32 | 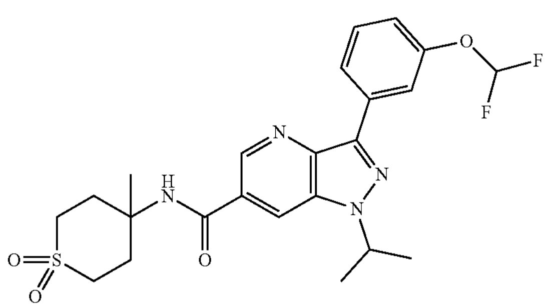 [SMILES: CC(C)n1nc(-c2cccc(OC(F)F)c2)c2ncc(C(=O)NC3(C)CCS(=O)(=O)CC3)cc21] | 3-(3-(difluoromethoxy)phenyl)-1-isopropyl-N-(4-methyl-1,1-dioxidotetrahydro-2H-thiopyran-4-yl)-1H-pyrazolo[4,3-b]pyridine-6-carboxamide | 493 | 4.3 |

-continued

| Example | Structure | Name | LCMS [M + 1] | Human DGAT2 IC$_{50}$ (nM) |
|---|---|---|---|---|
| 33 | 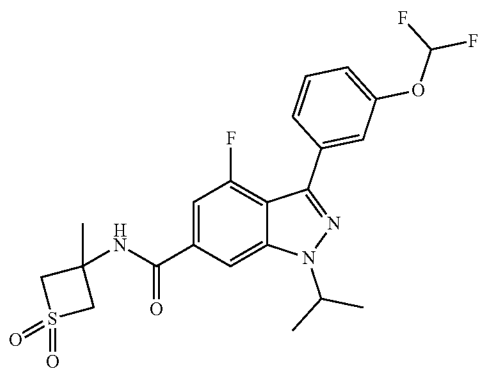 [SMILES: CC(C)n1nc(-c2cccc(OC(F)F)c2)c2c(F)cc(C(=O)NC3(C)CS(=O)(=O)C3)cc21] | 3-(3-(difluoromethoxy)phenyl)-4-fluoro-1-isopropyl-N-(3-methyl-1,1-dioxidothietan-3-yl)-1H-indazole-6-carboxamide | 482 | 1.0 |
| 34 | 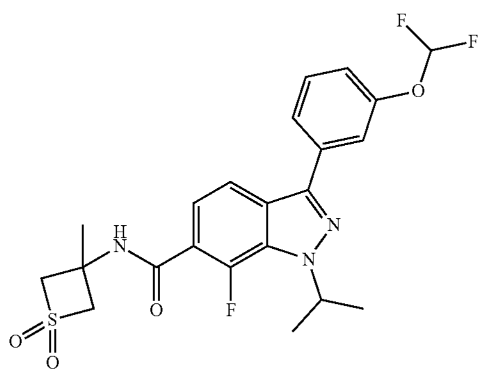 [SMILES: CC(C)n1nc(-c2cccc(OC(F)F)c2)c2ccc(C(=O)NC3(C)CS(=O)(=O)C3)c(F)c21] | 3-(3-(difluoromethoxy)phenyl)-7-fluoro-1-isopropyl-N-(3-methyl-1,1-dioxidothietan-3-yl)-1H-indazole-6-carboxamide | 482 | 5.2 |
| 35 | 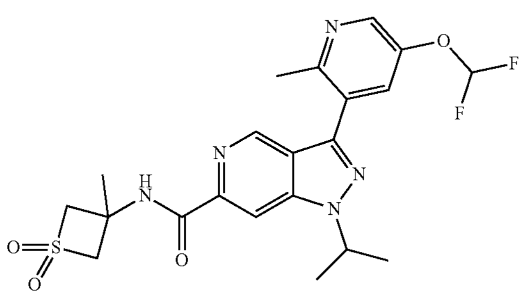 [SMILES: Cc1ncc(OC(F)F)cc1-c1nn(C(C)C)c2cc(C(=O)NC3(C)CS(=O)(=O)C3)ncc12] | 3-(5-(difluoromethoxy)-2-methylpyridin-3-yl)-1-isopropyl-N-(3-methyl-1,1-dioxidothietan-3-yl)-1H-pyrazolo[4,3-c]pyridine-6-carboxamide | 480 | 285 |
| 36 | 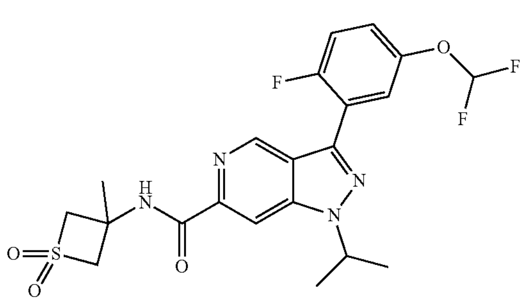 [SMILES: CC(C)n1nc(-c2cc(OC(F)F)ccc2F)c2cnc(C(=O)NC3(C)CS(=O)(=O)C3)cc21] | 3-(5-(difluoromethoxy)-2-fluorophenyl)-1-isopropyl-N-(3-methyl-1,1-dioxidothietan-3-yl)-1H-pyrazolo[4,3-c]pyridine-6-carboxamide | 483 | 1.7 |

| Example | Structure | Name | LCMS [M + 1] | Human DGAT2 IC$_{50}$ (nM) |
|---|---|---|---|---|
| 37 | 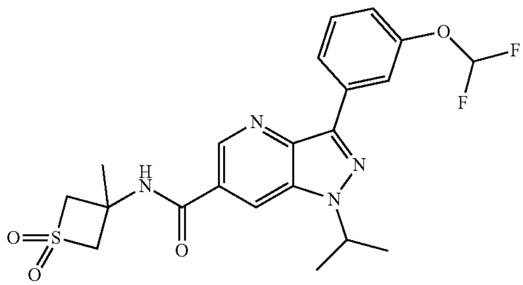 [SMILES: CC(C)n1nc(-c2cccc(OC(F)F)c2)c2ncc(C(=O)NC3(C)CS(=O)(=O)C3)cc21] | 3-(3-(difluoromethoxy)phenyl)-1-isopropyl-N-(3-methyl-1,1-dioxidothietan-3-yl)-1H-pyrrolo[3,2-b]pyridine-6-carboxamide | 464 | 50 |
| 38 | 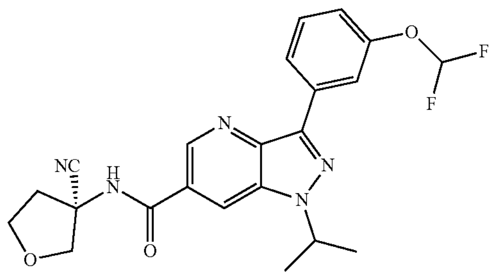 [SMILES: CC(C)n1nc(-c2cccc(OC(F)F)c2)c2ncc(C(=O)N[C@]3(C#N)CCOC3)cc21] | N-[(3S)-3-cyanotetrahydrofuran-3-yl]-3-[3-(difluoromethoxy)phenyl]-1-isopropyl-pyrazolo[4,3-b]pyridine-6-carboxamide | 442 | 11 |
| 39a | 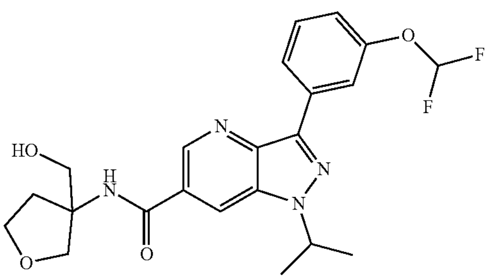 [SMILES: CC(C)n1nc(-c2cccc(OC(F)F)c2)c2ncc(C(=O)NC3(CO)CCOC3)cc21] | 3-[3-(difluoromethoxy)phenyl]-N-[3-(hydroxymethyl)tetrahydrofuran-3-yl]-1-isopropyl-pyrazolo[4,3-b]pyridine-6-carboxamide (faster eluting in OJ-H column, 25% MeOH/CO$_2$) | 447 | 19 |
| 39b | 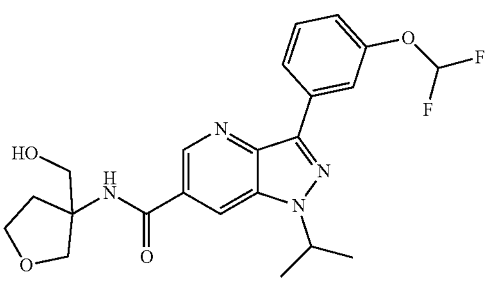 [SMILES: CC(C)n1nc(-c2cccc(OC(F)F)c2)c2ncc(C(=O)NC3(CO)CCOC3)cc21] | 3-[3-(difluoromethoxy)phenyl]-N-[3-(hydroxymethyl)tetrahydrofuran-3-yl]-1-isopropyl-pyrazolo[4,3-b]pyridine-6-carboxamide (slower eluting in OJ-H column, 25% MeOH/CO$_2$) | 447 | 38 |
| 40 | 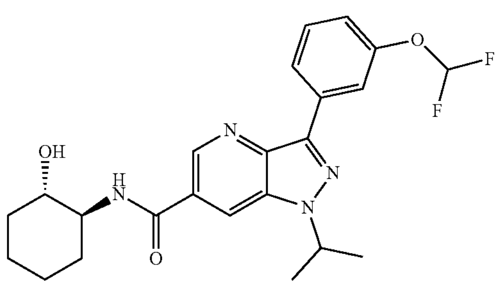 [SMILES: CC(C)n1nc(-c2cccc(OC(F)F)c2)c2ncc(C(=O)N[C@H]3CCCC[C@@H]3O)cc21] | 3-[3-(difluoromethoxy)phenyl]-N-[(1S,2S)-2-hydroxycyclohexyl]-1-isopropyl-pyrazolo[4,3-b]pyridine-6-carboxamide | 445 | 17 |

-continued

| Example | Structure | Name | LCMS [M + 1] | Human DGAT2 IC$_{50}$ (nM) |
|---|---|---|---|---|
| 41 | 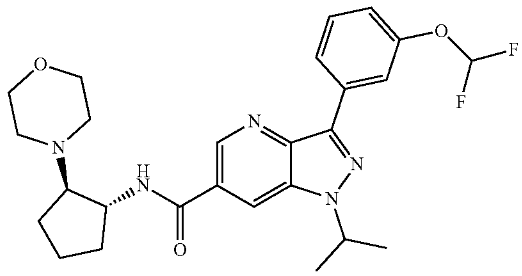 [SMILES: CC(C)n1nc(-c2cccc(OC(F)F)c2)c2ncc(C(=O)N[C@@H]3CCC[C@H]3N3CCOCC3)cc21] | 3-[3-(difluoromethoxy)phenyl]-1-isopropyl-N-[(1R,2R)-2-morpholinocyclopentyl]pyrazolo[4,3-b]pyridine-6-carboxamide | 500 | 72 |
| 42 | 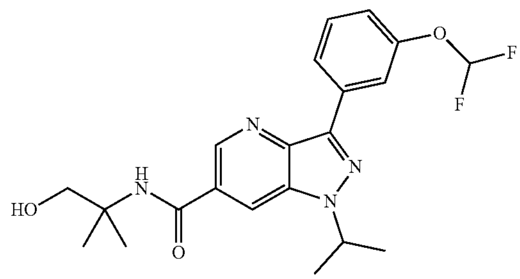 | 3-(3-(difluoromethoxy)phenyl)-N-(1-hydroxy-2-methylpropan-2-yl)-1-isopropyl-1H-pyrazolo[4,3-b]pyridine-6-carboxamide | 419 | 38 |
| 43 | 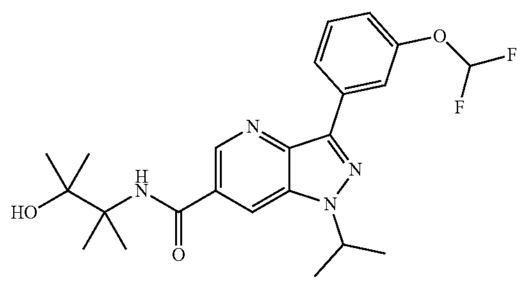 [SMILES: CC(C)n1nc(-c2cccc(OC(F)F)c2)c2ncc(C(=O)NC(C)(C)C(C)(C)O)cc21] | 3-(3-(difluoromethoxy)phenyl)-N-(3-hydroxy-2,3-dimethylbutan-2-yl)-1-isopropyl-1H-pyrazolo[4,3-b]pyridine-6-carboxamide | 447 | 148 |
| 44 | 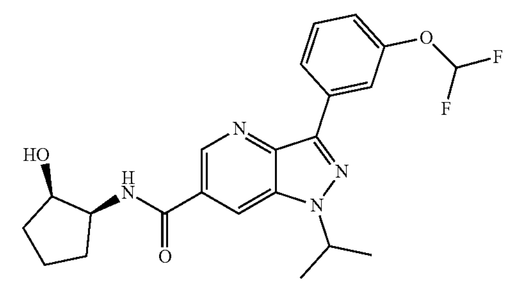 [SMILES: CC(C)n1nc(-c2cccc(OC(F)F)c2)c2ncc(C(=O)N[C@H]3CCC[C@H]3O)cc21] | 3-(3-(difluoromethoxy)phenyl)-N-((1S,2R)-2-hydroxycydopentyl)-1-isopropyl-1H-pyrazolo[4,3-b]pyridine-6-carboxamide | 431 | 64 |
| 45a | 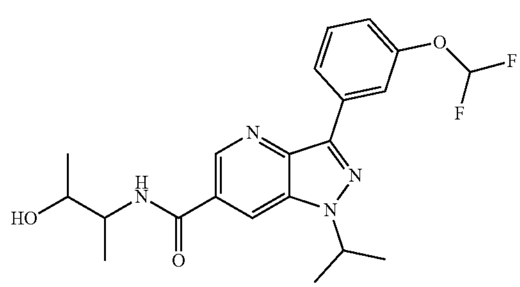 | 3-(3-(difluoromethoxy)phenyl)-N-(3-hydroxybutan-2-yl)-1-isopropyl-1H-pyrazolo[4,3-b]pyridme-6-carboxamide (1$^{st}$ faster eluting in AD-H column, 40% MeOH/CO$_2$) | 419 | 23 |

-continued

| Example | Structure | Name | LCMS [M + 1] | Human DGAT2 IC$_{50}$ (nM) |
| --- | --- | --- | --- | --- |
| 45b | 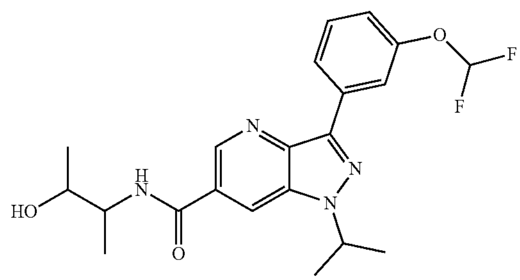 | 3-(3-(difluoromethoxy)phenyl)-N-(3-hydroxybutan-2-yl)-1-isopropyl-1H-pyrazolo[4,3-b]pyridine-6-carboxamide (2$^{nd}$ faster eluting in AD-H column, 40% MeOH/CO$_2$) | 419 | 520 |
| 45c | 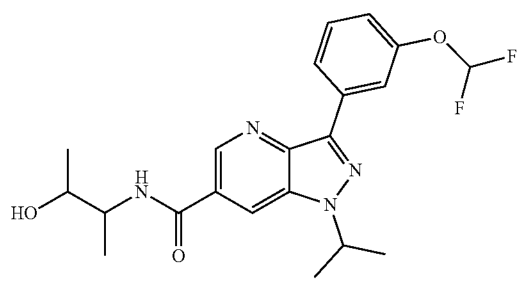 [SMILES: CC(O)C(C)NC(=O)c1cnc2c(-c3cccc(OC(F)F)c3)nn(C(C)C)c2c1] | 3-(3-(difluoromethoxy)phenyl)-N-(3-hydroxybutan-2-yl)-1-isopropyl-1H-pyrazolo[4,3-b]pyridine-6-carboxamide (3$^{rd}$ faster eluting in AD-H column, 40% MeOH/CO$_2$) | 419 | 498 |
| 45d | 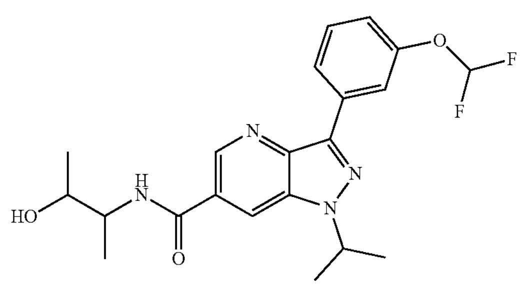 | 3-(3-(difluoromethoxy)phenyl)-N-(3-hydroxybutan-2-yl)-1-isopropyl-1H-pyrazolo[4,3-b]pyridine-6-carboxamide (slower eluting (last eluting) in AD-H column, 40% MeOH/CO$_2$) | 419 | 2725 |
| 46a | 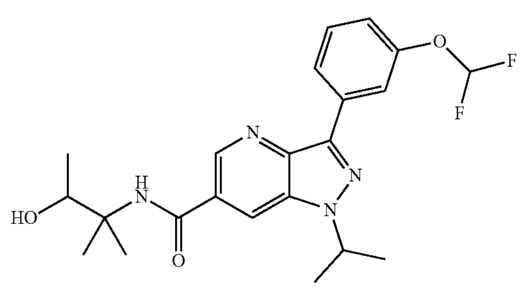 [SMILES: CC(C)n1nc(-c2cccc(OC(F)F)c2)c2ncc(C(=O)NC(C)(C)C(C)O)cc21] | 3-(3-(difluoromethoxy)phenyl)-N-(3-hydroxy-2-methylbutan-2-yl)-1-isopropyl-1H-pyrazolo[4,3-b]pyridine-6-carboxamide (faster eluting in OJ-H column, 25% MeOH/CO$_2$) | 433 | 15 |
| 46b | 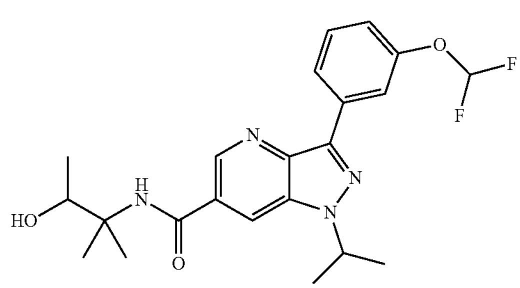 [SMILES: CC(C)n1nc(-c2cccc(OC(F)F)c2)c2ncc(C(=O)NC(C)(C)C(C)O)cc21] | 3-(3-(difluoromethoxy)phenyl)-N-(3-hydroxy-2-methylbutan-2-yl)-1-isopropyl-1H-pyrazolo[4,3-b]pyridine-6-carboxamide (slower eluting in OJ-H column, 25% MeOH/CO$_2$) | 433 | 13 |

-continued

| Example | Structure | Name | LCMS [M + 1] | Human DGAT2 IC$_{50}$ (nM) |
|---|---|---|---|---|
| 47a | 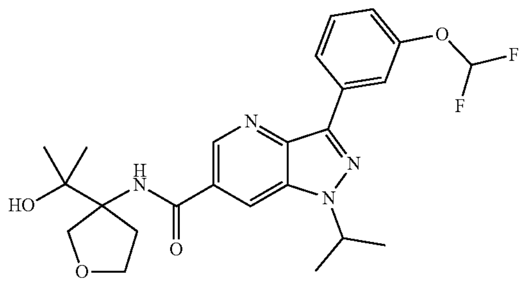 [SMILES: CC(C)n1nc(-c2cccc(OC(F)F)c2)c2ncc(C(=O)NC3(C(C)(C)O)CCOC3)cc21] | 3-(3-(difluoromethoxy)phenyl)-N-(3-(2-hydroxypropan-2-yl)tetrahydrofuran-3-yl)-1-isopropyl-1H-pyrazolo[4,3-b]pyridine-6-carboxamide (faster eluting in OD-H column, 25% MeOH/CO$_2$) | 475 | 1415 |
| 47b | 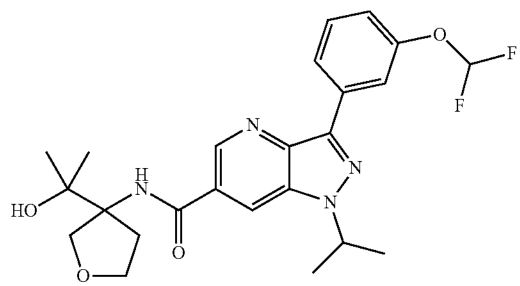 | 3-(3-(difluoromethoxy)phenyl)-N-(3-(2-hydroxypropan-2-yl)tetrahydrofuran-3-yl)-1-isopropyl-1H-pyrazolo[4,3-b]pyridine-6-carboxamide (slower eluting in OD-H column, 25% MeOH/CO$_2$) | 475 | 50 |
| 48a | 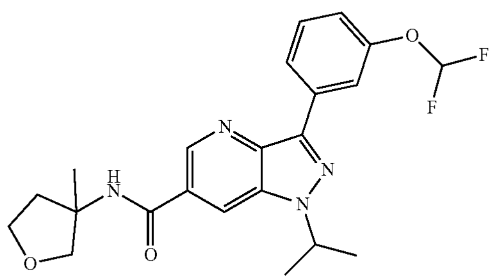 | 3-(3-(difluoromethoxy)phenyl)-1-isopropyl-N-(3-methyltetrahydrofuran-3-yl)-1H-pyrazolo[4,3-b]pyridine-6-carboxamide (faster eluting in OD-H column, 25% MeOH/CO$_2$) | 431 | 6.3 |
| 48b | 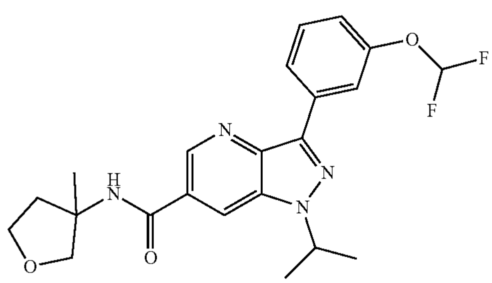 | 3-(3-(difluoromethoxy)phenyl)-1-isopropyl-N-(3-methyltetrahydrofuran-3-yl)-1H-pyrazolo[4,3-b]pyridine-6-carboxamide (slower eluting in OD-H column, 25% MeOH/CO$_2$) | 431 | 16 |
| 49 | 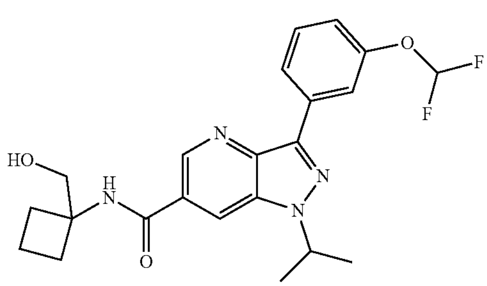 [SMILES: CC(C)n1nc(-c2cccc(OC(F)F)c2)c2ncc(C(=O)NC3(CO)CCC3)cc21] | 3-(3-(difluoromethoxy)phenyl)-N-(1-(hydroxymethyl)cyclobutyl)-1-isopropyl-1H-pyrazolo[4,3-b]pyridine-6-carboxamide | 431 | 6.1 |

-continued

| Example | Structure | Name | LCMS [M + 1] | Human DGAT2 IC$_{50}$ (nM) |
|---|---|---|---|---|
| 50a | 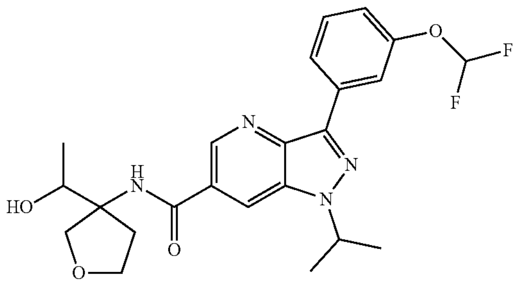 [SMILES: CC(C)n1nc(-c2cccc(OC(F)F)c2)c2ncc(C(=O)NC3(C(C)O)CCOC3)cc21] | 3-(3-(difluoromethoxy)phenyl)-N-(3-(1-hydroxyethyl)tetrahydrofuran-3-yl)-1-isopropyl-1H-pyrazolo[4,3-b]pyridine-6-carboxamide (1$^{st}$ faster eluting in OJ-H column, 30% MeOH/CO$_2$) | 461 | 132 |
| 50b | 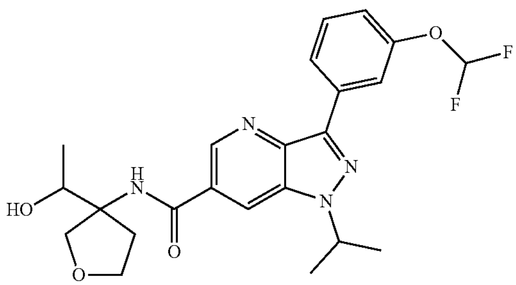 [SMILES: CC(C)n1nc(-c2cccc(OC(F)F)c2)c2ncc(C(=O)NC3(C(C)O)CCOC3)cc21] | 3-(3-(difluoromethoxy)phenyl)-N-(3-(1-hydroxyethyl)tetrahydrofuran-3-yl)-1-isopropyl-1H-pyrazolo[4,3-b]pyridine-6-carboxamide (2$^{nd}$ faster eluting in OJ-H column, 30% MeOH/CO$_2$) | 461 | 31 |
| 50c | 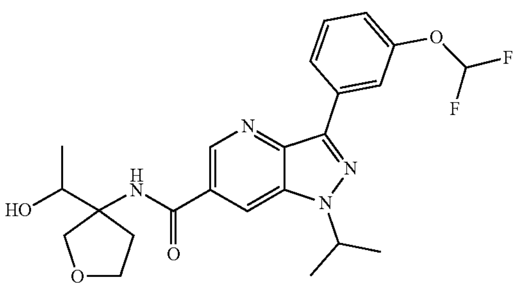 [SMILES: CC(C)n1nc(-c2cccc(OC(F)F)c2)c2ncc(C(=O)NC3(C(C)O)CCOC3)cc21] | 3-(3-(difluoromethoxy)phenyl)-N-(3-(1-hydroxyethyl)tetrahydrofuran-3-yl)-1-isopropyl-1H-pyrazolo[4,3-b]pyridine-6-carboxamide (3$^{rd}$ faster eluting in OJ-H column, 30% MeOH/CO$_2$) | 461 | 108 |
| 50d | 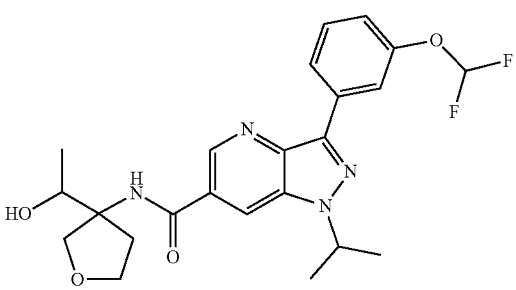 [SMILES: CC(C)n1nc(-c2cccc(OC(F)F)c2)c2ncc(C(=O)NC3(C(C)O)CCOC3)cc21] | 3-(3-(difluoromethoxy)phenyl)-N-(3-(1-hydroxyethyl)tetrahydrofuran-3-yl)-1-isopropyl-1H-pyrazolo[4,3-b]pyridine-6-carboxamide (slowest eluting in OJ-H column, 30% MeOH/CO$_2$) | 461 | 150 |
| 51 | 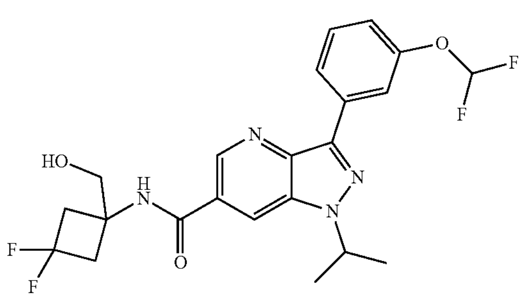 [SMILES: CC(C)n1nc(-c2cccc(OC(F)F)c2)c2ncc(C(=O)NC3(CO)CC(F)(F)C3)cc21] | N-(3,3-difluoro-1-(hydroxymethyl)cyclobutyl)-3-(3-(difluoromethoxy)phenyl)-1-isopropyl-1H-pyrazolo[4,3-b]pyridine-6-carboxamide | 467 | 17 |

-continued

| Example | Structure | Name | LCMS [M + 1] | Human DGAT2 IC$_{50}$ (nM) |
|---|---|---|---|---|
| 52 | 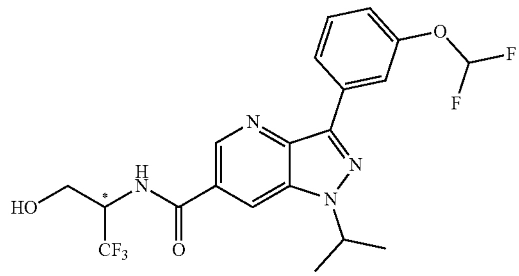 [SMILES: CC(C)n1nc(-c2cccc(OC(F)F)c2)c2ncc(C(=O)NC(CO)C(F)(F)F)cc21] | 3-(3-(difluoromethoxy)phenyl)-1-isopropyl-N-(1,1,1-trifluoro-3-hydroxypropan-2-yl)-1H-pyrazolo[4,3-b]pyridine-6-carboxamide(racemic mixture) | 459 | 41 |
| 53a | 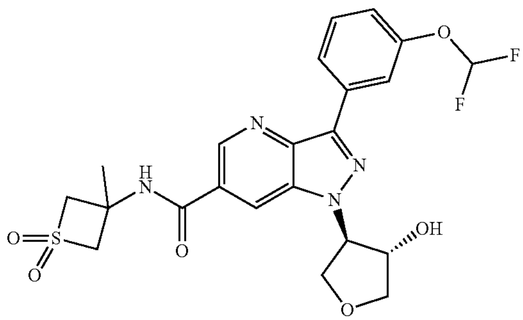 [SMILES: CC1(NC(=O)c2cnc3c(-c4cccc(OC(F)F)c4)nn([C@@H]4COC[C@H]4O)c3c2)CS(=O)(=O)C1] | 3-(3-(difluoromethoxy)phenyl)-1-((trans)-4-hydroxytetrahydrofuran-3-yl)-N-(3-methyl-1,1-dioxidothietan-3-yl)-1H-pyrazolo[4,3-b]pyridine-6-carboxamide (faster eluting in OJ-H column, 20% MeOH/CO$_2$) | 509 | 16 |
| 53b | 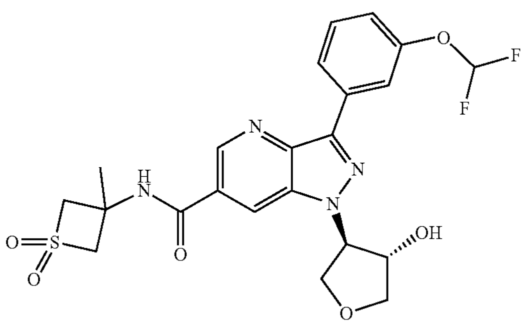 [SMILES: CC1(NC(=O)c2cnc3c(-c4cccc(OC(F)F)c4)nn([C@@H]4COC[C@H]4O)c3c2)CS(=O)(=O)C1] | 3-(3-(difluoromethoxy)phenyl)-1-((trans)-4-hydroxytetrahydrofuran-3-yl)-N-(3-methyl-1,1-dioxidothietan-3-yl)-1H-pyrazolo[4,3-b]pyridine-6-carboxamide (slower eluting in OJ-H column, 20% MeOH/CO$_2$) | 509 | 132 |
| 54 | 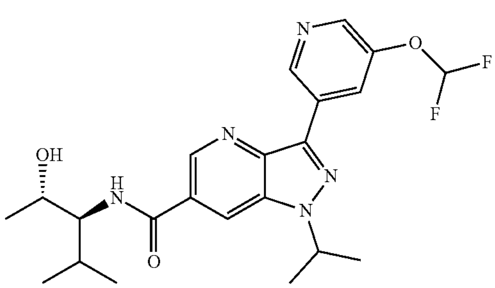 [SMILES: CC(C)[C@H](NC(=O)c1cnc2c(-c3cncc(OC(F)F)c3)nn(C(C)C)c2c1)[C@H](C)O] | 3-(5-(difluoromethoxy)pyridin-3-yl)-N-((2S,3S)-2-hydroxy-4-methylpentan-3-yl)-1-isopropyl-1H-pyrazolo[4,3-b]pyridine-6-carboxamide | 448 | 13 |

-continued

| Example | Structure | Name | LCMS [M + 1] | Human DGAT2 IC$_{50}$ (nM) |
|---|---|---|---|---|
| 55 | 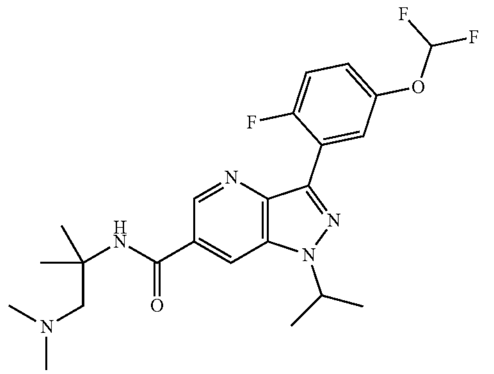 [SMILES: CC(C)n1nc(-c2cc(OC(F)F)ccc2F)c2ncc(C(=O)NC(C)(C)CN(C)C)cc21] | 3-(5-(difluoromethoxy)-2-fluorophenyl)-N-(1-(dimethylamino)-2-methylpropan-2-yl)-1-isopropyl-1H-pyrazolo[4,3-b]pyridine-6-carboxamide | 464 | 212 |
| 56 | 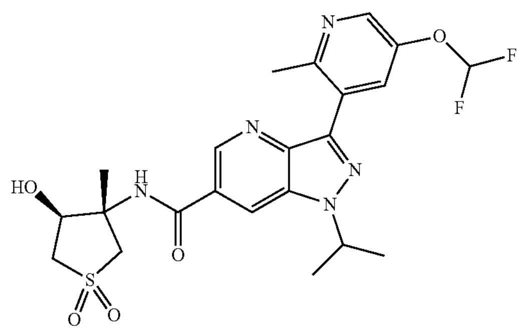 [SMILES: Cc1ncc(OC(F)F)cc1-c1nn(C(C)C)c2cc(C(=O)N[C@]3(C)CS(=O)(=O)C[C@H]3O)cnc12] | 3-(5-(difluoromethoxy)-2-methylpyridin-3-yl)-N-((3S,4S)-4-hydroxy-3-methyl-1,1-dioxidotetrahydrothiophen-3-yl)-1-isopropyl-1H-pyrazolo[4,3-b]pyridine-6-carboxamide | 510 | 209 |
| 57 | 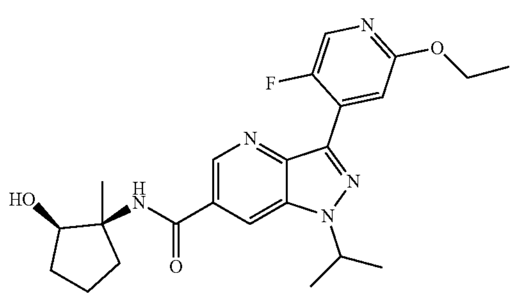 [SMILES: CCOc1cc(-c2nn(C(C)C)c3cc(C(=O)N[C@@]4(C)CCC[C@H]4O)cnc23)c(F)cn1] | 3-(2-ethoxy-5-fluoropyridin-4-yl)-N-((1S,2R)-2-hydroxy-1-methylcyclopentyl)-1-isopropyl-1H-pyrazolo[4,3-b]pyridine-6-carboxamide | 442 | 15 |
| 58 | 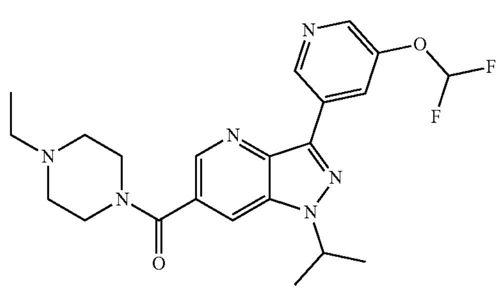 [SMILES: CCN1CCN(C(=O)c2cnc3c(-c4cncc(OC(F)F)c4)nn(C(C)C)c3c2)CC1] | (3-(5-(difluoromethoxy)pyridin-3-yl)-1-isopropyl-1H-pyrazolo[4,3-b]pyridin-6-yl)(4-ethylpiperazin-1-yl)methanone | 445 | >1000 |

Example 59: 1-cyclobutyl-3-(3-(difluoromethoxy)phenyl)-N-(3-methyl-1,1-dioxidothietan-3-yl)-1H-pyrazolo[4,3-b]pyridine-6-carboxamide

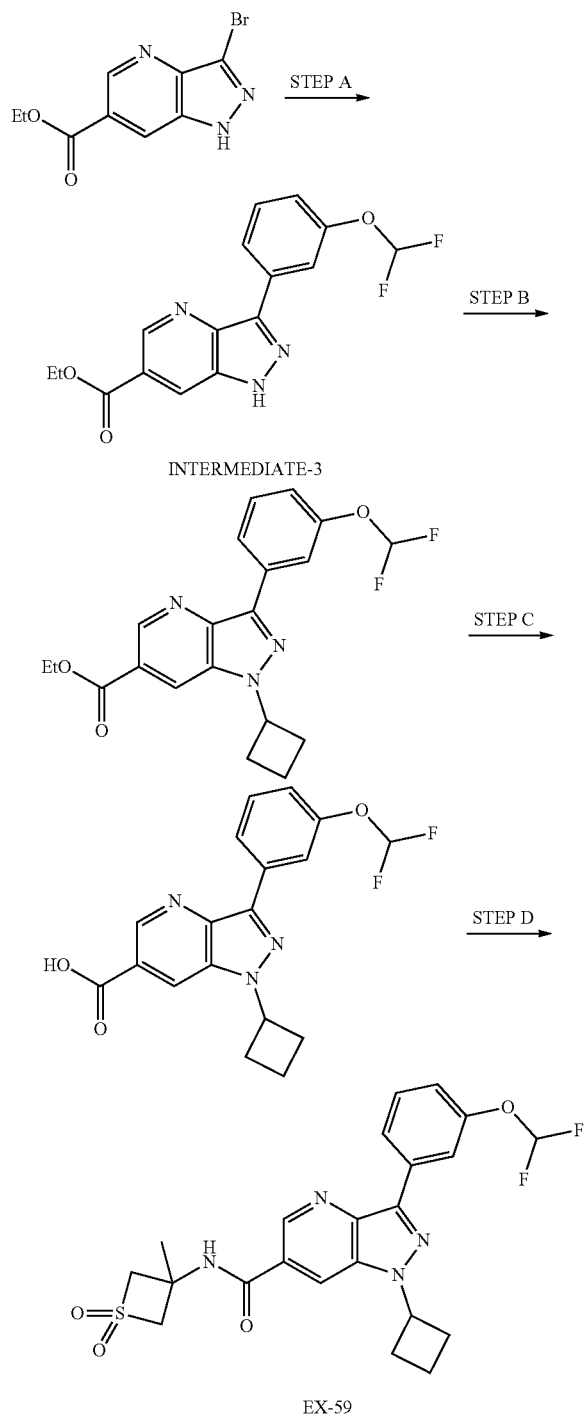

INTERMEDIATE-3

EX-59

Step A: Ethyl 3-(3-(difluoromethoxy)phenyl)-1H-pyrazolo[4,3-b]pyridine-6-carboxylate (Intermediate-3)

To a mixture of (3-(difluoromethoxy)phenyl)boronic acid (1.50 g, 7.97 mmol), ethyl 3-bromo-1H-pyrazolo[4,3-b]pyridine-6-carboxylate (1.96 g, 7.25 mmol), Pd(dppf)Cl$_2$ (1.33 g, 1.81 mmol), and Na$_2$CO$_3$ (1.54 g, 14.5 mmol) was added dioxane (58 mL), and water (15 mL). The reaction mixture was heated to 100° C. for 24 h, then cooled to RT and filtered. The resulting mixture was concentrated directly onto silica gel and purified by flash silica gel column chromatography (0-100% EtOAc/hexanes) to afford the title compound LC/MS=334 [M+1].

Step B: Ethyl 1-cyclobutyl-3-(3-(difluoromethoxy)phenyl)-1H-pyrazolo[4,3-b]pyridine-6-carboxylate To a mixture of ethyl 3-(3-(difluoromethoxy)phenyl)-1H-pyrazolo[4,3-b]pyridine-6-carboxylate (0.150 g, 0.45 mmol) and K$_3$CO$_2$ (0.124 g, 0.90 mmol) in DMF (1.5 mL) was added bromocyclobutane (0.079 g, 0.59 mmol). The reaction mixture was heated to 80° C. for 24 h, then cooled to RT and concentrated directly onto silica gel. The crude product was purified by flash silica gel column chromatography (0-100% EtOAc/hexanes) to afford the title compound. LC/MS=388 [M+1].

Step C: 1-Cyclobutyl-3-(3-(difluoromethoxy)phenyl)-1H-pyrazolo[4,3-b]pyridine-6-carboxylic acid To a solution of ethyl 1-cyclobutyl-3-(3-(difluoromethoxy)phenyl)-1H-pyrazolo[4,3-b]pyridine-6-carboxylate (0.091 g, 0.24 mmol) in THF (1.2 mL) was added 1 M aq. sodium hydroxide (2.40 mL, 2.40 mmol). The reaction was stirred at RT for 16 h, then concentrated to afford the crude title compound. LC/MS=360 [M+1].

Step D: 1-Cyclobutyl-3-(3-(difluoromethoxy)phenyl)-N-(3-methyl-1,1-dioxidothietan-3-yl)-1H-pyrazolo[4,3-b]pyridine-6-carboxamide To a solution of 1-cyclobutyl-3-(3-(difluoromethoxy)phenyl)-1H-pyrazolo[4,3-b]pyridine-6-carboxylic acid (0.084 g, 0.24 mmol), 3-amino-3-methylthietane 1,1-dioxide hydrochloride (52 mg, 0.31 mmol), and HATU (0.18 g, 0.47 mmol) in DMF (1.0 mL) was added DIPEA (0.12 mL, 0.71 mmol). The reaction mixture was stirred for 1 h, then filtered and purified by mass triggered reverse phase HPLC (ACN/water with 0.1% formic acid modifier) to afford the title compound. LC/MS=477 [M+1]. $^1$H NMR (600 MHz, Methanol-d4) δ 8.93 (d, J=1.9 Hz, 1H), 8.63 (d, J=1.9 Hz, 1H), 7.66 (q, J=7.9 Hz, 2H), 7.54 (d, J=7.9 Hz, 1H), 7.48 (s, 1H), 7.37 (dd, J=8.3, 2.1 Hz, 1H), 6.98 (t, J=73.7 Hz, 1H), 4.64 (d, J=14.7 Hz, 2H), 4.45 (d, J=7.1 Hz, 2H), 4.28-4.24 (m, 2H), 1.87 (s, 3H), 1.32 (ddt, J=12.4, 7.6, 3.8 Hz, 1H), 0.61-0.51 (m, 2H), 0.29 (q, J=4.8 Hz, 2H). Human DGAT2 IC$_{50}$=6.9 nM.

Intermediate 4 for Example 91: Methyl 4-cyano-3-iodo-1H-indazole-6-carboxylate

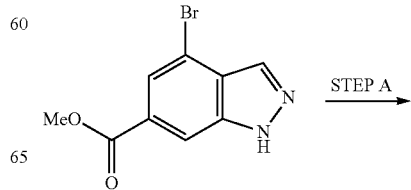

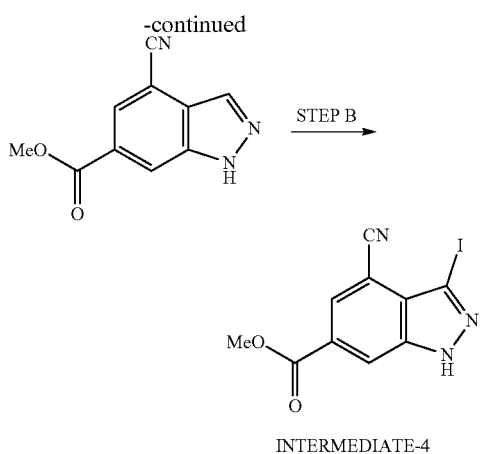

INTERMEDIATE-4

Step A: Methyl 4-cyano-1H-indazole-6-carboxylate

To a mixture of zinc cyanide (121 mg, 1.03 mmol), methyl 4-bromo-1H-indazole-6-carboxylate (263 mg, 1.03 mmol), and zinc (20.3 mg, 0.31 mmol) in DMF (5.2 mL) was added Pd(dppf)Cl$_2$ (169 mg, 0.20 mmol), and the resulting mixture was heated to 120° C. for 16 h. The reaction was cooled to room temperature, and then diluted with EtOAc, washed with sat. aq. NaHCO$_3$, and concentrated in vacuo. Purification by flash silica gel chromatography (0-100% EtOAc/hexanes) afforded the title compound. LC/MS=202 [M+1].

Step B: Methyl 4-cyano-3-iodo-1H-indazole-6-carboxylate

A solution of NIS (168 mg, 0.746 mmol) and methyl 4-cyano-1H-indazole-6-carboxylate (120 mg, 0.596 mmol) in DMF (3.0 mL) was heated to 80° C. for 8 h. The reaction mixture was cooled to RT, and water was added. The precipitate was collected by filtration to afford the crude title compound. LC/MS=327 [M+1].

By using procedures similar to those described in Example 59 with appropriate reagents, the following compounds were synthesized. These compounds were characterized by LC/MS.

| Example | Structure | Name | LCMS [M + 1] | Human DGAT2 IC$_{50}$ (nM) |
|---|---|---|---|---|
| 60a | 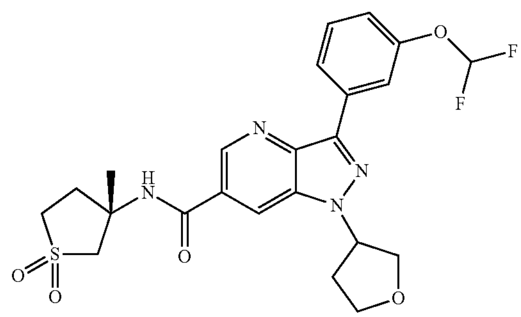 [SMILES: C[C@]1(NC(=O)c2cnc3c(-c4cccc(OC(F)F)c4)nn(C4CCOC4)c3c2)CCS(=O)(=O)C1] | 3-[3-(difluoromethoxy)phenyl]-N-[(3S)-3-methyl-1,1-dioxo-thiolan-3-yl]-1-tetrahydrofuran-3-yl-pyrazolo[4,3-b]pyridine-6-carboxamide (faster eluting in AS-H column, 25% iPrOH/CO$_2$) | 507 | 600 |
| 60b | 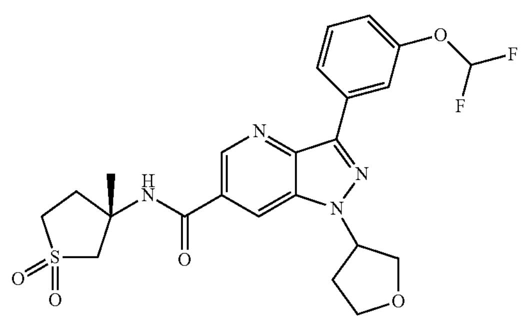 [SMILES: C[C@]1(NC(=O)c2cnc3c(-c4cccc(OC(F)F)c4)nn(C4CCOC4)c3c2)CCS(=O)(=O)C1] | 3-[3-(difluoromethoxy)phenyl]-N-[(3S)-3-methyl-1,1-dioxo-thiolan-3-yl]-1-tetrahydrofuran-3-yl-pyrazolo[4,3-b]pyridine-6-carboxamide (slower eluting in AS-H column, 25% iPrOH/CO$_2$) | 507 | 37 |
| 61 | 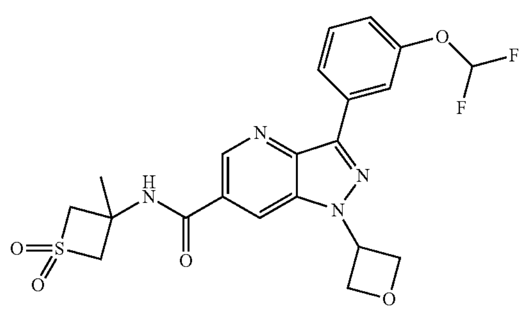 [SMILES: CC1(NC(=O)c2cnc3c(-c4cccc(OC(F)F)c4)nn(C4COC4)c3c2)CS(=O)(=O)C1] | 3-[3-(difluoromethoxy)phenyl]-N-(3-methyl-1,1-dioxo-thietan-3-yl)-1-(oxetan-3-yl)pyrazolo[4,3-b]pyridine-6-carboxamide | 479 | 65 |

| Example | Structure | Name | LCMS [M + 1] | Human DGAT2 IC$_{50}$ (nM) |
|---|---|---|---|---|
| 62a | 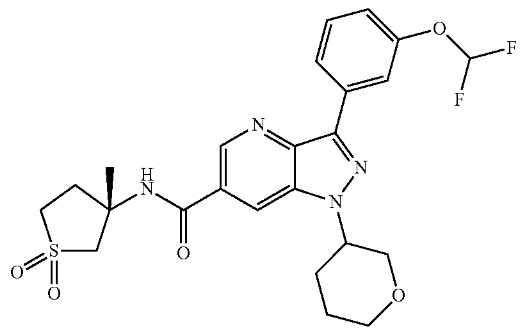 [SMILES: C[C@]1(NC(=O)c2cnc3c(-c4cccc(OC(F)F)c4)nn(C4CCCOC4)c3c2)CCS(=O)(=O)C1] | 3-[3-(difluoromethoxy)phenyl]-N-[(3S)-3-methyl-1,1-dioxo-thiolan-3-yl]-1-tetrahydropyran-3-yl-pyrazolo[4,3-b]pyridine-6-carboxamide (faster eluting in AD-H column, 30% MeOH/CO$_2$) | 521 | 59 |
| 62b | 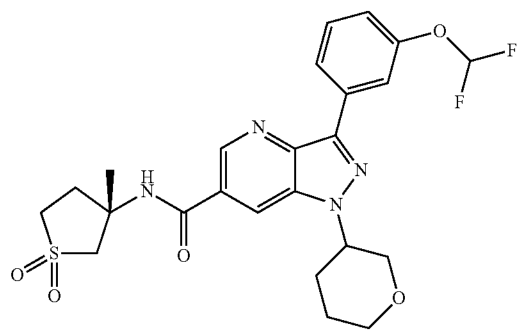 [SMILES: C[C@]1(NC(=O)c2cnc3c(-c4cccc(OC(F)F)c4)nn(C4CCCOC4)c3c2)CCS(=O)(=O)C1] | 3-[3-(difluoromethoxy)phenyl]-N-[(3S)-3-methyl-1,1-dioxo-thiolan-3-yl]-1-tetrahydropyran-3-yl-pyrazolo[4,3-b]pyridine-6-carboxamide (slower eluting in AD-H column, 30% MeOH/CO$_2$) | 521 | 116 |
| 63 | 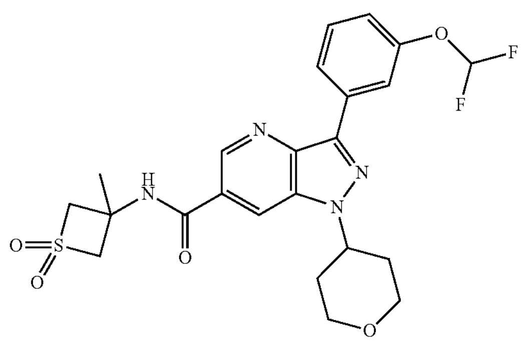 [SMILES: CC1(NC(=O)c2cnc3c(-c4cccc(OC(F)F)c4)nn(C4CCOCC4)c3c2)CS(=O)(=O)C1] | 3-(3-(difluoromethoxy)phenyl)-N-(3-methyl-1,1-dioxidothietan-3-yl)-1-(tetrahydro-2H-pyran-4-yl)-1H-pyrazolo[4,3-b]pyridine-6-carboxamide | 507 | 18 |
| 64 | 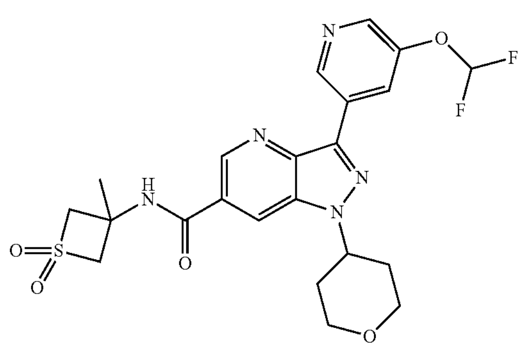 [SMILES: CC1(NC(=O)c2cnc3c(-c4cncc(OC(F)F)c4)nn(C4CCOCC4)c3c2)CS(=O)(=O)C1] | 3-[5-(difluoromethoxy)-3-pyridyl]-N-(3-methyl-1,1-dioxo-thietan-3-yl)-1-tetrahydropyran-4-yl-pyrazolo[4,3-b]pyridine-6-carboxamide | 507 | 177 |

-continued

| Example | Structure | Name | LCMS [M + 1] | Human DGAT2 IC$_{50}$ (nM) |
|---|---|---|---|---|
| 65 | 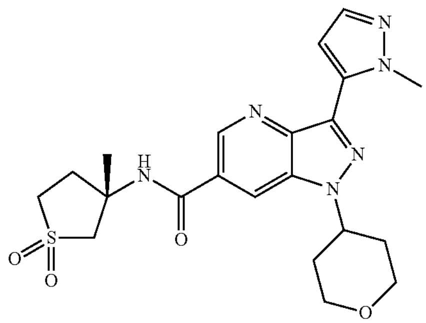 [SMILES: Cn1nccc1-c1nn(C2CCOCC2)c2cc(C(=O)N[C@@]3(C)CCS(=O)(=O)C3)cnc12] | N-[(3S)-3-methyl-1,1-dioxo-thiolan-3-yl]-3-(2-methylpyrazol-3-yl)-1-tetrahydropyran-4-yl-pyrazolo[4,3-b]pyridine-6-carboxamide | 458 | 10000 |
| 66a | 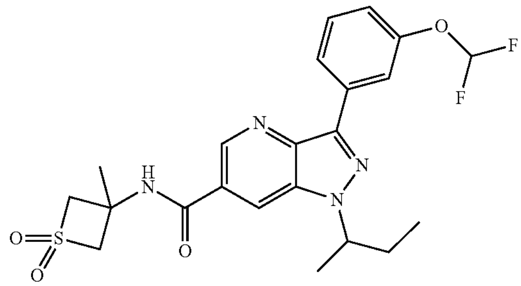 [SMILES: CCC(C)n1nc(-c2cccc(OC(F)F)c2)c2ncc(C(=O)NC3(C)CS(=O)(=O)C3)cc21] | 3-[3-(difluoromethoxy)phenyl]-N-(3-methyl-1,1-dioxo-thietan-3-yl)-1-sec-butyl-pyrazolo[4,3-b]pyridine-6-carboxamide (faster eluting in AD-H column, 20% MeOH/CO$_2$) | 479 | 71 |
| 66b | 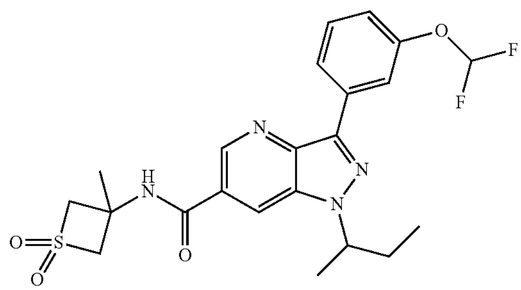 [SMILES: CCC(C)n1nc(-c2cccc(OC(F)F)c2)c2ncc(C(=O)NC3(C)CS(=O)(=O)C3)cc21] | 3-[3-(difluoromethoxy)phenyl]-N-(3-methyl-1,1-dioxo-thietan-3-yl)-1-sec-butyl-pyrazolo[4,3-b]pyridine-6-carboxamide (slower eluting in AD-H column, 20% MeOH/CO$_2$) | 479 | 1.5 |
| 67a | 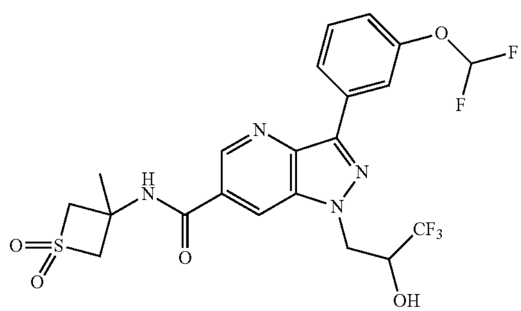 [SMILES: CC1(NC(=O)c2cnc3c(-c4cccc(OC(F)F)c4)nn(CC(O)C(F)(F)F)c3c2)CS(=O)(=O)C1] | 3-(3-(difluoromethoxy)phenyl)-N-(3-methyl-1,1-dioxidothietan-3-yl)-1-(3,3,3-trifluoro-2-hydroxypropyl)-1H-pyrazolo[4,3-b]pyridine-6-carboxamide (faster eluting in AD-H column, 20% MeOH/CO$_2$) | 535 | 73 |
| 67b | 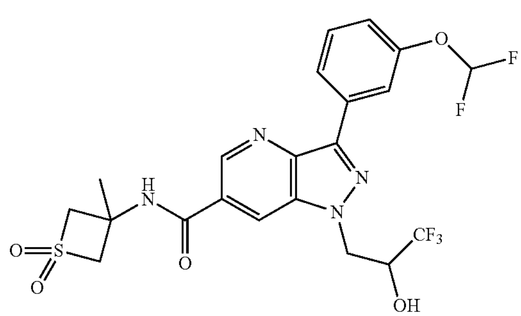 | 3-(3-(difluoromethoxy)phenyl)-N-(3-methyl-1,1-dioxidothietan-3-yl)-1-(3,3,3-trifluoro-2-hydroxypropyl)-1H-pyrazolo[4,3-b]pyridine-6-carboxamide (slower eluting in AD-H column, 20% MeOH/CO$_2$) | 535 | 90 |

| Example | Structure | Name | LCMS [M + 1] | Human DGAT2 IC$_{50}$ (nM) |
|---|---|---|---|---|
| 68a | 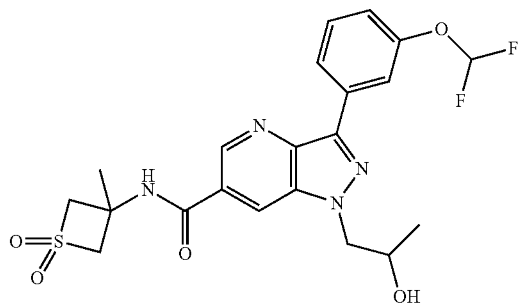 [SMILES: CC(O)Cn1nc(-c2cccc(OC(F)F)c2)c2ncc(C(=O)NC3(C)CS(=O)(=O)C3)cc21] | 3-(3-(difluoromethoxy)phenyl)-1-(2-hydroxypropyl)-N-(3-methyl-1,1-dioxidothietan-3-yl)-1H-pyrazolo[4,3-b]pyridine-6-carboxamide (faster eluting in AD-H column, 35% MeOH/CO$_2$) | 481 | 18 |
| 68b | 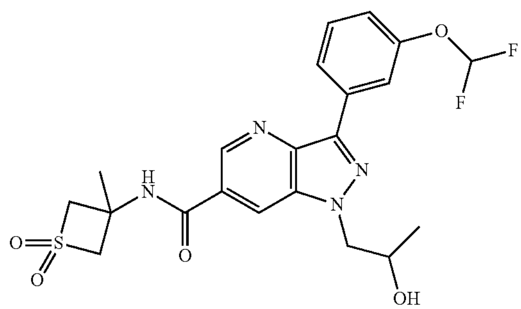 [SMILES: CC(O)Cn1nc(-c2cccc(OC(F)F)c2)c2ncc(C(=O)NC3(C)CS(=O)(=O)C3)cc21] | 3-(3-(difluoromethoxy)phenyl)-1-(2-hydroxypropyl)-N-(3-methyl-1,1-dioxidothietan-3-yl)-1H-pyrazolo[4,3-b]pyridine-6-carboxamide (slower eluting in AD-H column, 35% MeOH/CO$_2$) | 481 | 179 |
| 69 | 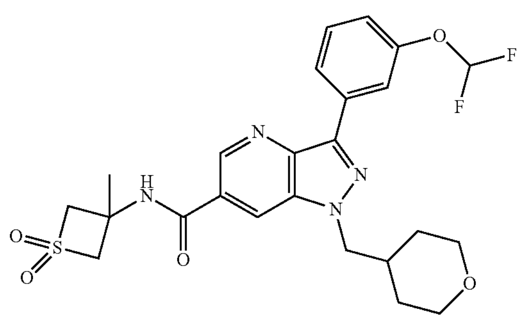 [SMILES: CC1(NC(=O)c2cnc3c(-c4cccc(OC(F)F)c4)nn(CC4CCOCC4)c3c2)CS(=O)(=O)C1] | 3-(3-(difluoromethoxy)phenyl)-N-(3-methyl-1,1-dioxidothietan-3-yl)-1-((tetrahydro-2H-pyran-4-yl)methyl)-1H-pyrazolo[4,3-b]pyridine-6-carboxamide | 521 | 59 |
| 70 | 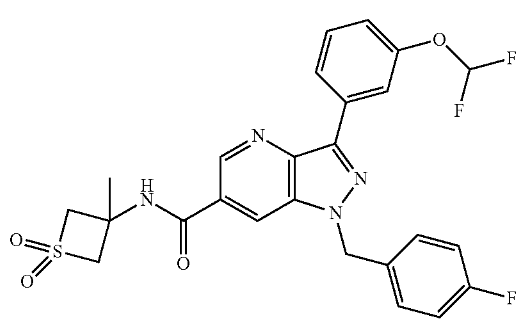 [SMILES: CC1(NC(=O)c2cnc3c(-c4cccc(OC(F)F)c4)nn(Cc4ccc(F)cc4)c3c2)CS(=O)(=O)C1] | 3-(3-(difluoromethoxy)phenyl)-1-(4-fluorobenzyl)-N-(3-methyl-1,1-dioxidothietan-3-yl)-1H-pyrazolo[4,3-b]pyridine-6-carboxamide | 531 | 40 |

| Example | Structure | Name | LCMS [M + 1] | Human DGAT2 IC$_{50}$ (nM) |
|---|---|---|---|---|
| 71 | 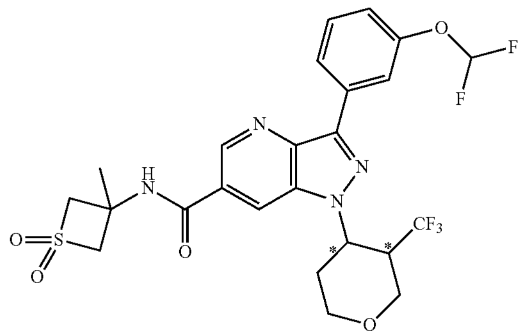 [SMILES: CC1(NC(=O)c2cnc3c(-c4cccc(OC(F)F)c4)nn(C4CCOCC4C(F)(F)F)c3c2)CS(=O)(=O)C1] | 3-(3-(difluoromethoxy)phenyl)-N-(3-methyl-1,1-dioxidothietan-3-yl)-1-(3-(trifluoromethyl)tetrahydro-2H-pyran-4-yl)-1H-pyrazolo[4,3-b]pyridine-6-carboxamide (mixture of diastereomers) | 576 | 95 |
| 72 | 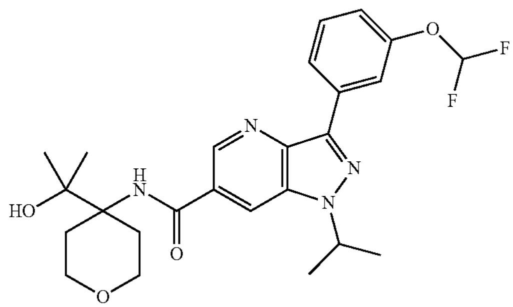 [SMILES: CC(C)n1nc(-c2cccc(OC(F)F)c2)c2ncc(C(=O)NC3(C(C)(C)O)CCOCC3)cc21] | 3-(3-(difluoromethoxy)phenyl)-N-(4-(2-hydroxypropan-2-yl)tetrahydro-2H-pyran-4-yl)-1-isopropyl-1H-pyrazolo[4,3-b]pyridine-6-carboxamide | 490 | 638 |
| 73a | 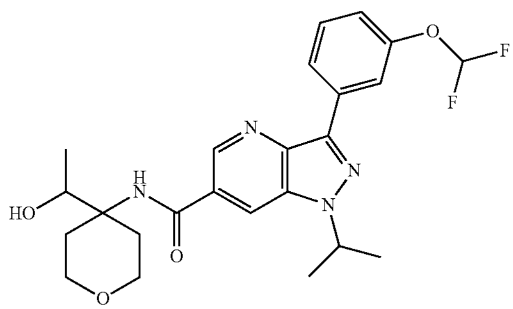 [SMILES: CC(C)n1nc(-c2cccc(OC(F)F)c2)c2ncc(C(=O)NC3(C(C)O)CCOCC3)cc21] | 3-(3-(difluoromethoxy)phenyl)-N-(4-(1-hydroxyethyl)tetrahydro-2H-pyran-4-yl)-1-isopropyl-1H-pyrazolo[4,3-b]pyridine-6-carboxamide (faster eluting in OJ-H column, 25% MeOH/CO$_2$) | 476 | 119 |
| 73b | 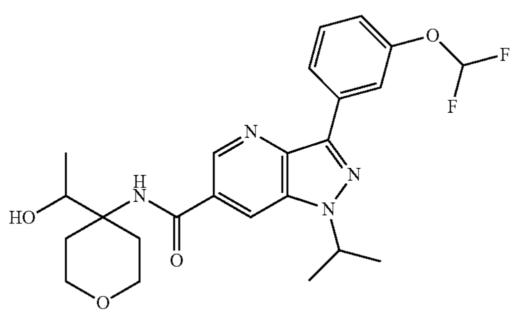 [SMILES: CC(C)n1nc(-c2cccc(OC(F)F)c2)c2ncc(C(=O)NC3(C(C)O)CCOCC3)cc21] | 3-(3-(difluoromethoxy)phenyl)-N-(4-(1-hydroxyethyl)tetrahydro-2H-pyran-4-yl)-1-isopropyl-1H-pyrazolo[4,3-b]pyridine-6-carboxamide (slower eluting in OJ-H column, 35% MeOH/CO$_2$) | 476 | 74 |

| Example | Structure | Name | LCMS [M + 1] | Human DGAT2 IC$_{50}$ (nM) |
|---|---|---|---|---|
| 74 | 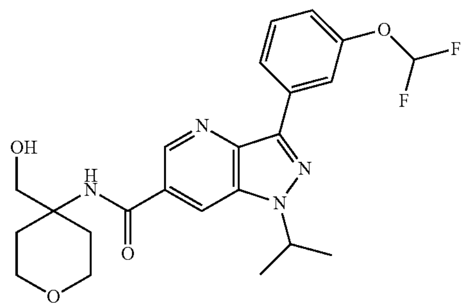 [SMILES: CC(C)n1nc(-c2cccc(OC(F)F)c2)c2ncc(C(=O)NC3(CO)CCOCC3)cc21] | 3-(3-(difluoromethoxy)phenyl)-N-(4-(hydroxymethyl)tetrahydro-2H-pyran-4-yl)-1-isopropyl-1H-pyrazolo[4,3-b]pyridine-6-carboxamide | 461 | 64 |
| 75a | 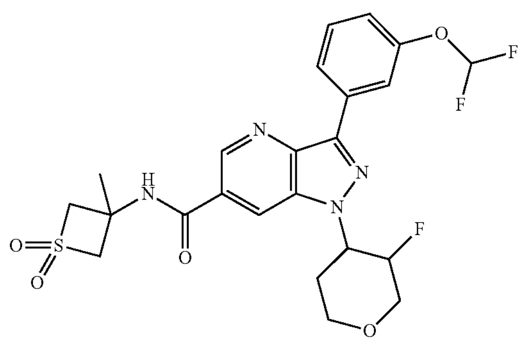 [SMILES: CC1(NC(=O)c2cnc3c(-c4cccc(OC(F)F)c4)nn(C4CCOCC4F)c3c2)CS(=O)(=O)C1] | 3-(3-(difluoromethoxy)phenyl)-1-(3-fluorotetrahydro-2H-pyran-4-yl)-N-(3-methyl-1,1-dioxidothietan-3-yl)-1H-pyrazolo[4,3-b]pyridine-6-carboxamide (faster eluting in IC-H column, 20% MeOH (0.1% DEA)/CO$_2$) | 526 | 29 |
| 75b | 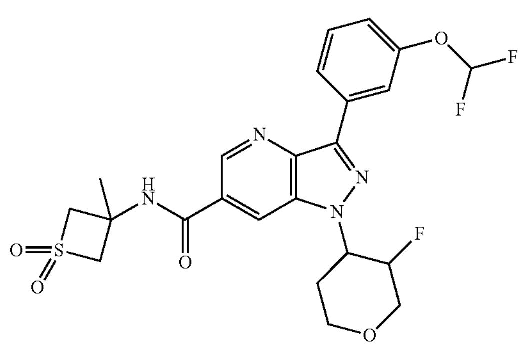 [SMILES: CC1(NC(=O)c2cnc3c(-c4cccc(OC(F)F)c4)nn(C4CCOCC4F)c3c2)CS(=O)(=O)C1] | 3-(3-(difluoromethoxy)phenyl)-1-(3-fluorotetrahydro-2H-pyran-4-yl)-N-(3-methyl-1,1-dioxidothietan-3-yl)-1H-pyrazolo[4,3-b]pyridine-6-carboxamide (slower eluting in IC-H column, 20% MeOH (0.1% DEA)/CO$_2$) | 526 | 9.0 |
| 76a | 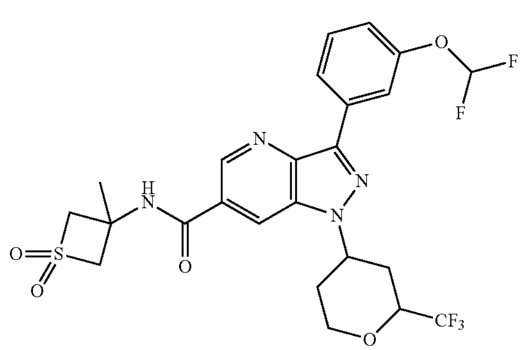 [SMILES: CC1(NC(=O)c2cnc3c(-c4cccc(OC(F)F)c4)nn(C4CCOC(C(F)(F)F)C4)c3c2)CS(=O)(=O)C1] | 3-(3-(difluoromethoxy)phenyl)-N-(3-methyl-1,1-dioxidothietan-3-yl)-1-(2-(trifluoromethyl)tetrahydro-2H-pyran-4-yl)-1H-pyrazolo[4,3-b]pyridine-6-carboxamide (faster eluting in AD-H column, 15% EtOH/CO$_2$) | 576 | 21 |

-continued

| Example | Structure | Name | LCMS [M + 1] | Human DGAT2 IC$_{50}$ (nM) |
|---|---|---|---|---|
| 76b | 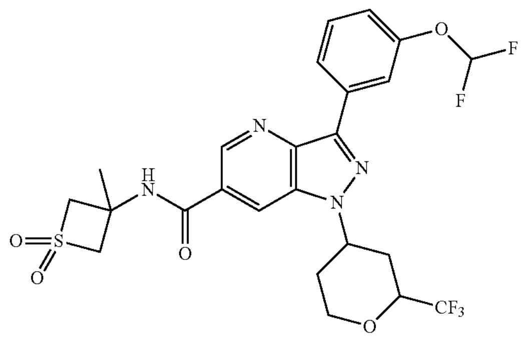 [SMILES: CC1(NC(=O)c2cnc3c(-c4cccc(OC(F)F)c4)nn(C4CCOC(C(F)(F)F)C4)c3c2)CS(=O)(=O)C1] | 3-(3-(difluoromethoxy)phenyl)-N-(3-methyl-1,1-dioxidothietan-3-yl)-1-(2-(trifluoromethyl)tetrahydro-2H-pyran-4-yl)-1H-pyrazolo[4,3-b]pyridine-6-carboxamide (slower eluting in AD-H column, 15% EtOH/CO$_2$) | 576 | 211 |
| 77a | 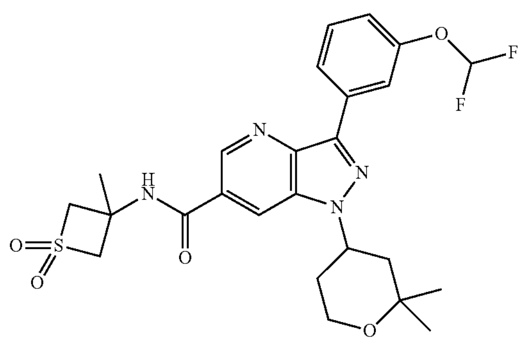 [SMILES: CC1(NC(=O)c2cnc3c(-c4cccc(OC(F)F)c4)nn(C4CCOC(C)(C)C4)c3c2)CS(=O)(=O)C1] | 3-(3-(difluoromethoxy)phenyl)-1-(2,2-dimethyltetrahydro-2H-pyran-4-yl)-N-(3-methyl-1,1-dioxidothietan-3-yl)-1H-pyrazolo[4,3-b]pyridine-6-carboxamide (faster eluting in AD-H column, 15% iPrOH/CO$_2$) | 536 | 140 |
| 77b | 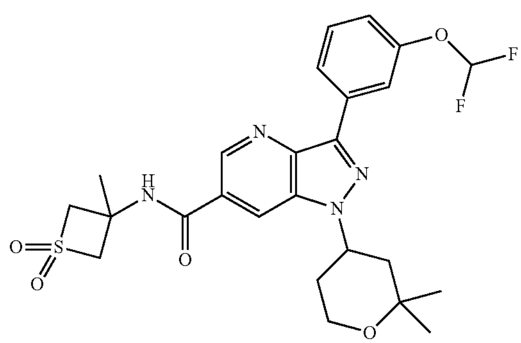 [SMILES: CC1(NC(=O)c2cnc3c(-c4cccc(OC(F)F)c4)nn(C4CCOC(C)(C)C4)c3c2)CS(=O)(=O)C1] | 3-(3-(difluoromethoxy)phenyl)-1-(2,2-dimethyltetrahydro-2H-pyran-4-yl)-N-(3-methyl-1,1-dioxidothietan-3-yl)-1H-pyrazolo[4,3-b]pyridine-6-carboxamide (slower eluting in AD-H column, 15% iPrOH/CO$_2$) | 536 | 7.4 |
| 78a | 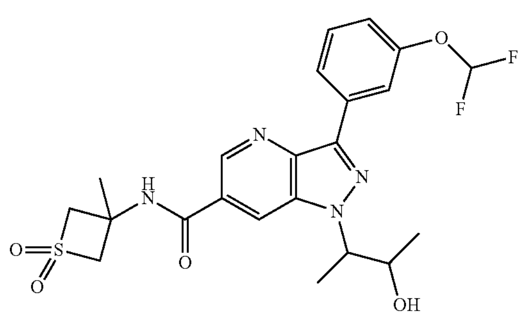 [SMILES: CC(O)C(C)n1nc(-c2cccc(OC(F)F)c2)c2ncc(C(=O)NC3(C)CS(=O)(=O)C3)cc21] | 3-(3-(difluoromethoxy)phenyl)-1-(3-hydroxybutan-2-yl)-N-(3-methyl-1,1-dioxidothietan-3-yl)-1H-pyrazolo[4,3-b]pyridine-6-carboxamide (1$^{st}$ faster eluting in AD-H column, 15% EtOH/CO$_2$) | 496 | 1733 |

| Example | Structure | Name | LCMS [M + 1] | Human DGAT2 IC$_{50}$ (nM) |
|---|---|---|---|---|
| 78b | 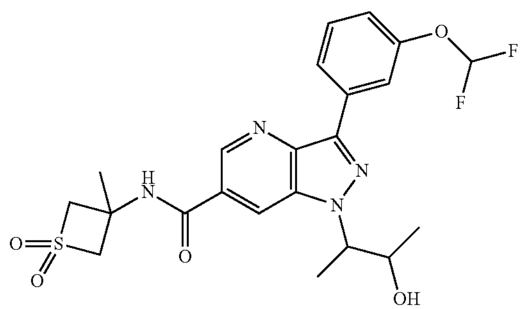 [SMILES: CC(O)C(C)n1nc(-c2cccc(OC(F)F)c2)c2ncc(C(=O)NC3(C)CS(=O)(=O)C3)cc21] | 3-(3-(difluoromethoxy)phenyl)-1-(3-hydroxybutan-2-yl)-N-(3-methyl-1,1-dioxidothietan-3-yl)-1H-pyrazolo[4,3-b]pyridine-6-carboxamide (2$^{nd}$ faster eluting in AD-H column, 15% EtOH/CO$_2$) | 496 | 4.4 |
| 78c | 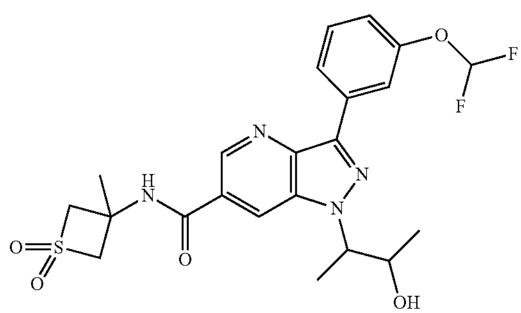 [SMILES: CC(O)C(C)n1nc(-c2cccc(OC(F)F)c2)c2ncc(C(=O)NC3(C)CS(=O)(=O)C3)cc21] | 3-(3-(difluoromethoxy)phenyl)-1-(3-hydroxybutan-2-yl)-N-(3-methyl-1,1-dioxidothietan-3-yl)-1H-pyrazolo[4,3-b]pyridine-6-carboxamide (3$^{rd}$ faster eluting in AD-H column, 15% EtOH/CO$_2$) | 496 | 121 |
| 78d | 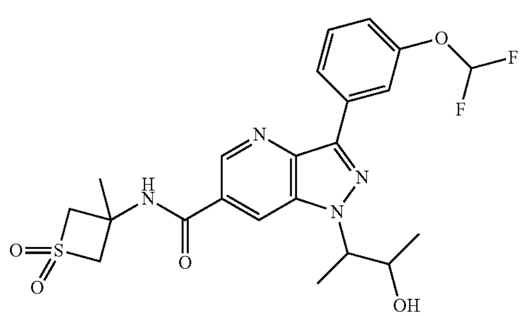 [SMILES: CC(O)C(C)n1nc(-c2cccc(OC(F)F)c2)c2ncc(C(=O)NC3(C)CS(=O)(=O)C3)cc21] | 3-(3-(difluoromethoxy)phenyl)-1-(3-hydroxybutan-2-yl)-N-(3-methyl-1,1-dioxidothietan-3-yl)-1H-pyrazolo[4,3-b]pyridine-6-carboxamide (slowest eluting in AD-H column, 15% EtOH/CO$_2$) | 496 | 47 |
| 79 | 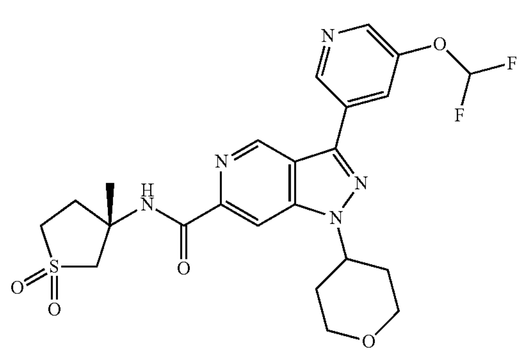 [SMILES: C[C@]1(NC(=O)c2cc3c(cn2)c(-c2cncc(OC(F)F)c2)nn3C2CCOCC2)CCS(=O)(=O)C1] | (S)-3-(5-(difluoromethoxy)pyridin-3-yl)-N-(3-methyl-1,1-dioxidotetrahydrothiophen-3-yl)-1-(tetrahydro-2H-pyran-4-yl)-1H-pyrazolo[4,3-c]pyridine-6-carboxamide | 522 | 10000 |

| Example | Structure | Name | LCMS [M + 1] | Human DGAT2 IC$_{50}$ (nM) |
|---|---|---|---|---|
| 80 | 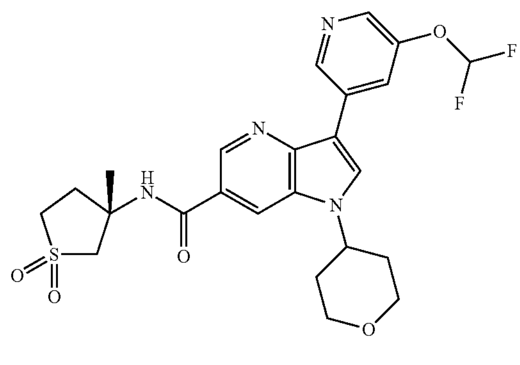 [SMILES: C[C@]1(NC(=O)c2cnc3c(-c4cncc(OC(F)F)c4)cn(C4CCOCC4)c3c2)CCS(=O)(=O)C1] | (S)-3-(5-(difluoromethoxy)pyridin-3-yl)-N-(3-methyl-1,1-dioxidotetrahydrothiophen-3-yl)-1-(tetrahydro-2H-pyran-4-yl)-1H-pyrrolo[3,2-b]pyridine-6-carboxamide | 522 | 875 |
| 81 | 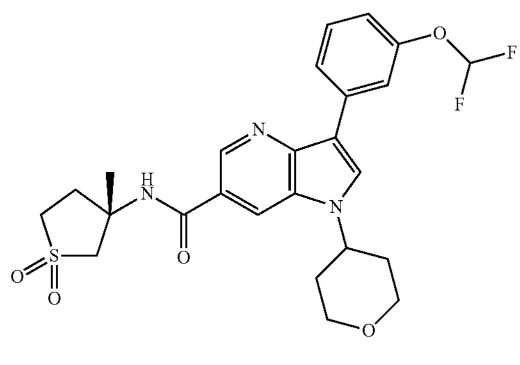 [SMILES: C[C@]1(NC(=O)c2cnc3c(-c4cccc(OC(F)F)c4)cn(C4CCOCC4)c3c2)CCS(=O)(=O)C1] | (S)-3-(3-(difluoromethoxy)phenyl)-N-(3-methyl-1,1-dioxidotetrahydrothiophen-3-yl)-1-(tetrahydro-2H-pyran-4-yl)-1H-pyrrolo[3,2-b]pyridine-6-carboxamide | 521 | 208 |
| 82 | 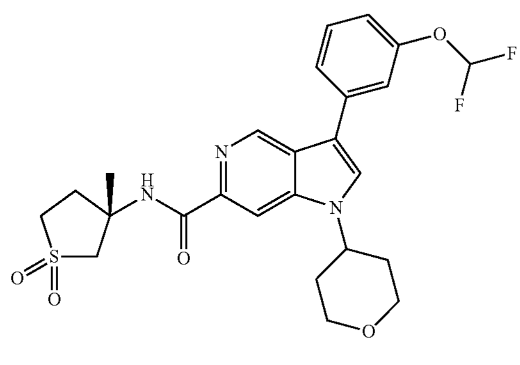 [SMILES: C[C@]1(NC(=O)c2cc3c(cn2)c(-c2cccc(OC(F)F)c2)cn3C2CCOCC2)CCS(=O)(=O)C1] | (S)-3-(3-(difluoromethoxy)phenyl)-N-(3-methyl-1,1-dioxidotetrahydrothiophen-3-yl)-1-(tetrahydro-2H-pyran-4-yl)-1H-pyrrolo[3,2-c]pyridine-6-carboxamide | 520 | 612 |
| 83 | 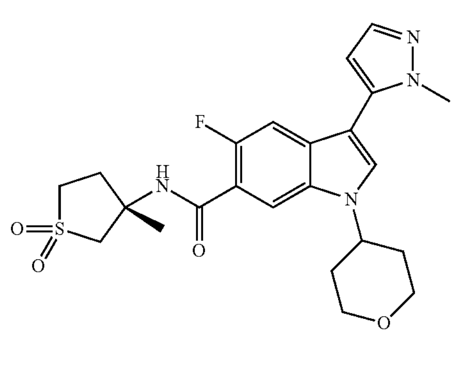 [SMILES: Cn1nccc1-c1cn(C2CCOCC2)c2cc(C(=O)N[C@@]3(C)CCS(=O)(=O)C3)c(F)cc12] | (S)-5-fluoro-N-methyl-1,1-dioxidotetrahydrothiophen-3-yl)-3-(1-methyl-1H-pyrazol-5-yl)-1-(tetrahydro-2H-pyran-4-yl)-1H-indole-6-carboxamide | 475 | 5434 |

| Example | Structure | Name | LCMS [M + 1] | Human DGAT2 IC$_{50}$ (nM) |
|---|---|---|---|---|
| 84 | 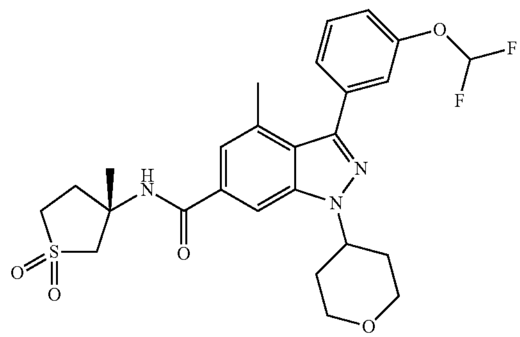 [SMILES: Cc1cc(C(=O)N[C@@]2(C)CCS(=O)(=O)C2)cc2c1c(-c1cccc(OC(F)F)c1)nn2C1CCOCC1] | (S)-3-(3-(difluoromethoxy)phenyl)-4-methyl-N-(3-methyl-1,1-dioxidotetrahydrothiophen-3-yl)-1-(tetrahydro-2H-pyran-4-yl)-1H-indazole-6-carboxamide | 534 | 13 |
| 85 | 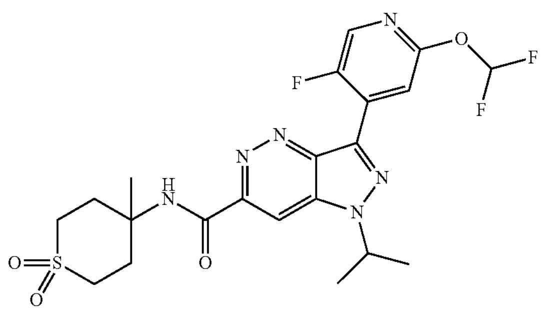 [SMILES: CC(C)n1nc(-c2cc(OC(F)F)ncc2F)c2nnc(C(=O)NC3(C)CCS(=O)(=O)CC3)cc21] | 3-(2-(difluoromethoxy)-5-fluoropyridin-4-yl)-1-isopropyl-N-(4-methyl-1,1-dioxidotetrahydro-2H-thiopyran-4-yl)-1H-pyrazolo[4,3-c]pyridazine-6-carboxamide | 513 | 143 |
| 86 | 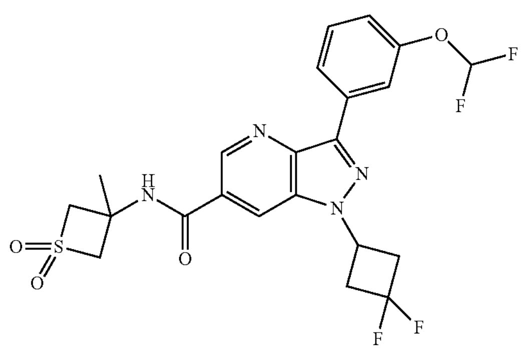 [SMILES: CC1(NC(=O)c2cnc3c(-c4cccc(OC(F)F)c4)nn(C4CC(F)(F)C4)c3c2)CS(=O)(=O)C1] | 1-(3,3-difluorocyclobutyl)-3-(3-(difluoromethoxy)phenyl)-N-(3-methyl-1,1-dioxidothietan-3-yl)-1H-pyrazolo[4,3-b]pyridine-6-carboxamide | 513 | 24 |
| 87a | 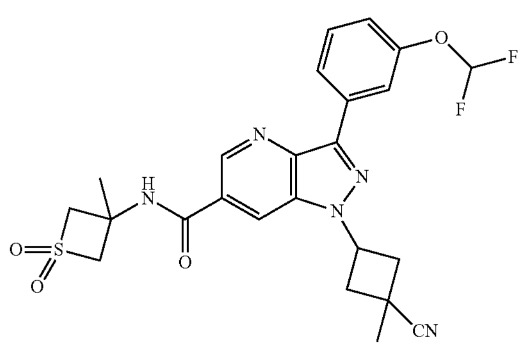 [SMILES: CC1(C#N)CC(n2nc(-c3cccc(OC(F)F)c3)c3ncc(C(=O)NC4(C)CS(=O)(=O)C4)cc32)C1] | 1-(3-cyano-3-methylcyclobutyl)-3-(3-(difluoromethoxy)phenyl)-N-(3-methyl-1,1-dioxidothietan-3-yl)-1H-pyrazolo[4,3-b]pyridine-6-carboxamide (diastereomer I) | 516 | 70 |

| Example | Structure | Name | LCMS [M + 1] | Human DGAT2 IC$_{50}$ (nM) |
|---|---|---|---|---|
| 87b | 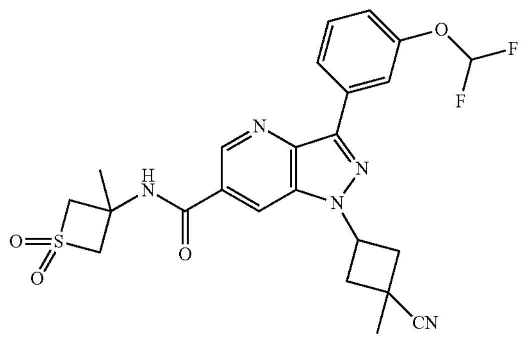 [SMILES: CC1(C#N)CC(n2nc(-c3cccc(OC(F)F)c3)c3ncc(C(=O)NC4(C)CS(=O)(=O)C4)cc32)C1] | 1-(3-cyano-3-methylcyclobutyl)-3-(3-(difluoromethoxy)phenyl)-N-(3-methyl-1,1-dioxidothietan-3-yl)-1H-pyrazolo[4,3-b]pyridine-6-carboxamide (diastereomer II) | 516 | 270 |
| 88 | 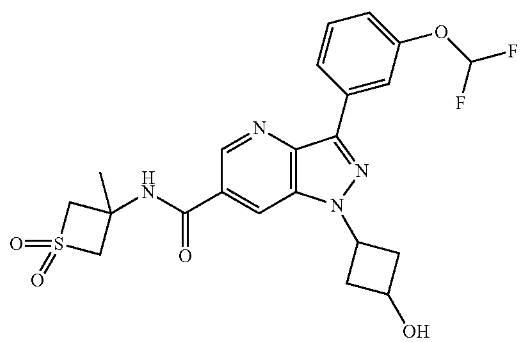 [SMILES: CC1(NC(=O)c2cnc3c(-c4cccc(OC(F)F)c4)nn(C4CC(O)C4)c3c2)CS(=O)(=O)C1] | 3-(3-(difluoromethoxy)phenyl)-1-(3-hydroxycyclobutyl)-N-(3-methyl-1,1-dioxidothietan-3-yl)-1H-pyrazolo[4,3-b]pyridine-6-carboxamide | 493 | 80 |
| 89 | 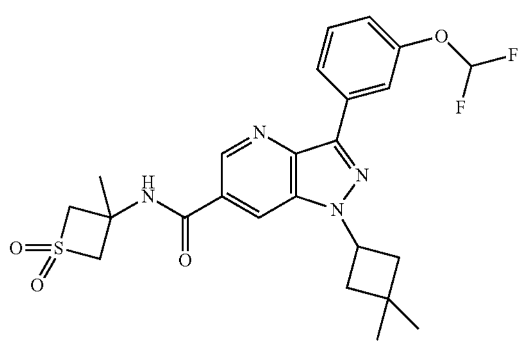 [SMILES: CC1(C)CC(n2nc(-c3cccc(OC(F)F)c3)c3ncc(C(=O)NC4(C)CS(=O)(=O)C4)cc32)C1] | 3-(3-(difluoromethoxy)phenyl)-1-(3,3-dimethylcyclobutyl)-N-(3-methyl-1,1-dioxidothietan-3-yl)-1H-pyrazolo[4,3-b]pyridine-6-carboxamide | 505 | 2.9 |
| 90 | 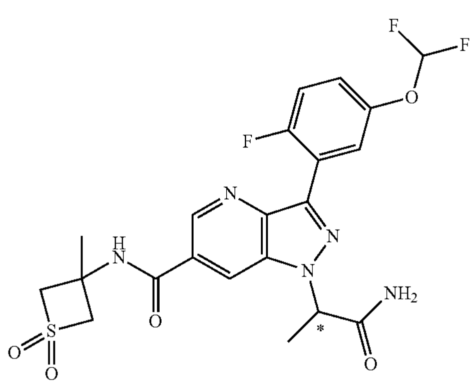 [SMILES: CC(C(N)=O)n1nc(-c2cc(OC(F)F)ccc2F)c2ncc(C(=O)NC3(C)CS(=O)(=O)C3)cc21] | 1-(1-amino-1-oxopropan-2-yl)-3-(5-(difluoromethoxy)-2-fluorophenyl)-N-(3-methyl-1,1-dioxidothietan-3-yl)-1H-pyrazolo[4,3-b]pyridine-6-carboxamide | 512 | 480 |

| Example | Structure | Name | LCMS [M + 1] | Human DGAT2 IC$_{50}$ (nM) |
|---|---|---|---|---|
| 91 | 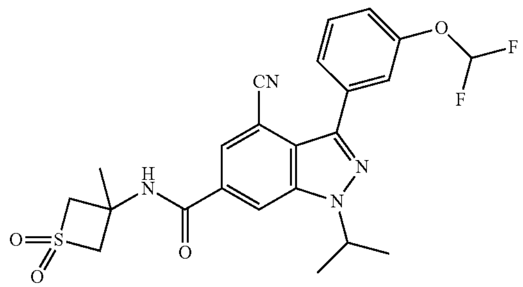 [SMILES: CC(C)n1nc(-c2cccc(OC(F)F)c2)c2c(C#N)cc(C(=O)NC3(C)CS(=O)(=O)C3)cc21] | 4-cyano-3-(3-(difluoromethoxy)phenyl)-1-isopropyl-N-(3-methyl-1,1-dioxidothietan-3-yl)-1H-indazole-6-carboxamide | 489 | 2.0 |

Example 92: 3-(3-cyclopropylphenyl)-1-isopropyl-N-(3-methyl-1,1-dioxidothietan-3-yl)-TH-pyrazolo[4,3-b]pyridine-6-carboxamide

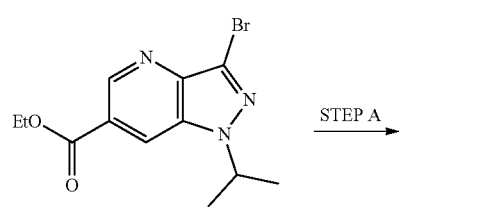

INTERMEDIATE-2

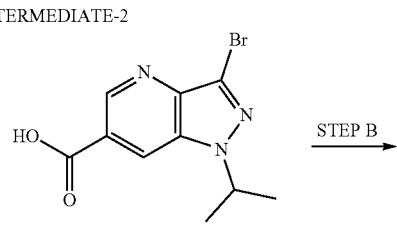

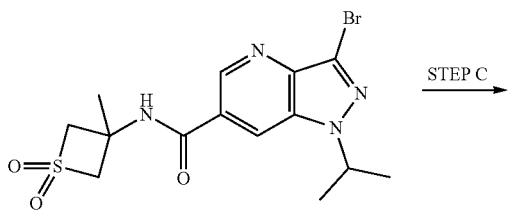

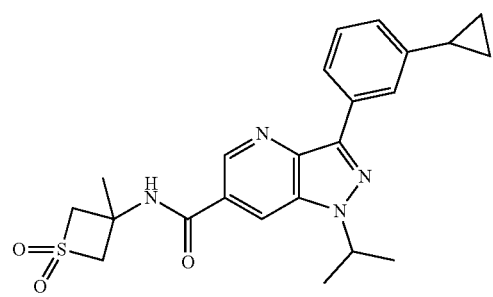

EX-92

Step A: 3-Bromo-1-isopropyl-1H-pyrazolo[4,3-b]pyridine-6-carboxylic acid

To a solution of ethyl 3-bromo-1-isopropyl-1H-pyrazolo[4,3-b]pyridine-6-carboxylate (0.261 g, 0.836 mmol) in THF (8.4 mL) was added aq. NaOH (1M, 8.4 mL, 8.4 mmol). The reaction was stirred at RT for 21 h, then diluted with 1 M aq. HCl and EtOAc. The layers were separated, and the organic layer was concentrated in vacuo to afford the crude title compound. LC/MS=283/285 [M+1].

Step B: 3-Bromo-1-isopropyl-N-(3-methyl-1,1-dioxidothietan-3-yl)-1H-pyrazolo[4,3-b]pyridine-6-carboxamide To a solution of 3-bromo-1-isopropyl-1H-pyrazolo[4,3-b]pyridine-6-carboxylic acid (0.191 g, 0.762 mmol), 3-amino-3-methylthietane 1,1-dioxide hydrochloride (0.138 g, 0.807 mmol), and HATU (0.511 g, 1.35 mmol) in DMF (6.7 mL) was added DIPEA (0.47 mL, 2.7 mmol). The reaction was stirred for 16 h, then concentrated directly onto silica gel and purified by flash silica gel column chromatography (0-100% EtOAc/hexanes) to afford the title compound. LC/MS=400/402 [M+1].

Step C: 3-(3-cyclopropylphenyl)-1-isopropyl-N-(3-methyl-1,1-dioxidothietan-3-yl)-1H-pyrazolo[4,3-b]pyridine-6-carboxamide To a mixture of 2-(3-cyclopropylphenyl)-4,4,5,5-tetramethyl-1,3,2-dioxaborolane (45.6 mg, 0.187 mmol) (0.046 g, 0.19 mmol), 3-bromo-1-isopropyl-N-(3-methyl-1,1-dioxidothietan-3-yl)-1H-pyrazolo[4,3-b]pyridine-6-carboxamide (0.050 g, 0.13 mmol), Pd(dppf)Cl$_2$ (0.009 g, 0.012 mmol), and Na$_2$CO$_3$ (0.033 g, 0.031 mmol) was added dioxane (0.5 mL), and water (0.10 mL). The reaction mixture was heated to 100° C. for 18 h, then cooled to RT and filtered. The crude residue was purified by mass triggered reverse phase HPLC (ACN/water with 0.10% NH$_4$OH modifier) to afford the title compound. LC/MS=439 [M+1]. $^1$H NMR (600 MHz, DMSO-d6) δ 9.29 (s, 1H), 9.03 (d, J=1.8 Hz, 1H), 8.66 (d, J=1.8 Hz, 1H), 8.24 (d, J=7.9 Hz, 1H), 8.22 (s, 1H), 7.40 (t, J=7.6 Hz, 1H), 7.10 (d, J=7.7 Hz, 1H), 5.13 (p, J=6.6 Hz, 1H), 4.61 (d, J=14.7 Hz, 2H), 4.37 (d, J=14.8 Hz, 2H), 2.04 (tt, J=8.9, 5.3 Hz, 1H), 1.78 (s, 3H), 1.59 (d, J=6.6 Hz, 6H), 1.04-0.99 (m, 2H), 0.76-0.72 (m, 2H). Human DGAT2 IC$_{50}$=31 nM.

By using procedures similar to those described in Example 92 with appropriate reagents, the following compounds were synthesized. These compounds were characterized by LC/MS.

| Example | Structure | Name | LCMS [M + 1] | Human DGAT2 IC$_{50}$ (nM) |
|---|---|---|---|---|
| 93 | 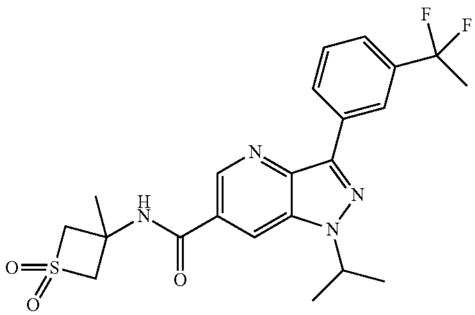 [SMILES: CC(C)n1nc(-c2cccc(C(C)(F)F)c2)c2ncc(C(=O)NC3(C)CS(=O)(=O)C3)cc21] | 3-[3-(1,1-difluoroethyl)phenyl]-1-isopropyl-N-(3-methyl-1,1-dioxo-thietan-3-yl)pyrazolo[4,3-b]pyridine-6-carboxamide | 463 | 210 |
| 94 | 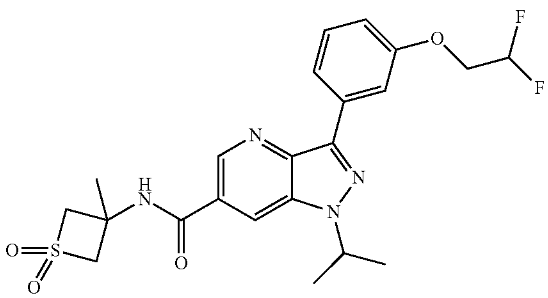 [SMILES: CC(C)n1nc(-c2cccc(OCC(F)F)c2)c2ncc(C(=O)NC3(C)CS(=O)(=O)C3)cc21] | 3-[3-(2,2-difluoroethoxy)phenyl]-1-isopropyl-N-(3-methyl-1,1-dioxo-thietan-3-yl)pyrazolo[4,3-b]pyridine-6-carboxamide | 479 | 7.0 |
| 95 | 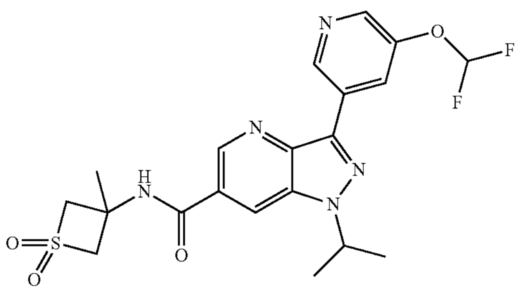 [SMILES: CC(C)n1nc(-c2cncc(OC(F)F)c2)c2ncc(C(=O)NC3(C)CS(=O)(=O)C3)cc21] | 3-[5-(difluoromethoxy)-3-pyridyl]-1-isopropyl-N-(3-methyl-1,1-dioxo-thietan-3-yl)pyrazolo[4,3-b]pyridine-6-carboxamide | 466 | 26 |
| 96 | 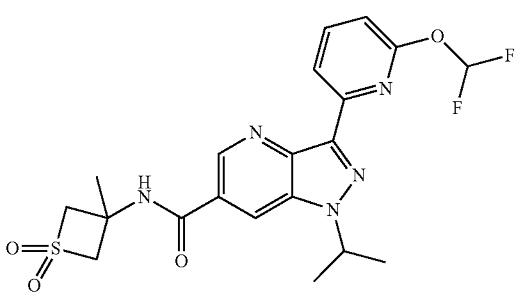 | 3-[6-(difluoromethoxy)-2-pyridyl]-1-isopropyl-N-(3-methyl-1,1-dioxo-thietan-3-yl)pyrazolo[4,3-b]pyridine-6-carboxamide | 466 | 5541 |
| 97 | 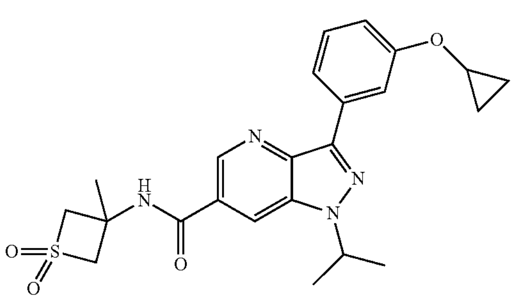 [SMILES: CC(C)n1nc(-c2cccc(OC3CC3)c2)c2ncc(C(=O)NC3(C)CS(=O)(=O)C3)cc21] | 3-[3-(cyclopropoxy)phenyl]-1-isopropyl-N-(3-methyl-1,1-dioxo-thietan-3-yl)pyrazolo[4,3-b]pyridine-6-carboxamide | 455 | 0.9 |

-continued

| Example | Structure | Name | LCMS [M + 1] | Human DGAT2 IC$_{50}$ (nM) |
|---|---|---|---|---|
| 98 | 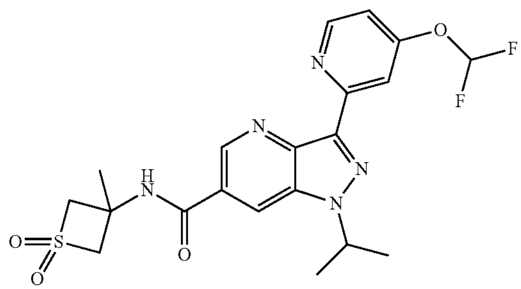 [SMILES: CC(C)n1nc(-c2cc(OC(F)F)ccn2)c2ncc(C(=O)NC3(C)CS(=O)(=O)C3)cc21] | 3-[4-(difluoromethoxy)-2-pyridyl]-1-isopropyl-N-(3-methyl-1,1-dioxo-thietan-3-yl)pyrazolo[4,3-b]pyridine-6-carboxamide | 466 | 690 |
| 99 | 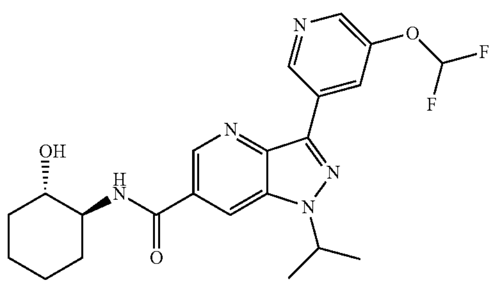 [SMILES: CC(C)n1nc(-c2cncc(OC(F)F)c2)c2ncc(C(=O)N[C@H]3CCCC[C@@H]3O)cc21] | 3-[5-(difluoromethoxy)-3-pyridyl]-N-[(1S,2S)-2-hydroxycyclohexyl]-1-isopropyl-pyrazolo[4,3-b]pyridine-6-carboxamide | 446 | 52 |
| 100 | 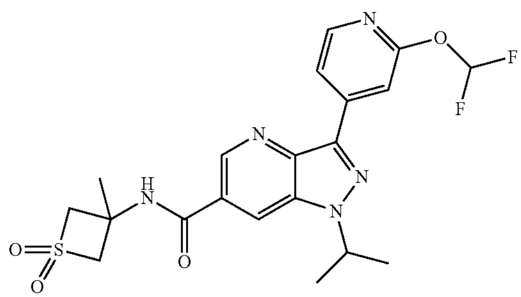 [SMILES: CC(C)n1nc(-c2ccnc(OC(F)F)c2)c2ncc(C(=O)NC3(C)CS(=O)(=O)C3)cc21] | 3-[2-(difluoromethoxy)-4-pyridyl]-1-isopropyl-N-(3-methyl-1,1-dioxo-thietan-3-yl)pyrazolo[4,3-b]pyridine-6-carboxamide | 466 | 139 |
| 101 | 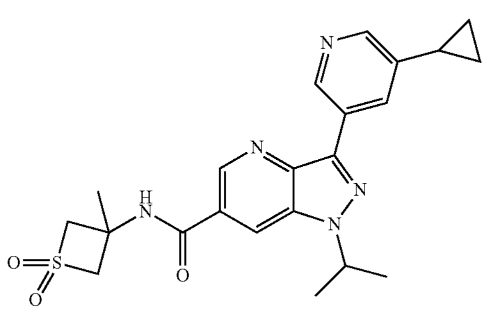 [SMILES: CC(C)n1nc(-c2cncc(C3CC3)c2)c2ncc(C(=O)NC3(C)CS(=O)(=O)C3)cc21] | 3-(5-cyclopropyl-3-pyridyl)-1-isopropyl-N-(3-methyl-1,1-dioxo-thietan-3-yl)pyrazolo[4,3-b]pyridine-6-carboxamide | 440 | 85 |
| 102 | 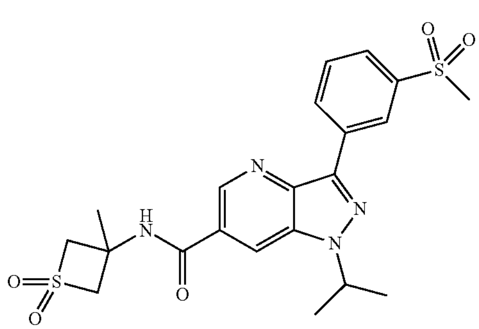 [SMILES: CC(C)n1nc(-c2cccc(S(C)(=O)=O)c2)c2ncc(C(=O)NC3(C)CS(=O)(=O)C3)cc21] | 1-isopropyl-N-(3-methyl-1,1-dioxo-thietan-3-yl)-3-(3-methylsulfonylphenyl)pyrazolo[4,3-b]pyridine-6-carboxamide | 477 | 7101 |

| Example | Structure | Name | LCMS [M + 1] | Human DGAT2 IC$_{50}$ (nM) |
|---|---|---|---|---|
| 103 | 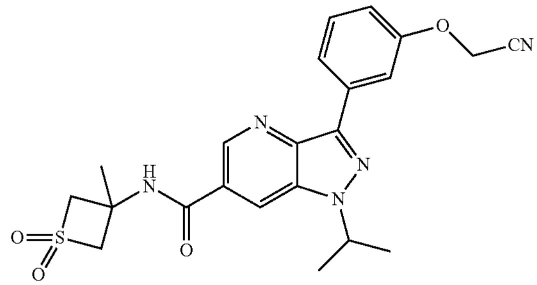 [SMILES: CC(C)n1nc(-c2cccc(OCC#N)c2)c2ncc(C(=O)NC3(C)CS(=O)(=O)C3)cc21] | 3-[3-(cyanomethoxy)phenyl]-1-isopropyl-N-(3-methyl-1,1-dioxo-thietan-3-yl)pyrazolo[4,3-b]pyridine-6-carboxamide | 417 | 142 |
| 104 | 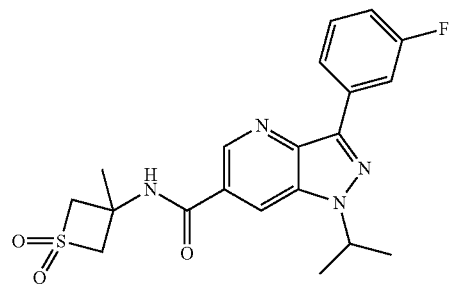 [SMILES: CC(C)n1nc(-c2cccc(F)c2)c2ncc(C(=O)NC3(C)CS(=O)(=O)C3)cc21] | 3-(3-fluorophenyl)-1-isopropyl-N-(3-methyl-1,1-dioxo-thietan-3-yl)pyrazolo[4,3-b]pyridine-6-carboxamide | 417 | 119 |
| 105 | 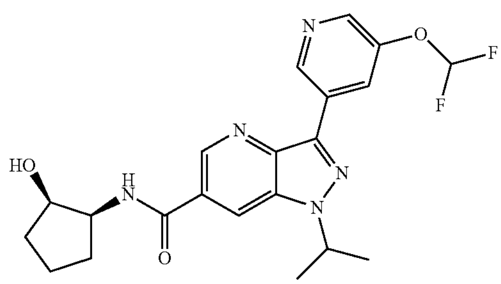 [SMILES: CC(C)n1nc(-c2cncc(OC(F)F)c2)c2ncc(C(=O)N[C@H]3CCC[C@H]3O)cc21] | 3-(5-(difluoromethoxy)pyridin-3-yl)-N-((1S,2R)-2-hydroxycyclopentyl)-1-isopropyl-1H-pyrazolo[4,3-b]pyridine-6-carboxamide | 432 | 78 |
| 106 | 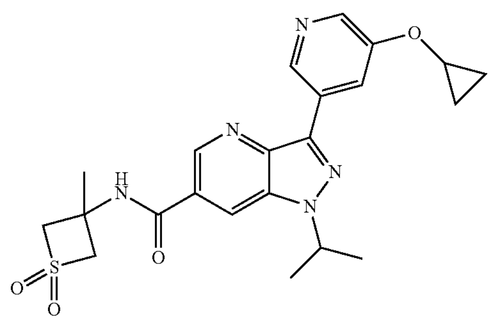 [SMILES: CC(C)n1nc(-c2cncc(OC3CC3)c2)c2ncc(C(=O)NC3(C)CS(=O)(=O)C3)cc21] | 3-(5-cyclopropoxypyridin-3-yl)-1-isopropyl-N-(3-methyl-1,1-dioxidothietan-3-yl)-1H-pyrazolo[4,3-b]pyridine-6-carboxamide | 456 | 46 |
| 107 | 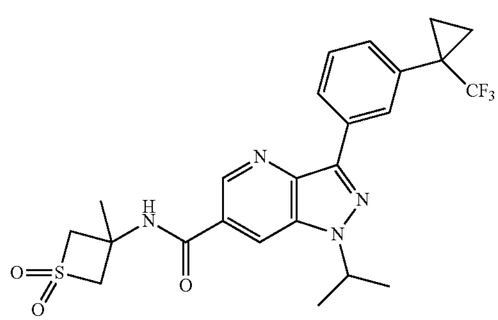 [SMILES: CC(C)n1nc(-c2cccc(C3(C(F)(F)F)CC3)c2)c2ncc(C(=O)NC3(C)CS(=O)(=O)C3)cc21] | 1-isopropyl-N-(3-methyl-1,1-dioxidothietan-3-yl)-3-(3-(1-(trifluoromethyl)cyclopropyl)phenyl)-1H-pyrazolo[4,3-b]pyridine-6-carboxamide | 507 | 2277 |

| Example | Structure | Name | LCMS [M + 1] | Human DGAT2 IC$_{50}$ (nM) |
|---|---|---|---|---|
| 108 | 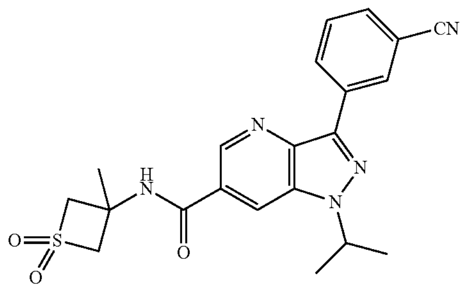 [SMILES: CC(C)n1nc(-c2cccc(C#N)c2)c2ncc(C(=O)NC3(C)CS(=O)(=O)C3)cc21] | 3-(3-cyanophenyl)-1-isopropyl-N-(3-methyl-1,1-dioxidothietan-3-yl)-1H-pyrazolo[4,3-b]pyridine-6-carboxamide | 424 | 109 |
| 109 | 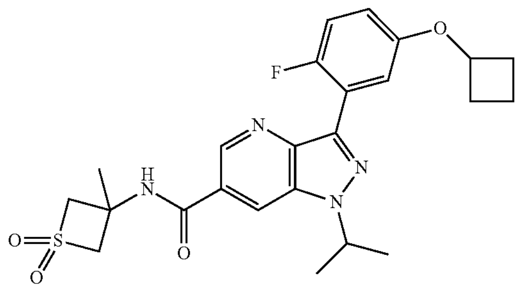 [SMILES: CC(C)n1nc(-c2cc(OC3CCC3)ccc2F)c2ncc(C(=O)NC3(C)CS(=O)(=O)C3)cc21] | 3-(5-cyclobutoxy-2-fluorophenyl)-1-isopropyl-N-(3-methyl-1,1-dioxidothietan-3-yl)-1H-pyrazolo[4,3-b]pyridine-6-carboxamide | 487 | 11 |
| 110 | 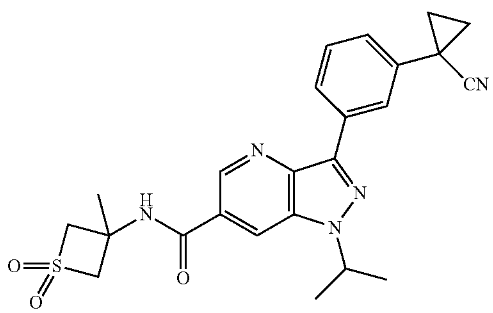 [SMILES: CC(C)n1nc(-c2cccc(C3(C#N)CC3)c2)c2ncc(C(=O)NC3(C)CS(=O)(=O)C3)cc21] | 3-(3-(1-cyanocyclopropyl)phenyl)-1-isopropyl-N-(3-methyl-1,1-dioxidothietan-3-yl)-1H-pyrazolo[4,3-b]pyridine-6-carboxamide | 464 | 1927 |
| 111 | 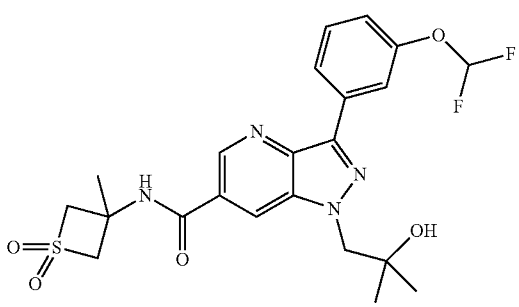 [SMILES: CC(C)(O)Cn1nc(-c2cccc(OC(F)F)c2)c2ncc(C(=O)NC3(C)CS(=O)(=O)C3)cc21] | 3-(3-(difluoromethoxy)phenyl)-1-(2-hydroxy-2-methylpropyl)-N-(3-methyl-1,1-dioxidothietan-3-yl)-1H-pyrazolo[4,3-b]pyridine-6-carboxamide | 495 | 22 |
| 112 | 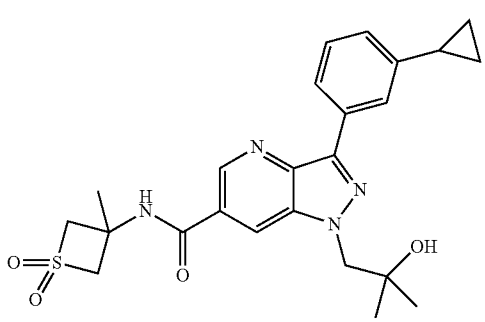 [SMILES: CC(C)(O)Cn1nc(-c2cccc(C3CC3)c2)c2ncc(C(=O)NC3(C)CS(=O)(=O)C3)cc21] | 3-(3-cyclopropylphenyl)-1-(2-hydroxy-2-methylpropyl)-N-(3-methyl-1,1-dioxidothietan-3-yl)-1H-pyrazolo[4,3-b]pyridine-6-carboxamide | 469 | 6.0 |

-continued

| Example | Structure | Name | LCMS [M + 1] | Human DGAT2 IC$_{50}$ (nM) |
|---|---|---|---|---|
| 113 | 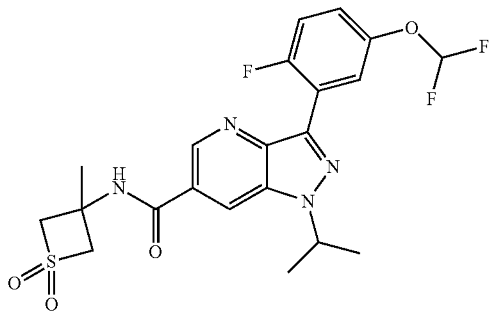 [SMILES: CC(C)n1nc(-c2cc(OC(F)F)ccc2F)c2ncc(C(=O)NC3(C)CS(=O)(=O)C3)cc21] | 3-(5-(difluoromethoxy)-2-fluorophenyl)-1-isopropyl-N-(3-methyl-1,1-dioxidothietan-3-yl)-1H-pyrazolo[4,3-b]pyridine-6-carboxamide | 483 | 1.0 |
| 114 | 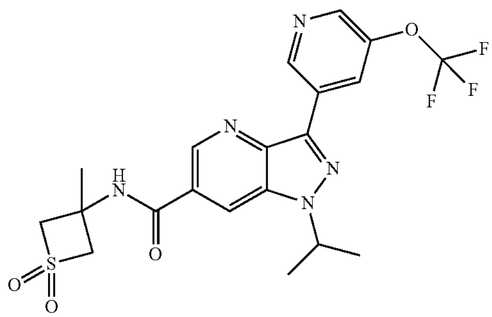 [SMILES: CC(C)n1nc(-c2cncc(OC(F)(F)F)c2)c2ncc(C(=O)NC3(C)CS(=O)(=O)C3)cc21] | 1-isopropyl-N-(3-methyl-1,1-dioxidothietan-3-yl)-3-(5-(trifluoromethoxy)pyridin-3-yl)-1H-pyrazolo[4,3-b]pyridine-6-carboxamide | 484 | 20 |
| 115 | 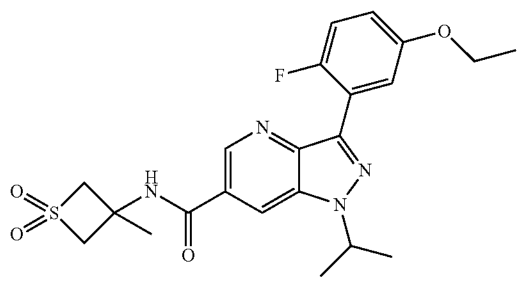 [SMILES: CCOc1ccc(F)c(-c2nn(C(C)C)c3cc(C(=O)NC4(C)CS(=O)(=O)C4)cnc23)c1] | 3-(5-ethoxy-2-fluorophenyl)-1-isopropyl-N-(3-methyl-1,1-dioxidothietan-3-yl)-1H-pyrazolo[4,3-b]pyridine-6-carboxamide | 461 | 3.3 |
| 116 | 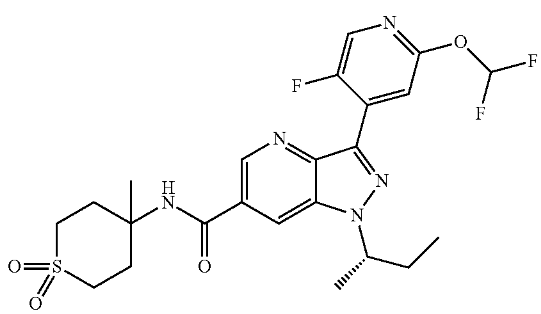 [SMILES: CC[C@H](C)n1nc(-c2cc(OC(F)F)ncc2F)c2ncc(C(=O)NC3(C)CCS(=O)(=O)CC3)cc21] | (S)-1-(sec-butyl)-3-(2-(difluoromethoxy)-5-fluoropyridin-4-yl)-N-(4-methyl-1,1-dioxidotetrahydro-2H-thiopyran-4-yl)-1H-pyrazolo[4,3-b]pyridine-6-carboxamide | 526 | 11.5 |
| 117 | 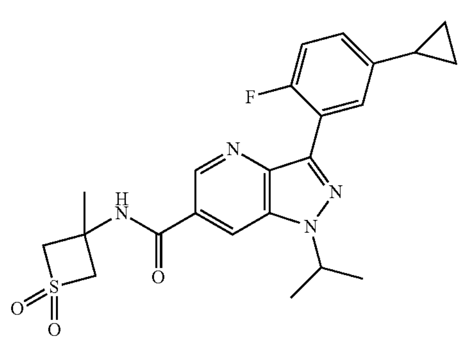 [SMILES: CC(C)n1nc(-c2cc(C3CC3)ccc2F)c2ncc(C(=O)NC3(C)CS(=O)(=O)C3)cc21] | 3-(5-cyclopropyl-2-fluorophenyl)-1-isopropyl-N-(3-methyl-1,1-dioxidothietan-3-yl)-1H-pyrazolo[4,3-b]pyridine-6-carboxamide | 457 | 9.6 |

-continued

| Example | Structure | Name | LCMS [M + 1] | Human DGAT2 IC$_{50}$ (nM) |
|---|---|---|---|---|
| 118 | 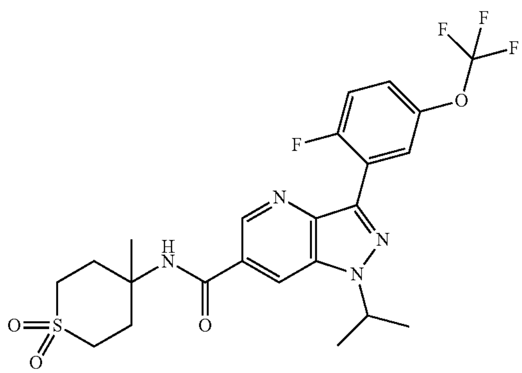 [SMILES: CC(C)n1nc(-c2cc(OC(F)(F)F)ccc2F)c2ncc(C(=O)NC3(C)CCS(=O)(=O)CC3)cc21] | 3-(2-fluoro-5-(trifluoromethoxy)phenyl)-1-isopropyl-N-(4-methyl-1,1-dioxidotetrahydro-2H-thiopyran-4-yl)-1H-pyrazolo[4,3-b]pyridine-6-carboxamide | 529 | 20 |
| 119 | 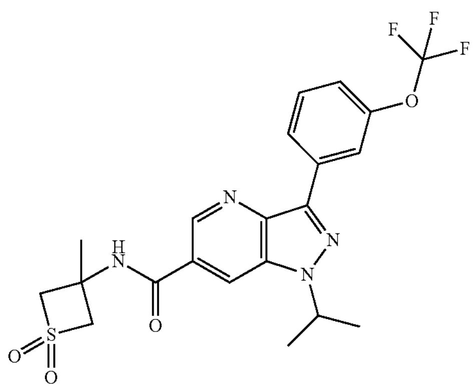 [SMILES: CC(C)n1nc(-c2cccc(OC(F)(F)F)c2)c2ncc(C(=O)NC3(C)CS(=O)(=O)C3)cc21] | 1-isopropyl-N-(3-methyl-1,1-dioxidothietan-3-yl)-3-(3-(trifluoromethoxy)phenyl)-1H-pyrazolo[4,3-b]pyridine-6-carboxamide | 483 | 97 |
| 120 | 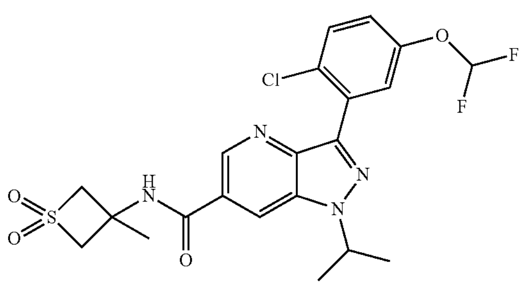 [SMILES: CC(C)n1nc(-c2cc(OC(F)F)ccc2Cl)c2ncc(C(=O)NC3(C)CS(=O)(=O)C3)cc21] | 3-(2-chloro-5-(difluoromethoxy)phenyl)-1-isopropyl-N-(3-methyl-1,1-dioxidothietan-3-yl)-1H-pyrazolo[4,3-b]pyridine-6-carboxamide | 499 | 7.2 |
| 121 | 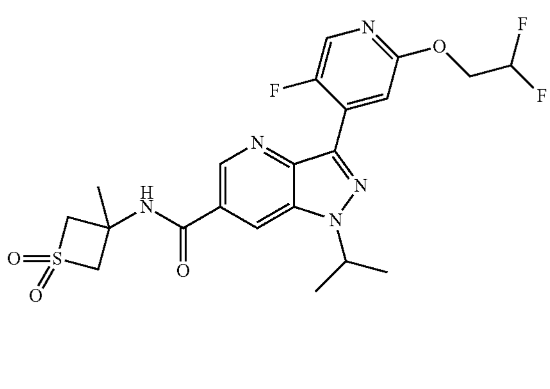 [SMILES: CC(C)n1nc(-c2cc(OCC(F)F)ncc2F)c2ncc(C(=O)NC3(C)CS(=O)(=O)C3)cc21] | 3-(2-(2,2-difluoroethoxy)-5-fluoropyridin-4-yl)-1-isopropyl-N-(3-methyl-1,1-dioxidothietan-3-yl)-1H-pyrazolo[4,3-b]pyridine-6-carboxamide | 498 | 8.3 |

-continued

| Example | Structure | Name | LCMS [M + 1] | Human DGAT2 IC$_{50}$ (nM) |
|---|---|---|---|---|
| 122 | 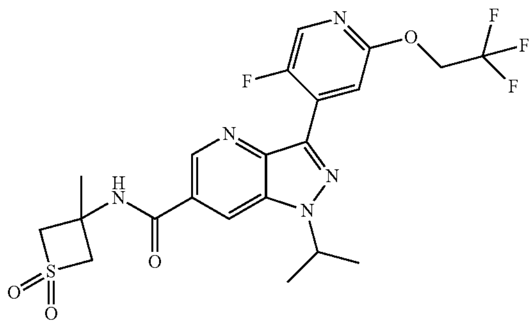 [SMILES: CC(C)n1nc(-c2cc(OCC(F)(F)F)ncc2F)c2ncc(C(=O)NC3(C)CS(=O)(=O)C3)cc21] | 3-(5-fluoro-2-(2,2,2-trifluoroethoxy)pyridin-4-yl)-1-isopropyl-N-(3-methyl-1,1-dioxidothietan-3-yl)-1H-pyrazolo[4,3-b]pyridine-6-carboxamide | 516 | 7.7 |
| 123 | 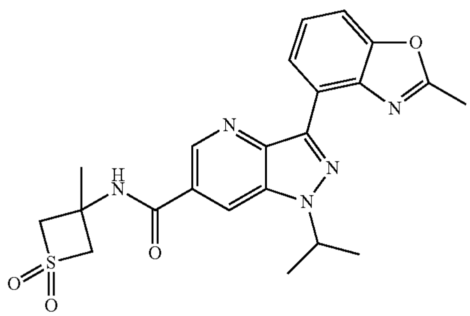 [SMILES: Cc1nc2c(-c3nn(C(C)C)c4cc(C(=O)NC5(C)CS(=O)(=O)C5)cnc34)cccc2o1] | 1-isopropyl-N-(3-methyl-1,1-dioxidothietan-3-yl)-3-(2-methylbenzo[d]oxazol-4-yl)-1H-pyrazolo[4,3-b]pyridine-6-carboxamide | 454 | 487 |
| 124 | 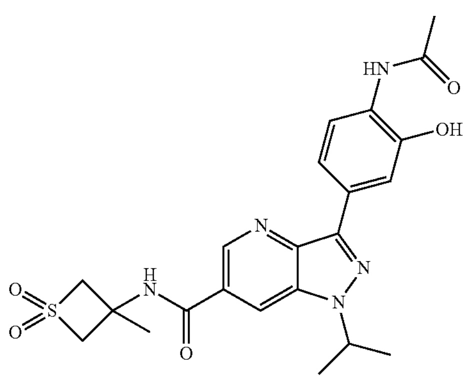 [SMILES: CC(=O)Nc1ccc(-c2nn(C(C)C)c3cc(C(=O)NC4(C)CS(=O)(=O)C4)cnc23)cc1O] | 3-(4-acetamido-3-hydroxyphenyl)-1-isopropyl-N-(3-methyl-1,1-dioxidothietan-3-yl)-1H-pyrazolo[4,3-b]pyridine-6-carboxamide | 472 | 620 |
| 125 | 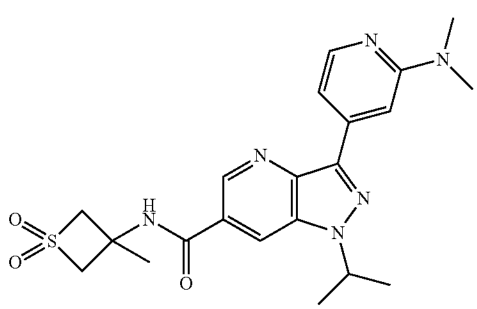 [SMILES: CC(C)n1nc(-c2ccnc(N(C)C)c2)c2ncc(C(=O)NC3(C)CS(=O)(=O)C3)cc21] | 3-(2-(dimethylamino)pyridin-4-yl)-1-isopropyl-N-(3-methyl-1,1-dioxidothietan-3-yl)-1H-pyrazolo[4,3-b]pyridine-6-carboxamide | 443 | >1000 |

Example 126: 3-(2-ethoxy-5-fluoropyridin-4-yl)-1-isopropyl-N-(3-methyl-1,1-dioxidothietan-3-yl)-1H-pyrazolo[4,3-b]pyridine-6-carboxamide

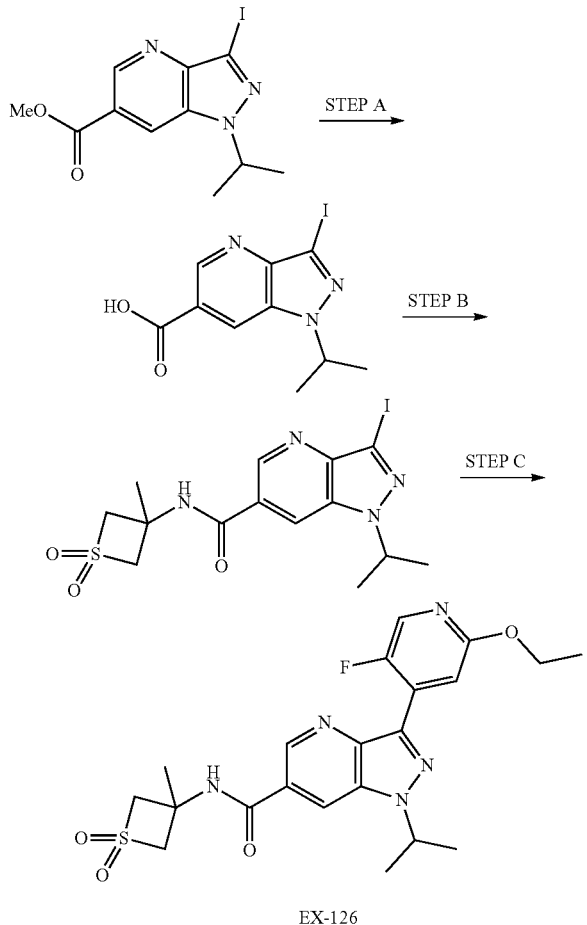

EX-126

Step A: 3-Iodo-1-isopropyl-1H-pyrazolo[4,3-b]pyridine-6-carboxylic acid

To a solution of methyl 3-iodo-1-isopropyl-1H-pyrazolo[4,3-b]pyridine-6-carboxylate (0.542 g, 1.57 mmol) in THF (6 mL) and MeOH (0.15 mL) was added LiOH (0.188 g, 7.85 mmol) and water (1.5 mL). The reaction was stirred at RT for 24 h, then diluted with 1 M aq. HCl. The mixture was extracted with EtOAc, and combined organic extracts were dried over $Na_2SO_4$, filtered, and concentrated in vacuo to afford the title compound. LC/MS=332 [M+1].

Step B: 3-Iodo-1-isopropyl-N-(3-methyl-1,1-dioxidothietan-3-yl)-1H-pyrazolo[4,3-b]pyridine-6-carboxamide To a solution of 3-iodo-1-isopropyl-1H-pyrazolo[4,3-b]pyridine-6-carboxylic acid (0.520 g, 1.57 mmol), 3-amino-3-methylthietane 1,1-dioxide hydrochloride (0.323 g, 1.89 mmol), and HATU (0.836 g, 2.20 mmol) in DMF (5.2 mL) was added DIPEA (0.69 mL, 3.9 mmol). The reaction was stirred at RT for 24 h, then diluted with water and extracted with EtOAc. The combined organic extracts were washed with brine, dried over $Na_2SO_4$, filtered, and concentrated in vacuo. The crude residue was purified by flash silica gel column chromatography (0-100% EtOAc/hexanes) to afford the title compound. LC/MS=449 [M+1].

Step C: 3-(2-ethoxy-5-fluoropyridin-4-yl)-1-isopropyl-N-(3-methyl-1,1-dioxidothietan-3-yl)-1H-pyrazolo[4,3-b]pyridine-6-carboxamide To a mixture of 2-ethoxy-5-fluoro-4-(4,4,5,5-tetramethyl-1,3,2-dioxaborolan-2-yl)pyridine (0.046 g, 0.17 mmol), 3-iodo-1-isopropyl-N-(3-methyl-1,1-dioxidothietan-3-yl)-1H-pyrazolo[4,3-b]pyridine-6-carboxamide (0.065 g, 0.15 mmol), $Pd(dppf)Cl_2$ (0.0053 mg, 0.0073 mmol), and $Na_2CO_3$ (0.031 g, 0.29 mmol) was added dioxane (0.5 mL), and water (0.20 mL). The reaction mixture was heated to 90° C. for 2 h, then cooled to RT and filtered. The crude residue was purified by mass triggered reverse phase HPLC (ACN/water with 0.1% $NH_4OH$ modifier) to afford the title compound. LC/MS=462 [M+1]. $^1$H NMR (500 MHz, DMSO-d6) δ 9.34 (s, 1H), 9.06 (d, J=1.6 Hz, 1H), 8.76 (d, J=1.7 Hz, 1H), 8.29 (d, J=2.3 Hz, 1H), 7.90 (d, J=5.0 Hz, 1H), 5.20 (p, J=6.2 Hz, 1H), 4.61 (d, J=14.7 Hz, 2H), 4.39-4.32 (m, 4H), 1.79 (s, 3H), 1.59 (d, J=6.6 Hz, 6H), 1.36 (t, J=7.0 Hz, 3H). Human DGAT2 $IC_{50}$=27 nM.

Example 127 and Example 128

3-(3-(1-Hydroxycyclopropyl)phenyl)-1-isopropyl-N-(3-methyl-1,1-dioxidothietan-3-yl)-1H-pyrazolo[4,3-b]pyridine-6-carboxamide (EXAMPLE 127) and 1-isopropyl-3-(3-(1-methoxycyclopropyl)phenyl)-N-(3-methyl-1,1-dioxidothietan-3-yl)-1H-pyrazolo[4,3-b]pyridine-6-carboxamide (Example 128)

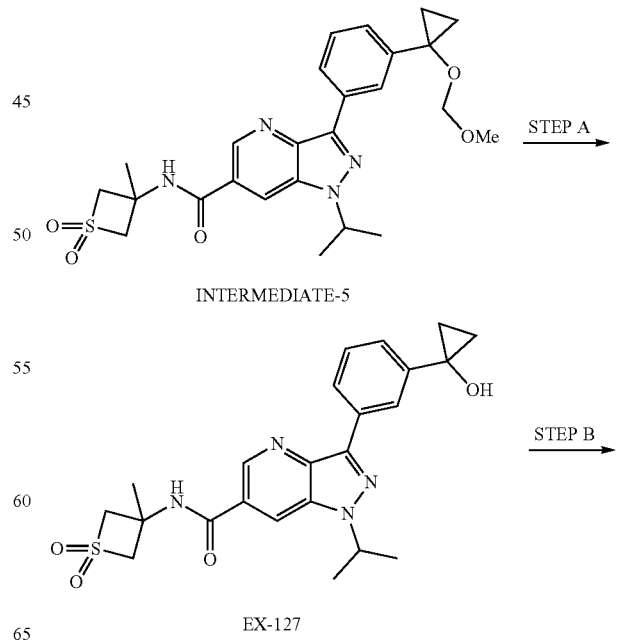

INTERMEDIATE-5

EX-127

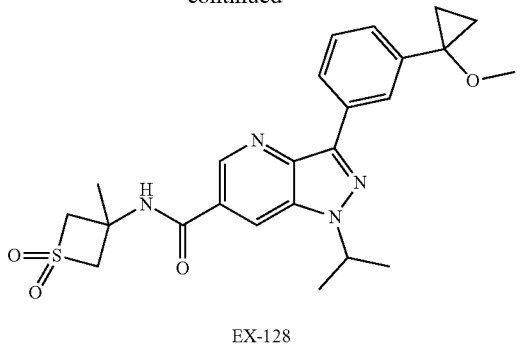

EX-128

INTERMEDIATE-5 was prepared by the synthetic procedures described for EXAMPLE 92 with appropriate reagent.

Step A: 3-(3-(1-Hydroxycyclopropyl)phenyl)-1-isopropyl-N-(3-methyl-1,1-dioxidothietan-3-yl)-1H-pyrazolo[4,3-b]pyridine-6-carboxamide (Example 127)

To a solution of 1-isopropyl-3-(3-(1-(methoxymethoxy)cyclopropyl)phenyl)-N-(3-methyl-1,1-dioxidothietan-3-yl)-1H-pyrazolo[4,3-b]pyridine-6-carboxamide (497 mg, 0.99 mmol) in dioxane (5 mL) was added HCl (0.75 mL, 4 M in dioxane). The reaction mixture was stirred for 2 h, then concentrated in vacuo. The crude residue was purified by flash silica gel chromatography (0-100% EtOAc/hexanes) to afford the title compound. LC/MS=455 [M+1].

$^1$H NMR (600 MHz, DMSO-d6) δ 9.28 (s, 1H), 9.03 (d, J=1.8 Hz, 1H), 8.66 (d, J=1.8 Hz, 1H), 8.45 (s, 1H), 8.30 (d, J=7.8 Hz, 1H), 7.44 (t, J=7.7 Hz, 1H), 7.20 (d, J=7.7 Hz, 1H), 6.04 (s, 1H), 5.14 (p, J=6.7 Hz, 1H), 4.61 (d, J=14.6 Hz, 2H), 4.37 (d, J=14.8 Hz, 2H), 1.78 (s, 3H), 1.59 (d, J=6.6 Hz, 7H), 1.18-1.14 (m, 2H), 1.04-0.97 (m, 2H). Human DGAT2 IC$_{50}$=298 nM.

Step B: 1-Isopropyl-3-(3-(1-methoxycyclopropyl)phenyl)-N-(3-methyl-1,1-dioxidothietan-3-yl)-1H-pyrazolo[4,3-b]pyridine-6-carboxamide (Example 128)

To a solution of 3-(3-(1-hydroxycyclopropyl)phenyl)-1-isopropyl-N-(3-methyl-1,1-dioxidothietan-3-yl)-1H-pyrazolo[4,3-b]pyridine-6-carboxamide (100 mg, 0.22 mmol) in THF (2.2 mL) at −78° C. was added NaH (26.4 mg, 0.66 mmol, 60 wt %). After stirring the mixture for 5 min, iodomethane (16 uL, 0.26 mmol) was added. After 1 h, the reaction mixture was quenched with sat. aq. NH$_4$Cl, warmed to room temperature, and extracted with EtOAc. The combined organic layers were dried over Na$_2$SO$_4$ and concentrated in vacuo. The crude residue was purified by mass triggered reverse phase HPLC (ACN/water with 0.1% NH$_4$OH modifier) to afford the title compound. LC/MS=469 [M+1]. $^1$H NMR (600 MHz, DMSO-d6) δ 9.29 (s, 1H), 9.05 (d, J=1.7 Hz, 1H), 8.67 (d, J=1.6 Hz, 1H), 8.46 (s, 1H), 8.34 (d, J=7.9 Hz, 1H), 7.50 (t, J=7.7 Hz, 1H), 7.28 (d, J=7.9 Hz, 1H), 5.21-5.09 (m, 1H), 4.61 (d, J=14.7 Hz, 2H), 4.37 (d, J=14.5 Hz, 2H), 3.21 (s, 3H), 1.78 (s, 3H), 1.59 (d, J=6.6 Hz, 6H), 1.24-1.19 (m, 2H), 1.06-1.01 (m, 2H). Human DGAT2 IC$_{50}$=5447 nM.

Example 129: 3-(3-(difluoromethoxy)phenyl)-1-(3-hydroxy-2,3-dimethylbutan-2-yl)-N-(3-methyl-1,1-dioxidothietan-3-yl)-1H-pyrazolo[4,3-b]pyridine-6-carboxamide

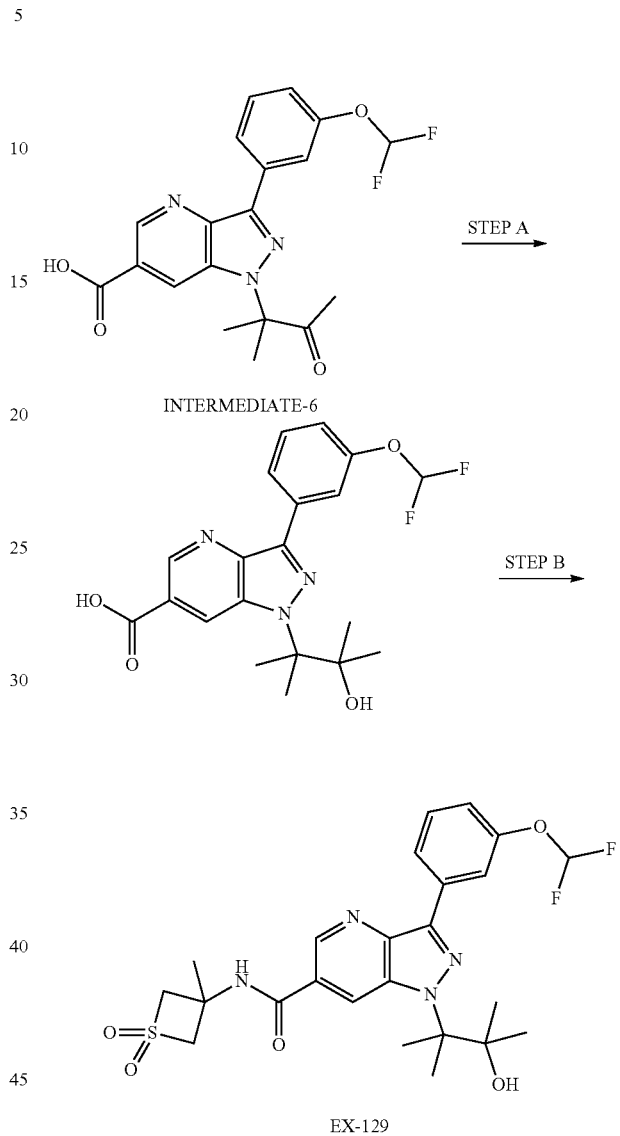

EX-129

INTERMEDIATE-6 was prepared by the synthetic procedures described for EXAMPLE 59 with appropriate reagents.

Step A: 3-(3-(difluoromethoxy)phenyl)-1-(3-hydroxy-2,3-dimethylbutan-2-yl)-1H-pyrazolo[4,3-b]pyridine-6-carboxylic acid To a solution of 3-(3-(difluoromethoxy)phenyl)-1-(2-methyl-3-oxobutan-2-yl)-1H-pyrazolo[4,3-b]pyridine-6-carboxylic acid (67 mg, 0.17 mmol) in THF (0.86 mL) at 0° C. was added MeMgBr (1.4 mL, 1 M). The resulting solution was stirred at room temperature for 2 h, then quenched with water (1 mL) and extracted with EtOAc. The organic layer was washed with brine, dried over Na$_2$SO$_4$, filtered, concentrated in vacuo to afford the crude title compound. LC/MS=406 [M+1].

Step B: 3-(3-(difluoromethoxy)phenyl)-1-(3-hydroxy-2,3-dimethylbutan-2-yl)-N-(3-methyl-1,1-dioxidothietan-3-yl)-TH-pyrazolo[4,3-b]pyridine-6-carboxamide To a solution of 3-(3-(difluoromethoxy)phenyl)-1-(3-hydroxy-2,3-dimethylbutan-2-yl)-TH-pyrazolo[4,3-b]pyridine-6-carboxylic acid (70 mg, 0.17 mmol), 3-amino-3-methylthietane 1,1-dioxide hydrochloride (35.5 mg, 0.207 mmol), and HATU (164 mg, 0.430 mmol) in DMF (2.0 mL) was added DIPEA (0.15 m, 0.86 mmol). The resulting mixture was stirred at RT for 18 h, then filtered and purified by mass triggered reverse phase HPLC (ACN/water with 0.1% formic acid modifier) to afford the title compound. LC/MS=524 [M+1]. $^1$H NMR (600 MHz, Methanol-d4) δ 8.99 (d, J=1.8 Hz, TH), 8.83 (d, J=1.8 Hz, TH), 8.38-8.34 (m, 2H), 8.30 (s, TH), 7.53 (t, J=8.0 Hz, TH), 7.18 (dd, J=8.1, 2.2 Hz, TH), 6.93 (t, J=74.2 Hz, TH), 4.66 (d, J=14.7 Hz, 2H), 4.29 (d, J=14.9 Hz, 2H), 2.00 (s, 6H), 1.90 (s, 3H), 1.21 (s, 6H). Human DGAT2 IC$_{50}$=97 nM.

By using procedures similar to those described in Example 129 with appropriate reagents, the following compounds were synthesized. These compounds were characterized by LC/MS.

| Example | Structure | Name | LCMS [M + 1] | DGAT2 IC$_{50}$ (nM) |
|---|---|---|---|---|
| 130a | 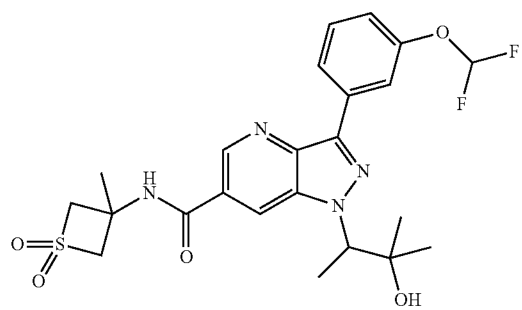 [SMILES: CC(n1nc(-c2cccc(OC(F)F)c2)c2ncc(C(=O)NC3(C)CS(=O)(=O)C3)cc21)C(C)(C)O] | 3-(3-(difluoromethoxy)phenyl)-1-(3-hydroxy-3-methylbutan-2-yl)-N-(3-methyl-1,1-dioxidothietan-3-yl)-1H-pyrazolo[4,3-b]pyridine-6-carboxamide (faster eluting in AD-H column, 25% MeOH (0.1% DEA)/CO$_2$) | 510 | 2.8 |
| 130b | 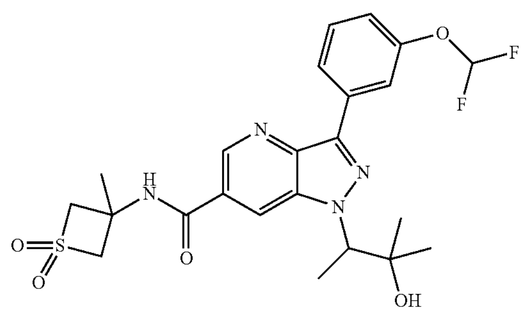 [SMILES: CC(n1nc(-c2cccc(OC(F)F)c2)c2ncc(C(=O)NC3(C)CS(=O)(=O)C3)cc21)C(C)(C)O] | 3-(3-(difluoromethoxy)phenyl)-1-(3-hydroxy-3-methylbutan-2-yl)-N-(3-methyl-1,1-dioxidothietan-3-yl)-1H-pyrazolo[4,3-b]pyridine-6-carboxamide (slower eluting in AD-H column, 25% MeOH (0.1% DEA)/CO$_2$) | 510 | 80 |
| 131a | 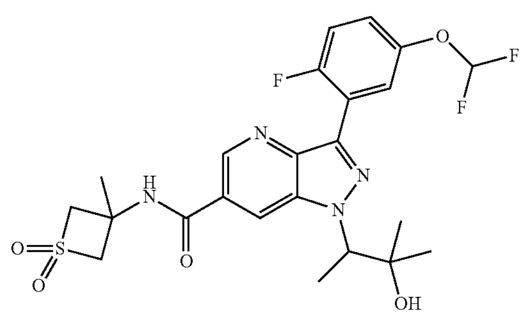 [SMILES: CC(n1nc(-c2cc(OC(F)F)ccc2F)c2ncc(C(=O)NC3(C)CS(=O)(=O)C3)cc21)C(C)(C)O] | 3-(5-(difluoromethoxy)-2-fluorophenyl)-1-(3-hydroxy-3-methylbutan-2-yl)-N-(3-methyl-1,1-dioxidothietan-3-yl)-1H-pyrazolo[4,3-b]pyridine-6-carboxamide (faster eluting in AD-H column, 25% MeOH (0.1% DEA)/CO$_2$) | 527 | 11 |
| 131b | 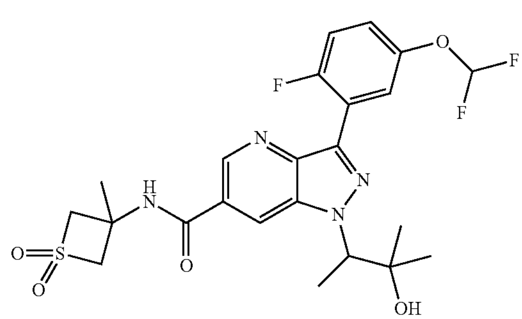 [SMILES: CC(n1nc(-c2cc(OC(F)F)ccc2F)c2ncc(C(=O)NC3(C)CS(=O)(=O)C3)cc21)C(C)(C)O] | 3-(5-(difluoromethoxy)-2-fluorophenyl)-1-(3-hydroxy-3-methylbutan-2-yl)-N-(3-methyl-1,1-dioxidothietan-3-yl)-1H-pyrazolo[4,3-b]pyridine-6-carboxamide (slower eluting in AD-H column, 25% MeOH (0.1% DEA)/CO$_2$) | 527 | 110 |

| Example | Structure | Name | LCMS [M + 1] | DGAT2 IC$_{50}$ (nM) |
|---|---|---|---|---|
| 132a | 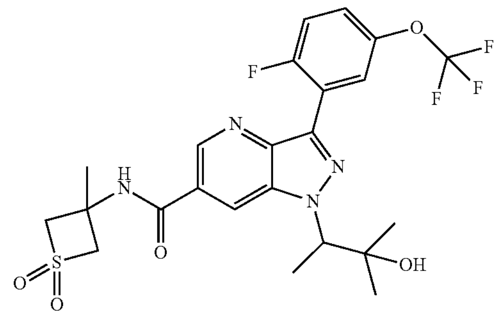 [SMILES: CC(n1nc(-c2cc(OC(F)(F)F)ccc2F)c2ncc(C(=O)NC3(C)CS(=O)(=O)C3)cc21)C(C)(C)O] | 3-(2-fluoro-5-(trifluoromethoxy)phenyl)-1-(3-hydroxy-3-methylbutan-2-yl)-N-(3-methyl-1,1-dioxidothietan-3-yl)-1H-pyrazolo[4,3-b]pyridine-6-carboxamide(faster eluting in AD-H column, 25% MeOH (0.1% DEA)/CO$_2$) | 545 | 231 |
| 132b | 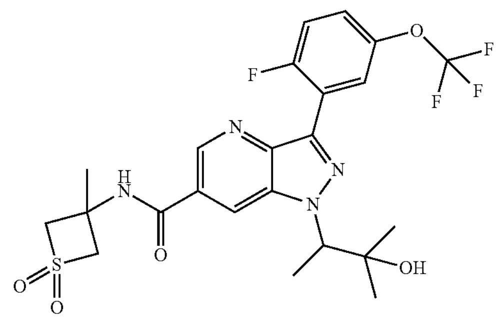 [SMILES: CC(n1nc(-c2cc(OC(F)(F)F)ccc2F)c2ncc(C(=O)NC3(C)CS(=O)(=O)C3)cc21)C(C)(C)O] | 3-(2-fluoro-5-(trifluoromethoxy)phenyl)-1-(3-hydroxy-3-methylbutan-2-yl)-N-(3-methyl-1,1-dioxidothietan-3-yl)-1H-pyrazolo[4,3-b]pyridine-6-carboxamide(slower eluting in AD-H column, 25% MeOH (0.1% DEA)/CO$_2$) | 545 | 215 |
| 133a | 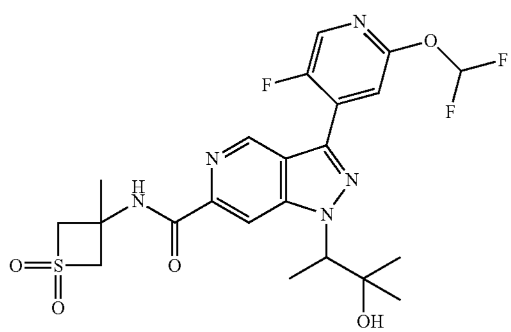 [SMILES: CC(n1nc(-c2cc(OC(F)F)ncc2F)c2cnc(C(=O)NC3(C)CS(=O)(=O)C3)cc21)C(C)(C)O] | 3-(2-(difluoromethoxy)-5-fluoropyridin-4-yl)-1-(3-hydroxy-3-methylbutan-2-yl)-N-(3-methyl-1,1-dioxidothietan-3-yl)-1H-pyrazolo[4,3-c]pyridine-6-carboxamide (faster eluting in AD-H column, 25% MeOH (0.1% DEA)/CO$_2$) | 528 | 862 |
| 133b | 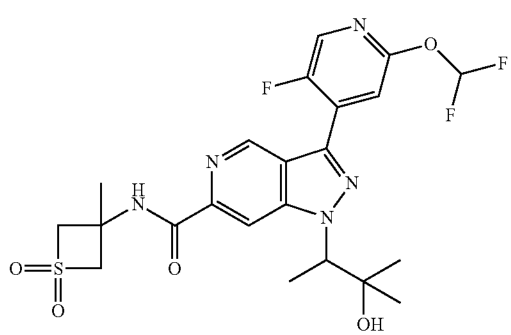 [SMILES: CC(n1nc(-c2cc(OC(F)F)ncc2F)c2cnc(C(=O)NC3(C)CS(=O)(=O)C3)cc21)C(C)(C)O] | 3-(2-(difluoromethoxy)-5-fluoropyridin-4-yl)-1-(3-hydroxy-3-methylbutan-2-yl)-N-(3-methyl-1,1-dioxidothietan-3-yl)-1H-pyrazolo[4,3-c]pyridine-6-carboxamide (slower eluting in AD-H column, 25% MeOH (0.1% DEA)/CO$_2$) | 528 | 15 |

Example 134: 3-(3-(Difluoromethoxy)phenyl)-N-(3-methyl-1,1-dioxidothietan-3-yl)-1-(1-methylpiperidin-4-yl)-1H-pyrazolo[4,3-b]pyridine-6-carboxamide

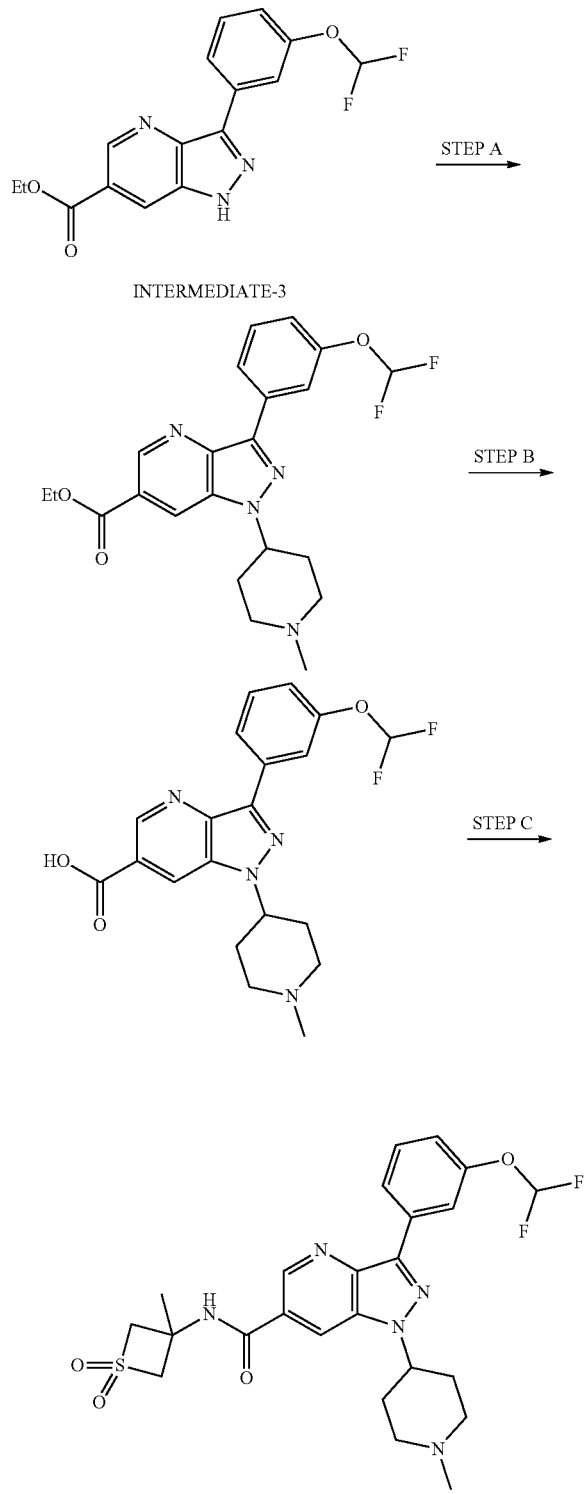

INTERMEDIATE-3

EX-134

Step A: Ethyl 3-(3-(difluoromethoxy)phenyl)-1-(1-methylpiperidin-4-yl)-1H-pyrazolo[4,3-b]pyridine-6-carboxylate To a solution of ethyl 3-(3-(difluoromethoxy)phenyl)-1H-pyrazolo[4,3-b]pyridine-6-carboxylate (100 mg, 0.30 mmol), 1-methylpiperidin-4-ol (69.1 mg, 0.60 mmol), and PPh$_3$ (157 mg, 0.60 mmol) in THF (1.5 mL) was added diisopropyl azodicarboxylate (0.117 mL, 0.60 mmol), and the reaction mixture was stirred for 4 d at RT. The reaction mixture was used in the next step without purification. LC/MS=431 [M+1].

Step B: 3-(3-(Difluoromethoxy)phenyl)-1-(1-methylpiperidin-4-yl)-1H-pyrazolo[4,3-b]pyridine-6-carboxylic acid To a solution ethyl 3-(3-(difluoromethoxy)phenyl)-1-(1-methylpiperidin-4-yl)-1H-pyrazolo[4,3-b]pyridine-6-carboxylate (0.13 g, 0.30 mmol) in THF (1.5 mL) was added aq. NaOH (1 M, 3.0 mL, 3.0 mmol). The reaction was stirred at RT for 24 h, then concentrated to afford the crude title compound. LC/MS=403 [M+1].

Step C: 3-(3-(Difluoromethoxy)phenyl)-N-(3-methyl-1,1-dioxidothietan-3-yl)-1-(1-methylpiperidin-4-yl)-1H-pyrazolo[4,3-b]pyridine-6-carboxamide To a solution of 3-(3-(difluoromethoxy)phenyl)-1-(1-methylpiperidin-4-yl)-1H-pyrazolo[4,3-b]pyridine-6-carboxylic acid (0.121 g, 0.30 mmol), 3-amino-3-methylthietane 1,1-dioxide hydrochloride (0.056 g, 0.33 mmol), and HATU (0.23 g, 0.60 mmol) in DMF (2.0 mL) was added DIPEA (0.11 mL, 0.60 mmol). The reaction was stirred for 1 h at RT, then purified by mass triggered reverse phase HPLC (ACN/water with 0.10% NH$_4$OH modifier) to afford the title compound. LC/MS=520 [M+1]. $^1$H NMR (600 MHz, Methanol-d4) δ 9.08 (d, J=1.8 Hz, 1H), 8.63 (d, J=1.8 Hz, 1H), 8.48 (s, 1H), 8.41 (d, J=8.0 Hz, 1H), 8.30 (s, 1H), 7.55 (t, J=8.0 Hz, 1H), 7.21 (dd, J=8.1, 2.2 Hz, 1H), 6.94 (t, J=74.1 Hz, 1H), 4.98 (dt, J=11.2, 6.9 Hz, 1H), 4.67 (d, J=14.7 Hz, 2H), 4.32 (d, J=14.9 Hz, 2H), 3.48 (d, J=12.3 Hz, 2H), 2.94 (t, J=11.3 Hz, 2H), 2.75 (s, 3H), 2.63-2.55 (m, 2H), 2.30 (d, J=11.8 Hz, 2H), 1.91 (s, 3H). Human DGAT2 IC$_{50}$=33 nM.

By using procedures similar to those described in Example 134 with appropriate reagents, the following compounds were synthesized. These compounds were characterized by LC/MS.

| Example | Structure | Name | LCMS [M + 1] | Human DGAT2 IC$_{50}$ (nM) |
|---|---|---|---|---|
| 135 | 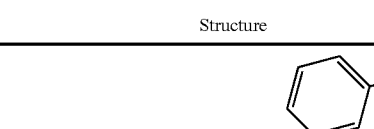 | 1-(1-acetylazetidin-3-yl)-3-(3-(difluoromethoxy)phenyl)-N-(3-methyl-1,1-dioxidothietan-3-yl)-1H-pyrazolo[4,3-b]pyridine-6-carboxamide | 521 | 7936 |

Assays

Insect Cell Expression and Membrane Preparation

Sf-9 insect cells were maintained in Grace's insect cell culture medium with 10% heated-inactivated fetal bovine serum, 1% Pluronic F-68 and 0.14 µg/ml Kanamycine sulfate at 27° C. in a shaker incubator. After infection with untagged baculovirus expressing human DGAT2 (hDGAT2) at multiplicity of infection (MOI) 3 for 48 hours, cells were harvested. Cell pellets were suspended in buffer containing 10 mM Tris-HCl pH 7.5, 1 mM EDTA, 250 mM sucrose and Complete Protease Inhibitor Cocktail (Sigma Aldrich), and sonicated on ice. Cell debris were removed by centrifugation at 2000×g for 15 minutes. Membrane fractions were isolated by ultracentrifugation (100,000×g), resuspended in the same buffer, and frozen (−80° C.) for later use. The protein concentration was determined with the Pierce™ BCA Protein Assay Kit (Thermo Fisher Scientific). Expression of protein levels was analyzed by immunoblotting with rabbit anti-DGAT2 antibody (Abcam, ab102831) and donkey anti-rabbit IgG H&L Alexa Fluor® 647 (Abcam, ab150075) followed by detection using Typhoon FLA9000 (GE Healthcare).

LC/MS/MS Analysis Method

LC/MS/MS analyses were performed using Thermal Fisher's LX4-TSQ Vantage system. This system consists of an Agilent binary high-performance liquid chromatography (HPLC) pumps and a TSQ Vantage triple quadrupole MS/MS instrument. For each sample, 2 µL samples from the top organic layer of in-plate liquid-liquid extraction were injected onto a Thermo Betabasic C4 column (2.1 mm×20 mm, 5 µm particle size). The samples were then eluted using the following conditions; mobile phase: Isopropanol:acetonitrile/10 mM ammonium formate=50/35/15 (v/v/v), flow rate: 0.8 mL/min, temperature: 25° C. Data was acquired in positive mode using a heated electrospray ionization (HESI) interface. The operational parameters for the TSQ Vantage MS/MS instrument were a spray voltage of 3000 V, capillary temperature of 280° C., vaporizer temperature 400° C., sheath gas 45 arbitrary unit, Aux gas 10 arbitrary units, S-lens 165 and collision gas 1.0 mTorr. Standard reference material (SRM) chromatograms of $^{13}C_{18}$-triolein (Q1: 920.8>Q3:621.3) and internal standard $^{13}C_{21}$-triolein (Q1: 923.8>Q3:617.3) were collected for 33 sec. The peak area was integrated by Xcalibur Quan software. The ratio between the $^{13}C_{18}$triolein generated in the reaction and spiked in internal standard $^{13}C_{21}$-triolein was used to generate percentage inhibition and IC$_{50}$ values. Compound percentage inhibition was calculated by the following formula: Inhibition %=1-[(compound response–low control)/(high control–low control)]×100%. Potent compounds were titrated and IC$_{50}$ were calculated by 4 parameter sigmoidal curve fitting formula.

DGAT2 Enzymatic Activity Assay

DGAT2 activity was determined by measuring the amount of enzymatic product $^{13}C_{18}$-triolein ($^{13}C$-1,2,3-Tri(cis-9-octadecenoyl)glycerol) using the membrane prep mentioned above. The assay was carried out in ABgene 384-well assay plates in a final volume of 25 µL at rt. The assay mixture contained the following: assay buffer (100 mM Tris·Cl, pH 7.0, 20 mM MgCl$_2$, 5% ethanol), 25 µM of diolein, 5 µM of $^{13}C$ oleoyl-CoA and 8 ng/µL of DGAT2 membrane.

What is claimed is:

1. A compound of Formula I,

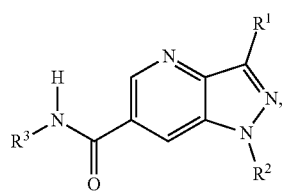

or a pharmaceutically acceptable salt thereof, wherein R$^1$ is

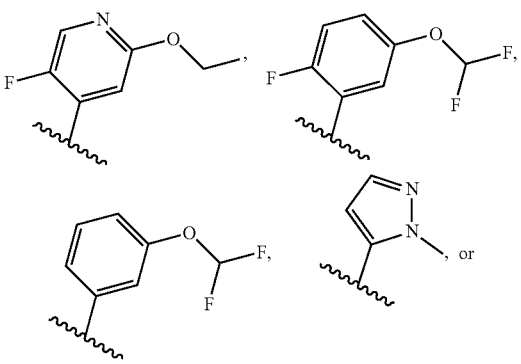

-continued

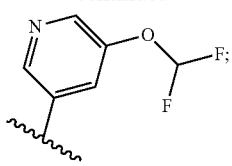

R² is

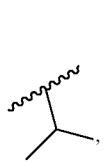 , 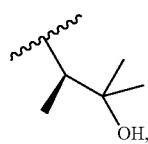 , 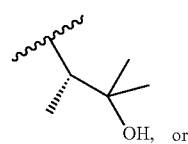 or

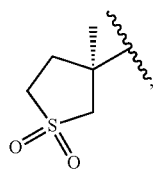 ;

and
R³ is

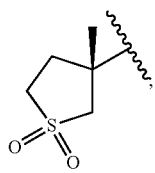 , 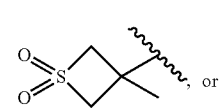 , or

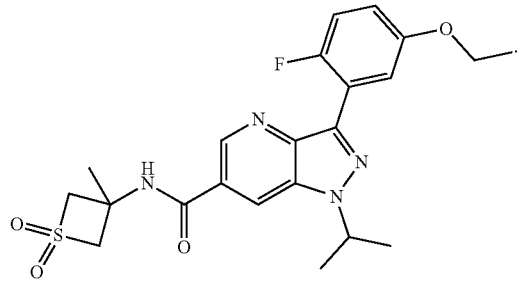 .

2. The compound of claim 1, or a pharmaceutically acceptable salt thereof, which is

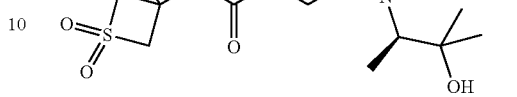

3. The compound of claim 1, or a pharmaceutically acceptable salt thereof, which is

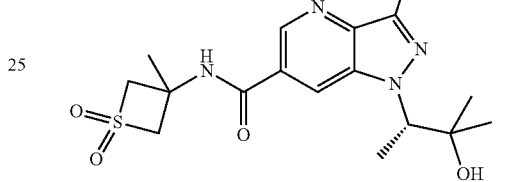

4. The compound of claim 1, or a pharmaceutically acceptable salt thereof, which is

5. The compound of claim 1, or a pharmaceutically acceptable salt thereof, which is

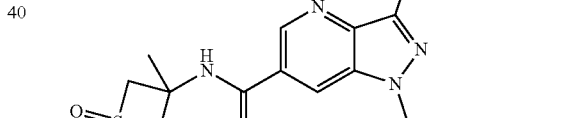

6. The compound of claim 1, or a pharmaceutically acceptable salt thereof, which is

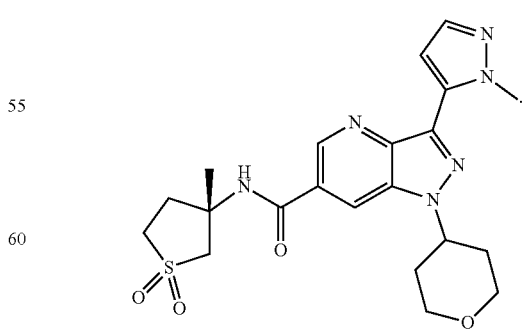

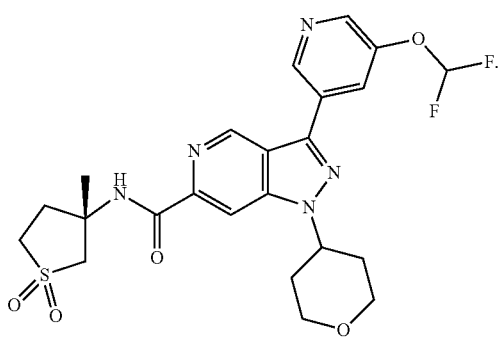 [SMILES: C[C@]1(NC(=O)c2cc3c(cn2)c(-c2cncc(OC(F)F)c2)nn3C2CCOCC2)CCS(=O)(=O)C1]

7. A composition comprising a pharmaceutically acceptable carrier and a compound according to claim 1, or a pharmaceutically acceptable salt thereof.

8. A method for treating a condition selected from hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases and heart failure comprising administering to a patient in need thereof a compound of claim 1, or a pharmaceutically acceptable salt thereof.

9. A compound of Formula I:

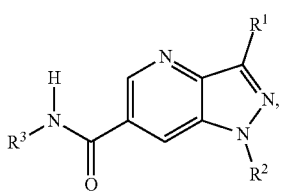

or a pharmaceutically acceptable salt thereof, wherein
$R^1$ is
- (a) phenyl optionally substituted with one to three substituents independently selected from halogen, hydroxy, $N(C_{1-3}alkyl)_2$, CN, $C_{1-6}alkyl$, $C_{1-6}haloalkyl$, $C_{3-6}cycloalkyl$, $OC_{1-6}alkyl$, $OC_{1-6}haloalkyl$, $OC_{3-6}cycloalkyl$, $S(O)_2C_{1-6}alkyl$, $OC_{1-6}alkyl-CN$, $C_{1-6}alkyl-CN$, or $NHC(O)C_{1-6}alkyl$, and wherein the cycloalkyl is optionally substituted with $C_{1-6}alkyl$, $C_{1-6}haloalkyl$, CN, OH, or $OC_{1-6}alkyl$;
- (b) 6 membered heteroaryl containing one nitrogen atom optionally substituted with one to three substituents independently selected from halogen, hydroxy, $C_{1-6}alkyl$, $C_{1-6}haloalkyl$, $C_{3-6}cycloalkyl$, $OC_{1-6}alkyl$, $OC_{1-6}haloalkyl$, $O-C_{3-6}cycloalkyl$, $OC_{1-6}alkyl-CN$ or CN, and when the cycloalkyl is cyclopropyl, the cyclopropyl is optionally substituted with halogen, $C_{1-6}alkyl$, $C_{1-6}haloalkyl$, CN, OH, or $OC_{1-6}alkyl$; or
- (c) 5 membered heteroaryl containing 2 N atoms optionally substituted with $C_{1-6}alkyl$;

$R^2$ is:
- (a) 4 to 6 membered heterocycle containing one oxygen atom optionally mono-substituted or disubstituted with halogen, $C_{1-6}haloalkyl$, $C_{1-6}alkyl$, $C(O)C_{1-6}alkyl$, or OH, or
- (b) $C_{1-6}alkyl$ unsubstituted or optionally mono-substituted, disubstituted or trisubstituted with halogen, OH, $CF_3$, or CN; and $R^3$ is a 4, 5, or 6 membered heterocyclyl containing 1 sulfur atom optionally mono-substituted, disubstituted, trisubstituted, or quad-substituted with oxo, $CH_3$, or OH.

10. The compound of claim 9 of Formula I,

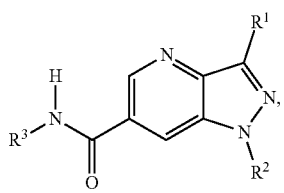

or a pharmaceutically acceptable salt thereof, wherein $R^1$ is

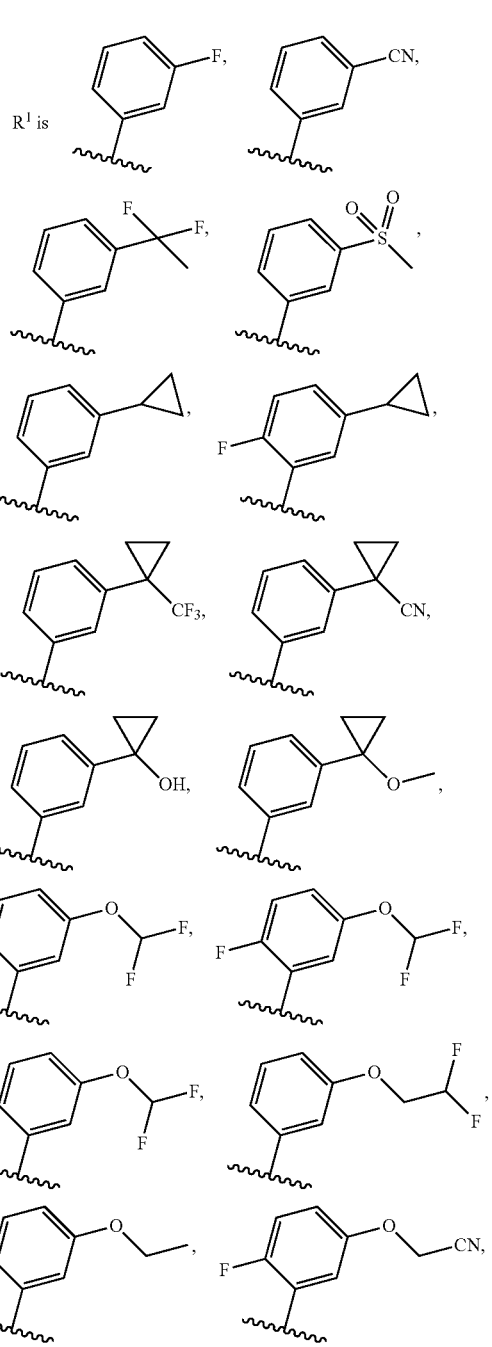

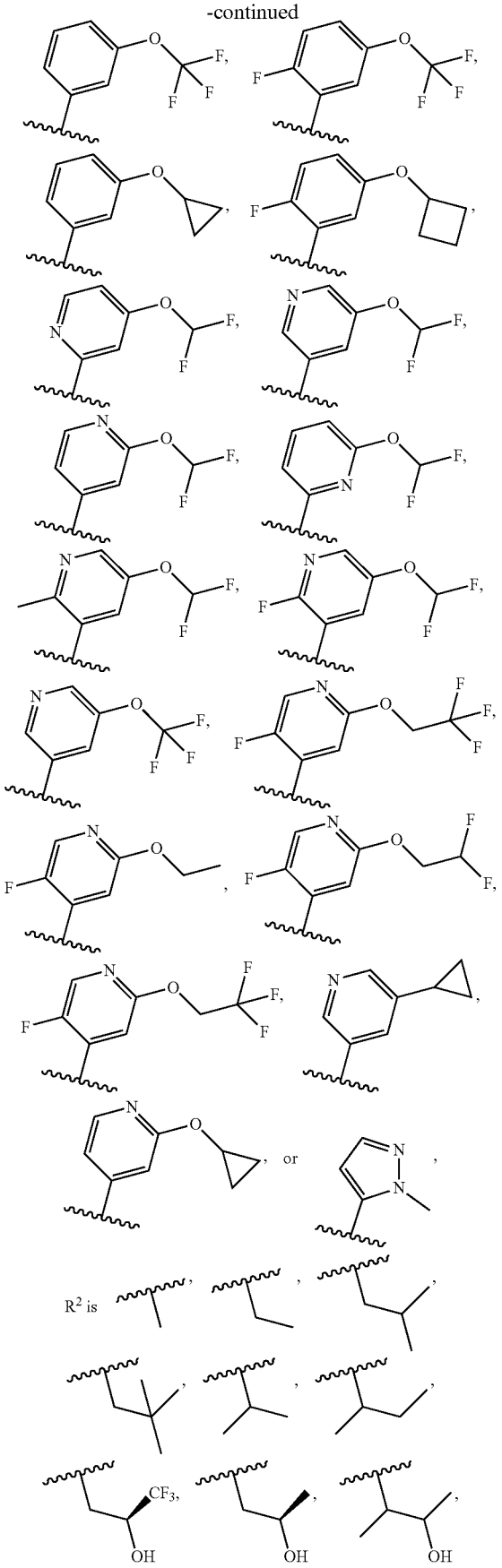
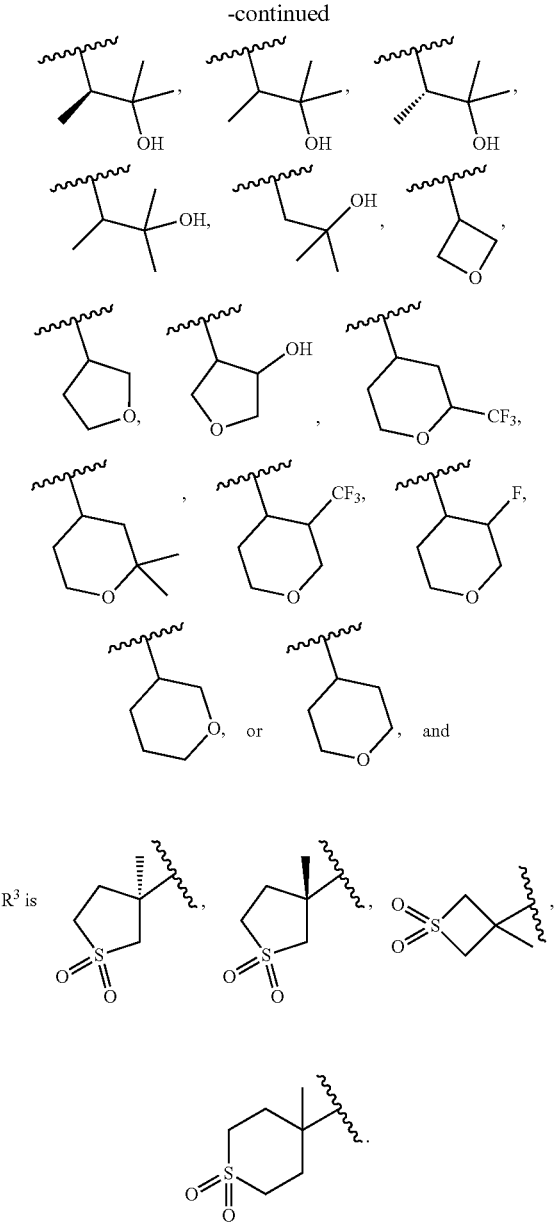
11. A composition comprising a pharmaceutically acceptable carrier and a compound according to claim 9, or a pharmaceutically acceptable salt thereof.
12. The compound of claim 9, or a pharmaceutically acceptable salt thereof, which is:
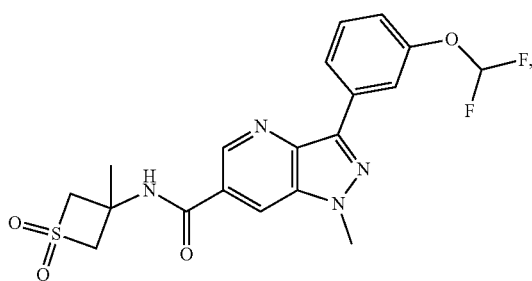

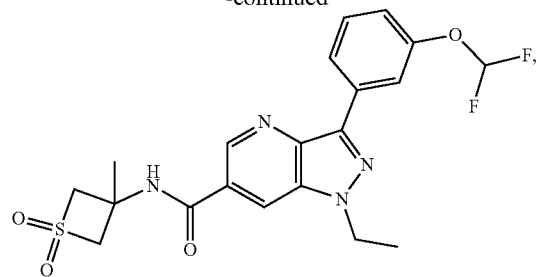
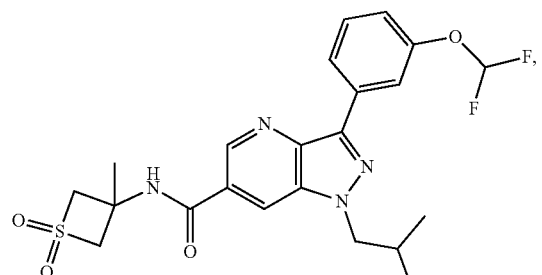
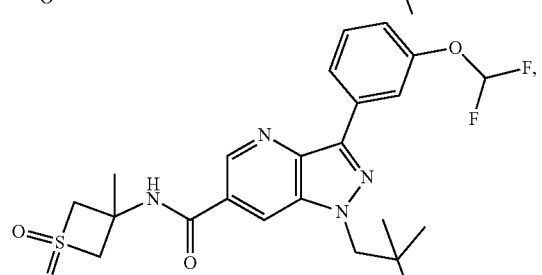
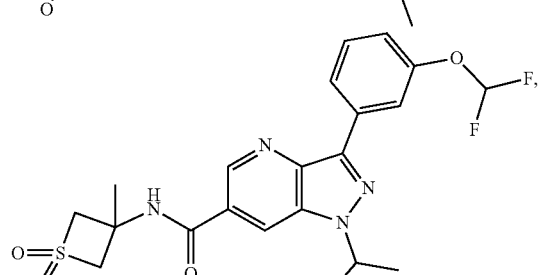
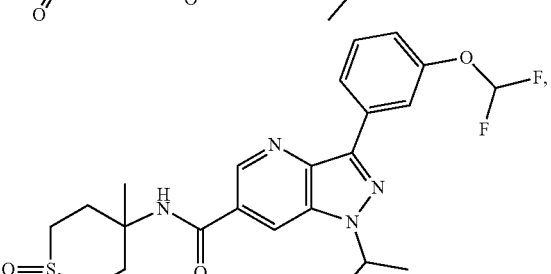
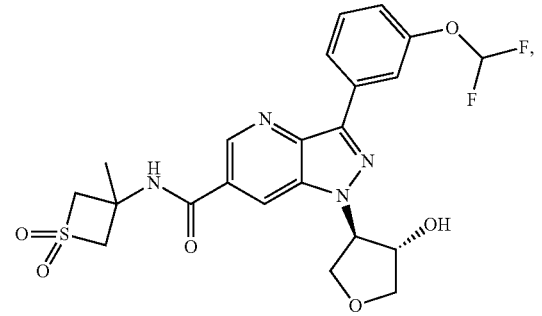 [SMILES: CC1(NC(=O)c2cnc3c(-c4cccc(OC(F)F)c4)nn([C@@H]4COC[C@H]4O)c3c2)CS(=O)(=O)C1]
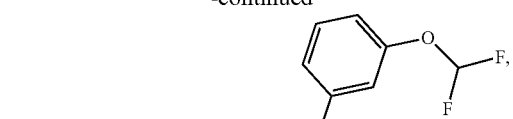
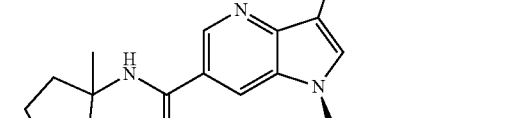
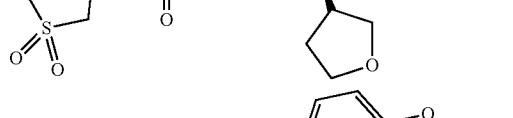
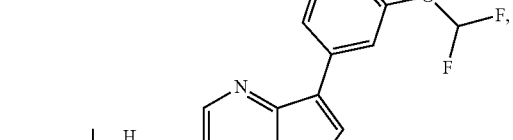
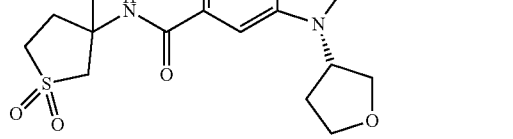
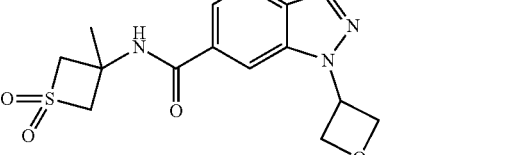
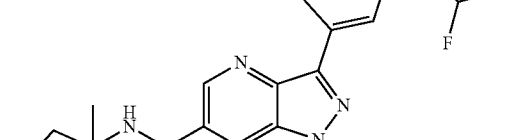
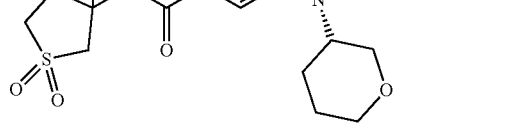
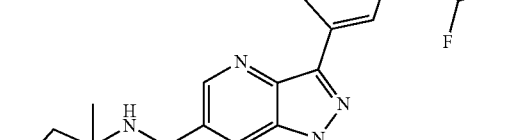

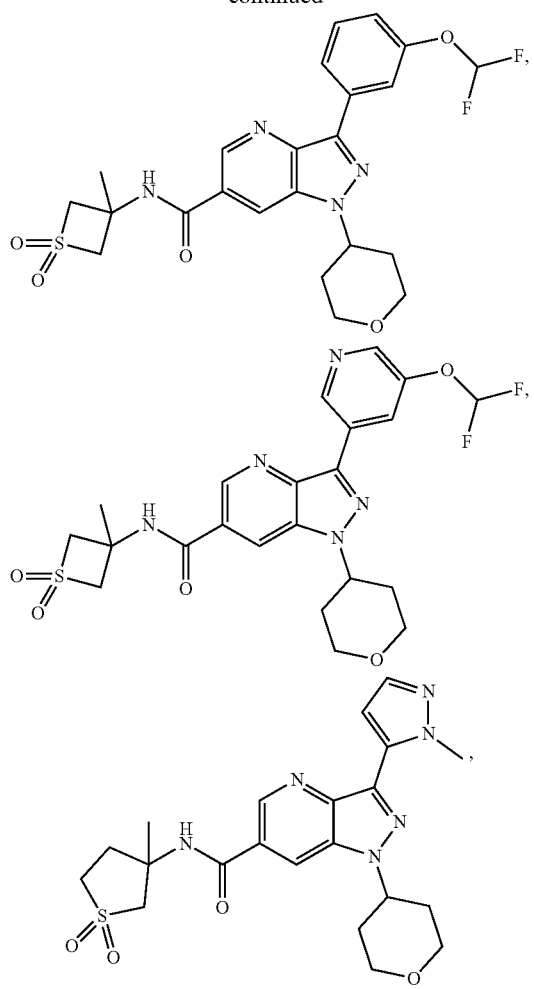

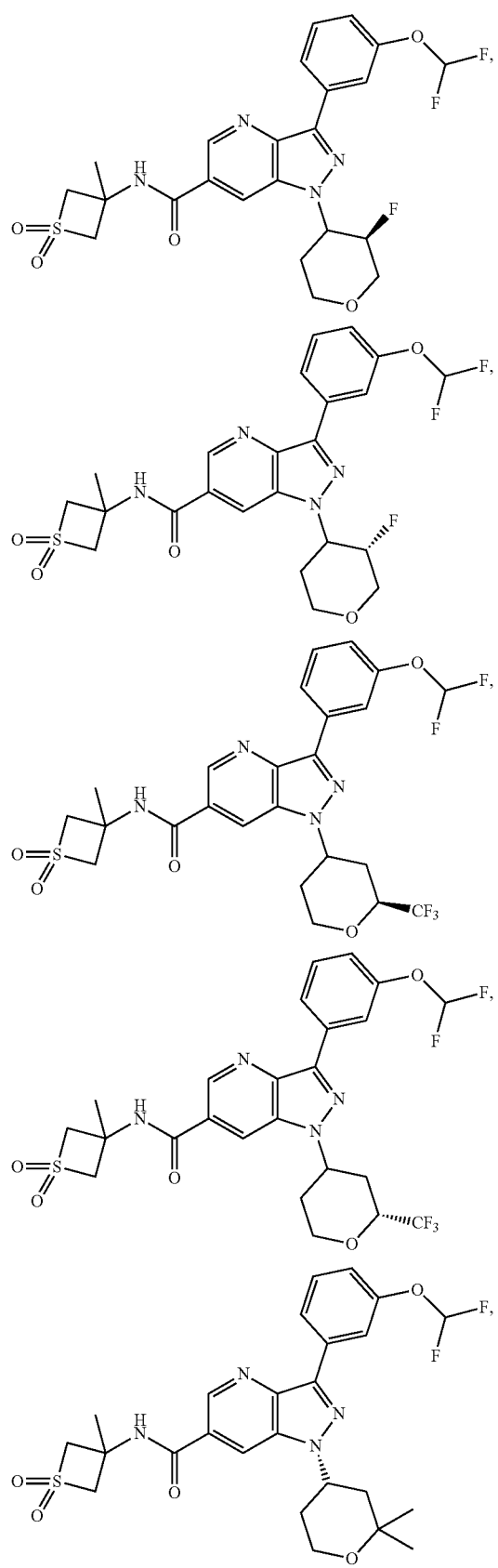
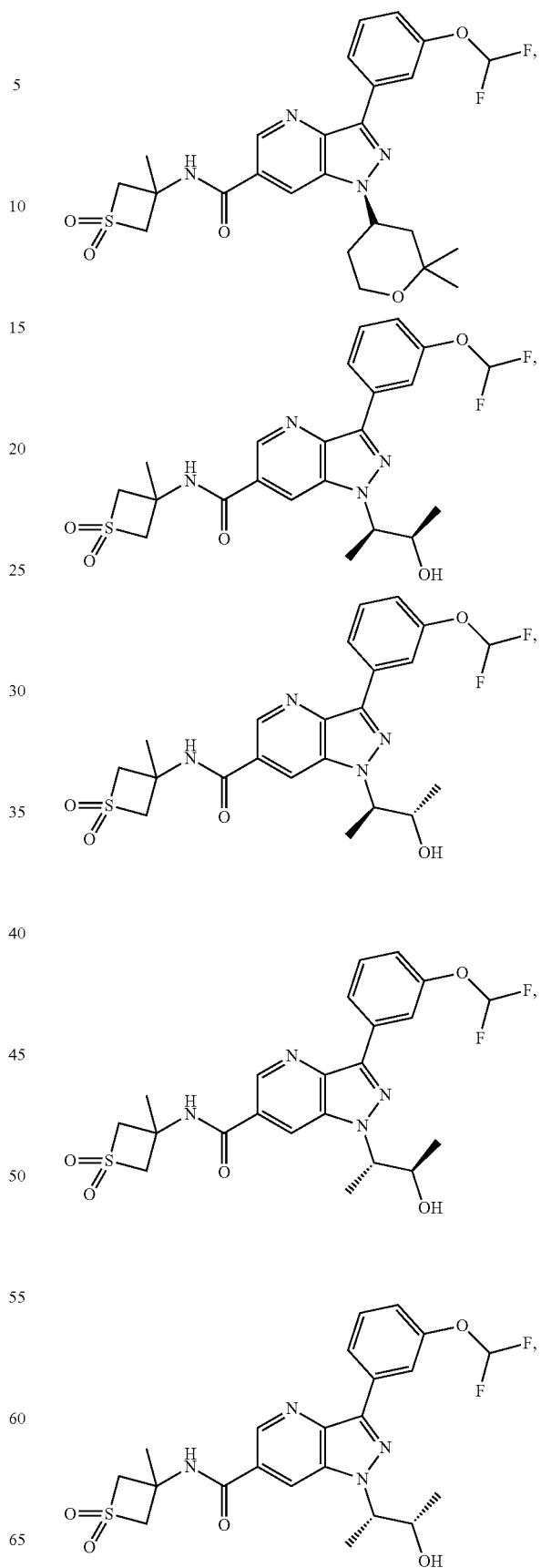

191
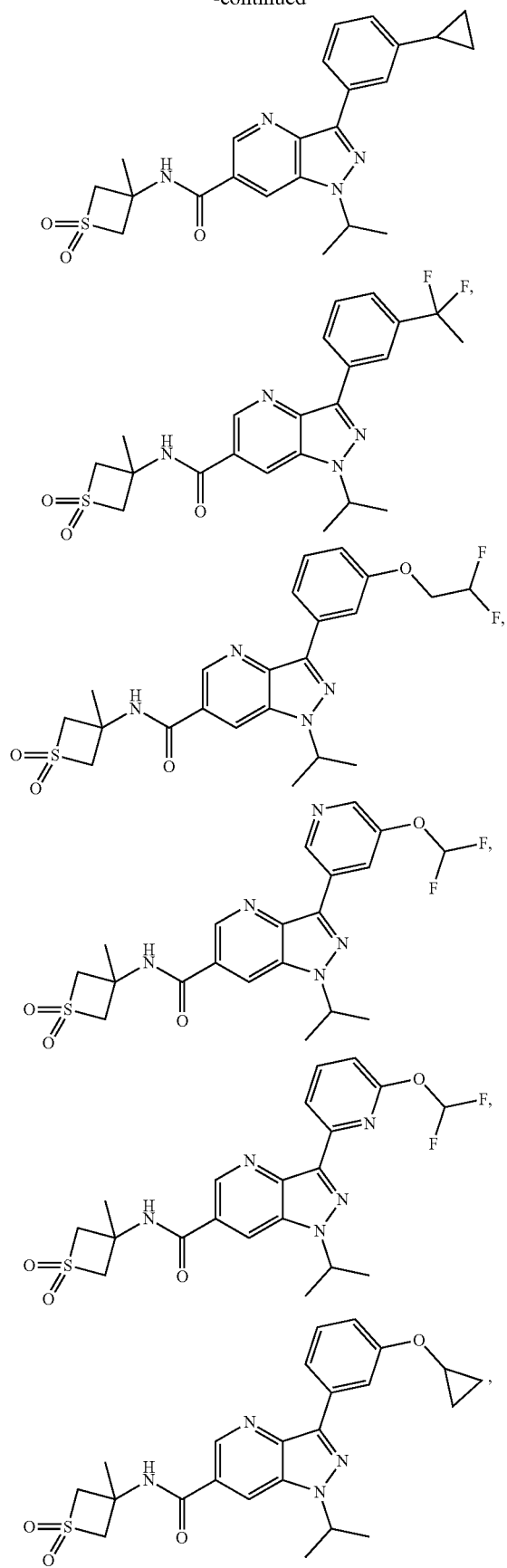
192
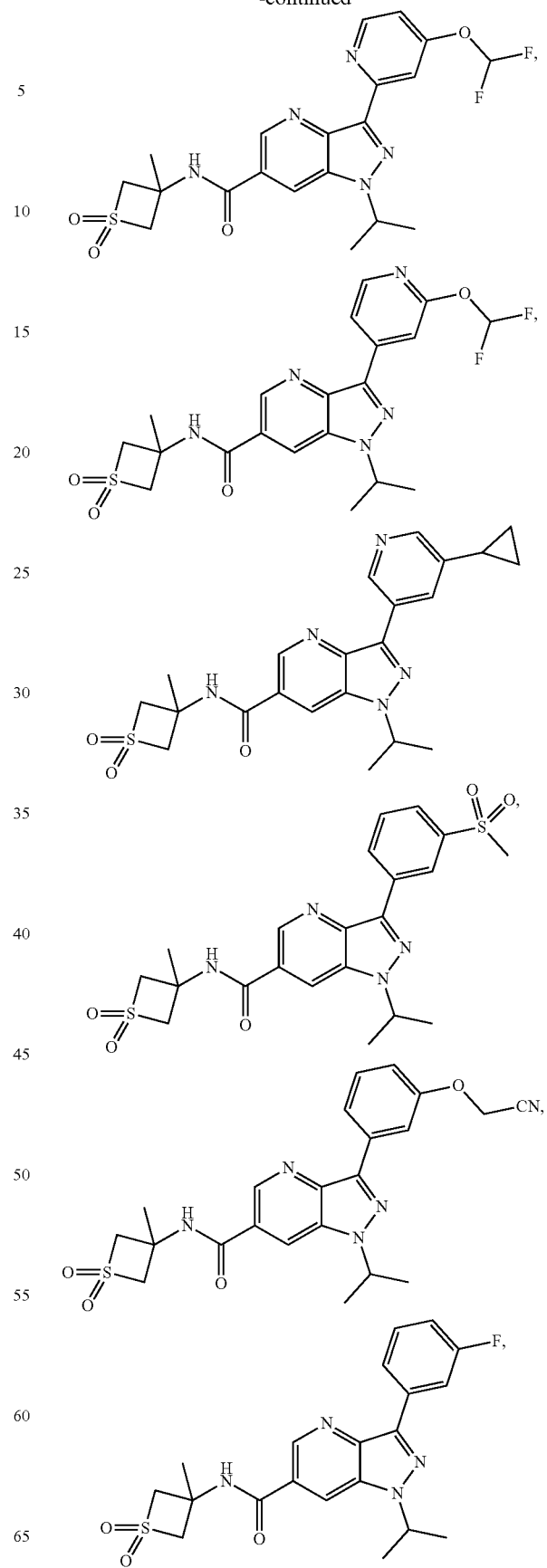

193
-continued
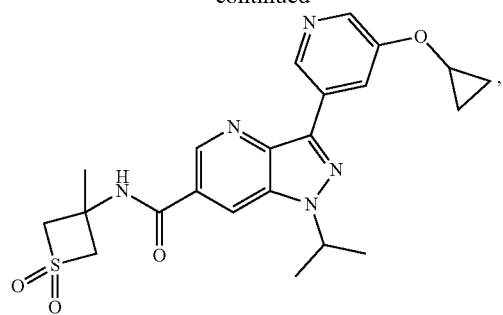
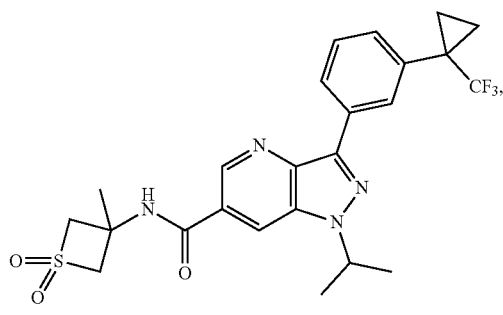
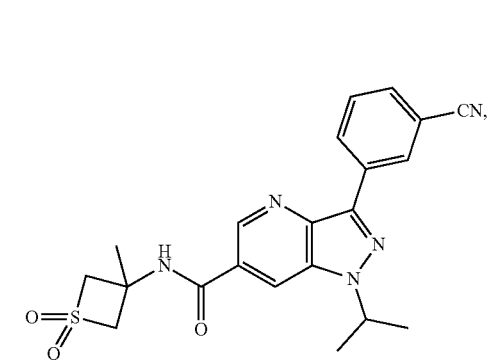
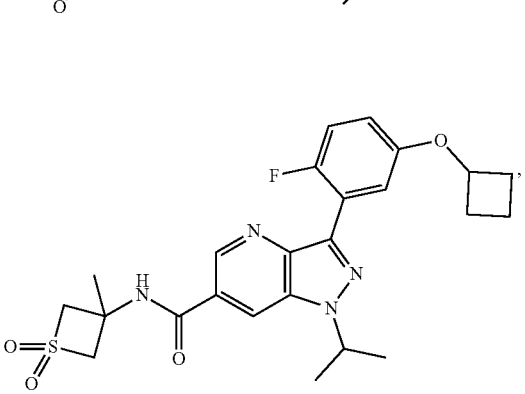
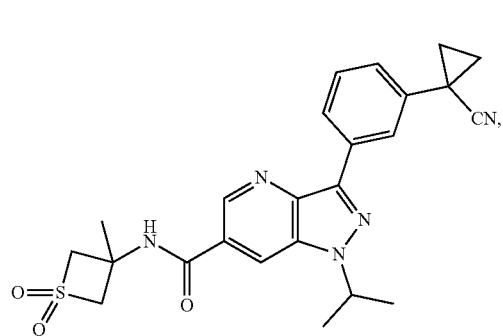
194
-continued
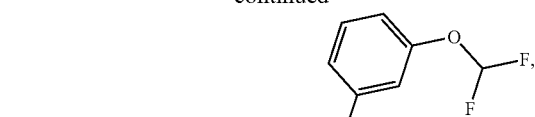
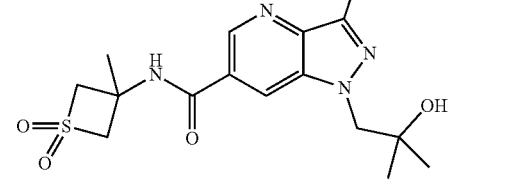
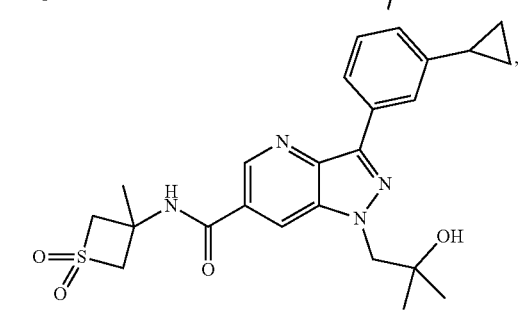
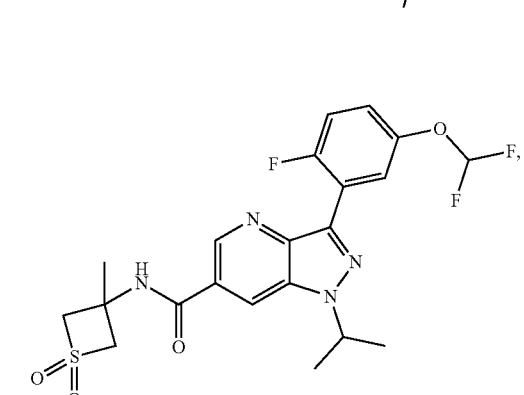
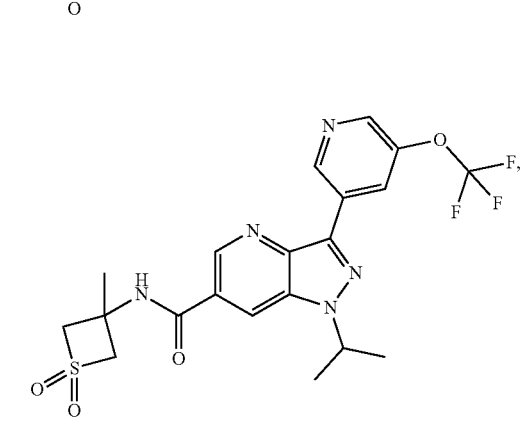
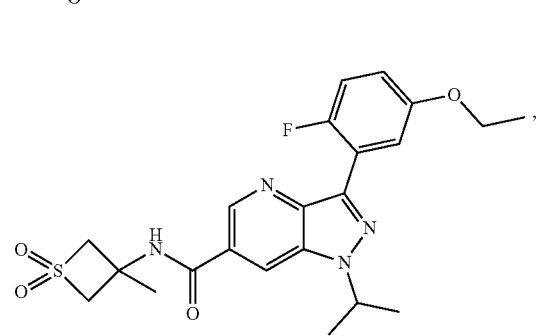

-continued
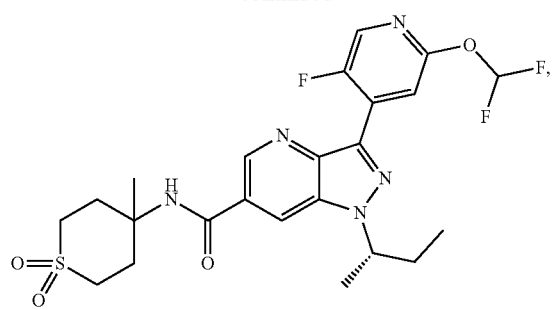
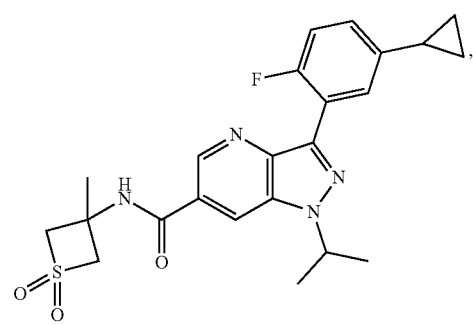
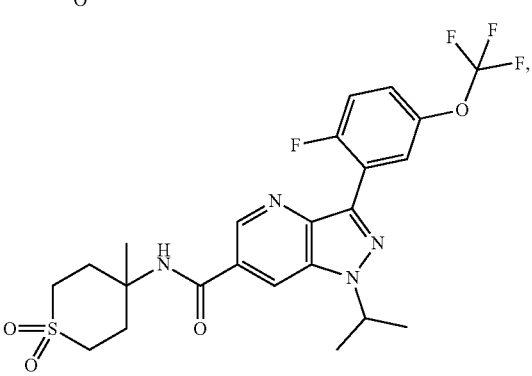
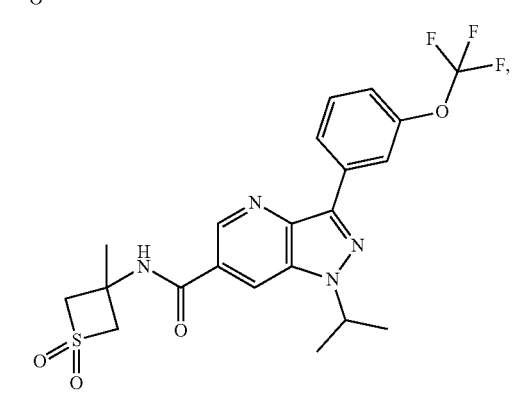
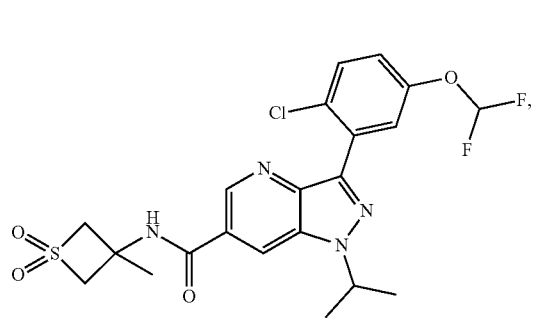
-continued
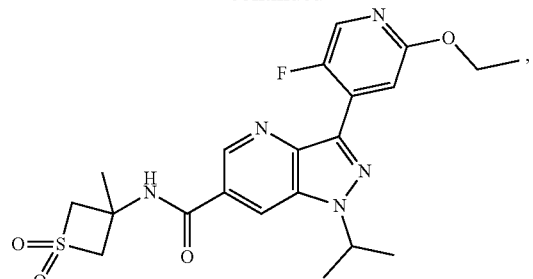
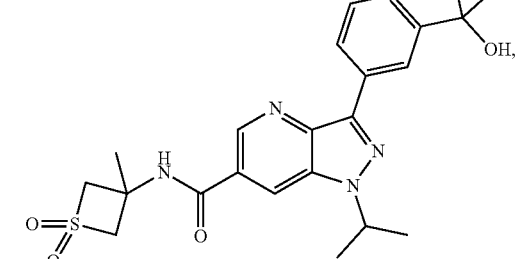
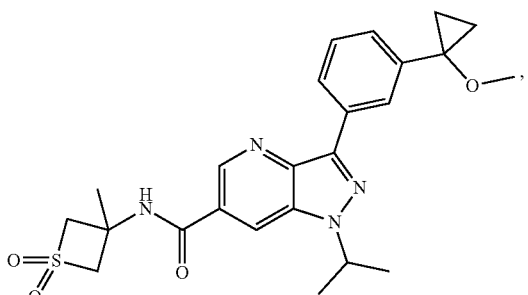
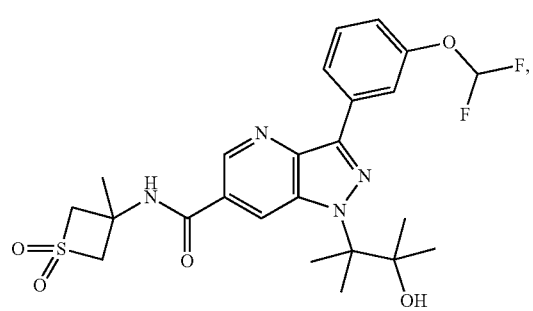
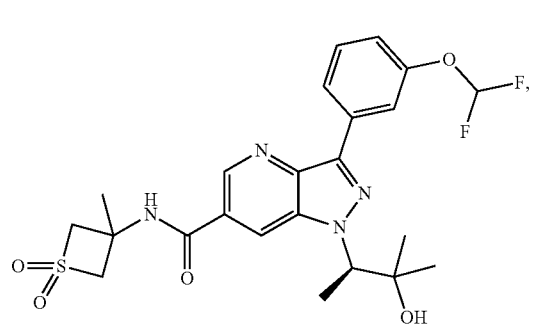

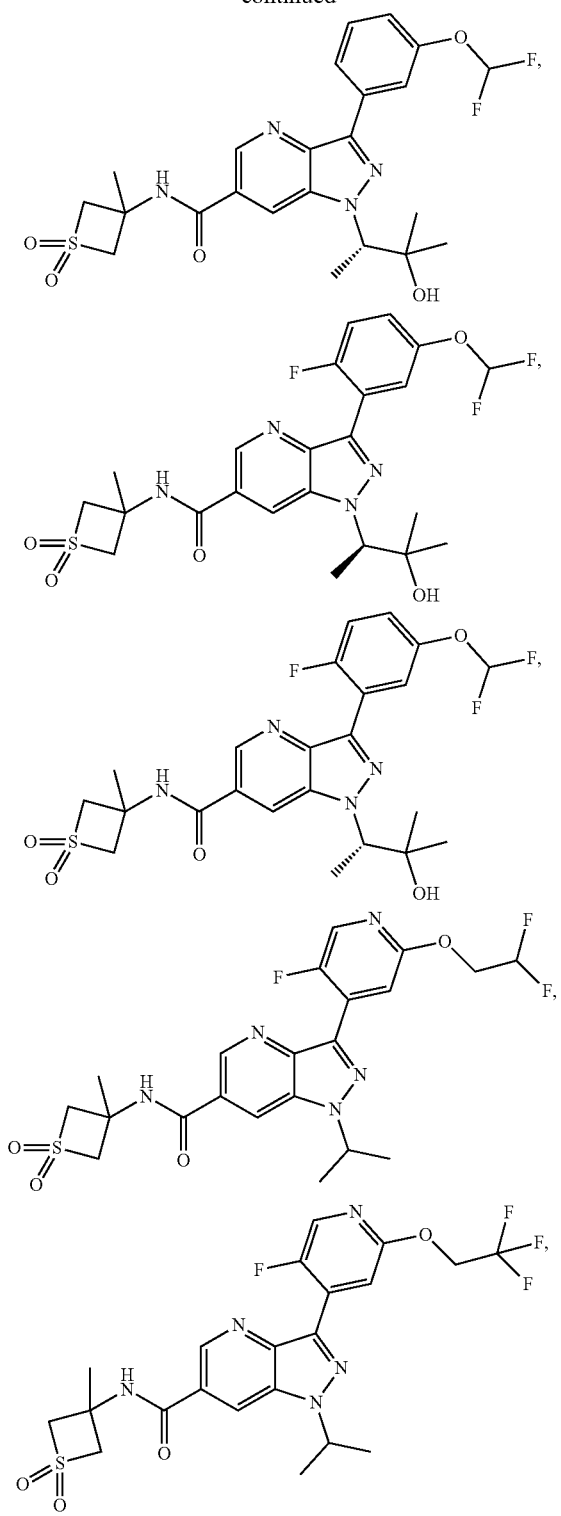

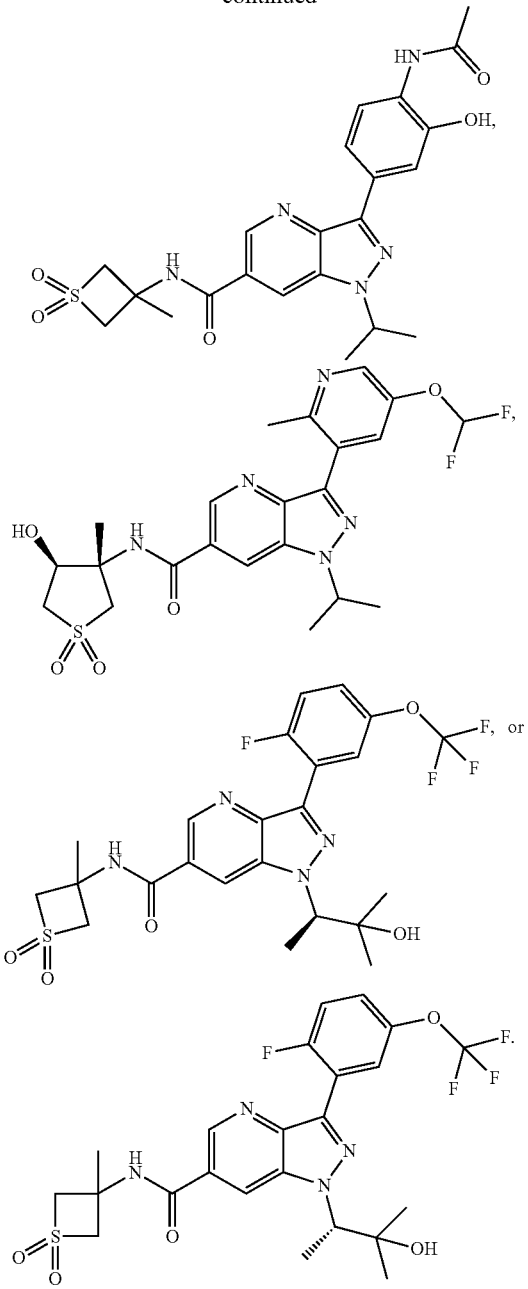

13. A method for treating a condition selected from hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases and heart failure comprising administering to a patient in need thereof a compound of claim 9, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 11,787,810 B2 | Page 1 of 1 |
| APPLICATION NO. | : 17/319121 | |
| DATED | : October 17, 2023 | |
| INVENTOR(S) | : Yeon-Hee Lim et al. | |

It is certified that error appears in the above-identified patent and that said Letters Patent is hereby corrected as shown below:

On the Title Page

Item (71) Applicant
Please correct "Merck Sharp & Dohme Corp" to read "Merck Sharp & Dohme LLC"

Signed and Sealed this
Twelfth Day of November, 2024

*Katherine Kelly Vidal*
Katherine Kelly Vidal
*Director of the United States Patent and Trademark Office*